(12) United States Patent
Riddell et al.

(10) Patent No.: US 11,723,962 B2
(45) Date of Patent: Aug. 15, 2023

(54) CELL-BASED NEOANTIGEN VACCINES AND USES THEREOF

(71) Applicant: FRED HUTCHINSON CANCER CENTER, Seattle, WA (US)

(72) Inventors: Stanley R. Riddell, Sammamish, WA (US); Joshua Veatch, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 189 days.

(21) Appl. No.: 16/098,808

(22) PCT Filed: May 4, 2017

(86) PCT No.: PCT/US2017/031171
§ 371 (c)(1),
(2) Date: Nov. 2, 2018

(87) PCT Pub. No.: WO2017/192924
PCT Pub. Date: Nov. 9, 2017

(65) Prior Publication Data
US 2019/0224236 A1    Jul. 25, 2019

Related U.S. Application Data

(60) Provisional application No. 62/331,906, filed on May 4, 2016.

(51) Int. Cl.
| | | |
|---|---|---|
| A01N 63/00 | (2020.01) | |
| C12N 15/85 | (2006.01) | |
| C07H 21/04 | (2006.01) | |
| A61K 39/00 | (2006.01) | |
| A61K 35/17 | (2015.01) | |
| A61P 31/12 | (2006.01) | |
| A61P 37/06 | (2006.01) | |
| A61P 35/02 | (2006.01) | |
| A61P 31/04 | (2006.01) | |
| A61K 39/39 | (2006.01) | |
| C07K 14/255 | (2006.01) | |
| C07K 14/535 | (2006.01) | |
| C07K 14/54 | (2006.01) | |
| C12N 15/86 | (2006.01) | |

(52) U.S. Cl.
CPC .......... *A61K 39/0011* (2013.01); *A61K 35/17* (2013.01); *A61K 39/39* (2013.01); *A61P 31/04* (2018.01); *A61P 31/12* (2018.01); *A61P 35/02* (2018.01); *A61P 37/06* (2018.01); *C07K 14/255* (2013.01); *C07K 14/535* (2013.01); *C07K 14/5434* (2013.01); *A61K 2039/5154* (2013.01); *A61K 2039/5156* (2013.01); *A61K 2039/5158* (2013.01); *A61K 2039/55522* (2013.01); *A61K 2039/55533* (2013.01); *A61K 2039/55538* (2013.01); *C07H 21/04* (2013.01); *C12N 15/85* (2013.01); *C12N 15/86* (2013.01); *C12N 2510/00* (2013.01); *Y02A 50/30* (2018.01)

(58) Field of Classification Search
CPC ........ C12N 15/63; C12N 15/85; C12N 15/86; C12N 2510/00; A61K 39/39; A61K 2039/5158; C07H 21/04
See application file for complete search history.

(56) References Cited

U.S. PATENT DOCUMENTS

| | | | |
|---|---|---|---|
| 5,283,173 | A | 2/1994 | Fields et al. |
| 5,468,614 | A | 11/1995 | Fields et al. |
| 10,828,352 | B2 | 11/2020 | Berger et al. |
| 2002/0155093 | A1 | 10/2002 | Houghton et al. |
| 2004/0087025 | A1 | 5/2004 | June et al. |
| 2005/0129671 | A1 | 6/2005 | Cooper et al. |
| 2009/0324630 | A1 | 12/2009 | Jensen |
| 2011/0189141 | A1 | 8/2011 | Kieback et al. |
| 2011/0243972 | A1 | 10/2011 | Jaffee |
| 2014/0080208 | A1* | 3/2014 | Deisseroth et al. |

FOREIGN PATENT DOCUMENTS

| | | |
|---|---|---|
| CN | 103502439 A | 1/2014 |
| JP | 2007/535924 A | 12/2007 |
| JP | 2008-539751 A | 11/2008 |
| JP | 2013-116891 A | 6/2013 |
| WO | 97/09433 | 3/1997 |
| WO | 97/41210 | 11/1997 |
| WO | 2004/035768 A1 | 4/2004 |
| WO | 2005/107381 A2 | 11/2005 |
| WO | 2006/120439 A2 | 11/2006 |
| WO | 2012/129514 A1 | 9/2012 |
| WO | 2014/134165 A1 | 9/2014 |
| WO | 2014/153270 A1 | 9/2014 |

(Continued)

OTHER PUBLICATIONS

Adham et al., 2011, Journal of Biomedicine and Biotechnology, vol. 2011, Article 417403, p. 1-7.*
Nakazawa et al., 2009, Journal of immunotherapy, vol. 32, No. 8, p. 826-836.*
Altschul et al., "Basic Local Alignment Search Tool," *Journal of Molecular Biology* 225:403-410, 1990.

(Continued)

*Primary Examiner* — Shin Lin Chen
(74) *Attorney, Agent, or Firm* — Seed IP Law Group

(57) ABSTRACT

The present disclosure relates to immune cells that express an exogenous neoantigen and an immunogenicity enhancer, or to T cells that express an exogenous neoantigen, and their use in treating a disease or disorder, such as cancer for tumor associated neoantigens. Related expression constructs, kits, host cells, pharmaceutical compositions, and methods are also provided.

22 Claims, 26 Drawing Sheets
Specification includes a Sequence Listing.

(56) References Cited

FOREIGN PATENT DOCUMENTS

| WO | 2014/165707 A2 | 10/2014 |
|---|---|---|
| WO | 2014/168874 A2 | 10/2014 |
| WO | 2015/142963 A1 | 9/2015 |
| WO | 2016/040900 A1 | 3/2016 |
| WO | 2016/054555 A2 | 4/2016 |
| WO | 2016/054638 A1 | 4/2016 |
| WO | 2016/069641 A1 | 5/2016 |
| WO | 2016/069647 A1 | 5/2016 |
| WO | 2016/182959 A1 | 11/2016 |
| WO | 2017/059186 A1 | 4/2017 |
| WO | 2017/077008 A1 | 5/2017 |

OTHER PUBLICATIONS

Altschul et al., "Gapped BLAST and PSI-BLAST: a new generation of protein database search programs, " *Nucleic Acids Research* 25(17):3389-3402, 1997.

Andreatta et al., "Gapped sequence alignment using artificial neural networks: application to the MHC class I system," *Bioinformatics* 32(4):511-517, 2016.

Applequist et al., "Activation of Innate Immunity, Inflammation, and Potentiation of DNA Vaccination through Mammalian Expression of the TLR5 Agonist Flagellin," *The Journal of Immunology* 175:3882-3891, 2005,.

Bear et al., "T Cells as Vehicles for Cancer Vaccination," *Journal of Biomedicine and Biotechnology* 2011(417403):1-7, 2011. (8 pages).

Berger et al., "Analysis of transgene-specific immune responses that limit the in vivo persistence of adoptively transferred HSV-TK-modified donor T cells after allogeneic hematopoietic cell transplantation," *Blood* 107(6):2294-2302, Mar. 15, 2006. (10 pages).

Berger et al., "Nonmyeloablative Immunosuppressive Regimen Prolongs In Vivo Persistence of Gene-Modified Autologous T Cells in a Nonhuman Primate Model," *Journal of Virology* 75(2):799-808, Jan. 2001.

Berger et al., "Pharmacologically regulated Fas-mediated death of adoptively transferred T cells in a nonhuman primate model," *Blood* 103(4):1261-1269, Feb. 15, 2004. (10 pages).

Bleakley et al., "Leukemia-associated minor histocompatibility antigen discovery using T-cell clones isolated by in vitro stimulation of naive CD8⁺ T cells," *Blood* 115(23):4923-4933, Jun. 10, 2010. (12 pages).

Broz, "Caspase target drives pyroptosis," *Nature* 526:642-643, Oct. 29, 2015. (2 pages).

Bui et al., "Automated generation and evaluation of specific MHC binding predictive tools: ARB matrix applications," *Immunogenetics* 57:304-314, May 3, 2005. (12 pages).

Carreno et al., "A dendritic cell vaccine increases the breadth and diversity of melanoma neoantigen-specific T cells," *Science* 348(6236):803-808, May 15, 2015. (8 pages).

Chen et al., "Molecular mechanisms of T cell co-stimulation and co-inhibition," *Nat. Rev. Immunol.* 13(4):227-242, Apr. 2013. (30 pages).

Cibulskis et al., "Sensitive detection of somatic point mutations in impure and heterogeneous cancer samples," *Nature Biotechnology* 31(3), Mar. 2013. (9 pages).

Deniger et al., "Stable, Nonviral Expression of Mutated Tumor Neoantigen-specific T-cell Receptors Using the *Sleeping Beauty* Transposon/Transposase System," *Molecular Therapy* 24(6):1078-1089, Jun. 2016.

Ding et al., "Efficient Transposition of the *piggyBac* (*PB*) Transposon in Mammalian Cells and Mice," *Cell* 122:473-483, Aug. 12, 2005.

Dranoff, "Experimental mouse tumour models: what can be learnt about human cancer immunology?," *Nature Reviews* 12:61-66, Jan. 2012.

Engels et al., "Retroviral Vectors for High-Level Transgene Expression in T Lymphocytes," *Human Gene Therapy* 14:1155-1168, Aug. 10, 2003.

Fontana et al., "Peripheral blood lymphocytes genetically modified to express the self/tumor antigen MAGE-A3 induce antitumor immune responses in cancer patients," *Blood* 113(8):1651-1660, Feb. 19, 2009. (11 pages).

Fritsch et al., "HLA-Binding Properties of Tumor Neoepitopes in Humans," *Cancer Immunol. Res.* 2(6):522-529, Jun. 2014. (9 pages).

Galvan et al., "Genome-Wide Mapping of *PiggyBac* Transposon Integrations in Primary Human T Cells," *J. Immunother* 32(8):837-844, Oct. 2009. (19 pages).

Genbank, NCBI Reference Sequence: NC_003197.2, "*Salmonella enterica* subsp. enterica serovar Typhimurium str. LT2, complete genome," Accession No. NC_003197, Sep. 28, 2017. (2 pages).

Genbank, NCBI Reference Sequence: NP_006862.2, "receptor-interacting serine/threonine-protein kinase 3 [*Homo sapiens*]," Accession No. NP_006862, Jun. 25, 2021. (4 pages).

Gubin et al., "Checkpoint Blockade Cancer Immunotherapy Targets Tumour-Specific Mutant Antigens," *Nature* 575(7528):577-581, Nov. 27, 2014. (32 pages).

Gubin et al., "Tumor neoantigens: building a framework for personalized cancer immunotherapy," *The Journal of Clinical Investigation* 125(9):3413-3421, Sep. 2015. (10 pages).

Hong, "Stimulatory versus suppressive effects of GM-CSF on tumor progression in multiple cancer types," *Experimental & Molecular Medicine* 48:e242, 2016. (8 pages).

Hoof et al., "NetMHCpan, a method for MHC class I binding prediction beyond humans," *Immunogenetics* 67(1):1-13, Jan. 2009. (24 pages).

Hsieh et al., "Development of $T_H1$ CD4⁺ T Cells Through IL-12 Produced by *Listeria*-Induced Macrophages," *Science* 260:541-549, Apr. 23, 1993. (4 pages).

Ivics et al., "Molecular Reconstruction of *Sleeping Beauty*, a Tc1-like Transposon from Fish, and Its Transposition in Human Cells," *Cell* 91:501-510, Nov. 14, 1997.

Kennedy et al., "Direct Cross-Priming by Th Lymphocytes Generates Memory Cytotoxic T Cell Responses," *The Journal of Immunology* 174:3961-3911, 2005. (12 pages).

Kim et al., "RIP kinase 3 in necroptosis: does it take two or more to kill?," *Cell Death and Differentiation* 21:1505-1507, 2014.

Koboldt et al., "VarScan 2: Somatic mutation and copy number alteration discovery in cancer by exome sequencing," *Genome Research* 22:568-576, Feb. 2, 2012. (10 pages).

Koboldt et al., "VarScan: variant detection in massively parallel sequencing of individual and pooled samples," *Bioinformatics* 25(17):2283-2285, Jun. 2009.

Kreiter et al., "Increased Antigen Presentation Efficiency by Coupling Antigens to MHC Class I Trafficking Signals," *The Journal of Immunology* 180:309-318, 2008. (12 pages).

Ledbetter et al., "CD28 Ligation in T-Cell Activation: Evidence for Two Signal Transduction Pathways," *Blood* 75(7):1531-1539, Apr. 1, 1990. (10 pages).

Lehninger, *The Molecular Basis of Cell Structure and Function* (2nd Edition), Worth Publication, New York, pp. 71-77, 1975.

Levin et al., "Exploiting a natural conformational switch to engineer an Interleukin-2 superkine," *Nature* 484(7395):529-533, Oct. 26, 2012. (12 pages).

Liebig et al., "Generation of Human CD40-activated B cells," *Journal of Visualized Experiments*, Oct. 16, 2009. (3 pages).

Lombardo et al., "Gene editing in human stem cells using zinc finger nucleases and integrase-defective lentiviral vector delivery," *Nature Biotechnology* 25(11):1298-1306, Nov. 2007.

Lynn et al., "Peptide-TLR-7/8a conjugate vaccines chemically programmed for nanoparticle self-assembly enhance CD8 T cell immunity to tumor antigens," *Nature Biotechnology* 38(3):320-332, Mar. 2020. (34 pages).

McSorley et al., "Bacterial Flagellin is an Effective Adjuvant for CD4⁺ T Cells In Vivo," *The Journal of Immunology* 169:3914-3919, 2002.

Morgan, "Risky business: target choice in adoptive cell therapy," *Blood* 122(20):3392-3394, Nov. 14, 2013.

Murphy et al., "The Pseudokinase MLKL Mediates Necroptosis via a Molecular Switch Mechanism," *Immunity* 39:443-453, Sep. 19, 2013.

(56) References Cited

OTHER PUBLICATIONS

Nielsen et al., "NetMHCpan-3.0; improved prediction of binding to MHC class I molecules integrating information from multiple receptor and peptide length datasets," *Genome Medicine 8*(33), 2016. (9 pages).
Nielsen et al., "Reliable prediction of T-cell epitopes using neural networks with novel sequence representations," *Protein Science 12*:1007-1017, 2003.
Orozco et al., "RIPK1 both positively and negatively regulates RIPK3 oligomerization and necroptosis," *Cell Death and Differentiation 21*:1511-1521, 2014.
Pan et al., "Cancer Immunotherapy Using a Membrane-bound Interleukin-12 With B7-1 Transmembrane and Cytoplasmic Domains," *Molecular Therapy*, Feb. 14, 2012. (11 pages).
Park et al., "CD4 T-cells transduced with CD80 and 4-1BBL mRNA induce long-term CD8 T-cell responses resulting in potent antitumor effects," *Vaccine 32*:6919-6926, Nov. 3, 2014.
Patel et al., "T-Cell Therapy for Multiple Myeloma Using NY-ESO-1(+) T-Cell Antigen Presenting Cells (T-APC) Combined with Adoptive Cellular Transfer (ACT) to Augment Immunotherapy," *Blood 124*(21), Dec. 6, 2014. (Abstract Only) (1 page).
Pennock et al., "T cell Vaccinology: Beyond the Reflection of Infectious Responses," *Trends Immunol. 37*(3):170-180, Mar. 2016. (20 pages).
Peters et al., "Generating quantitative models describing the sequence specificity of biological processes with the stabilized matrix method," *BMC Bioinformatics 6*(132), May 31, 2005. (9 pages).
Rajasagi et al, "Systematic identification of personal tumor-specific neoantigens in chronic lymphocytic leukemia," *Blood 124*(3):453-462, Jul. 17, 2014. (20 pages).
Riddell et al., "Restoration of Viral Immunity in Immunodeficient Humans by the Adoptive Transfer of T Cell Clones," *Science 257*(5067):238-241, Jul. 10, 1992, (5 pages).
Riddell et al., "T-cell mediated rejection of gene-modified HIV-specific cytotoxic T lymphocytes in HIV-infected patients," *Nature Medicine 2*(2):216-223, Feb. 1996.
Rizvi et al., "Mutational landscape determines sensitivity to PD-1 blockade in non-small cell lung cancer," *Science 348*(6230):124-128, Apr. 3, 2015. (6 pages).
Rosenberg et al., "Adoptive cell transfer as personalized immunotherapy for human cancer," *Science 348*(6230):62-68, Apr. 3, 2015. (8 pages).
Russo et al., "Clinical and immunologic responses in melanoma patients vaccinated with MAGE-A3-genetically modified lymphocytes," *Int. J. Cancer 132*:2551-2566, 2013.
Russo et al., "Lymphocytes genetically modified to express tumor antigens target DCs in vivo and induce antitumor immunity," *The Journal of Clinical Investigation 117*(10):3087-3096, Oct. 2007.
Saha et al., "*piggyBac* Transposon System Modification of Primary Human T Cells," *J. Vis. Exp.* (69):eA235, Nov. 5, 2012. (5 pages).
Saunders et al., "Strelka: accurate somatic small-variant calling from sequenced tumor-normal sample pairs," *Bioinformatics 28*(14):1811-1817, 2012.
Scholten et al., "Codon modification of T cell receptors allows enhanced functional expression in transgenic human T cells," *Clinical Immunology* (119):135-145, Feb. 2, 2006.
Schumacher et al., "Neoantigens in cancer immunotherapy," *Science 348*(6230):69-74, Apr. 3, 2015. (7 pages).
Segal et al., "Epitope Landscape in Breast and Colorectal Cancer," *Cancer Res. 68*(3):889-892, Feb. 1, 2008. (5 pages).
Shi et al., "Cleavage of GSDMD by inflammatory caspases determines pyroptotic cell death," *Nature 526*:660-665, Oct. 29, 2015. (17 pages).
Snyder et al., "Genetic Basis for Clinical Response to CTLA-4 Blockade in Melanoma," *The New England Journal of Medicine 371*(23):2189-2199, Dec. 4, 2014.
Szolek et al., "OptiType: precision HLA typing from next-generation sequencing data," *Bioinformatics 30*(23):3310-3316, 2014.

Tran et al., "Cancer Immunotherapy Based on Mutation-Specific CD4+ T Cells in a Patient with Epithelial Cancer," *Science 344*:641-645, May 9, 2014. (6 pages).
Tran et al., "T-Cell Transfer Therapy Targeting Mutant KRAS in Cancer," *The New England Journal of Medicine 375*(23):2255-2262, Dec. 8, 2016.
Trolle et al., "Automated benchmarking of peptide-MHC class I binding predictions," *Bioinformatics*, Feb. 25, 2015. (9 pages).
Tumeh et al., "PD-1 blockade induces responses by inhibiting adaptive immune resistance," *Nature 515*(7528):568-571, Nov. 27, 2014. (24 pages).
Tüting et al., "Autologous Human Monocyte-Derived Dendritic Cells Genetically Modified to Express Melanoma Antigens Elicit Primary Cytotoxic T Cell Responses In Vitro: Enhancement by Cotransfection of Genes Encoding the Th1-Biasing Cytokines IL-12 and IFN-$\alpha^1$," *The Journal of Immunology* 160:1139-1147, 1998. (11 pages).
Van Buuren et al., "High sensitivity of cancer exome-based CD8 T cell neo-antigen identification," *OncoImmunology 3*(5):e28836, May 14, 2014. (7 pages).
Van Craenenbroeck et al., "Episomal vectors for gene expression in mammalian cells," *Eur. J. Biochem. 267*:5665-5678, 2000.
Veatch et al., "A therapeutic cancer vaccine delivers antigens and adjuvants to lymphoid tissues using genetically modified T cells," *J. Clin. Invest. 131*(16):e144195, Aug. 16, 2021. (w/Supplemental Data) (26 pages).
Wang et al., "Homology-driven genome editing in hematopoietic stem and progenitor cells using zinc finger nuclease mRNA and AAV6 donors," *Nature Biotechnology 33*(12):1256-1263, Dec. 2015. (26 pages).
Xing et al., "T-Cell Tolerance: Central and Peripheral," *Cold Spring Harbor Perspectives in Biology* 4:a006957, 2012. (16 pages).
Yatim et al., "RIPK1 and NF-κB signaling in dying cells determines cross-priming of $CD8^+$ T cells," *Science 350*(6258):328-334, Sep. 24, 2015. (8 pages).
Yatim et al., "Supplementary Materials for RIPK1 and NF-κB-signaling in dying cells determines cross-priming of $CD8^+$ T cells," *Science*, Sep. 24, 2015. (20 pages).
Aggen et al., "Single-chain VαVβ T-cell receptors function without mispairing with endogenous TCR chains," *Gene Therapy 19*:365-374, 2012. (10 pages).
Barrett et al., "Chimeric Antigen Receptor Therapy for Cancer," *Annu Rev Med. 65*:333-347, 2014. (18 pages).
Bear et al., "T Cells as Vehicles for Cancer Vaccination," *Journal of Biomedicine and Biotechnology 2011*(Article ID 417403):1-7, 2011. (8 pages).
Berger et al., "A nonhuman primate model for analysis of safety, persistence, and function of adoptively transferred T cells," *J Med Primatol. 40*(2):88-103, 2011. (21 pages).
Berger et al., "Safety of targeting ROR1 in primates with chimeric antigen receptor-modified T cells," *Cancer Immunol Res. 3*(2):206-216, 2015. (24 pages).
Carreno et al., "A dendritic cell vaccine increases the breadth and diversity of melanoma neoantigen-specific T cells," *Science 348*(6236):803-808, 2015. (8 pages).
Caruana Ignazio et al., "Boosting In Vivo CAR-Redirected Virus-Specific CTLs With Universal-Artificial Antigen Presenting Cells," *Blood 122*(21):4204, 2013. Database Biosis, Database AN PREV201400362624, Abstract (1 page).
Cavallo et al., "2011: the immune hallmarks of cancer," *Cancer Immunol Immunother 60*:319-326, 2011. (8 pages).
Chan et al., "Flow cytometric detection of degranulation reveals phenotypic heterogeneity of degranulating CMV-specific CD8+ T lymphocytes in rhesus macaques," *J. Immunol. Methods 325*(1-2):20-34, 2007. (23 pages).
Chmielewski et al., "Antigen-specific T-cell activation independently of the MHC: chimeric antigen receptor-redirected T cells," *Frontiers in Immunology 4*(371), 2013. (7 pages).
Cho et al., "CD4 T cells transduced with CD80 and 4-1BBL mRNA induce long-term CD8 T cell responses resulting in potent antitumor effects," *Journal for ImmunoTherapy of Cancer 2*(Suppl 3):264, 2014, (1 page).

(56) References Cited

OTHER PUBLICATIONS

Chothia et al., "The outline structure of the T-cell αβ receptor," *The EMBO Journal* 7(12):3745-3755, 1988.
Cooper et al., "Enhanced antilymphoma efficacy of CD19-redirected influenza MP1-specific CTLs by cotransfer of T cells modified to present influenza MP1," *Blood* 105(4):1622-1631, 2005.
Cruz et al., "Infusion of donor-derived CD19-redirected virus-specific T cells for B-cell malignancies relapsed after allogeneic stem cell transplant: a phase 1 study," *Blood* 122(17):2965-2973, 2013.
Dossett et al., "Adoptive Immunotherapy of Disseminated Leukemia With TCR-transduced, $CD8^+$ T Cells Expressing a Known Endogenous TCR," *Molecular Therapy* 17(4):742-749, 2009.
Duong et al., "Engineering T Cell Function Using Chimeric Antigen Receptors Identified Using a DNA Library Approach," *PLoS ONE* 8(5): e63037, 2013. (10 pages).
Fontana et al., "Peripheral blood lymphocytes genetically modified to express the self/tumor antigen MAGE-A3 induce antitumor immune responses in cancer patients," *Blood* 113(8):1651-1660, 2009. (11 pages).
Govers et al., "T Cell Receptor Fused to CD3ζ: Transmembrane Domain of CD3ζ Prevents TCR Mis-Pairing, Whereas Complete CD3ζ Directs Functional TCR Expression," *The Open Gene Therapy Journal* 4:11-22, 2011.
Hanahan et al., "Hallmarks of Cancer: The Next Generation," *Cell* 144:646-674, 2011.
Hanahan et al., "The Hallmarks of Cancer," *Cell* 100:57-70, 2000.
Hudecek et al., "The B-cell tumor-associated antigen ROR1 can be targeted with T cells modified to express a ROR1-specific chimeric antigen receptor," *Blood* 116(22):4532-4541, 2010. (18 pages).
International Search Report and Written Opinion, dated Sep. 21, 2017, for International Patent Application No. PCT/US2017/031171, 24 pages.
Jiang et al. "Combination of Vaccination and Chimeric Receptor Expressing T Cells Provides Improved Active Therapy of Tumors" *The Journal of Immunology* 177:4288-4298, 2006.
Jores et al., "Resolution of hypervariable regions in T-cell receptor β chains by a modified Wu-Kabat index of amino acid diversity," *Proc. Natl. Acad. Sci. USA* 87:9138-9142, 1990.
Jurgens et al., "Transduction of Primary Lymphocytes with Epstein-Barr Virus (EBV) Latent Membrane Protein-Specific T-Cell Receptor Induces Lysis of Virus-Infected Cells: A Novel Strategy for the Treatment of Hodgkin's Disease and Nasopharyngeal Carcinoma," *Journal of Clinical Immunology* 26(1):22-32, 2006.
Kalos et al., "T Cells with Chimeric Antigen Receptors Have Potent Antitumor Effects and Can Establish Memory in Patients with Advanced Leukemia," *Sci Transl Med.* 3(95):95ra73, 2011. (21 pages).
Kochenderfer et al., "Treating B-cell cancer with T cells expressing anti-CD19 chimeric antigen receptors," *Nat Rev Clin Oncol.* 10(5):267-276, 2013. (24 pages).
Kreiter et al., "Mutant MHC class II epitopes drive therapeutic immune responses to cancer," *Nature* 520:692-696, 2015. (17 pages).
Kuball et al., "Facilitating matched pairing and expression of TCR chains introduced into human T cells," *Blood.* 109(6)2331-2338, 2007. (17 pages).
Kyrgidis et al., "Melanoma: Stem cells, sun exposure and hallmarks for carcinogenesis, molecular concepts and future clinical implications," *J. Carcinog.* 9:3, 2010. (26 pages).
Kyte et al., "Phase I/II trial of melanoma therapy with dendritic cells transfected with autologous tumor-mRNA," *Cancer Gene Therapy* 13:905-918, 2006.
Lamers et al., "Treatment of Metastatic Renal Cell Carcinoma With CAIX CAR-engineered T cells: Clinical Evaluation and Management of On-target Toxicity," *Molecular Therapy* 21(4):904-912, 2013.

Liang et al., "In vitro induction of specific anti-tumoral immunity against laryngeal carcinoma by using human interleukin-12 gene-transfected dendritic cells," *Chinese Medical Journal* 124(9):1357-1361, 2011.
Lou et al., "Dendritic Cells Strongly Boost the Antitumor Activity of Adoptively Transferred T Cells In vivo," *Cancer Research* 64:6783-6790, 2004.
Maher, "Immunotherapy of Malignant Disease Using Chimeric Antigen Receptor Engrafted T Cells," *ISRN Oncology*, 2012. (23 pages).
Mauri et al., "Antigen-presenting T cells induce the development of cytotoxic CD4+ T cells. I. Involvement of the CD80-CD28 adhesion molecules," *J. Immunol.* 155(1): 118-127, 1995. (Abstract only, 5 pages).
Maus et al., "Antibody-modified T cells: CARs take the front seat for hematologic malignancies," *Blood* 123(17):2625-2635, 2014. (22 pages).
Melenhorst et al., "Robust expansion of viral antigen-specific CD4+ and CD8+ T cells for adoptive T cell therapy using gene-modified activated T cells as antigen presenting cells," *J. Immunother.* 29(4):436-43, 2006. (Abstract only, 2 pages).
Melief, "'License to Kill' Reflects Joint Action of CD4 and CD8 T Cells," *Clin Cancer Res* 19(16):4295-4296, 2013. (3 pages).
Morgan et al., "Case Report of a Serious Adverse Event Following the Administration of T Cells Transduced With a Chimeric Antigen Receptor Recognizing ERBB2," *Molecular Therapy* 18(4):843-851, 2010.
Nakazawa et al., "Optimization of the *PiggyBac* Transposon System for the Sustained Genetic Modification of Human T-Lymphocytes," *J. Immunother.* 32(8):826-836, 2009. (18 pages).
Palmer et al., "Vaccine-Stimulated, Adoptively Transferred $CD8^+$ T Cells Traffic Indiscriminately and Ubiquitously while Mediating Specific Tumor Destruction," *J Immunol.* 173:7209-7216, 2004. (9 pages).
Park et al., "Cancer Stem Cell-Directed Therapies: Recent Data From the Laboratory and Clinic," *Molecular Therapy* 17(2):219-230, 2009.
Patel Krina K et al., "T-Cell Therapy for Multiple Myeloma Using NY-ESO-1(+) T-Cell Antigen Presenting Cells (T-APC) Combined with Adoptive Cellular Transfer (ACT) to Augment Immunotherapy," *Blood* 124(21), 2014. Database Biosis, Database AN PREV201500277242, Abstract (1 page).
Penix et al., "Two Essential Regulatory Elements in the Human Interferon Gamma Promoter Confer Activation Specific Expression in T cells," *The Journal of Experimental Medicine* 178:1483-1496, 1993.
Ribas, "Genetically Modified Dendritic Cells for Cancer Immunotherapy," *Current Gene Therapy* 5(6):619-628, 2005.
Russo et al., "Clinical and immunologic responses in melanoma patients vaccinated with MAGE-A3-genetically modified lymphocytes," *International Journal of Cancer* 132:2557-2566, 2013.
Russo et al., "Lymphocytes genetically modified to express tumor antigens target DCs in vivo and induce antitumor immunity," *The Journal of Clinical Investigation* 117(10):3087-3096, 2007.
Sadelain et al., "The Basic Principles of Chimeric Antigen Receptor Design," *Cancer Discovery* 3(4):388-398, 2013. (12 pages).
Schmitt et al., "T Cell Receptor Gene Therapy for Cancer," *Human Gene Therapy* 20:1240-1248, 2009.
Schreibelt et al., "Abstract IA44: Cancer prevention: Dendritic cell enhanced immune responses towards neoantigens in patients with Lynch syndrome," *Cancer Immunol. Res.* 4(1 Suppl):Abstract nrIA44, 2016. (4 pages).
Stone et al., "A novel T cell receptor single-chain signaling complex mediates antigen-specific T cell activity and tumor control," *Cancer Immunol Immunother* 63:1163-1176, 2014.
Sun et al., "Listeriolysin O as a strong immunogenic molecule for the development of new anti-tumor vaccines," *Human Vaccines & Immunotherapeutics* 9(5):1058-1068, 2013.
Tanimoto et al., "Genetically engineered fixed K562 cells: potent "off-the-shelf" antigen-presenting cells for generating virus-specific T cells," *Cytotherapy* 16:135-146, 2014.

(56) References Cited

OTHER PUBLICATIONS

Thompson et al., "cis-Acting Sequences Required for Inducible Interleukin-2 Enhancer Function Bind a Novel Ets-Related Protein, Elf-1," *Molecular and Cellular Biology* 12(3):1043-1053, 1992.

Till et al., "Adoptive immunotherapy for indolent non-Hodgkin lymphoma and mantle cell lymphoma using genetically modified autologous CD20-specific T cells," *Blood* 112(6):2261-2271, 2008. (25 pages).

Todd et al., "Transcription of the Interleukin 4 Gene is Regulated by Multiple Promoter Elements," *J. Exp. Med.* 177:1663-1674, 1993.

Toobiak et al., "Carbon Monoxide Induced Erythroid Differentiation of K562 Cells Mimics the Central Macrophage Milieu in Erythroblastic Islands," *PLoS ONE* 7(3):e33940, 2012. (8 pages).

Torikai et al., "A foundation for universal T-cell based immunotherapy: T cells engineered to express a CD19-specific chimeric-antigen-receptor and eliminate expression of endogenous TCR," *Blood* 119(24):5697-5705, 2012. (10 pages).

Wang Xiuli et al., "Enhanced Antitumor Efficacy of Adoptively Transferred CD19-Redirected CMV Specific Central Memory T Cells by CMV Vaccine," *Blood* 120(21):3014, 2012. Database Biosis, Database AN PREV201300229759, Abstract (1 page).

Wilgenhof et al., "Therapeutic Vaccination With an Autologous mRNA Electroporated Dendritic Cell Vaccine in Patients With Advanced Melanoma," *J. Immunother.* 34(5):448-456, 2011.

Wolff et al., "Monoclonal Antibody Homodimers: Enhanced Anti-tumor Activity in Nude Mice," *Cancer Research* 53:2560-2565, 1993. (7 pages).

Zhang et al., "Optimizing DC Vaccination by Combination With Oncolytic Adenovirus Coexpressing IL-12 and GM-CSF," *Molecular Therapy* 19(8):1558-1568, 2011.

Olsen et al., "TANTIGEN: a comprehensive database of tumor T cell antigens," *Cancer Immunol Immunother* 66:731-735, Mar. 9, 2017.

Vigneron et al., "Database of T cell-defined human tumor antigens: the 2013 update," *Cancer Immunity* 13:15, Jul. 15, 2013. (6 pages).

"TANTIGEN: Classification of tumor antigens," Dec. 1, 2009, URL=http://projects.met-hilab.org/tadb/HTML/classification.php, download date Dec. 28, 2022. (1 page).

Chang et al., "Peptide length-based prediction of peptide-MHC class II binding," *Bioinformatics* 22(22):2761-2767, 2006.

Chicz et al., "Predominant naturally processed peptides bound to HLA-DR1 are derived from MHC-related molecules and are heterogeneous in size," *Nature* 358:764-768, Aug. 27, 1992.

Goodyear et al., "Dominant responses with conservation of T-cell receptor usage in the CD8+ T-cell recognition of a cancer testis antigen peptide presented through HLA-Cw7 in patients with multiple myeloma," *Cancer Immunol Immunother* 60:1751-1761, 2011.

Nelde et al., "HLA class I-restricted MYD88 L265P-derived peptides as specific targets for lymphoma immunotherapy," *Oncoimmunology* 6(3):e1219825, 2017. (11 pages).

Nelde et al., "Identification and Characterization of HLA Class I-Restricted MYD88 L265P-Derived Peptides as Tumor-Specific Targets for Immunotherapy," *Blood* 126(23):2750, 2015.

Neumann et al., "A peptide epitope derived from the cancer testis antigen HOM-MEL-40/SSX2 capable of inducing CD4+ and CD8+ T-cell as well as B-cell responses," *Cancer Immunol Immunother* 60:1333-1346, 2011.

Rogel et al., "A long peptide from MELOE-1 contains multiple HLA class II T cell epitopes in addition to the HLA-A*0201 epitope: an attractive candidate for melanoma vaccination," *Cancer Immunol Immunother* 60:3217-337, 2011.

Vigneron et al., "Insights into the processing of MHC class I ligands gained from the study of human tumor epitopes," *Cell. Mol. Life Sci.* 68:1503-1520, 2011.

Yamazoe et al., "Identification of HLA-A*0201- and A*2402-Restricted Epitopes of Mucin 5AC Expressed in Advanced Pancreatic Cancer," *Pancreas* 40:896-904, 2011.

\* cited by examiner

CELL-BASED NEOANTIGEN VACCINES AND USES THEREOF

STATEMENT OF GOVERNMENT INTEREST

This invention was made with government support under CA114536 and CA136551 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_440_USPC_SEQUENCE_LISTING.txt. The text file is 181 KB, was created on Mar. 6, 2019, and is being submitted electronically via EFS-Web.

BACKGROUND

The potential for T cells to recognize and eliminate human cancers of different histologies has been recognized. For example, antibodies that block T cell regulatory molecules (immune checkpoint molecules) have been shown to enhance immune function and have anti-tumor activity (Brahmer et al., *N Engl J Med* 366: 2455, 2012; Topalian et al., *N Engl J Med* 366: 2443, 2012). However, a majority of cancer patients do not achieve durable immune responses when treated with inhibitors of immune checkpoint molecules, perhaps because many patients lack a functional T cell response to tumor antigens that can be induced or rescued (Tumeh et al., *Nature* 515: 568, 2014). Accordingly, methods for eliciting or boosting robust T cell responses to tumor antigens are needed.

Traditional peptide- and dendritic cell-based vaccination platforms have struggled to produce clinically effective T cell responses (Pennock et al., *Trends Immunol* 37: 170, 2016). Autologous T cells may be a useful platform for a cell-based cancer vaccine. T cells modified to express a foreign protein are highly immunogenic in animals (Berger et al., *Blood* 103: 1261, 2004; Russo et al., *J Clin Invest.* 117: 3087, 2007) and humans (Berger et al., *Blood* 107: 2294, 2006; Berger et al., *J Virol* 75: 799, 2001; Riddell et al., *Nat Med* 2: 216, 1996), and elicit high frequency, durable T cell responses to peptide epitopes derived from the foreign protein. Transferred T cells migrate efficiently to secondary lymphoid organs where antigen priming occurs and can be further genetically modified to increase immunogenicity (Russo et al., *J Clin Invest.* 117: 3087, 2007).

One issue that must be addressed during the design of a cancer vaccine is the selection of tumor-associated antigens to target with the vaccine. Many "self" antigens expressed by tumors are generally poor candidates for inclusion in a vaccine due to immune tolerance (see, e.g., Xing and Hogquist, *Cold Spring Harb. Perspect. Biol.* 4:a006957, 2012) and also on-target off-tumor toxicity (see, e.g., Morgan, *Blood* 20:3392 (2013)). But, mutations are a hallmark of cancer, and cancers that are associated with carcinogenic exposures or genomic instability can accumulate large numbers of somatic mutations. While some of these mutations in highly mutated cancers occur in oncogenes and tumor suppressor genes and promote tumor growth, the vast majority are "passenger" mutations and lead to no observable phenotype when re-introduced into normal cells. Passenger mutations are distributed at random throughout the genomes of these cancers and form the bulk of expressed amino acid changes, and can be sampled and recognized by T cells as "foreign." These somatic mutations produce neoantigens and, because the majority are passenger mutations, most neoantigens will be unique to an individual patient's tumor (Schumacher and Schreiber, *Science* 348:69, 2015). Tumor-specific neoantigens may lead to clinically effective T cell responses, and may be better targets for cancer vaccines than some cancer-specific or overexpressed self-antigens that have traditionally been the targets for cancer vaccination (Schumacher and Schreiber, 2015).

Neoantigen vaccine approaches using peptides (Gubin et al., *Nature* 515: 577, 2014) and liposomal RNA preparations (Kreiter et al., *Nature* 520: 692, 2015) have been used in multiple transplantable mouse cancer models, and a peptide-pulsed dendritic cell vaccine has been found to stimulate neoantigen responses in patients with melanoma (Carreno et al., *Science* 348: 803, 2015). Despite evidence supporting a potentially important role for neoantigens in an immune response to highly mutated solid tumors, a reproducible strategy for exploiting the neoantigen repertoire in an individual's tumor to elicit broadly directed and potent immune responses is lacking.

Therefore, there remains a need for cell-based vaccines that generate immune responses to neoantigens associated with diseases or disorders, such as tumor-specific neoantigens. The embodiments of the present disclosure address such needs, and further provide other related advantages.

BRIEF SUMMARY

In one aspect, the present disclosure provides a T cell, comprising a polynucleotide encoding an exogenous neoantigen associated with a disease or disorder, and a polynucleotide encoding an immunogenicity enhancer.

In another aspect, provided is an immune cell, comprising an exogenous neoantigen associated with a disease or disorder and an immunogenicity enhancer comprising an IL-12 fusion protein that localizes to the cell surface of the T cell, wherein the immune cell is selected from a B cell, a natural killer cell, a dendritic cell, a macrophage, a monocyte, a megakaryocyte, a mast cell, a thrombocyte, an erythrocyte, and a granulocyte.

In a further aspect, a composition comprising a T cell or an immune cell of the present disclosure and a pharmaceutically acceptable carrier, diluent, or excipient is provided.

In another aspect, the present disclosure provides methods of treating a disease or disorder, wherein the methods comprise administering to a human subject in need thereof an effective amount of a T cell, an immune cell, or a composition as described herein.

In yet another aspect, methods are provided for treating a human subject having a disease or disorder associated with expression of a neoantigen, comprising administering to the subject an effective amount of a T cell, of an immune cell, or of a composition as described herein.

In still another aspect, the present disclosure provides a transposon expression construct, comprising a nucleic acid molecule encoding a neoantigen. A kit comprising a transposon expression construct of the present disclosure is also provided.

In another aspect, a host cell, comprising a transposon expression construct of the present disclosure is provided. Compositions comprising a host cell of the present disclosure and a pharmaceutically acceptable carrier, diluent, or excipient are also provided.

In a further aspect, the present disclosure provides a method of preparing a T cell, comprising introducing into the T cell (a) a piggyBac transposon plasmid containing a nucleic acid molecule encoding a neoantigen identified in a sample of a subject; and (b) a plasmid comprising a nucleic acid molecule encoding a piggyBac transposase, thereby preparing the T cell.

In yet another aspect, a method of preparing an immune cell is provided, comprising introducing into the immune cell (a) a piggyBac transposon plasmid containing a nucleic acid molecule encoding a neoantigen identified in a sample of a subject, (b) a plasmid comprising a nucleic acid molecule encoding a piggyBac transposase, and (c) a plasmid comprising a nucleic acid molecule encoding an IL-12 fusion protein that localizes to the cell surface of the T cell, thereby preparing the immune cell.

DETAILED DESCRIPTION

Figure 1:
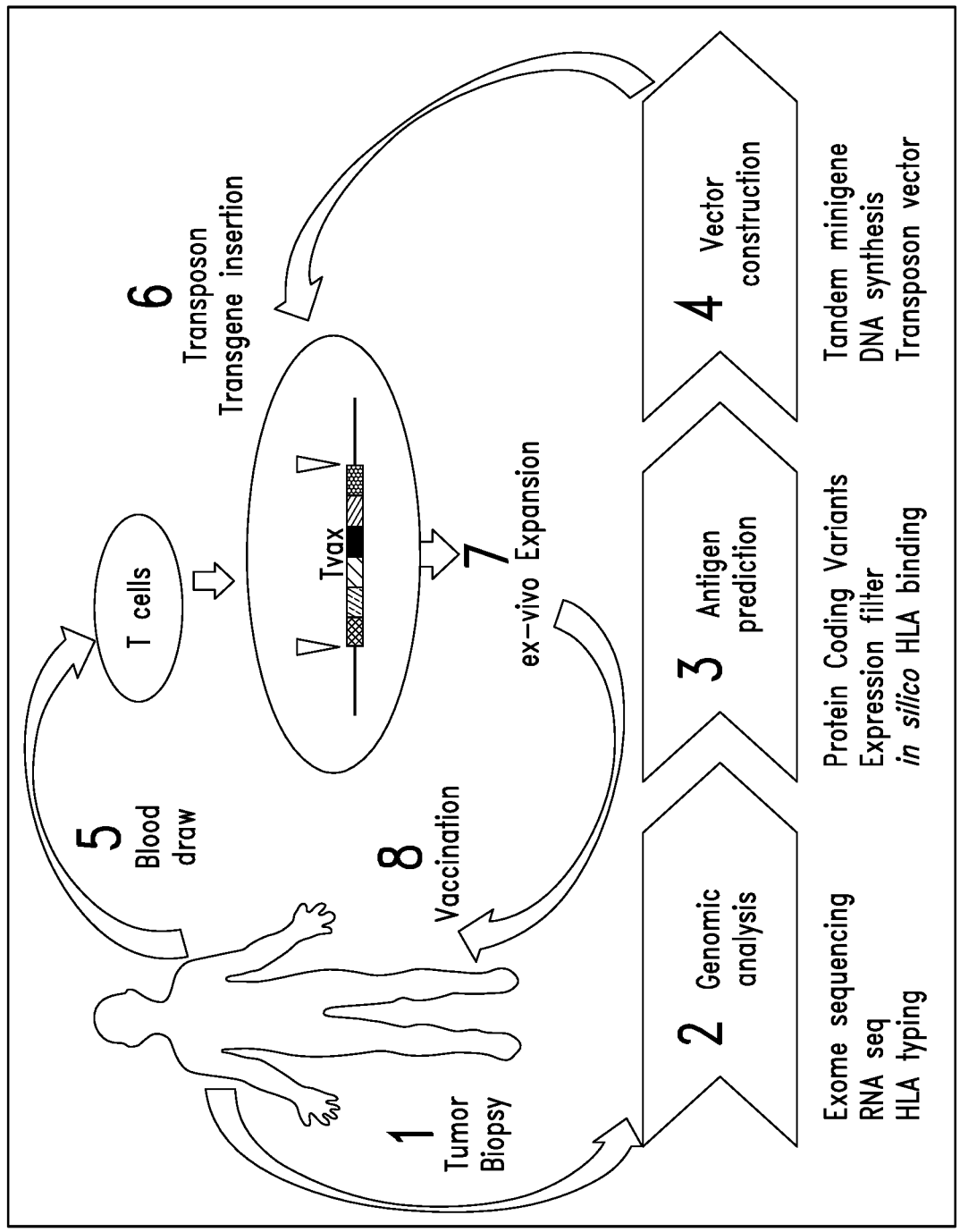
FIG. 1 shows a schematic of a method of this disclosure for developing a personalized T cell vaccine based on tumor-specific neoantigens. Because the majority of neoantigens are unique to an individual patient's cancer, the "mutanome" of each patient's tumor is determined, allowing for the identification of candidate neoantigens to be targeted by the vaccine. T cells may be obtained from the patient, modified to express the neoantigen, expanded ex vivo, and administered to the patient.

The present disclosure provides immunogenic compositions and cell-based vaccines for eliciting or boosting immune responses to neoantigens. In certain embodiments, immune cells (e.g., T lymphocytes) comprising one or more polynucleotides encoding exogenous neoantigens and encoding one or more, expression constructs that encode the one or more neoantigens, host cells comprising such expression constructs, and methods for using the same, are provided. The immune and host cells provided herein are modified to express an exogenous neoantigen, such as a tumor neoantigen. In certain embodiments, the immune cells and host cells are further modified to express one or more immunogenicity enhancers (e.g., foreign or helper antigen, IL-12 (such as a membrane-tethered IL-12), GM-CSF) to augment an immune response against the one or more exogenous neoantigens.

The immune cells or host cells may be used in a personalized, cell-based vaccine for inducing an immune response to one or more neoantigens produced by a particular subject, which may provide a functional T cell response to the neoantigen(s) that can be induced or rescued. In certain embodiments, a neoantigen is a tumor neoantigen. Neoantigens have the advantage of being found in only one or a few specific individuals, not being found in normal tissues (and, therefore, having reduced off-target immunogenicity), and not being subject to central tolerance mechanisms.

Prior to setting forth this disclosure in more detail, it may be helpful to an understanding thereof to provide definitions of certain terms used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated.

As used herein, the term "about" means±20% of the indicated range, value, or structure, unless otherwise indicated.

It should be understood that the terms "a" and "an" as used herein refer to "one or more" of the enumerated components. The use of the alternative (e.g., "or") should be understood to mean either one, both, or any combination thereof of the alternatives.

In addition, it should be understood that the individual features or groups of features, derived from the various combinations of the compositions and substituents described herein, are disclosed by the present application to the same extent as if each feature or group of features was set forth individually. Thus, selection of particular structures or particular substituents is within the scope of the present disclosure.

As used herein, the terms "include," "have," and "comprise" are used synonymously, which terms and variants thereof are intended to be construed as non-limiting.

The term "consisting essentially of" limits the scope of a claim to the specified materials or steps, or to those that do not materially affect the basic characteristics of the claimed subject matter. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, an "immune cell" or "immune system cell" means any cell of the immune system that originates from a hematopoietic stem cell in the bone marrow, which gives rise to two major lineages, a myeloid progenitor cell (which gives rise to myeloid cells such as monocytes, macrophages, dendritic cells, megakaryocytes, mast cells, thrombocytes, erythrocytes, and granulocytes) and a lymphoid progenitor cell (which gives rise to lymphoid cells, or "lymphocytes"). As used herein, the term "lymphocyte" refers to a subtype of white blood cell of a vertebrate immune system that is characterized by its predominant presence in lymph and, generally, by a large nucleus. Lymphocytes include, for example, T cells (CD4$^+$ T cells, CD8$^+$ T cells, CD4$^-$ CD8$^-$ double-negative T cells, γδ T cells, regulatory T cells), B cells, and natural killer (NK) cells. Other exemplary immune system cells include macrophages and dendritic cells, as well as other myeloid cells as described herein. Macrophages and dendritic cells may be referred to as "professional antigen presenting cells" (or "professional APCs"), which are specialized cells that can activate T cells when a major histocompatibility complex (MHC) receptor on the surface of the APC interacts with a TCR on the surface of a T cell. Alternatively, any hematopoietic stem cell or immune system cell can be converted into an APC by introducing a nucleic acid molecule that expresses an antigen recognized by a TCR or by another antigen binding protein (e.g., chimeric antigen receptor or antibody). Immune cells or lymphocytes used in vaccine compositions or methods of treatment of this disclosure may be autologous, allogeneic, or syngeneic to a subject to receive the composition or the method of treatment.

A "T cell" (or "T lymphocyte") is an immune system cell that matures in the thymus and produces T cell receptors (TCRs), which can be obtained (enriched or isolated) from, for example, peripheral blood mononuclear cells (PBMCs) and are referred to herein as "bulk" T cells. After isolation of T cells, both cytotoxic (CD8+) and helper (CD4+) T cells, can be sorted into naïve, memory, and effector T cell subpopulations, either before or after expansion. T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{CM}$). Effector T cells ($T_E$) refers to antigen-experienced CD8+ cytotoxic T lymphocytes that has decreased expression of CD62L, CCR7, CD28, and are positive for granzyme and perforin as compared to $T_{CM}$. Helper T cells ($T_h$) are CD4+ cells that influence the activity of other immune cells by releasing cytokines. CD4+ T cells can activate and suppress an adaptive immune response, and which action is induced will depend on presence of other cells and signals. T cells can be collected in accordance with known techniques, and the various subpopulations or combinations thereof can be enriched or depleted by known techniques, such as by affinity binding to antibodies, flow cytometry, or immunomagnetic selection.

"T cell receptor" (TCR) refers to an immunoglobulin superfamily member (having a variable binding domain, a constant domain, a transmembrane region, and a short cytoplasmic tail; see, e.g., Janeway et al., *Immunobiology: The Immune System in Health and Disease*, 3$^{rd}$ Ed., Current Biology Publications, p. 4:33, 1997) capable of specifically binding to an antigen peptide bound to a MHC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). Like immunoglobulins, the extracellular portion of TCR chains (e.g., α-chain, β-chain) contain two immunoglobulin domains, a variable domain (e.g., α-chain variable domain or $V_\alpha$, β-chain variable domain or $V_\beta$; typically amino acids 1 to 116 based on Kabat numbering, Kabat et al., "Sequences of Proteins of Immunological Interest," US Dept. Health and Human Services, Public Health Service National Institutes of Health, 1991, 5$^{th}$ ed.) at the N-terminus, and one constant domain (e.g., α-chain constant domain or $C_\alpha$, typically amino acids 117 to 259 based on Kabat, β-chain constant domain or $C_\beta$, typically amino acids 117 to 295 based on Kabat) adjacent to the cell membrane. Also like immunoglobulins, the variable domains contain complementary determining regions (CDRs) separated by framework regions (FRs) (see, e.g., Jores et al., *Proc. Nat'l Acad. Sci. U.S.A.* 87: 9138, 1990; Chothia et al., *EMBO J.* 7: 3745, 1988; see also Lefranc et al., *Dev. Comp. Immunol.* 27: 55, 2003). In certain embodiments, a TCR is found on the surface of T cells (or "T lymphocytes") and associates with the CD3 complex. The source of a TCR as used in the present disclosure may be from various animal species, such as a human, mouse, rat, rabbit or other mammal.

"Antigen" or "Ag" as used herein refers to an immunogenic molecule that provokes an immune response and this immune response may involve antibody production, activation of specific immunologically-competent cells (e.g., T cells), or both. An antigen may be, for example, a peptide, glycopeptide, polypeptide, glycopolypeptide, polynucleotide, polysaccharide, lipid or the like. An antigen can be synthesized, produced recombinantly, or derived from a biological sample using methods known in the art. For example, novel antigens can be generated using methods known in the art such as chromosome rearrangement or breakage. Exemplary biological samples that can contain one or more antigens include tissue samples, tumor samples, cells, biological fluids, or combinations thereof. Antigens can be produced by cells that have been modified or genetically engineered to express an antigen. Exemplary antigens include α-fetoprotein (AFP), B7H4, BTLA, CD3, CD19, CD20, CD25, CD22, CD28, CD30, CD40, CD44v6, CD52, CD56, CD79b, CD80, CD81, CD86, CD134 (OX40), CD137 (4-1BB), CD151, CD276, CA125, CEA, CEACAM6, c-Met, CT-7, CTLA-4, EGFR, EGFRvIII, ErbB2, ErbB3, ErbB4, EphA2, FLT1, FLT4, Frizzled, O-acetyl-GD2, GD2, GHRHR, GHR, GITR, gp130, HVEM, IGF1R, IL6R, KDR, L1CAM, Lewis A, Lewis Y, LTβR, LIFRβ, LRP5, MAGE, mesothelin, MUC1, NY-ESO-1, a cancer-specific neoantigen, OSMRβ, PD1, PD-L1, PD-L2, PSMA, PTCH1, RANK, Robo1, ROR1, TERT, TGFBR2, TGFBR1, TLR7, TLR9, TNFRSF4, TNFR1, TNFR2, tyrosinase, TWEAK-R, or WT-1, including immunogenic portions or fragments thereof.

As used herein, a "tumor antigen" or "tumor-associated antigen" or "TAA" refers to a mutated protein found in an oncogenic or tumor cell that elicits a humoral immune response, a cellular immune response, or both, which may be found only in tumor cells or may be found in tumor cells and other normal cells. A TAA may be a product of a mutated oncogene (e.g., p53, raf, ras, myc, EGFR), a mutated tumor suppressor gene (e.g., pRb, TP53, PTEN, CD95), a mutated gene that overexpresses or aberrantly expresses a cellular protein, or the like.

As used herein, a "neoantigen" refers to a host cellular product containing a structural change, alteration or mutation that creates a new antigen or antigenic epitope that has not previously been observed in the subject's genome (i.e., in a sample of healthy tissue from the subject) or been "seen" or recognized by the host's immune system. Neoantigens may originate, for example, from coding polynucleotides having alterations (substitution, addition, deletion) that result in an altered or mutated product, or from the insertion of an exogenous nucleic acid molecule or protein into a cell, or from exposure to environmental factors (e.g., chemical, radiological) resulting in a genetic change. Neoantigens may arise separately from a tumor antigen, or may arise from or be associated with a tumor antigen. "Tumor neoantigen" (or "tumor-specific neoantigen") refers to a protein comprising a neoantigenic determinant associated with, arising from, or arising within a tumor cell or plurality of cells within a tumor. Tumor neoantigenic determinants are found on, for example, antigenic tumor proteins or peptides that contain one or more somatic mutations encoded by the DNA of tumor cells, as well as proteins or peptides from viral open reading frames associated with virus-associated tumors (e.g., cervical cancers, some head and neck cancers). For example, tumor neoantigens may arise within or from any of the exemplary tumor or other antigens, as well as from "driver" cancer antigens (e.g., G12D neoantigen from KRAS described in Tran et al., *N. Eng. J. Med.* 375:2255-2262 (2016)), as well as in mutated B-Raf, SF31, MYD88, DDX3X, MAPK1, GNB1, and others).

As used herein, an "immunogenicity enhancer" comprises a molecule encoded by a polynucleotide contained in a host cell, such as a T cell, that enhances immunogenicity of an exogenous neoantigen encoded by a polynucleotide contained in the cell. An immunogenicity enhancer encoded by a host cell can provide localized and concentrated adjuvant activity that improves an immune response against a neoantigen. Exemplary immunogenicity enhancers include an IL-12 (such as a membrane-tethered IL-12), a GM-CSF, an inducible cell death factor, a bacterial flagellin, a CD80, a CD137L, a CD40L, a secreted IL-2, a secreted IL-2 that binds T cells independent of CD25, a secreted IL-15, a secreted IL-15-IL-15Rα complex, a secreted IFNβ, a secreted IFN-α1, a secreted IL-7, or any combination thereof. An immunogenicity enhancer may be endogenously expressed by the host cell (e.g., the host cell may endogenously express, for example, GM-CSF), in which case the host cell may be engineered to increase the expression of the immunogenicity enhancer, or the immunogenicity enhancer may be exogenous to the host cell.

As used herein, a "$T_{VAX}$ cell" refers to a T cell comprising a heterologous polynucleotide that encodes one or more neoantigens, wherein the T cell delivers an antigen systemically when administered to a host, such as a human. Such a $T_{VAX}$ cell may further comprise a polynucleotide that encodes an immunogenicity enhancer, wherein the immunogenicity of the neoantigen expressed in the T cell is statistically significantly improved as compared to a T cell encoding one or more neoantigens without the immunogenicity enhancer. Systemic administration of $T_{VAX}$ cells of the present disclosure may result in systemic neoantigen presentation or localized neoantigen presentation, such as for example, localized or concentrated neoantigen presentation at tumor sites or in secondary lymphoid tissues.

A "binding domain" or "binding region," as used herein, refers to a protein, polypeptide, oligopeptide, or peptide (e.g., antibody, receptor) or portion thereof that possesses the ability to specifically recognize and bind to a target (e.g., antigen, ligand). A binding domain includes any naturally occurring, synthetic, semi-synthetic, or recombinantly produced (i.e., engineered by a human) binding partner for a biological molecule or another target of interest. Exemplary binding domains include immunoglobulin light and heavy chain variable regions (e.g., domain antibodies, single chain Fv fragment (scFv or sFv), Fab, F(ab')$_2$), receptor ectodomains, or ligands (e.g., cytokines, such as IL-12). Immunoglobulin variable domains (e.g., scFv, Fab) are referred to herein as "immunoglobulin-based binding domains." A variety of assays are known for identifying binding domains that specifically bind a particular target, including Western blot, ELISA, and Biacore® analysis. In certain embodiments, a binding domain is part of a larger polypeptide or protein and is referred to as a "binding protein."

Sources of binding domains include antibody variable regions from various species (which can be formatted as antibodies, sFvs or scFvs, Fabs, or soluble $V_H$ domain or domain antibodies), including human, rodent, avian, leporine, and ovine. Additional sources of binding domains include variable regions of antibodies from other species, such as camelid (from camels, dromedaries, or llamas; Ghahroudi et al., *FEBS Letters* 414:521, 1997; Vincke et al., *J. Biol. Chem.* 284:3273, 2009; Hamers-Casterman et al., *Nature* 363:446, 1993; Nguyen et al., *J. Mol. Biol.* 275:413, 1998; nurse sharks (Roux et al., *Proc. Nat'l. Acad. Sci. (USA)* 95:11804, 1998), spotted ratfish (Nguyen et al., *Immunogenetics* 54:39, 2002), or lamprey (Herrin et al., *Proc. Nat'l. Acad. Sci. (USA)* 105:2040, 2008; Alder et al., *Nature Immunol.* 9:319, 2008). These antibodies can apparently form antigen-binding regions using only heavy chain variable region, i.e., these functional antibodies are homodimers of heavy chains only (referred to as "heavy chain antibodies") (Jespers et al., *Nature Biotechnol.* 22:1161, 2004; Cortez-Retamozo et al., *Cancer Res.* 64:2853, 2004; Baral et al., *Nature Med.* 12:580, 2006; Barthelemy et al., *J. Biol. Chem.* 283:3639, 2008).

As used herein, "specifically binds" or "specific for" refers to an association or union of a binding protein (e.g., a receptor, an antibody, CAR, or TCR) or a binding component (or fusion protein thereof) to a target molecule with an affinity or $K_a$ (i.e., an equilibrium association constant of a particular binding interaction with units of 1/M) equal to or greater than $10^5$ M$^{-1}$ (which equals the ratio of the on-rate [$k_{on}$] to the off-rate [$k_{off}$] for this association reaction), while not significantly associating or uniting with any other molecules or components in a sample. Binding proteins or binding domains (or fusion proteins thereof) may be classified as "high affinity" binding proteins or binding domains (or fusion proteins thereof) or as "low affinity" binding proteins or binding domains (or fusion proteins thereof). "High affinity" binding proteins or binding domains refer to those binding proteins or binding domains having a $K_a$ of at least $10^7$ M$^{-1}$, at least $10^8$ M$^{-1}$, at least $10^9$M$^{-1}$, at least $10^{10}$ M$^{-1}$, at least $10^{11}$ M$^{-1}$, at least $10^{12}$M$^{-1}$, or at least $10^{13}$M$^{-1}$. "Low affinity" binding proteins or binding domains refer to those binding proteins or binding domains having a $K_a$ of up to $10^7$ M$^{-1}$, up to $10^6$M$^{-1}$, up to $10^5$ M$^{-1}$. Alternatively, affinity may be defined as an equilibrium dissociation constant ($K_d$) of a particular binding interaction with units of M (e.g., $10^{-5}$ M to $10^{-13}$M).

A variety of assays are known for identifying binding domains of the present disclosure that specifically bind a particular target, as well as determining binding domain or fusion protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173; 5,468,614, or the equivalent).

Terms understood by those in the art of antibody technology are each given the meaning acquired in the art, unless expressly defined differently herein. The term "antibody" refers to an intact antibody comprising at least two heavy (H) chains and two light (L) chains inter-connected by disulfide bonds, as well as any antigen-binding portion or fragment of an intact antibody that has or retains the ability to bind to the antigen target molecule recognized by the intact antibody, such as an scFv, Fab, or Fab'2 fragment. Thus, the term "antibody" herein is used in the broadest sense and includes polyclonal and monoclonal antibodies, including intact antibodies and functional (antigen-binding) antibody fragments thereof, including fragment antigen binding (Fab) fragments, F(ab')$_2$ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

A monoclonal antibody or antigen-binding portion thereof may be non-human, chimeric, humanized, or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988).

For example, the terms "$V_L$" and "$V_H$" refer to the variable binding region from an antibody light and heavy chain, respectively. The variable binding regions are made up of discrete, well-defined sub-regions known as "complementarity determining regions" (CDRs) and "framework regions" (FRs). The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 of the heavy chain linked to the light chain via an inter-chain disulfide bond.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al., "Sequences of Proteins of Immunological Interest" (5th Ed. Public Health Service, National Institutes of Health, Bethesda, Md., 1991) ("Kabat" numbering scheme), Al-Lazikani, et al. (*J. Mol. Biol.* 273: 927, 1997) ("Chothia" numbering scheme), MacCallum, et al. (*J. Mol. Biol.* 262: 732, 1996) ("Contact" numbering scheme), Lefranc, et al. (*Dev. Comp. Immunol.* 27: 55, 2003) ("IMGT" numbering scheme), and Honegger & Plückthun (*J. Mol. Biol.* 309: 657, 2001) ("Aho" numbering scheme). The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table 1, below, lists exemplary position boundaries of CDR-L1, CDR-L2, CDR-L3 and CDR-H1, CDR-H2, CDR-H3 as identified by Kabat, Chothia, and Contact schemes, respectively. For CDR-H1, residue numbering is listed using both the Kabat and Chothia numbering schemes. FRs are located between CDRs, for example, with FR-L1 located between CDR-L1 and CDR-L2, and so forth. It is noted that because the shown Kabat numbering scheme places insertions at H35A and H35B, the end of the Chothia CDR-H1 loop, when numbered using the shown Kabat numbering convention, varies between H32 and H34, depending on the length of the loop.

TABLE 1

Exemplary CDR Position Boundaries

| CDR | Kabat | Chothia | Contact |
|---|---|---|---|
| CDR-L1 | L24--L34 | L24--L34 | L30--L36 |
| CDR-L2 | L50--L56 | L50--L56 | L46--L55 |
| CDR-L3 | L89--L97 | L89--L97 | L89--L96 |
| CDR-H1 (Kabat Numbering[1]) | H31--H35B | H26--H32..34 | H30--H35B |
| CDR-H1 (Chothia Numbering[2]) | H31--H35 | H26--H32 | H30--H35 |
| CDR-H2 | H50--H65 | H52--H56 | H47--H58 |
| CDR-H3 | H95--H102 | H95--H102 | H93--H101 |

[1]Kabat et al., "Sequences of Proteins of Immunological Interest," 5th Ed. Public Health Service, National Institutes of Health, Bethesda, MD, 1991.
[2]Al-Lazikani et al., *J. Mol. Biol.* 273: 927, 1997.

Thus, unless otherwise specified, a "CDR" or "complementary determining region," or individual specified CDRs (e.g., CDR-H1, CDR-H2), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given $V_H$ or $V_L$ amino acid sequence, it is understood that such a CDR has a sequence of the corresponding CDR (e.g., CDR-H3) within the variable region, as defined by any of the aforementioned schemes. In some embodiments, specified CDR sequences are specified. Likewise, unless otherwise specified, a FR or individual specified FR(s) (e.g., FR-H1, FR-H2), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, or Contact method. In other cases, the particular amino acid sequence of a CDR or FR is given.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g., scFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In certain embodiments, the antibodies are recombinantly produced fragments, such as fragments comprising arrangements that do not occur naturally, such as those with two or more antibody regions or chains joined by synthetic linkers, e.g., peptide linkers. In certain embodiments, antibodies are produced by enzyme digestion of a naturally-occurring intact antibody. In some aspects, antibody fragments are scFvs.

As used herein, "Fc region portion" refers to the heavy chain constant region segment of the Fc fragment (the "fragment crystallizable" region or Fc region) from an antibody, which can in include one or more constant domains, such as CH2, CH3, CH4, or any combination thereof. In certain embodiments, an Fc region portion includes the CH2 and CH3 domains of an IgG, IgA, or IgD antibody or any combination thereof, or the CH3 and CH4 domains of an IgM or IgE antibody and any combination thereof. In other embodiments, a CH2CH3 or a CH3CH4 structure has sub-region domains from the same antibody isotype and are human, such as human IgG1, IgG2, IgG3, IgG4, IgA1, IgA2, IgD, IgE, or IgM (e.g., CH2CH3 from human IgG1). By way of background, an Fc region is responsible for the effector functions of an immunoglobulin, such as ADCC (antibody-dependent cell-mediated cytotoxicity), CDC (complement-dependent cytotoxicity) and complement fixation, binding to Fc receptors (e.g., CD16, CD32, FcRn), greater half-life in vivo relative to a polypeptide lacking an Fc region, protein A binding, and perhaps even placental transfer (see Capon et al., *Nature* 337:525, 1989). In certain embodiments, an Fc region portion found in immunoglobulin-like binding proteins of the present disclosure will be capable of mediating one or more of these effector functions, or will lack one or more or all of these activities by way of, for example, one or more mutations known in the art.

In addition, antibodies have a hinge sequence that is typically situated between the Fab and Fc region (but a lower section of the hinge may include an amino-terminal portion of the Fc region). By way of background, an immunoglobulin hinge acts as a flexible spacer to allow the Fab portion to move freely in space. In contrast to the constant regions, hinges are structurally diverse, varying in both sequence and length between immunoglobulin classes and even among subclasses. For example, a human IgG1 hinge region is freely flexible, which allows the Fab fragments to rotate about their axes of symmetry and move within a sphere centered at the first of two inter-heavy chain disulfide bridges. By comparison, a human IgG2 hinge is relatively short and contains a rigid poly-proline double helix stabilized by four inter-heavy chain disulfide bridges, which restricts the flexibility. A human IgG3 hinge differs from the other subclasses by its unique extended hinge region (about four times as long as the IgG1 hinge), containing 62 amino acids (including 21 prolines and 11 cysteines), forming an inflexible poly-proline double helix and providing greater flexibility because the Fab fragments are relatively far away from the Fc fragment. A human IgG4 hinge is shorter than IgG1 but has the same length as IgG2, and its flexibility is intermediate between that of IgG1 and IgG2.

As used herein, unless otherwise provided, a position of an amino acid residue in the constant region of human IgG1 heavy chain is numbered assuming that the variable region of human IgG1 is composed of 128 amino acid residues according to the Kabat numbering convention. The numbered constant region of human IgG1 heavy chain is then used as a reference for numbering amino acid residues in constant regions of other immunoglobulin heavy chains. A position of an amino acid residue of interest in a constant region of an immunoglobulin heavy chain other than human IgG1 heavy chain is the position of the amino acid residue in human IgG1 heavy chain with which the amino acid residue of interest aligns. Alignments between constant regions of human IgG1 heavy chain and other immunoglobulin heavy chains may be performed using software programs known in the art, such as the Megalign program (DNASTAR Inc.) using the Clustal W method with default parameters. According to the numbering system described herein, for example, although human IgG2 $C_{H2}$ region may have an amino acid deletion near its amino-terminus compared with other $C_{H2}$ regions, the position of the "N" located at 296 in human IgG2 $C_{H2}$ is still considered position 297 because this residue aligns with "N" at position 297 in human IgG1 $C_{H2}$.

The term "epitope" includes any amino acid sequence or protein determinant capable of specific binding to an immunoglobulin, receptor or other binding domain or binding protein. Epitopic determinants generally contain chemically active surface groupings of molecules, such as amino acids or sugar side chains, and can have specific three dimensional structural characteristics, as well as specific charge characteristics.

The terms "polypeptide" and "peptide" as used herein refer to a compound made up of amino acid residues that are linked by peptide bonds. The term "protein" may be synonymous with the term "polypeptide" or may refer, in addition, to a complex of two or more polypeptides. A polypeptide may further contain other components (e.g., covalently bound), such as a tag, a label, a bioactive molecule, or any combination thereof. In certain embodiments, a polypeptide may be a fragment. As used herein, a "fragment" means a polypeptide that is lacking one or more amino acids that are found in a parent polypeptide. A fragment can comprise a binding domain, antigen, or epitope found in a parent polypeptide. In certain embodiments, a fragment of a polypeptide can have at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more of amino acids of the amino acid sequence of the parent polypeptide.

As described herein, a "variant" polypeptide species has one or more non-natural amino acids, one or more amino acid substitutions, one or more amino acid insertions, one or more amino acid deletions, or any combination thereof at one or more sites relative to a reference polypeptide as presented herein. In certain embodiments, "variant" means a polypeptide having a substantially similar activity (e.g., enzymatic function, immunogenicity) or structure relative to a reference polypeptide. A variant of a reference polypeptide can have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity to the amino acid sequence for the reference polypeptide as determined by sequence alignment programs and parameters known in the art. The variant can result from, for example, a genetic polymorphism or human manipulation. Conservative substitutions of amino acids are well known and may occur naturally or may be introduced when a protein is recombinantly produced. Amino acid substitutions, deletions, and additions may be introduced into a protein using mutagenesis methods known in the art (see, e.g., Sambrook et al., *Molecular Cloning: A Laboratory Manual*, 3d ed., Cold Spring Harbor Laboratory Press, NY, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare polypeptide variants (see, e.g., Sambrook et al., supra).

The terms "identical" or "percent identity," in the context of two or more polypeptide or nucleic acid molecule sequences, means two or more sequences or subsequences that are the same or have a specified percentage of amino acid residues or nucleotides that are the same over a specified region (e.g., 60%, 65%, 70%, 75%, 80%, 85%, 90%, 91%, 92%, 93%, 94%, 95%, 96%, 97%, 98%, 99%, or 100% identity), when compared and aligned for maximum correspondence over a comparison window, or designated region, as measured using methods known in the art, such as a sequence comparison algorithm, by manual alignment, or by visual inspection. For example, preferred algorithms suitable for determining percent sequence identity and sequence similarity are the BLAST and BLAST 2.0 algorithms, which are described in Altschul et al. (*Nucleic Acids Res.* 25:3389, 1977) and Altschul et al. (*J. Mol. Biol.* 215:403, 1990), respectively.

As used herein, a "fusion protein" comprises a single chain polypeptide having at least two distinct domains, wherein the domains are not naturally found together in a protein. A nucleic acid molecule encoding a fusion protein may be constructed using PCR, recombinantly engineered, or the like, or such fusion proteins can be made synthetically. A fusion protein may further contain other components (e.g., covalently bound), such as a tag or bioactive molecule.

A "nucleic acid molecule" or "polynucleotide" refers to a single- or double-stranded linear or circular polynucleotide containing either deoxyribonucleotides or ribonucleotides that are linked by 3'-5'-phosphodiester bonds. A nucleic acid molecule includes RNA, DNA, genomic DNA, mitochondrial DNA, cDNA, or vector DNA. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides, morpholinos), or a combination of both. Modified nucleotides can have modifications in, or replacement of, sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like.

In certain embodiments, polynucleotides encoding peptides or proteins of the disclosure may be codon optimized to enhance or maximize expression in certain types of cells (e.g., Scholten et al., *Clin. Immunol.* 119:135-145, 2006). As used herein a "codon optimized" polynucleotide is a heterologous polypeptide having codons modified with silent mutations corresponding to the abundances of host cell tRNA levels.

Variants of the polynucleotides of this disclosure are also contemplated. Variant polynucleotides are at least 80%, 85%, 90%, 95%, 99%, or 99.9% identical to a reference polynucleotide as described herein, or that hybridizes to a reference polynucleotide of defined sequence under stringent hybridization conditions of 0.015M sodium chloride, 0.0015M sodium citrate at about 65°-68° C. or 0.015M sodium chloride, 0.0015M sodium citrate, and 50% formamide at about 42° C. The polynucleotide variants retain the capacity to encode an immunoglobulin binding protein or antigen-binding fragment thereof having the functionality described herein.

The term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the co-existing materials in the natural system, is isolated. Such polynucleotide may be part of a vector and/or such polynucleotide or polypeptide may be part of a composition (e.g., a cell lysate), and still be isolated in that such vector or composition is not part of the natural environment for the nucleic acid or polypeptide.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid molecule may be incorporated into the genome of a cell (e.g., chromosome, plasmid, plastid, or mitochondrial DNA), converted into an autonomous replicon, comprised in an episomal expression vector (see, e.g., Van Caenenbroeck et al., *Eur. J. Biochem.* 267:5665 (2000)), or transiently expressed (e.g., transfected mRNA).

As used herein, "heterologous" or "exogenous" nucleic acid molecule, construct or sequence refers to a nucleic acid molecule or portion of a nucleic acid molecule that is not native to a host cell, but may be homologous to a nucleic acid molecule or portion of a nucleic acid molecule from the host cell. The source of the heterologous or exogenous nucleic acid molecule, construct or sequence may be from a different genus or species. In certain embodiments, a heterologous or exogenous nucleic acid molecule is added (i.e., not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, "heterologous" or "exogenous" refers to a non-native enzyme, protein, or other activity encoded by an exogenous nucleic acid molecule introduced into the host cell, even if the host cell encodes a homologous protein or activity.

In certain embodiments, more than one heterologous nucleic acid molecules can be introduced into a host cell as separate nucleic acid molecules, as a polycistronic nucleic acid molecule, as a single nucleic acid molecule encoding a fusion protein (e.g., a plurality of neoantigens), or any combination thereof, and still be considered as more than one heterologous nucleic acid. For example, as disclosed herein, an immune cell can be modified to contain two or more heterologous or exogenous nucleic acid molecules that encode one or more desired neoantigens or that encode one or more neoantigens and an immunogenicity enhancer (e.g., flagellin, IL-12, GM-CSF). When two or more exogenous nucleic acid molecules encoding a neoantigen or an immunogenicity enhancer are introduced into a host cell, it is understood that the two or more exogenous nucleic acid molecules can be introduced as a single nucleic acid molecule (e.g., on a single vector), or as more than one nucleic acid molecule (e.g., on separate vectors), and can be comprised in an episomal expression vector, or integrated into the host chromosome at a single site or multiple sites, and still be considered two or more exogenous nucleic acid molecules. Thus, the number of referenced heterologous nucleic acid molecules or encoded biological activities refers to the number of encoding nucleic acid molecules or the number of protein activities, not the number of separate nucleic acid molecules introduced into a host cell.

As used herein, the term "endogenous" or "native" refers to a gene, protein, or activity that is normally present in a host cell. Moreover, a gene, protein, or activity that is mutated, overexpressed, shuffled, duplicated, or otherwise altered as compared to a parent gene, protein, or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

As used herein, the term "recombinant" refers to a cell, microorganism, nucleic acid molecule, or vector that has been modified by introduction of an exogenous nucleic acid molecule through human intervention, or refers to a cell or microorganism that has been altered such that expression of an endogenous nucleic acid molecule or gene is controlled, deregulated or constitutive, where such alterations or modifications are introduced or induced through human intervention (e.g., by genetic engineering). Genetic alterations may include, for example, modifications introducing nucleic acid molecules (which may include an expression control element, such as a promoter) encoding one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule. A cell, microorganism, nucleic acid molecule, or vector that has been modified by introduction of an exogenous nucleic acid molecule may be referred to as "recombinant" or "non-naturally occurring" or "genetically engineered" or "transformed" or "transgenic".

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one to three codons or amino acids, a deletion of one to about five codons or amino acids, or a combination thereof.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, N.Y., pp. 71-77, 1975; Lewin, Genes IV, Oxford University Press, NY and Cell Press, Cambridge, Mass., p. 8, 1990).

Neoantigens

In some aspects, the present disclosure provides immunogenic compositions or vaccines comprising immune cells, such as T cells, that express one or more exogenous neoantigens.

In certain embodiments, a neoantigen is associated with a hyperproliferative disease or disorder (e.g., cancer), such as a tumor neoantigen. Because tumor neoantigens often arise from somatic "passenger" mutations in the DNA of tumor cells, many tumor neoantigens are unique to an individual patient's cancer. Therefore, in certain embodiments, developing an immunogenic composition or vaccine disclosed herein comprises determining the "mutanome" of an individual patient's tumor, identifying candidate tumor neoantigens, and expressing the tumor neoantigens in immune cells to be delivered to a subject (FIG. 1). In certain embodiments, a neoantigen comprises an antigenic peptide or epitope from a protein encoded by a nucleic acid molecule having a missense mutation, nonstop mutation, splice variant, gene fusion, frameshift mutation (e.g., addition or deletion), or combinations thereof, as compared to the wild-type nucleic acid molecule.

Neoantigens may be identified using any of several well-known techniques (see, e.g., Rajasagi et al., *Blood* 124:453, 2014). By way of background and not wishing to be bound by theory, generally, a relatively small fraction of mutations in a malignant clone are able to elicit a new immune response. To be immunogenic, a mutation must change the amino acid sequence of an expressed protein, and the resulting protein must be proteolytically processed into peptides that contain the amino acid change, bind to MHC molecules, and be detected as foreign by the individual's T cells. The resulting mutation can potentially activate a T cell response if it alters processing and binding of the peptide to MHC, or alters the MHC-peptide-T cell receptor (TCR) interaction in a way that promotes specific binding (Gubin et al., *J. Clin. Invest.* 125:3413, 2015). Computational algorithms have been developed to predict proteasome processing as well as peptide binding to MHC.

Exemplary prediction tools for identifying potential peptide binding to MHC in silico include, for example, NetMHC (for predicting MHC class I binding for particular human MHC alleles using artificial neural networks (ANNs)) (Andreatta et al., *Bioinformatics* 32(4):511-517 (2016); Segal et al., *Cancer Res* 68(3):889-892 (2008); Nielsen et al., *Protein Sci.* 12(5): 1007-1017 (2003); NetMHCpan (for predicting MHC class I binding for any allele of known sequence) (Nielsen & Andreatta, *Genome Medicine* 8(1):33 (2016); Hoof et al., *Immunogenetics* 61(1): 1-13 (2009), the Stabilized Matrix Method (SMM) (Peters & Sette, *BMC Bioinformatics* 6:132 (2005), and Average Relative Binding (ARB) matrix methods (Bui et al., *Immunogenetics* 57(5):304-314 (2005) (see also Fritsch et al., *Cancer Immunol Res* 2(6):522-529 (2014); van Buuren et al., *Oncoimmunology* 3: e28836 (2014); Trolle et al., *Bioinformatics* 39(5):764-768 (2015)). For example, mutations (e.g., missense and frameshift) can be analyzed for formation of novel peptides predicted to bind autologous MHC alleles using NetMHCpan (Trolle et al., *Bioinformatics* 39(5):764-768 (2015).). In addition, HLA typing may be obtained from next generation or exome sequencing using OptiType (see, e.g., Szolek et al., *Bioinformatics* 30(23): 3310-3316 (2014)).

A candidate neoantigen for use in an immunogenic composition or a vaccine of the present disclosure may be identified by isolating DNA from a tumor sample; sequencing expressed genes using exome capture, RNA sequencing, whole genome sequencing, or combinations thereof; and using bioinformatics to identify somatic mutations (e.g., point mutations) that are predicted to produce candidate neoantigens.

Neoantigen and Immunogenicity Enhancer Expressing Cells

In certain aspects, the present disclosure provides immune cells (e.g., T cells) comprising one or more exogenous neoantigens and an immunogenicity enhancer. In some embodiments, an immune cell comprising an exogenous neoantigen and an immunogenicity enhancer as disclosed herein may be used in an immunogenic composition or a vaccine for eliciting or boosting an immune response against the neoantigen. For example, in any of the embodiments described herein, T cells are modified to express an exogenous neoantigen. Neoantigens delivered by such engineered T cells will be highly immunogenic when administered to a subject, which can elicit a high frequency, durable T cell response against one or more epitopes of the neoantigen(s). Transferred T cells, to a subject known to have cells producing the neoantigen, can migrate efficiently to secondary lymphoid organs where neoantigen priming can occur, and may activate other T cells indirectly (mediated by dendritic cells) or directly against cells producing the neoantigen. Additionally, the generation of a durable T cell response may prevent relapse or recurrence of a disease associated with a neoantigen (e.g., tumor neoantigen).

Vaccines based on T cells may offer additional practical advantages compared to other approaches, particularly in the context of personalized neoantigen-based vaccines and immunogenic compositions, such as ease of design, production, and administration. By way of background, vaccines based on naked peptides or nucleic acid molecules are easy to construct and administer, but have not been highly effective. Moreover, increasing their immunogenicity is limited to adding systemic adjuvants, which can be toxic, be of limited efficacy, or both. Dendritic cells are difficult to isolate, genetically modify, or expand to large numbers ex vivo. In contrast, T cells are readily isolated, easily genetically modified, and can be expanded ex vivo, and there is clinical precedent for adoptively transferring T cells. As described herein, T cells for use in an immunogenic composition or a vaccine of this disclosure may also be modified to increase the potency of specific anti-cancer immune responses that are elicited.

In certain embodiments, the present disclosure provides an immune cell or lymphocyte comprising a nucleic acid molecule encoding an exogenous neoantigen and an immunogenicity enhancer, wherein the nucleic acid molecule encodes one or more exogenous neoantigens. For example, a nucleic acid molecule may encode one, two, three, four, five, six, seven, eight, nine, ten, 11, 12, 13, 14, 15, 16, 17, 18, 19 or 20 neoantigens. In certain embodiments, an immune cell comprises a nucleic acid molecule encoding two to about five exogenous neoantigens, or two to about ten exogenous neoantigens, or two to about 20 exogenous neoantigens. In certain other embodiments, an immune cell or lymphocyte comprises separate nucleic acid molecules that each independently encode one or more exogenous neoantigens, such as two to about five exogenous neoantigens or two to about ten exogenous neoantigens or two to about 20 exogenous neoantigens (e.g., each nucleic acid molecule may encode a different number of neoantigens).

In certain embodiments, an immune cell or lymphocyte of the present disclosure comprises a polynucleotide encoding an exogenous neoantigen comprising an epitope that is specifically bound by $CD8^+$ T cell, a $CD4^+$ T cell, or both. In certain embodiments, an immune cell or lymphocyte of the present disclosure comprises a polynucleotide encoding an exogenous neoantigen that is specifically bound by a $CD8^+$ T cell, and comprises a polynucleotide encoding an antigen or neoantigen that is specifically bound by a $CD4^+$ T cell. In further embodiments, the encoded $CD4^+$ antigen or neoantigen is exogenous to the immune cell or lymphocyte. In other embodiments, an immune cell or lymphocyte comprises a polynucleotide encoding an exogenous neoantigen that is specifically bound by a $CD4^+$ T cell, and comprises a polynucleotide encoding an antigen or neoantigen that is specifically bound by a $CD8^+$ T cell. In further embodiments, the encoded $CD8^+$ antigen or neoantigen is exogenous to the immune cell or lymphocyte. Without wishing to be bound by theory, co-stimulation of CD8 and CD4 activity of a T cell can enhance the immune response against a neoantigen.

In any of the aforementioned embodiments, an immune cell or lymphocyte (e.g., T cell) of the present disclosure comprises an exogenous neoantigen and an immunogenicity enhancer. In any of the aforementioned embodiments, an immune cell or lymphocyte comprises a polynucleotide encoding an exogenous neoantigen and a polynucleotide encoding an immunogenicity enhancer. Exemplary immunogenicity enhancers include an IL-12 (including a membrane-tethered IL-12), a GM-CSF, an inducible cell death factor, an antigen (e.g., bacterial flagellin), or any combination thereof.

In any of the aforementioned embodiments, an exogenous neoantigen-containing immune cell or lymphocyte of the present disclosure may contain an immunogenicity enhancer that comprises a pathogen-associated molecule, such as those recognized by toll-like receptors (TLRs). For example, DNA-encoded TLR agonists may function as immunogenicity enhancers (i.e., molecular adjuvants) for use with an immunogenic composition or a vaccine of this disclosure (see Applequist et al., *J. Immunol.* 175:3882, 2005). An exemplary immunogenicity enhancer comprises a bacterial flagellin protein. Expression of a bacterial flagellin protein at the cell surface has been shown to enhance immune responses (Applequist et al., 2005). In some embodiments, an encoded immunogenicity enhancer comprises a bacterial flagellin or immunogenicity enhancing fragment thereof. In certain embodiments, an immune cell or lymphocyte comprising a nucleic acid molecule encoding an exogenous neoantigen and a nucleic acid molecule encoding a bacterial flagellin or immunogenicity enhancing fragment thereof is provided. In particular embodiments, a bacterial flagellin comprises a *Salmonella* phase 1 flagellin. In other embodiments, a bacterial flagellin comprises an amino acid sequence encoded by a nucleic acid molecule as set forth in GenBank Accession No. NC_003197.1 (which sequence is incorporated herein by reference in its entirety). In further embodiments, a bacterial flagellin comprises a bacterial flagellin fusion protein that localizes to the cell surface of a lymphocyte (i.e., a membrane-tethered bacterial flagellin fusion protein). For example, in certain embodiments, a bacterial flagellin fusion protein comprises (a) a bacterial flagellin domain; and (b) a transmembrane domain. In certain embodiments, a bacterial flagellin fusion protein further comprises (c) a signal domain that directs the fusion protein to a secretory pathway. In particular embodiments, a transmembrane domain comprises a PDGF transmembrane domain. In certain embodiments, a transmembrane domain comprises an amino acid sequence as set forth in SEQ ID NO.:5, or a fragment thereof. In further embodiments, a signal domain comprises an Igκ-chain leader sequence. In certain embodiments, a signal domain comprises an amino acid sequence as set forth in SEQ ID NO.:1. In still further embodiments, a bacterial flagellin domain may be modified to remove eukaryotic glycosylation sites. In certain embodiments, a bacterial flagellin domain comprises an amino acid sequence as set forth in SEQ ID NO.:4. In other embodiments, a bacterial flagellin fusion protein further comprises a tag. In some embodiments, a tag included in a bacterial flagellin fusion protein comprises an amino acid sequence as set forth in SEQ ID NO.:2.

In certain embodiments, a bacterial flagellin fusion protein comprises an amino acid sequence encoded by a nucleic acid molecule as set forth in SEQ ID NO.:3.

In any of the aforementioned embodiments, an exogenous neoantigen-containing immune cell or lymphocyte of the present disclosure contains an immunogenicity enhancer that is an IL-12, such as human IL-12. By way of background, IL-12 has been shown to stimulate the priming of Th1 pro-inflammatory responses at the site of antigen delivery (Hsieh et al., *Science* 260:547, 1993), while limiting systemic toxicity. For example, membrane-bound IL-12 can stimulate immune responses to transplanted tumor cell lines (Pan et al., *Mol. Ther.* 20:927, 2012). In certain embodiments disclosed herein, an immune cell or lymphocyte comprising an exogenous neoantigen and an exogenous IL-12 or functional fragment thereof is provided. A nucleic acid sequence encoding human IL-12 is set forth in SEQ ID NO.: 7, and an amino acid sequence of human IL-12 is set forth in SEQ ID NO.: 8. In certain embodiments, an immune cell or lymphocyte comprising a nucleic acid molecule encoding an exogenous neoantigen and a nucleic acid molecule encoding an IL-12 is provided. In certain embodiments, an IL-12 comprises a single-chain (sc) IL-12. Construction of a single-chain IL-12 is described in, for example, Pan et al., *Mol. Ther.* 20(5):927-937 (2012). In further embodiments, an IL-12 comprises an IL-12 fusion protein that localizes to the cell surface of the immune cell or lymphocyte (i.e., a membrane-tethered IL-12). In certain embodiments, an IL-12 fusion protein comprises (a) an IL-12 domain; and (b) a transmembrane domain. In certain embodiments, an IL-12 transmembrane domain of B7, CD2, CD3ε, CD3ζ, CD3, CD25, CD27, CD28, CD40, CD47, CD79A, CD79B, CD80, CD86, CD95 (Fas), CD134 (OX40), CD137 (4-1BB), CD150 (SLAMF1), CD152 (CTLA4), CD200R, CD223 (LAG3), CD270 (HVEM), CD272 (BTLA), CD273 (PD-L2), CD274 (PD-L1), CD278 (ICOS), CD279 (PD-1), TIM3, CD300, CD357 (GITR), A2aR, DAP10, FcRα, FcRβ, FcRγ, Fyn, GAL9, KIR, Lck, LAT, LPA5, LRP, NKG2D, NOTCH1, NOTCH2, NOTCH3, NOTCH4, PTCH2, ROR2, Ryk, Slp76, SIRPα, pTα, TCRα, TCRβ, TIM3, TRIM, or Zap70. In certain embodiments, an IL-12 fusion protein further comprises (c) a signal peptide that directs the fusion protein to a secretory pathway (i.e., to localize to the cell membrane).

In any of the aforementioned embodiments, an exogenous neoantigen-containing immune cell or lymphocyte of the present disclosure contains an immunogenicity enhancer that is a Granulocyte-Macrophage Colony Stimulating Factor (GM-CSF). By way of background, GM-CSF is secreted by multiple cell types in response to cytokine signaling and, among other functions, stimulates production of granulocytes and monocytes, which subsequently mature into macrophages and DCs. GM-CSF plays a role in immune modulation and has been used as an immunogenicity enhancer in cancer immunotherapies. See, e.g., Hong, *Exp. Mol. Med.* 48(7):e242 (2016).

In any of the aforementioned embodiments, the present disclosure provides an immune cell or lymphocyte comprising an exogenous neoantigen and an immunogenicity enhancer, or a polynucleotide encoding an exogenous neoantigen and a polynucleotide encoding an immunogenicity enhancer, wherein the immune cell or lymphocyte comprises a T cell.

Phagocytosis of dying cells by dendritic cells will activate CD8$^+$ T cells by cross-priming (Yatim et al., *Science* 350: 328, 2015). Thus, the ability to selectively induce apoptosis or necroptosis in a neoantigen-containing immune cell or lymphocyte of this disclosure may allow for enhanced immunogenicity of the cell, by activating an inflammatory cell death pathway and increasing neoantigen cross-presentation. In certain embodiments, an immune cell or lymphocyte comprises an exogenous neoantigen and an exogenous inducible cell death factor. In certain embodiments, an immune cell or lymphocyte comprises a nucleic acid molecule encoding an exogenous neoantigen and a nucleic acid molecule encoding an exogenous inducible cell death factor.

An "inducible cell death factor" refers to a molecule that is capable of triggering or promoting cell death, and which activity can be selectively induced. In some embodiments, an inducible cell death factor is a fusion protein comprising a cell death signaling domain and a multimerization domain.

A "multimerization domain," as used herein, refers to a polypeptide molecule or region that preferentially interacts or associates with another polypeptide molecule or region, directly or indirectly, wherein the interaction of multimerization domains substantially contribute to or efficiently promote multimerization (i.e., the formation of a dimer, trimer, tetramer, or higher order multimers, which may be a homodimer, heterodimer, homotrimer, heterotrimer, homomultimer, heteromultimer, or the like). For example, multimerization may be due to one or more types of molecular forces, including covalent bonds (e.g., disulfide bonds or bridges), ionic bonds, metallic bonds, electrostatic interactions, salt bridges, dipole-dipole forces, hydrogen bonding, Van der Waals forces, hydrophobic interactions, or any combination thereof. A multimer is stable under appropriate conditions (e.g., physiological conditions, in an aqueous solution suitable for expressing, purifying, or storing recombinant or engineered proteins, or under conditions for non-denaturing or non-reducing electrophoresis). Exemplary multimerization domains associate via a multimerization promoting molecule, such as chemically induced multimerization, wherein multimerization is minimal or does not occur in the absence of the multimerization promoting molecule.

In certain embodiments, an inducible cell death factor is a receptor interacting serine/threonine kinase 3 (RIPK3) (see, e.g., Yatim et al., *Science* 350:328, 2015). In particular embodiments, RIPK3 comprises an amino acid sequence encoded by a nucleic acid molecule as set forth in GenBank Accession No. NP_006862 (which sequence is incorporated herein by reference in its entirety). When activated, RIPK3 can trigger necroptosis through the TNF receptor-driven cell death pathway, and chemically enforced oligomerization of RIPK3 can induce necroptosis (Orozco et al., *Cell Death Differ.* 21:1511, 2014). Accordingly, in certain embodiments, an inducible cell death factor is a fusion protein comprising, for example, a RIPK3 cell death signaling domain and a multimerization domain. In certain embodiments, a RIPK3 cell death signaling domain comprises a RIPK3 kinase domain and a multimerization domain comprises an FK506-binding protein or multimerizing portion thereof. The FK506-binding protein binds with high affinity to a synthetic bivalent homologue of rapamycin, resulting in rapid dimerization (Yatim et al., supra; Orozco et al., supra). In further embodiments, a multimerization promoting molecule comprises rapamycin or analog or derivative thereof. Other molecules that are associated with a protein interaction that leads to cell death include mixed lineage kinase domain-like (MLKL) (see Murphy et al., *Immunity* 39:443, 2013) and caspase and GSDMD (see Shi et al., *Nature* 526:660, 2015). Immune cells, lymphocytes or T cells comprising an exogenous neoantigen and an inducible MLKL, caspase, or GSMD are also within the scope of this disclosure. Immune cells, lymphocytes or T cells comprising a nucleic acid molecule encoding an exogenous neoantigen and a nucleic acid molecule encoding an inducible MLKL, caspase, or GSMD are also provided.

Other immunogenicity enhancers for use in the cells and methods disclosed herein include, for example, a CD80, a CD137L, a CD40L, a secreted IL-2, a secreted IL-2 that binds T cells independent of CD25, a secreted IL-15, a secreted IL-15-IL-15Rα complex, a secreted IFNβ, a secreted IFN-α1, a secreted IL-7, or any combination thereof.

In any of the aforementioned embodiments, the present disclosure provides an immune cell or lymphocyte comprising an exogenous neoantigen and an exogenous inducible cell death factor, or a polynucleotide encoding an exogenous neoantigen and a polynucleotide encoding an exogenous inducible cell death factor, wherein the immune cell or lymphocyte comprises a T cell.

In any of the aforementioned embodiments, an exogenous neoantigen-containing immune cell or lymphocyte of the present disclosure may further comprise a costimulatory molecule. In certain embodiments, an immune cell or lymphocyte comprising a nucleic acid molecule encoding an exogenous neoantigen and a nucleic acid molecule encoding a costimulatory molecule is provided. A "costimulatory molecule" as used herein refers to a receptor, ligand, or cell-surface molecule that can deliver or transduce signals into T cells to positively modulate T cell activation (Chen and Flies, *Nat. Rev. Immunol.* 13:227, 2013). By way of background, T cell activation and proliferation requires two signals mediated through engagement of the T cell antigen-specific receptor (TCR) and a costimulatory signal, most typically binding of CD28 by CD80 and CD86 (Ledbetter et al., *Blood* 75:1531, 1990). Costimulatory ligands and counter-receptors are frequently expressed on APCs or other cells that interact with T cells, and provide costimulatory signaling by interacting with cell-surface receptors found on T cells. In some embodiments, an immune cell or lymphocyte comprising an exogenous neoantigen and an exogenous costimulatory molecule is provided, wherein the costimulatory molecule is selected from a CD80, a CD86, a B7RP1, a CD137L, an OX40L, a CD70, a CD30L, a CD154, an ICAM-1, a CD2BP2, a LIGHT, a KLRD1, a ligand that specifically binds to a CD83, or any combination thereof. In particular embodiments, the costimulatory molecule comprises a CD80. In further embodiments, the costimulatory molecule comprises a CD137L. In still further embodiments, the costimulatory molecule localizes to the cell surface of the immune cell or lymphocyte.

In any of the aforementioned embodiments, the present disclosure provides an immune cell or lymphocyte comprising an exogenous neoantigen and an exogenous costimulatory molecule, or a polynucleotide encoding an exogenous neoantigen and a polynucleotide encoding an exogenous costimulatory molecule, wherein the immune cell or lymphocyte comprises a T cell.

In any of the aforementioned embodiments, an exogenous neoantigen-containing immune cell or lymphocyte comprises an exogenous neoantigen associated with a disease or disorder. In some embodiments, a neoantigen is associated with a hyperproliferative disease or disorder, such as cancer. In certain embodiments, a neoantigen comprises a tumor neoantigen. In particular embodiments, a neoantigen comprises a tumor neoantigen from a protein encoded by a nucleic acid molecule having a missense mutation or frame-shift mutation, as compared to the protein encoded by a wild-type nucleic acid molecule.

In any of the aforementioned embodiments, an exogenous neoantigen, an exogenous immunogenicity enhancer, an exogenous inducible cell death factor, or an exogenous costimulatory molecule may be introduced into the immune cell by methods known in the art, such as transfection, transduction, or electroporation of a DNA molecule encoding one or more of the neoantigen(s), immunogenicity enhancer, inducible cell death factor, and costimulatory molecule. In some embodiments, an expression construct is used to introduce a polynucleotide encoding the neoantigen, immunogenicity enhancer, inducible cell death factor, or costimulatory molecule into the immune cell. For example, in some embodiments, one or more of the exogenous neoantigen, exogenous immunogenicity enhancer, exogenous inducible cell death factor, or exogenous costimulatory molecule are introduced into an immune cell, lymphocyte or T cell using a transposon vector or expression construct.

Expression Constructs and Host Cells

In further aspects, the present disclosure provides nucleic acid molecules encoding one or more neoantigens and immunogenicity enhancers, and expression constructs for expressing such neoantigens and immunogenicity enhancers in a host cell (e.g., T cell).

As used herein, "expression construct" refers to a DNA construct containing a nucleic acid molecule that is operably-linked to a suitable control sequence capable of effecting the expression of the nucleic acid molecule in a suitable host. An expression construct may be present in a vector (e.g., a bacterial vector, a viral vector) or may be integrated into a genome. The term "operably linked" refers to the association of two or more polynucleotides on a single polynucleotide fragment so that the function of one is affected by the other. For example, a promoter is operably-linked with a coding sequence when it is capable of affecting the expression of that coding sequence (i.e., the coding sequence is under the transcriptional control of the promoter). The term "expression control sequence" (also called a regulatory sequence) refers to polynucleotide sequences that effect the expression and processing of coding sequences to which they are operably linked. For example, expression control sequences may include transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion.

In certain embodiments, an expression construct is present in a vector. A "vector" is a nucleic acid molecule that is capable of transporting another nucleic acid. A vector may be, for example, a plasmid, cosmid, virus, RNA vector, or linear or circular DNA or RNA molecule that may include chromosomal, non-chromosomal, semi-synthetic, or synthetic nucleic acids. Exemplary vectors are those capable of autonomous replication (episomal vectors) or expression of nucleic acids to which they are linked (expression vectors). Exemplary viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, Retroviridae: The viruses and their replication, in Fundamental Virology, Third Edition, B. N. Fields et al., Eds., Lippincott-Raven Publishers, Philadelphia, 1996). In some embodiments, the vector is a plasmid vector (such as sleeping beauty, piggyBac, or other transposon vectors). In some embodiments, the vector is a viral vector. In some such embodiments, the viral vector is a lentiviral vector or a γ-retroviral vector. In some embodiments, a viral or plasmid vector further comprises a gene marker transduction (e.g., green fluorescent protein, huEGFRt).

In certain other aspects, the disclosure provides a host cell comprising an expression construct or vector, or a polynucleotide provided by an expression construct as described herein. As used herein, the term "host" refers to a cell (e.g., T cell, hematopoietic progenitor cell) or microorganism targeted for genetic modification with a heterologous or exogenous nucleic acid molecule to produce a peptide of interest (e.g., a neoantigen). In certain embodiments, a host cell may optionally already possess or be modified to include other genetic modifications that confer desired properties related or unrelated to biosynthesis of the heterologous or exogenous neoantigen peptide or immunogenicity enhancer (e.g., inclusion of a detectable marker). More than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. When two or more exogenous nucleic acid molecules are introduced into a host cell, it is understood that the two more exogenous nucleic acid molecules can be introduced as a single nucleic acid molecule (e.g., on a single vector), on separate vectors, integrated into the host chromosome at a single site or multiple sites. The number of referenced heterologous nucleic acid molecules or protein activities refers to the number of encoding nucleic acid molecules or the number of protein activities, not the number of separate nucleic acid molecules introduced into a host cell.

In certain embodiments, an exogenous neoantigen or immunogenicity enhancer is introduced to a host cell using a transposon expression construct. A "transposon" (or "transposable element") refers to a mobile genetic unit that can move positions within a DNA molecule in the presence of a transposase. Transposons mobilize through a cut-and-paste mechanism wherein a transposase enzyme binds to DNA at inverted repeats and catalyzes the excision of the element from a DNA molecule and inserts it in another location. This process of horizontal gene transfer can be used to introduce a gene into a cell. As used herein, a "transposon system" refers to a plasmid-based gene transfer system comprising a transposon and a transposase. Transposons that may be used to introduce an exogenous gene into a cell include, for example, the sleeping beauty transposon (Ivies et al., Cell 91:501, 1997) and the piggyBac transposon (Ding et al., Cell 122:473, 2005). In the piggyBac transposon system, a gene of interest is flanked by transposon inverted terminal repeat (IR) elements, and the construct is typically electroporated into cells along with a plasmid expressing the transposase enzyme. This leads to efficient stable integration into primary human T cells associated with retroviral vectors (Nakazawa et al., J. Immunother. 32:826, 2009), and has the advantages of ease of use, low cost of naked DNA, and less theoretical risk for integration related transformation events (Galvan et al., J. Immunother. 32:837, 2009).

In certain embodiments, a transposon expression construct, comprising a nucleic acid molecule encoding a neoantigen, is provided. In further embodiments, the transposon expression construct comprises a sleeping beauty transposon or a piggyBac transposon. In particular embodiments, a transposon expression construct comprises (a) a promoter; (b) a first piggyBac transposon inverted repeat; (b) a nucleic acid molecule encoding a neoantigen; and (c) a second piggyBac transposon inverted repeat; wherein the nucleic acid molecule that encodes the neoantigen is positioned between the first piggyBac transposon inverted repeat and the second piggyBac transposon inverted repeat.

In any of the aforementioned embodiments, a transposon expression construct may be present in a plasmid or delivered to a cell in a plasmid.

In any of the aforementioned embodiments, a transposon expression construct may comprise a minigene, wherein the minigene comprises a nucleic acid molecule encoding a neoantigen. In any of the aforementioned embodiments, a transposon expression construct may comprise tandem minigenes, wherein each minigene comprises a nucleic acid molecule encoding a neoantigen. For example, the tandem minigenes may comprise nucleic acid molecules encoding from two to about 20 neoantigens, or from two to about 10 neoantigens, or from two to about five neoantigens.

In any of the aforementioned embodiments, a transposon expression construct may further comprise a reporter gene. In certain embodiments, the reporter gene is a green fluorescent protein (GFP) gene. In certain embodiments, a transposon expression construct further comprises a nucleic acid molecule encoding a cell surface marker. For example, in particular embodiments, a cell surface marker comprises a truncated human CD19, a truncated human EGFR, a truncated human CD34, a truncated human NGFR, or any other transduction marker known in the art.

In any of the aforementioned embodiments, a transposon expression construct may further comprise a nucleic acid molecule encoding an immunogenicity enhancer, wherein the immunogenicity enhancer is selected from an IL-12 (such as a membrane-tethered IL-12), and a GM-CSF, an inducible cell death factor, an antigen (e.g., bacterial flagellin), or any combination thereof.

In any of the aforementioned embodiments, a transposase expression construct may further comprise a nucleic acid molecule encoding a piggyBac transposase. For example, a transposase may be encoded by the same expression construct as the other exogenous genes and the piggyBac transposon inverted repeats. In other embodiments, a transposase is encoded by a nucleic acid molecule contained in a different expression construct. For example, in particular embodiments, a transposase is encoded by a nucleic acid molecule in an expression construct present in a different plasmid.

In another aspect, host cells comprising a transposon expression construct as described herein are provided. In some embodiments, the host cell comprises a transposon expression vector of any of the aforementioned embodiments. In certain embodiments, the host cell further comprises a piggyBac transposase enzyme expression construct, wherein the piggyBac transposase enzyme construct comprises a nucleic acid molecule encoding a piggyBac transposase. In particular embodiments, the first and second constructs are present in different plasmids.

In any of the aforementioned embodiments, a host cell may be an immune system cell. In some embodiments, the host cell comprises a dendritic cell. In other embodiments, the host cell comprises a T cell. In further embodiments, the host cell comprises a T cell selected from a naïve T cell, central memory T cell, naïve and central memory T cells, effector memory T cells, or any combination thereof. In particular embodiments, a host cell is a CD4$^+$ T cell or a CD8$^+$ T cell or both.

In any of the aforementioned embodiments, a host cell may comprise a human cell, such as a human T cell.

In any of the aforementioned embodiments, a polynucleotide encoding an exogenous neoantigen, an exogenous immunogenicity enhancer, an exogenous inducible cell death factor, or an exogenous costimulatory molecule is delivered to a host cell via a viral vector. In some embodiments, the viral vector is a retroviral vector or a lentiviral vector.

In any of the aforementioned embodiments, a viral vector to be used to deliver a polynucleotide of this disclosure, comprises a polynucleotide encoding an immunogenicity enhancer selected from, for example, an IL-12 (such as a membrane-tethered IL-12), a GM-CSF, an inducible cell death factor, an antigen (e.g., bacterial flagellin), or any combination thereof. In any of the aforementioned embodiments, a viral vector to be used to deliver a polynucleotide of this disclosure, comprises a polynucleotide that encodes a CD80, CD137, CD140L, secreted IL-2, IL-2 modified to be CD25 independent in T cell binding (see Levin et al., Nature 484(7395):529-33, 2012), IL-15, IL-15-IL-15 receptor alpha complex, IFN-B, IFN-A1, IL-7, an inducible death switch such as small molecule dimerizable RIPK3, or any combination thereof.

In any of the aforementioned embodiments, a host cell encoding a neoantigen (e.g., a lymphocyte such as a T cell) further comprises a nucleic acid molecule encoding a costimulatory molecule delivered via a viral vector. In some embodiments, a viral vector comprises a nucleic acid molecule encoding a CD80, a CD86, a B7RP1, a CD137L, an OX40L, a CD70, a CD30L, a CD154, an ICAM-1, a CD2BP2, a LIGHT, a KLRD1, a ligand that specifically binds to a CD83, an agonist of CD137 (4-1BB), an agonist of CD134 (OX-40), an agonist of CD27, an agonist of CD28, an agonist of CD40, an agonist of CD122, an agonist of GITR, an agonist of ICOS, or any combination thereof. In particular embodiments, a viral vector comprises a nucleic acid molecule encoding a CD80. In other particular embodiments, a viral vector comprises a nucleic acid molecule encoding a CD137L. In certain embodiments, a costimulatory molecule localizes to the cell surface of the host cell, such as a T cell.

Methods and Kits

In further aspects, methods and kits for preparing an immune cell or lymphocyte that expresses an exogenous neoantigen and an immunogenicity enhancer, and optionally any other active molecules, are provided.

In certain embodiments, a method for preparing an immune cell or lymphocyte that comprises an exogenous neoantigen is provided, the method comprising introducing into a lymphocyte (a) a transposon plasmid (e.g., piggyBac) containing a nucleic acid molecule encoding a neoantigen (e.g., identified in a sample of a particular subject) and (b) a plasmid comprising a nucleic acid molecule encoding a transposase (e.g., piggyBac), thereby preparing the lymphocyte that comprises an exogenous neoantigen.

In further embodiments, a nucleic acid molecule encodes two or more neoantigens or neoantigens are contained in a tandem minigene. For example, a tandem minigene may be used to express multiple neoantigens contained the same plasmid.

In certain embodiments, an immune cell or lymphocyte expressing a neoantigen prepared by the methods described herein is syngeneic, allogeneic, or autologous to the subject to be treated. In particular embodiments, an immune cell or lymphocyte expressing a neoantigen is autologous to the subject to be treated. In certain embodiments, a transposon plasmid (e.g., piggyBac) and the plasmid comprising a nucleic acid molecule encoding a transposase (e.g., piggyBac) are introduced into an immune cell or lymphocyte (e.g., T cell) ex vivo. In some embodiments, a nucleic acid molecule encoding a neoantigen or an immunogenicity enhancer is introduced into the genome of an immune cell or a lymphocyte using known genome editing techniques, such as by use of a CRISPR-Cas9 system or a zinc finger nuclease (ZNF) system. See, e.g., Wang et al., Nat. Biotech 33:1256 (2015); see also Lombardo et al., Nat. Biotech. 11:1298 (2007) and PCT Patent Application US/2016/031366.

In certain embodiments, a kit comprising the above components or a transposon expression construct as disclosed herein is provided.

Pharmaceutical Compositions and Methods of Use

In some aspects, pharmaceutical compositions, immunogenic, compositions, and vaccines are provided. In some embodiments, a therapeutic vaccine for eliciting or boosting a robust immune cell response is provided. In certain embodiments, the vaccine comprises an immune cell modified to express an exogenous neoantigen.

In certain embodiments, the present disclosure provides a composition, comprising a an immune cell or lymphocyte (e.g., T cell) as disclosed herein, and a pharmaceutically acceptable carrier, diluent, or excipient. Pharmaceutically acceptable carriers for diagnostic and therapeutic use are well known in the pharmaceutical art, and are described, for example, in Remington's Pharmaceutical Sciences, Mack Publishing Co. (A. R. Gennaro (Ed.), 18th Edition, 1990) and in CRC Handbook of Food, Drug, and Cosmetic Excipients, CRC Press LLC (S. C. Smolinski, ed., 1992). Exemplary pharmaceutically acceptable carriers include any adjuvant, carrier, excipient, glidant, diluent, preservative, dye/colorant, surfactant, wetting agent, dispersing agent, suspending agent, stabilizer, isotonic agent, solvent, emulsifier, or any combination thereof. For example, sterile saline and phosphate buffered saline at physiological pH can be suitable pharmaceutically acceptable carriers. Preservatives, stabilizers, dyes or the like may also be provided in the pharmaceutical composition. In addition, antioxidants and suspending agents may also be used. Pharmaceutical compositions may also contain diluents such as water, buffers, antioxidants such as ascorbic acid, low molecular weight polypeptides (less than about 10 residues), proteins, amino acids, carbohydrates (e.g., glucose, sucrose, dextrins), chelating agents (e.g., EDTA), glutathione and other stabilizers and excipients. Neutral buffered saline or saline mixed with nonspecific serum albumin are exemplary diluents.

In another aspect, methods for treating a disease or disorder comprising administering compositions disclosed herein are provided. In certain embodiments, the present disclosure provides a method for treating a disease or disorder, comprising administering to a human subject in need thereof an effective amount of a lymphocyte as disclosed herein or a composition as disclosed herein.

In another aspect, methods for treating a human subject having a disease or disorder associated with expression of a neoantigen are provided, comprising administering to a human subject in need thereof an effective amount of an immune cell or lymphocyte as disclosed herein or a composition as disclosed herein. In any of the methods disclosed herein, an immune cell or lymphocyte maybe autologous to the subject, syngeneic to the subject, or allogeneic to the subject. In any of the methods disclosed herein, a lymphocyte comprises a T cell.

In another aspect, methods for preventing relapse or recurrence of a disease or disorder (e.g., cancer, infection) in a human subject having the disease or disorder are provided, comprising administering to a human subject in need thereof an effective amount of a lymphocyte, such as a T cell, containing or expressing a neoantigen and an immunogenicity enhancer as disclosed herein or a composition as disclosed herein. In any of the aforementioned embodiments, a disease or disorder may be a viral infection, bacterial infection, hyperproliferative disorder, or inflammatory or autoimmune disease.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses, such as adenovirus, bunyavirus, herpesvirus, papovavirus, papillomavirus (e.g., HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., HIV), flavivirus (e.g., HCV, HBV) or the like. In certain embodiments, infection with cytosolic pathogens whose antigens are processed and displayed with HLA (MHC) Class I molecules, are treated with fusion proteins of this disclosure.

A wide variety of cancers, including solid tumors and leukemias, are amenable to the compositions and methods disclosed herein. Exemplary types of cancer that may be treated include adenocarcinoma of the breast, prostate, and colon; all forms of bronchogenic carcinoma of the lung; myeloid leukemia; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated include histiocytic disorders; malignant histiocytosis; leukemia; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leiomyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Exemplifying the variety of hyperproliferative disorders amenable to treatment are B-cell lymphomas (such as various forms of Hodgkin's disease, non-Hodgkin's lymphoma (NHL) or central nervous system lymphomas), leukemias (such as acute lymphoblastic leukemia (ALL), chronic lymphocytic leukemia (CLL), Hairy cell leukemia, B cell blast transformation of chronic myeloid leukemia) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Inflammatory and autoimmune diseases include arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant), non-specific interstitial pneumonia (NSIP), Guillain-Barré Syndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans.

In particular embodiments, the disease or disorder is a hyperproliferative disease or disorder selected from a hematological malignancy or a solid cancer. In certain embodiments, the hyperproliferative disease or disorder is a hematological malignancy selected from acute lymphoblastic leukemia (ALL), acute myeloid leukemia (AML), chronic myelogenous leukemia (CML), chronic eosinophilic leukemia (CEL), myelodysplastic syndrome (MDS), non-Hodgkin's lymphoma (NHL), and multiple myeloma (MM). In some embodiments, the hyperproliferative disease or disorder is a solid cancer selected from biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, malignant melanoma, neuroblastoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, and uterine cancer. In certain embodiments, the disorder or disease being treated is lung cancer. In certain embodiments, the disorder or disease being treated is malignant melanoma.

In certain embodiments, a method for treating a hyperproliferative disease or disorder is provided, wherein the hyperproliferative disease or disorder is a hematological malignancy selected from acute lymphoblastic leukemia (ALL), acute myeloid leukemia (AML), chronic myelogenous leukemia (CML), chronic eosinophilic leukemia (CEL), myelodysplastic syndrome (MDS), non-Hodgkin's lymphoma (NHL), and multiple myeloma (MM).

In further embodiments, a method for treating a hyperproliferative disease or disorder is provided, wherein the hyperproliferative disease or disorder is a solid cancer selected from biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, malignant melanoma, neuroblastoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, and uterine cancer.

In any of the aforementioned embodiments, the composition may comprise a lymphocyte or host cell, and the lymphocyte or host cell is syngeneic, allogeneic, or autologous to the human subject. In some embodiments, the composition may comprise a lymphocyte or host cell, and the lymphocyte or host cell is autologous to the human subject.

Compositions of this disclosure may be administered in a manner appropriate to the disease or condition to be treated (or prevented) as determined by persons skilled in the medical art. An appropriate dose, suitable duration, and frequency of administration of the compositions will be determined by such factors as the condition of the patient, size, type and severity of the disease, particular form of the active ingredient, and the method of administration. In certain embodiments, cells or compositions of the present disclosure may be administered in an initial "priming" dose, followed by one or more "boost" dose in an amount and at a frequency, and for a duration, appropriate to the circumstances. In certain embodiments, a one or both of a priming dose and a boost dose comprises a lymphocyte comprising an exogenous neoantigen and one or more exogenous immunogenicity enhancer (e.g., an mtIL-12 and secreted GM-CSF).

The present disclosure provides pharmaceutical compositions comprising cells expressing a fusion protein as disclosed herein and a pharmaceutically acceptable carrier, diluents, or excipient. Suitable excipients include water, saline, dextrose, glycerol, or the like and combinations thereof.

In any of the aforementioned embodiments, the method may further comprise administering an additional therapeutic agent or adjunctive agent. In certain embodiments, a modified lymphocyte (e.g., T cell) comprising a neoantigen and an adjuvant or a composition thereof is administered simultaneously or sequentially with the additional therapeutic or adjunctive agent.

In certain embodiments, an additional therapeutic agent comprises a chemotherapy; an inhibitor of an immune checkpoint molecule; a costimulatory molecule; a molecule that enhances immunogenicity; a cellular therapy; or a vaccine.

In certain embodiments, the additional therapeutic agent comprises a chemotherapy. Exemplary chemotherapeutic agents include, for example, alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSKTM; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins, capecitabine; and pharmaceutically acceptable salts, acids or derivatives of any of the above.

In certain embodiments, the additional therapeutic agent comprises an inhibitor of an immune checkpoint molecule. In certain embodiments, the inhibitor of an immune checkpoint molecule comprises an agent that blocks the activity or expression of the immune checkpoint molecule. In some embodiments, the immune checkpoint molecule comprises a PD-1, PD-L1, PD-L2, LAG3, CTLA4, B7-H3, B7-H4, CD244/2B4, HVEM, BTLA, CD160, TIM3, GALS, KIR, PVR1G (CD112R), PVRL2, adenosine, A2aR, immunosuppressive cytokines (e.g., IL-10, IL-4, IL-IRA, IL-35), IDO, arginase, VISTA, TIGIT, LAIR1, CEACAM-1, CEACAM-3, CEACAM-5, Treg cells, or any combination thereof. In some embodiments, the agent blocks the activity or expression of a PD-1, PD-L1, or PD-L2. In some embodiments In some embodiments, the agent blocks the activity of the immune checkpoint molecule, and the agent comprises an antagonistic antibody or binding fragment thereof, an aptamer, ribozyme, a dominant-negative inhibitor, or a small molecule inhibitor. In some embodiments, the agent blocks the expression of the immune checkpoint molecule, and the agent is a siRNA, a shRNA, an RNAi, an antisense, a CRISPR/Cas system, a zinc finger nuclease, or a TALEN. In some embodiments, the agent is an antibody that blocks the activity of a PD-1, PD-L1, or PD-L2, comprising an antibody that binds to a PD-1.

In some embodiments, an additional therapeutic agent comprises a costimulatory molecule. In some embodiments, the costimulatory molecule comprises a CD80, a CD86, a B7RP1, a CD137L, an OX40L, a CD27, a CD28, a CD122, a GITR, an ICOS, a CD40, a CD70, a CD30L, a CD154, an ICAM-1, a CD2BP2, a LIGHT, KLRD1, or a ligand that specifically binds to a CD83. In particular embodiments, the costimulatory molecule comprises a CD80. In still further embodiments, the costimulatory molecule comprises a CD137L. In some embodiments, an additional therapeutic agent comprises an agonist of a costimulatory molecule. For example, an additional therapeutic agent may comprise a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2), an agonist of GITR (such as, for example, humanized monoclonal antibodies described in PCT Patent Publication No. WO 2016/054638), an agonist of ICOS, or any combination thereof.

In certain embodiments, an additional therapeutic agent comprises a molecule that enhances immunogenicity, such as a bacterial flagellin, an IL-12, a GM-CSF, an helper antigen, or any combination thereof. In some embodiments, the bacterial flagellin comprises a *Salmonella* phase 1 flagellin. In other embodiments, a bacterial flagellin, IL-12, GM-CSF, helper antigen, or any combination thereof is combined with an adjuvant.

In certain embodiments, an additional therapeutic agent comprises a cellular therapy, such as an immune cell comprising an engineered TCR, a chimeric antigen receptor (CAR), or both. In further embodiments, an additional therapeutic agent comprises a vaccine, such as a peptide vaccine, DNA vaccine, RNA vaccine, cellular vaccine, or any combination thereof. In still further embodiments, a vaccine is administered with an additional therapeutic agent or an adjunctive agent. Exemplary additional therapeutic agents or adjunctive agents may be comprised of a B-Raf inhibitor, a MEK inhibitor, a tyrosine kinase inhibitor, a cytotoxic agent, alum or an aluminum salt, GM-CSF, gamma inulin, ISCOMs, liposomes, MF59, monophosphoryl lipid A, virosomes and other virus-like particles, or Aquila's QS-21 stimulon, CD80, CD137, CD140L, or secretion of IL-2, IL-2 modified to be CD25 independent in T cell binding (see Levin et al., 2012), IL-15, IL-15-IL-15 receptor alpha complex, IFN-B, IFN-A1, IL-7, inducible death switches such as small molecule dimerizable RIPK3, or any combination thereof.

Administration of immune cells, lymphocytes, T cells, and compositions thereof of this disclosure, as well as cell-based additional therapies (e.g., an immune cell comprising an engineered TCR or a chimeric antigen receptor (CAR)), will generally be performed via injection (e.g., parenteral). The term "parenteral" as used herein includes subcutaneous injections, intravenous, intramuscular, intrasternal injection, or infusion techniques. Administration of other additional therapies or their pharmaceutically acceptable salts, in pure form or in an appropriate pharmaceutical composition, can be carried out using any mode of administration for agents serving similar utilities. For example, immune-enhancing agents of this disclosure can be delivered via injection or using a appropriate pharmaceutically acceptable carrier, diluent or excipient, and may be formulated into preparations in solid, semi solid, liquid or gaseous forms, such as tablets, capsules, powders, granules, ointments, solutions, suppositories, injections, inhalants, gels, microspheres, and aerosols. Exemplary routes of administering such pharmaceutical compositions include oral, topical, transdermal, inhalation, parenteral, sublingual, buccal, rectal, vaginal, and intranasal.

Compositions of this disclosure are formulated to allow the active ingredients contained therein to be bioavailable upon administration of the composition to a patient. Compositions that will be administered to a subject or patient take the form of one or more dosage units, where for example, a tablet may be a single dosage unit, and a container of a compound of this disclosure in aerosol form may hold a plurality of dosage units. Actual methods of preparing such dosage forms are known, or will be apparent, to those skilled in this art (see, e.g., Remington: The Science and Practice of Pharmacy, 22nd Edition (Pharmaceutical Press, 2012). The composition to be administered will, in any event, contain a therapeutically effective amount of an immune cell or lymphocyte of this disclosure.

EXAMPLES

Example 1

T Cells Expressing an Exogenous Antigen can Prime and Boost Responses to the Antigen In Vivo A mouse model for investigating vaccination with autologous T cells genetically engineered to express candidate neoantigens ("$T_{VAX}$") was developed. The model can be used to study the mechanisms of $T_{VAX}$ action and to evaluate strategies for augmenting vaccine immunity. Ovalbumin ("OVA") was used as a model antigen because reagents are readily available to quantify OVA-specific T cells, and OVA-expressing tumors are widely used to investigate immune mechanisms of tumor eradication (Dranoff, Nat. Rev. Immunol. 12: 61, 2012). To determine whether murine T cells transduced to express OVA would be immunogenic, wild-type B6 mice (The Jackson Laboratory, USA) were seeded with a small number of CD45.1 congenically marked naïve OVA-specific OT-1 CD8+ T cells and then vaccinated with one of two dose levels of wild-type T cells expressing full-length OVA (referred to herein as "$T_{OVA}$" cells), or control T cells expressing GFP. Expansion of antigen specific OT-1 cells in vivo was followed with the congenic CD45.1 marker.

Figure 2:
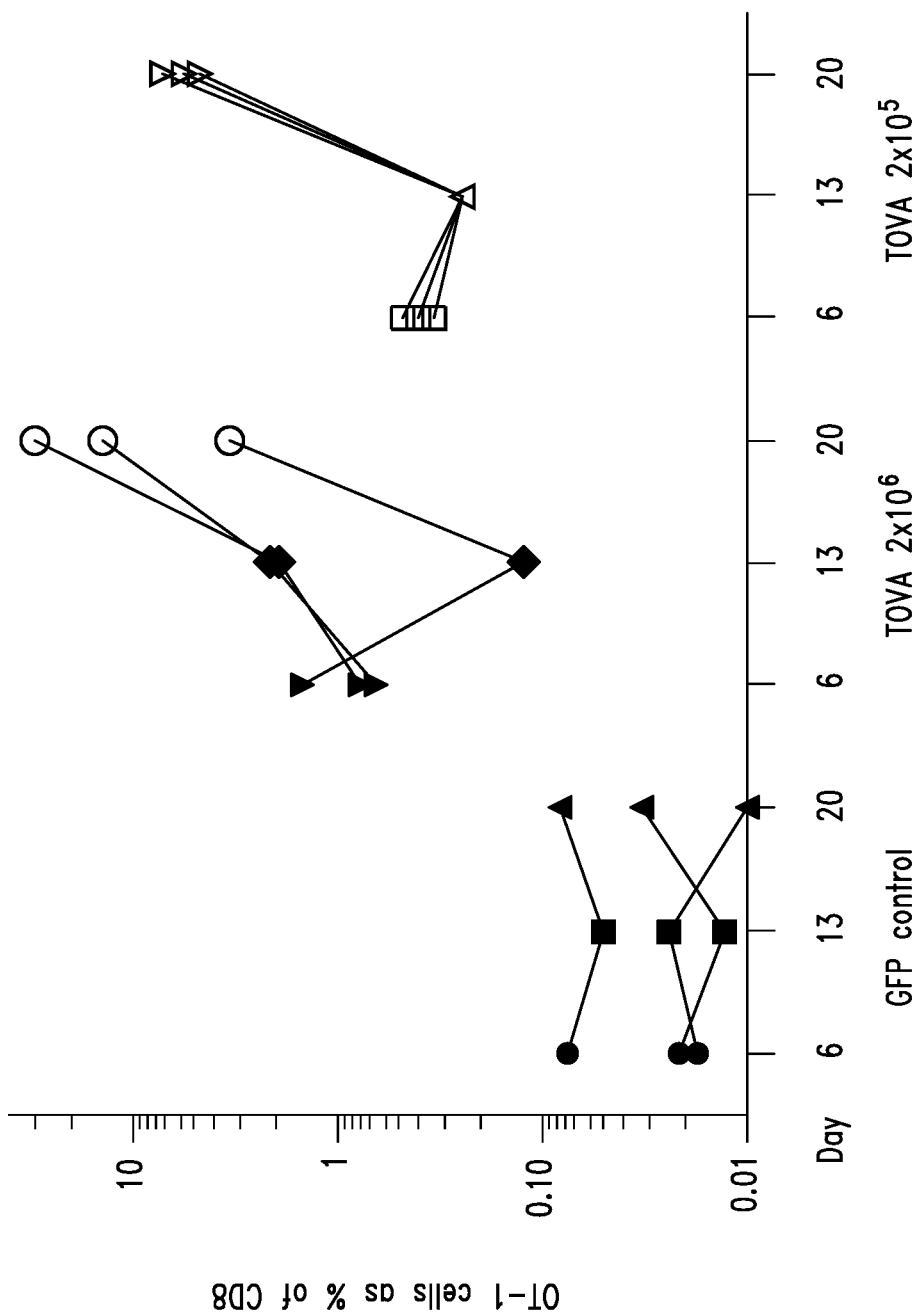
FIG. 2 shows that treatment with $T_{VAX}$ cells engineered to express ovalbumin (referred to as "$T_{OVA}$" cells) efficiently induces CD8$^+$ responses to ovalbumin ("OVA") in mice. Six-week-old male C57BL/6 mice were injected with $2\times10^4$ congenic (CD45.1) naïve OT-1 cells on day −1, and injected with $T_{OVA}$ on days 0 and 14. The frequency of OT-1 cells was determined on days 6, 13, and 20. OVA-specific T cells showed dose-dependent priming after administration of as few as $2\times10^5$ $T_{OVA}$ cells and efficient boosting of the response to 5-10% of circulating T cells 7 days following a second $2\times10^5$ $T_{OVA}$ cell dose at day 14.

Dose-dependent priming of OVA-specific T cells after administration of as few as 200,000 $T_{OVA}$ and efficient boosting of the response to 5-10% of circulating T cells seven days following a second 200,000 $T_{OVA}$ cell dose at day 14 were observed (FIG. 2). The $T_{OVA}$ model system allows for T cell responses to be primed and boosted with modest doses of $T_{OVA}$, and can be used to explore the ability of additional genetic modifications to the $T_{OVA}$ cells to enhance the efficiency of priming, boosting, and memory formation of the T cell vaccine.

Example 2

Murine Model for Developing a T Cell-Based Vaccine

Murine models, such as the $T_{OVA}$ model in Example 1, may be used to elucidate mechanisms underlying the effects of $T_{VAX}$, develop T cell-based vaccine regimens, and identify additional genetic modifications that potentially enhance the ability of T cells to elicit immune responses to tumor-associated antigens. Examples 3-8 describe a series of experiments using the $T_{OVA}$ mouse model. The following materials and methods were used.

Mice

All mouse experiments were performed in 6-week-old male C57BL/6 mice as described above in Example 1. In some experiments, T cell donors for constructing the vaccine were obtained from B6 background mice that express chicken ovalbumin under the control of the beta actin promoter (The Jackson Laboratory). OT-I mice transgenic for a TCR specific for the ovalbumin SIINFEKL (SEQ ID NO: 513) epitope (used herein as a model neoantigen) were crossed with CD45.1 mice (Both obtained from The Jackson Laboratory) to make mice that were heterozygous for the OT-I transgenic TCR and homozygous for the congenic CD45.1 marker.

DNA Constructs

The coding sequence of an mtIL12 construct (Pan et al., Mol. Ther. 20(5):927-937 (2012)) was amplified by PCR and cloned into the NotI-EcoRI sites of the retroviral vector MP71 (Engels et al., Hum. Gene Ther. 14(12):1155-1168 (2003)) using the NEBuilder cloning kit (NEB) to make the plasmid pJV1. Synthetic DNA fragments encoding a codon-optimized murine GM-CSF were synthesized (Life Sciences) and cloned into the NotI-EcoRI sites of MP71 to make pJV8. Plasmid pJV99 was made by fusing a linear DNA fragment encoding a truncated form of murine CD19 fused at the N-terminus to a linear sequence encoding the SIINFEKL (SEQ ID NO: 513) epitope from chicken ovalbumin and the LLO190 epitope (NEKYAQAYPNVS) (SEQ ID NO: 514) of Listeria monocytogenes listerolysin O (epitopes connected a glycine-serine linker), and cloning this into the NotI-EcoRI sites of the retroviral vector MP71. Plasmid pJV94 was obtained by replacing the SIINFEKL (SEQ ID NO: 513) sequence of pJV72 with sequences containing mutated epitopes in the murine Lama4 and Alg8 genes identified by Robert Schrieber and colleagues (Gubin et al., Nature 515(7528):577-581 (2014)). The plasmids, constructs, vectors, and the sequences thereof from the above-noted references and sources are herein incorporated by reference in their entireties.

Gene Modification of T Cells

Total T cells from 5-10 week old mouse donors were isolated from spleen using the EasySep™ mouse CD8 purification kit (STEMCELL Technologies, Vancouver, BC, Canada) and stimulated with murine CD3/CD28 dynabeads (Thermo Fisher Scientific (Waltham, Mass., USA)) in murine T cell medium supplemented with murine IL-2. Retrovirus was produced by transfecting Plat-E cells (Cell Biolabs, Inc., San Diego, Calif., USA) with plasmid retroviral constructs using calcium phosphate transfection, and harvesting viral supernatant on days +2 and +3 from transfection. Viral supernatant with concentrated by centrifugation onto retronectin, and T cells were transduced with virus on days +1 and +2 of stimulation. Transduction of antigens was monitored by mCD19 expression; membrane tethered IL-12 with anti-IL12 antibody (Biolegend), and GM-CSF by ELISA. Cells were moved to medium supplemented with murine IL-15 on day +3 of stimulation, beads were removed on day +5 of stimulation, and cells were cryopreserved or transferred into mice on day +6 of stimulation. For some experiments, T cells from donors constitutively expressing OVA were co-transduced with viruses containing membrane tethered IL-12 and/or secreted GM-CSF. For other experiments, T cell from wildtype donors were transduced with a combination of viruses containing membrane tethered IL-12 and/or secreted GM-CSF and/or viruses containing antigens.

Vaccination Experiments

In experiments involving OT-I mice, CD8+ cells were isolated using the EasySep kit, and 500 cells were transferred per mouse the day prior to vaccination for vaccination experiments, and 100 cells per mouse for the B16 tumor experiment. $2\times10^5$ vaccine cells are transferred for priming dose, and in tumor experiments this was repeated every 14 days. Boost doses were performed using cryopreserved cells that were rested overnight in medium containing murine IL15 prior to injection.

In experiments with OT-I cells, peripheral blood white blood cells were stained with the congenic marker CD45.1 following erythroid lysis. In some experiments, endogenous T cell responses to antigens were detected by staining with tetramers specific for SIINFEKL, mutated Alg8, mutated Lama4 (obtained from the Fred Hutchinson Cancer Research Center Immune Monitoring Lab) or LLO190 (obtained from the NIH Tetramer Core Facility) following erythroid lysis.

To determine effective prime-boost regimens for vaccination with transgenic T cells, $T_{OVA}$ cells from B6 mice were expanded in culture and administered intravenously to mice in various prime-boost regimens. OVA-specific CD8+ and CD4+ T cell responses are measured using standard assays with congenic markers, and their function was assessed by intracellular cytokine staining. CD8+ T cell responses were examined by transferring 200,000 CD45.1 congenically marked OVA-specific OT-1 T cells into B6 mice prior to vaccination. Expanded OT-1 cells were measured on a weekly basis in the peripheral blood. To examine CD4+ responses, CD45.1 congenically marked OVA-specific CD4+ OT-II cells were transferred prior to vaccination in a similar way. Groups of mice were vaccinated with different schedules of priming and boosting (every week, every 2 weeks, and monthly) (3 mice per group). The methods were also repeated without OT-1/OT-II T cell transfer in order to assess responses of endogenous T cells.

Example 3

Expression of Immunogenicity Enhancers Improves $T_{VAX}$ Immune Response

Figure 5A:
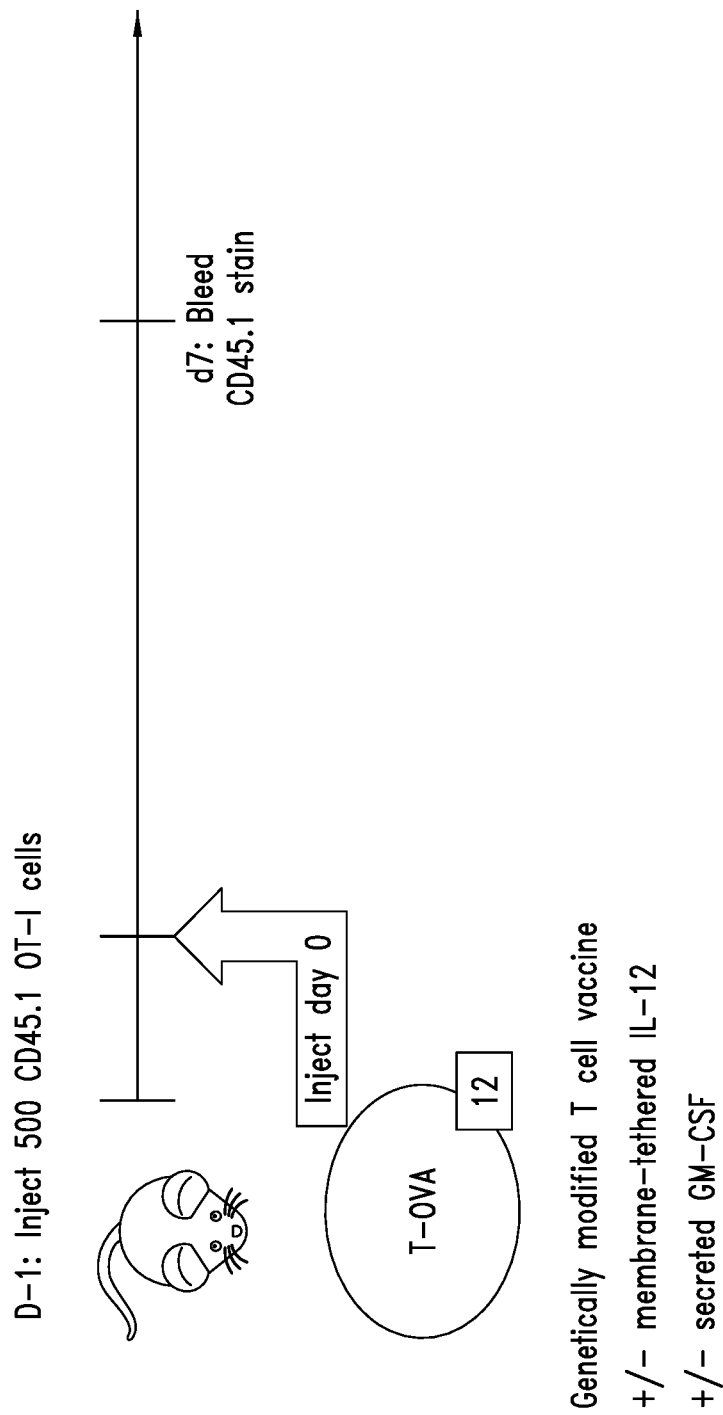
FIGS. 5A to 5B show that expression of adjuvant molecules by $T_{VAX}$ enhances priming of CD8$^+$ T cells. (A) Design scheme of an experiment in which 6-week-old male C57BL/6 mice were injected at day −1 with 500 transgenic donor CD4.5$^{+/+}$ TCR$_{OT-1}$$^{+/-}$ CD8$^+$ T cells (with TCRs specific for the ovalbumin antigen peptide SIINFEKL). At day 0, mice received a T-cell vaccine ($2\times10^5$ T cells expressing full-length ovalbumin, referred to as $T_{OVA}$ cells). Three groups of the injected $T_{OVA}$ cells were transduced to further express a membrane-tethered IL-12 (mtIL-12), secreted GM-CSF, or both. Mice were then bled at day +7 and T cells were stained for CD45.1. (B) Percentages of CD8$^+$ T cells with OT-1-specific TCRs from each tested group.
Figure 5B:
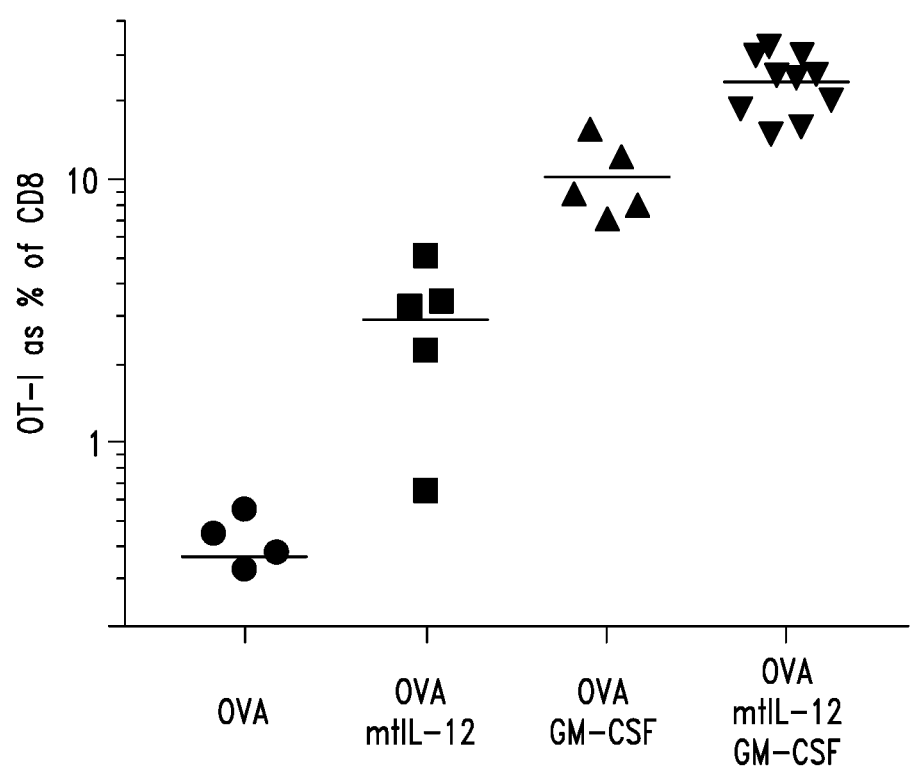

Without wishing to by bound by theory, $T_{VAX}$ cells of the present disclosure may localize and concentrate neoantigen presentation in, e.g., secondary lymphoid tissues and tumor sites. T cell-based vaccines presenting model TAAs had previously showed some efficacy in a murine melanoma model, but a large number of pre-existing antigen-specific T cells was required for this effect. We investigated whether $T_{vax}$ cells may be modified to increase their immunogenicity and thereby overcome this requirement. In this experiment, mice were injected with 500 transgenic donor CD45.1+/+ TCR$^{OT-1+/-}$ CD8+ T cells. At day +1 following injection, the mice were administered a T-cell vaccine ($2\times10^5$ $T_{OVA}$ cells). Three groups of the $T_{OVA}$ cells further expressed a membrane-tethered IL-12, secreted GM-CSF, or both. Mice were then bled at day +7 and T cells were stained for CD45.1. FIG. 5A. Data from this experiment is shown in FIG. 5B. Animals injected with $T_{OVA}$ cells expressing either or both immunogenicity enhancers showed significant increases in OT-1 specific CD8+ T cells relative to animals receiving unmodified $T_{OVA}$. Co-expression of mtIL-12 and secreted GM-CSF produced the strongest optimization effect. These data show that $T_{VAX}$ cells modified to express immunogenicity enhancer molecules such as mtIL-12 and GM-CSF induce robust proliferation and memory formation. Such cells may be useful to achieve therapeutic benefits without the need for high numbers of pre-existing antigen-specific T cells.

Other modifications to enhance $T_{VAX}$ immunogenicity include, for example, expression of an inducible cell death factor. Induction of necroptosis in T cells through, for example, an inducible RIPK3 can be used to enhance immunogenicity of priming and boosting doses of $T_{VAX}$. $T_{VAX}$ cells are modified to express an inducible RIPK3, which activates an inflammatory cell death pathway and increases antigen cross-presentation (Yatim et al., Science 350(6258):328-334 (2015)). Further, this may be tested in a transgenic mouse that expresses the small molecule-inducible allele of RIPK3 in T cells. Vaccination and expansion is performed as described above to measure the expansion and persistence of OVA-specific CD8+ and CD4+ responses to vaccination with necroptotic cell death induced in the setting of priming, boosting, or both.

Other immunogenicity enhancers, such as a pathogenic membrane protein, which can be a membrane-tethered bacterial flagellin, may also be used in $T_{vax}$ of the present disclosure. Antigen presenting cells can be activated in vivo by an innate inflammatory signal to the site of antigen presentation, caused by a membrane-tethered bacterial flagellin. This can be tested in $T_{VAX}$ cells by using a retroviral vector to introduce the membrane-tethered version of bacterial flagellin on the surface of $T_{OVA}$ cells. The resulting $T_{VAX}$ cells are characterized in priming and boosting regimens as above.

Additional approaches for enhancing host immunogenic response against $T_{VAX}$ include, for example, CD80, CD137, CD140L, secreted IL-2, IL-2 modified to be CD25 independent in T cell binding (see Levin et al., 2012), IL-15, IL-15-IL-15 receptor alpha complex, IFN-B, IFN-A1, and IL-7.

Example 4

Figure 6A:
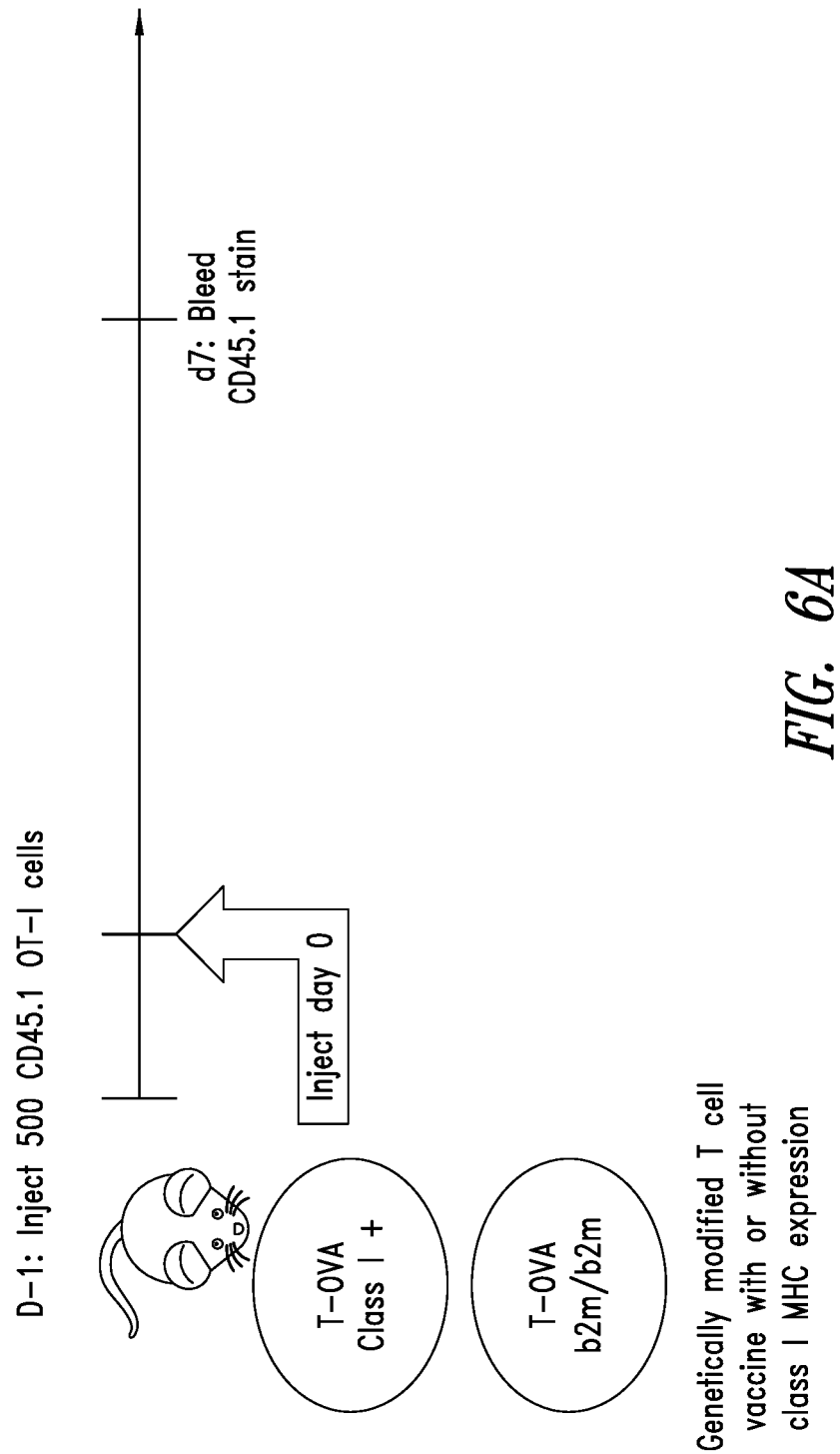
FIGS. 6A and 6B show that T priming of CD8$^+$ T cells occurs by cross-presentation. (A) Six-week-old male C57BL/6 mice were injected with 500 CD4.5$^{+/+}$ TCR$_{OT-1}$$^{+/-}$ CD8$^+$ T cells, vaccinated with $2\times10^5$ Class I MHC$^+$ or b2 m$^{-/-}$ $T_{OVA}$ cells, bled, and stained for CD45.1. (B) Percentages of CD8$^+$ T cells with OT-1-specific TCRs from each tested group.
Figure 6B:
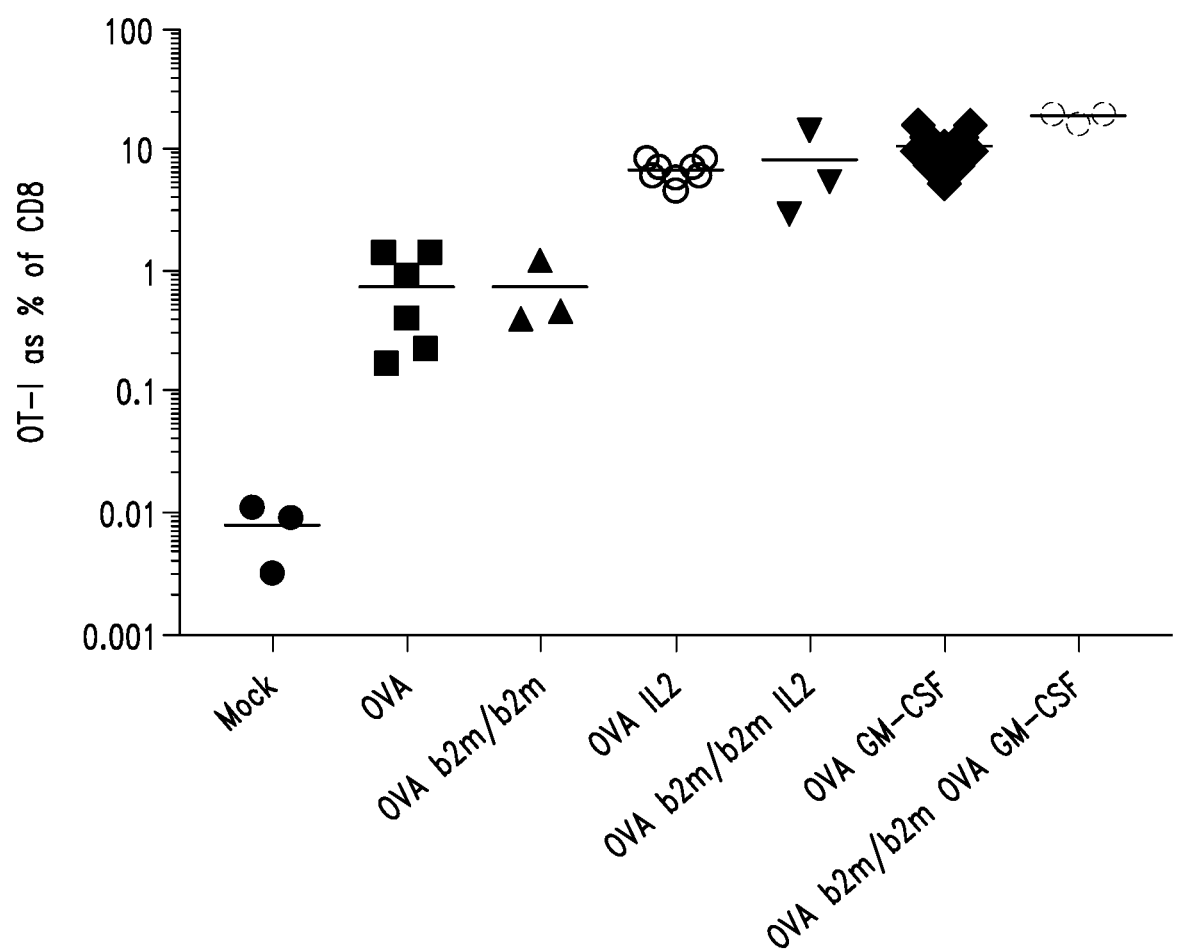

CD8 Priming by $T_{VAX}$ Cells Occurs by Cross-Presentation $T_{VAX}$ priming or boosting may occur through direct presentation by $T_{VAX}$ or by cross-presentation from host DCs. In order to test whether direct presentation by $T_{VAX}$ occurs, mice were injected with 500 CD4.5+/+ TCROT-1+/- CD8+ T cells, then vaccinated with $2\times10^5$ Class I MHC+ or b2 m-/- $T_{OVA}$ cells, bled, and stained for CD45.1 (FIG. 6A). As shown in FIG. 6B, no significant difference was seen between the groups injected with MHC I+ and b2 m-/- $T_{OVA}$ cells, and percentage of OT-1-specific CD8+ T cells increased with expression of the immune enhancer molecules. These data show that direct presentation by $T_{VAX}$ is not required for CD8 priming.

Example 5

$T_{VAX}$ Primes Endogenous CD8 and CD4 Responses

Figure 7A:
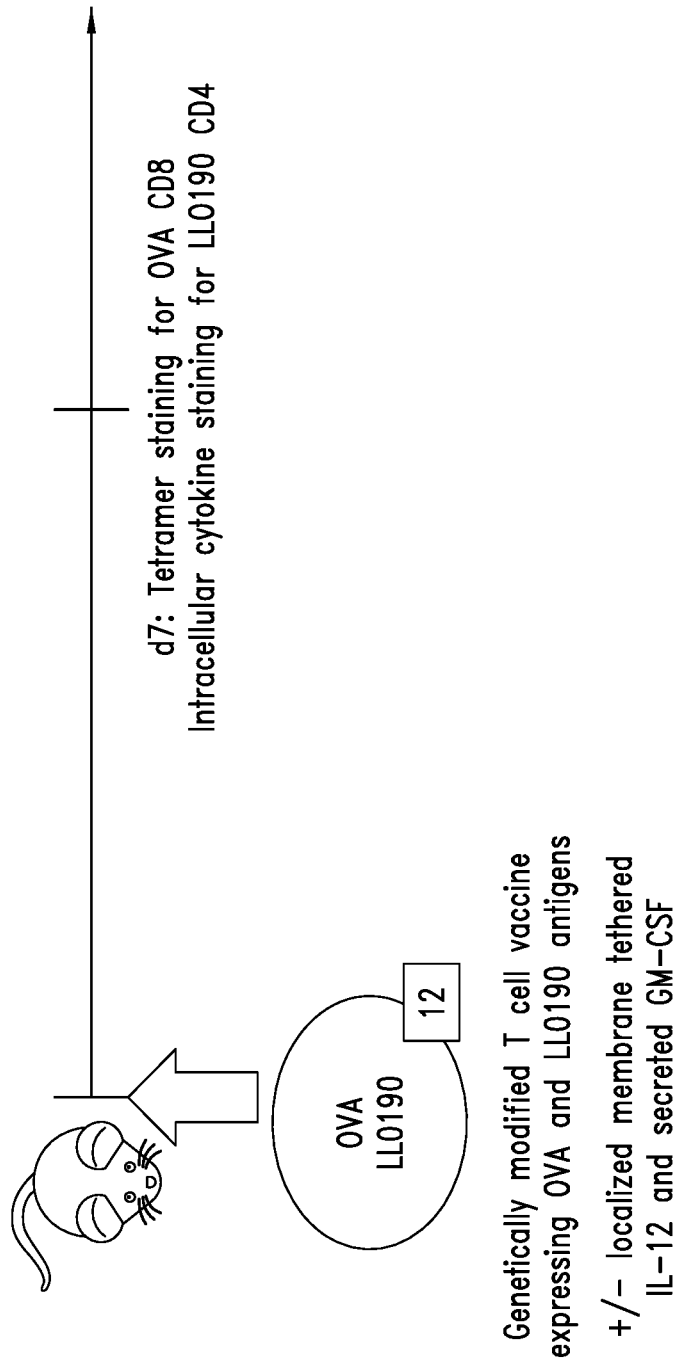
FIGS. 7A-7C illustrate that $T_{VAX}$ cells expressing two antigens can prime endogenous CD4$^+$ and CD8$^+$ responses. (A) 6-week-old male C57BL/6 mice were vaccinated using $T_{OVA}$ cells that were further transduced with a virus encoding CD4 antigen LLO190 (from *Listeria monocytogenes*). Two groups of CD8$^+$ cells and one group of CD4$^+$ cells further expressed mtIL-12 and GM-CSF. At day +7, cells were stained (OVA/CD8 tetramers; intracellular cytokine staining for LLO190/CD4) and sorted. (B) OVA/CD8-positive tetramer cells as a percentage of CD8$^+$ T cells. (C) Intracellular interferon-positive cells as a percentage of CD4$^+$ T cells.
Figure 7B:
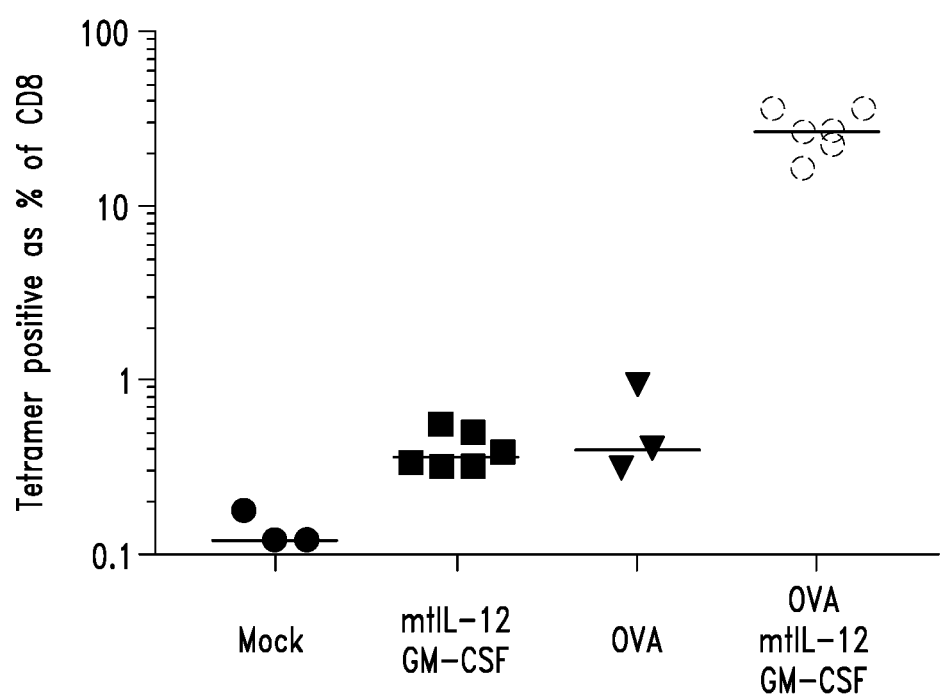
Figure 7C:
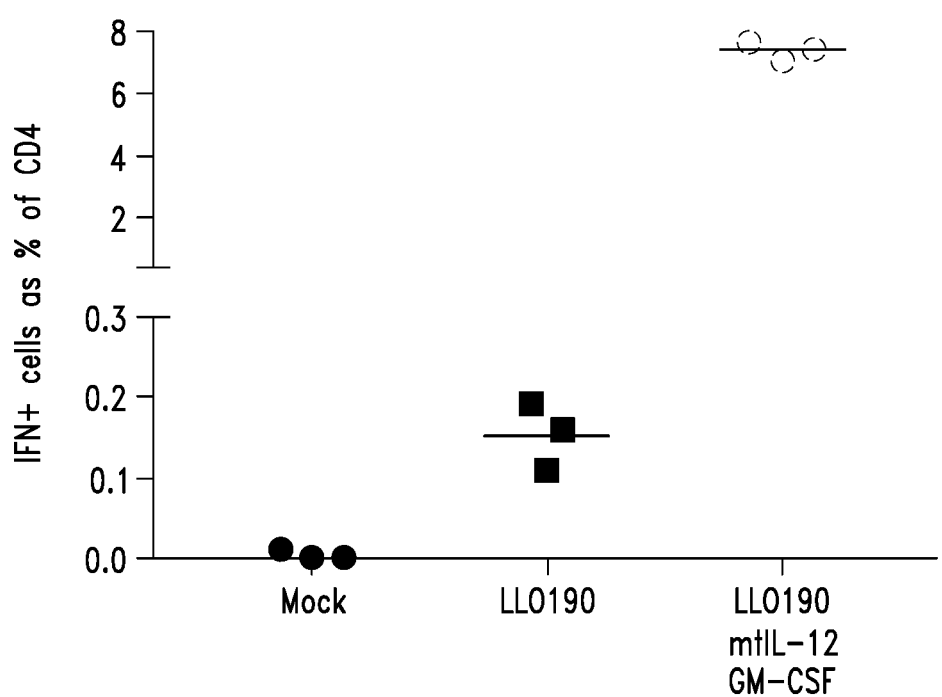

Next, we asked whether $T_{VAX}$ could prime endogenous CD8 and CD4 responses. For the CD8 experiment, mice were injected with mock control, T cells expressing mtIL-12 and GM-CSF but no antigen, T cells expressing OVA alone, or T cells expressing the antigen and both immunogenicity enhancer molecules. At day +7 following injection, tetramer staining for OVA-specific CD8+ T cells was performed. For the CD4 experiment, mice were injected with a mock control, T cells expressing the virally transduced CD4 model antigen (LLO190) but no immunogenicity enhancers, or T cells expressing antigen and adjuvant molecules. On day +7, intracellular interferon staining was performed (FIG. 7A). As shown in FIG. 7B, co-expression of the antigen with immunogenicity enhancer molecules showed significantly higher CD8 tetramer staining than the other tested groups. A similar result was seen in the CD4 experiment, where injection with T cells co-expressing antigen and immunogenicity enhancers resulted in much higher levels of intracellular cytokines (FIG. 7C).

Example 6

$T_{VAX}$ with mtIL12 is Therapeutically Effective in a Transplantable Tumor Model The effectiveness of Tvax when directed against neoantigens may be tested in a transplantable tumor model. The B16F10 transplantable melanoma model is a heavily mutated tumor. While a transplantable model does not fully address issues of tolerance to chronic antigen exposure, the B16 model is poorly immunogenic and is therefore thought to be a relatively stringent test of immune therapies.

Figure 8A:
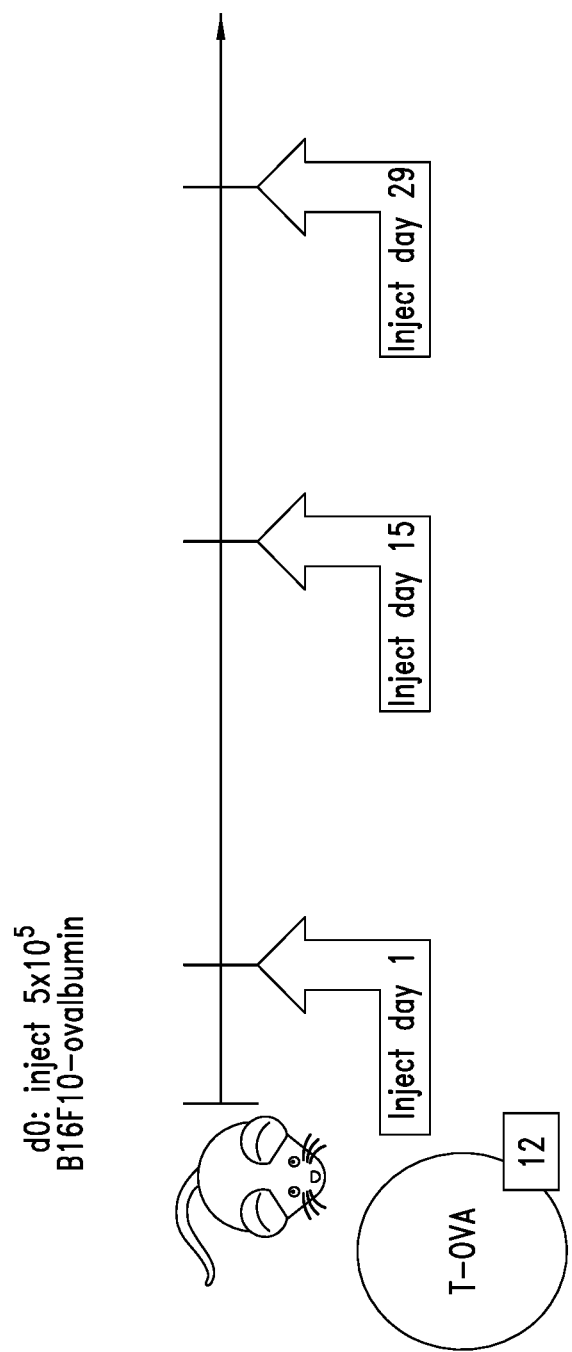
FIGS. 8A-8C illustrate that $T_{VAX}$ cells engineered to express mtIL-12 and containing OVA as a model antigen have therapeutic efficacy in a transplantable mouse melanoma model. (A) Six-week-old male C57BL/6 mice were injected with $5\times10^5$ cells from the B16F10-ovalbumin mouse melanoma cell line. At day +1, mice received $2\times10^5$ $T_{OVA/mt-IL12}$ cells, with booster administrations (same dosage) at days +15, and +29. Animals were sacrificed at days +10, +14, +17, and +21, and tumor size was measured. (B) Tumor size (mm$^3$) for each tested group following injection. (C) Percent survival of each tested group.
Figure 8B:
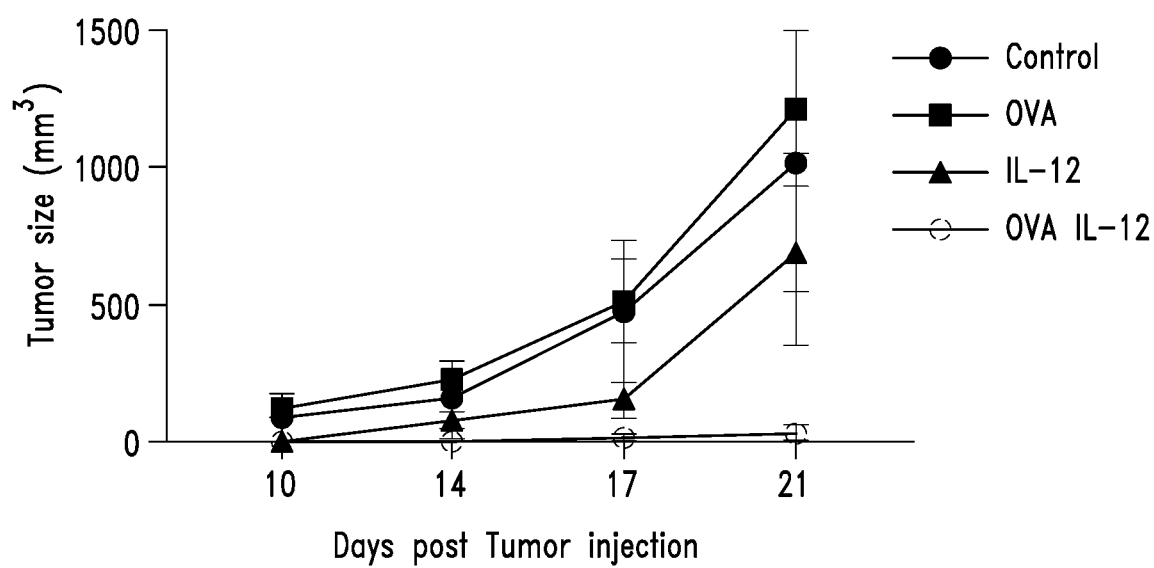
Figure 8C:
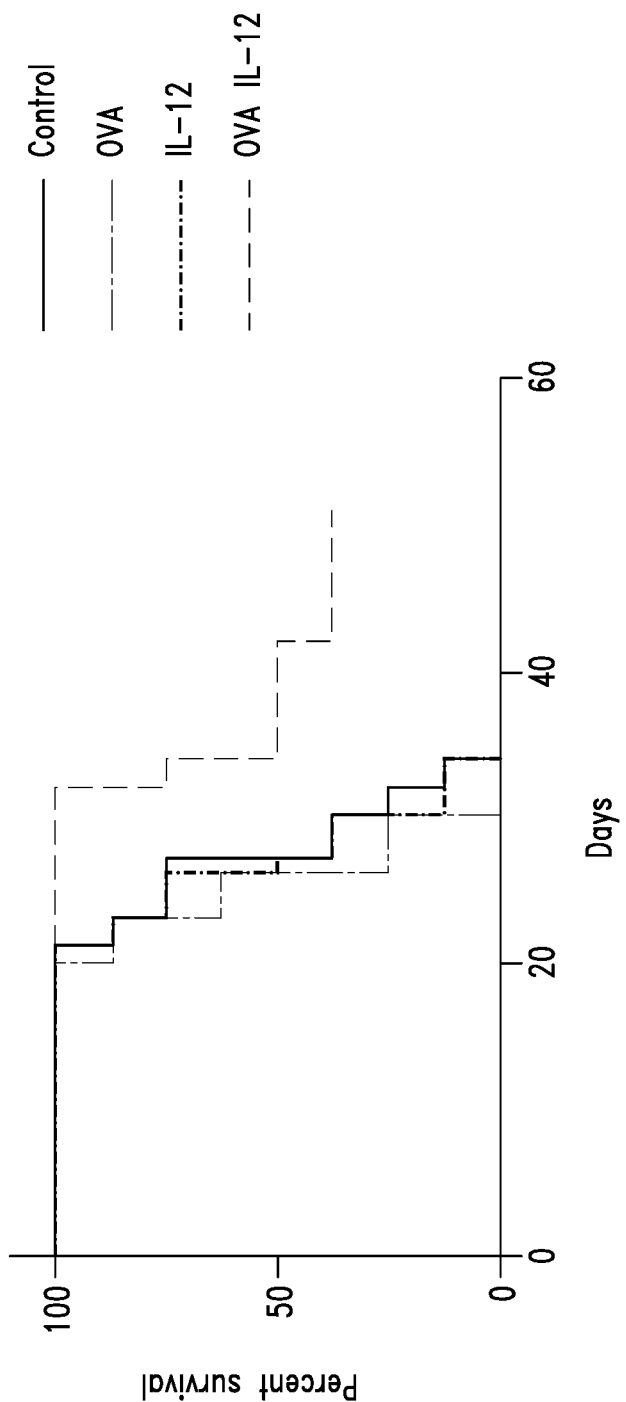

B6F10 cells also expressing ovalbumin ($5 \times 10^5$) were injected into male C57BL/6 mice. The following day, the mice were primed with $2 \times 10^5$ $T_{OVA}$ cells expressing mtIL12. Boost injections (same dosage) were administered at days 15 and 29 after tumor injection. FIG. 8A. Tumor size (mm³) was measured at 10, 14, 17, and 29 days following tumor injection, and survival of the animals was followed for 60 days. As shown in FIG. 8B, the group receiving $T_{OVA}$/mtIL12 cells experienced a low level of tumor growth, in sharp contrast to the other tested groups. The $T_{OVA}$/mtIL12-treated group also had a significantly higher survival rate, with 50% of the animals alive at day 40, while the other groups reached 50% survival before day 30 (FIG. 8C). These data show that $T_{VAX}$ including mt12 is therapeutically effective in a transplantable tumor model.

Example 7

$T_{VAX}$ Induces Immune Response Against Murine Neoantigens

Figure 9A:
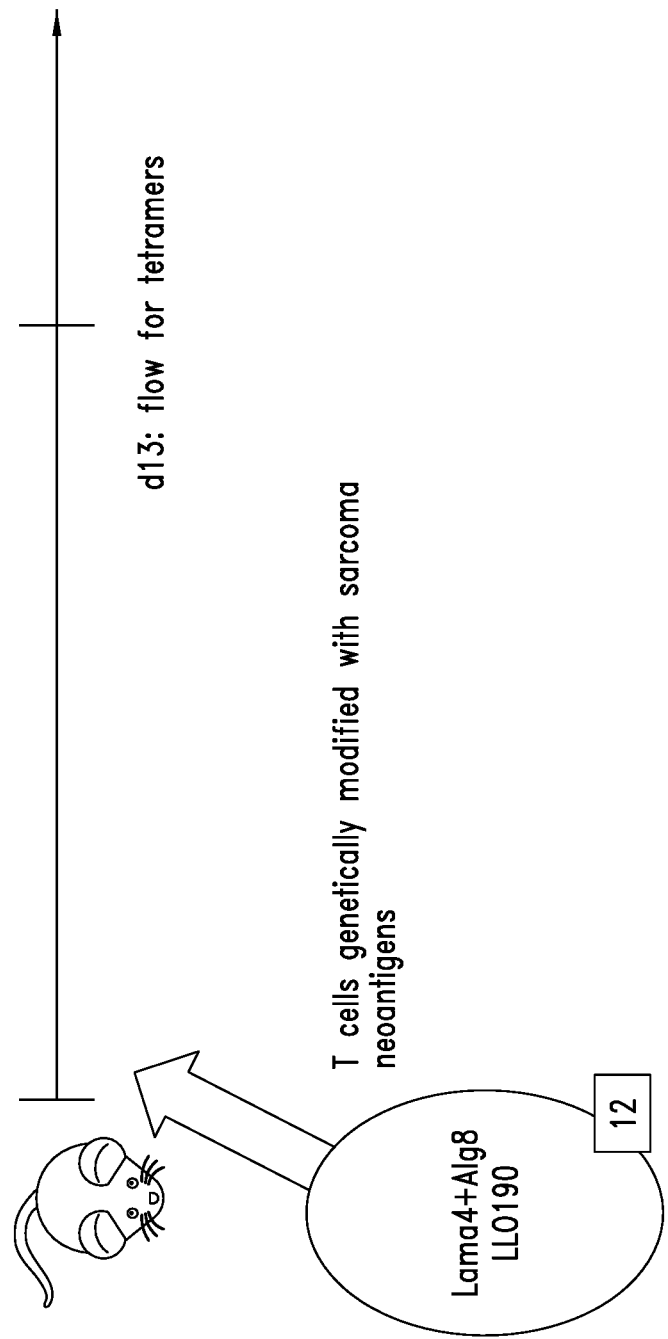
FIGS. 9A-9C show that $T_{VAX}$ cells induce responses against murine sarcoma neoantigens. (A) Six-week-old male C57BL/6 mice were vaccinated with T cells transduced with a viral vector encoding linked murine neoantigens Lama4 and Alg8. Subsets of the $T_{VAX}$ cells were transduced to further express *L. monocytogenes* antigen LLO190, mtIL-12+GM-CSF, or both. At day +13, tetramer staining was performed. (B) Tetramer-positive cells as a percentage of CD8$^+$ T cells for each tested group. (C) In a follow-up experiment, vaccinated mice received an initial priming dose of $2\times10^5$ syngeneic T cells modified to express Alg8, Lama4, mt-IL12, and GM-CSF, followed by a "boost" injection ($4\times10^5$ cells) at day +28. Tetramer staining was performed at the indicated time points. The limit of detection for these tetramers in this experiment as compared to mock vaccinated animals was 0.1%. N=3 per group. Error bars represent standard error of the mean.
Figure 9B:
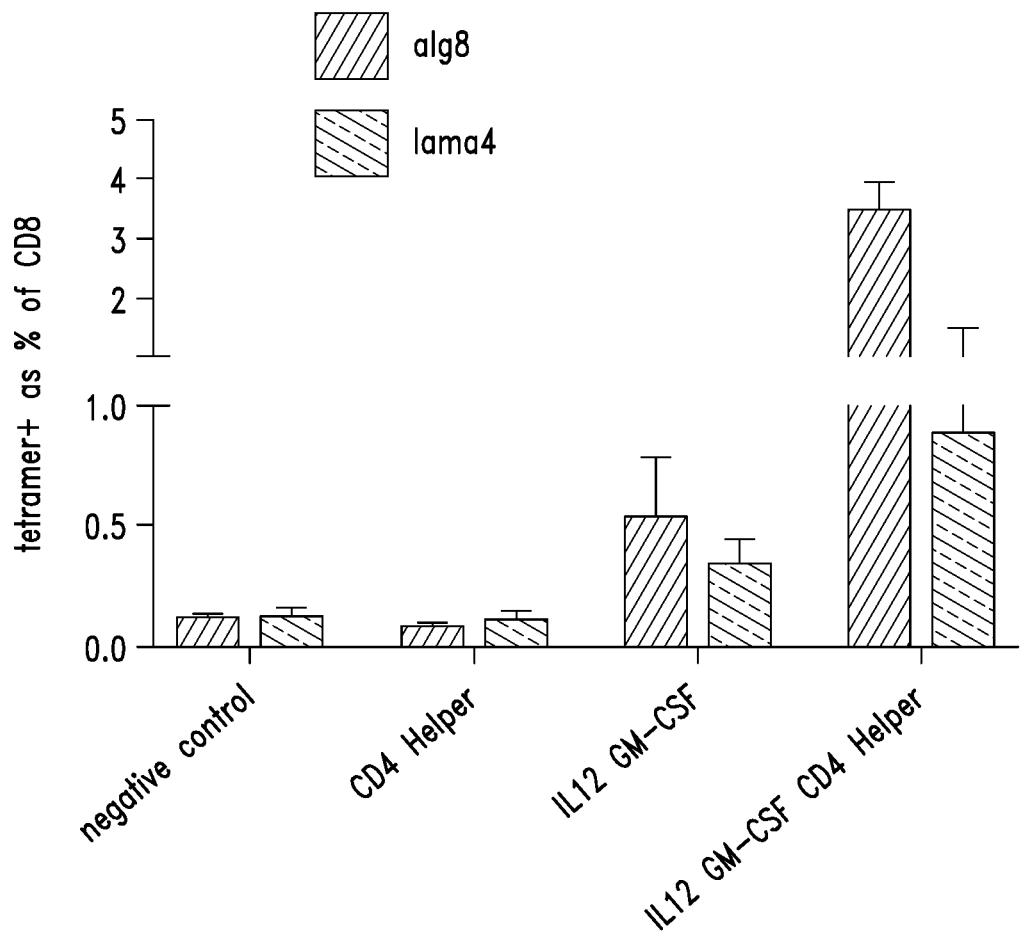

T cell responses to model antigens such as OVA are easier to provoke than responses against antigens present in cancer. To evaluate the effectiveness of neoantigen-specific T cells, mtIL12+GM-CSF+ T cells were transduced to express the murine sarcoma neoantigens Lama4 or Alg8 (described in Gubin et al., Nature 515(7528): 577-581 (2014)) and, optionally, the CD4 helper antigen LLO190 (FIG. 9A). Mice were bled at the indicated days and antigen specific cells were measured as a fraction of the CD8+ T cells in the blood that were tetramer positive. The limit of detection for these tetramers in this experiment from analyzing mock vaccinated animals was 0.1%. N=3 per group. Error bars represent standard error of the mean. At day 13 following injection, tetramer staining was performed. Results are shown in FIG. 9B. T cells expressing the adjuvant molecules induced a robust vaccine response against both neoantigens, with the highest level of tetramer staining (as a percentage of CD8+ T cells) seen in the additional presence of the helper antigen.

Example 8

TOVA-Induced Immune Response is Enhanced by Vaccine Boost

Figure 9C:
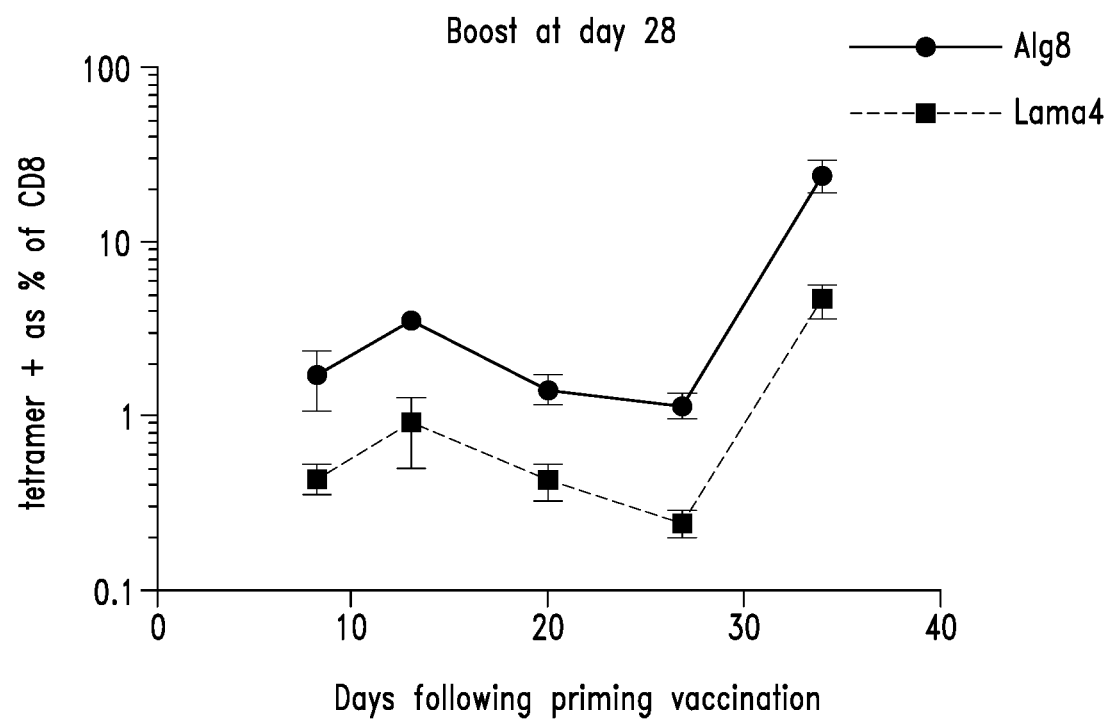

Vaccine regimens often consist of an initial priming administration followed by one or more subsequent boost injections. Following on the experiment described in Example 7, mice were primed by intravenous injection of $2 \times 10^5$ syngeneic T cells transduced with a virus encoding a tandem minigene of alg8 and lama4 neoantigens fused to the LLO190 CD4 antigen, as well as 2 additional viruses encoding membrane tethered IL-12 and secreted GM-CSF. At day +28, mice were boosted by intravenous injection of $4 \times 10^5$ syngeneic T cells retrovirally transduced with a virus encoding the neoantigens alg8 and lama4. Data are shown in FIG. 9C. Mice were bled at the indicated days and antigen-specific cells were measured as a fraction of the CD8+ T cells in the blood that were tetramer positive. The limit of detection for these tetramers in this experiment from analyzing mock vaccinated animals was 0.1%. N=3 per group. Error bars represent standard error of the mean. As shown in FIG. 9C, the boost injection significantly increased the immune response.

Example 9

Transposon System for Stable Integration of Exogenous Genes in Human T Cells

To develop a personalized cancer vaccine, a new vaccine construct needs to be created for each patient based on predicted neoantigens in the patient's tumor. As a result, production of a clinical grade retrovirus for T cell genetic modification is not feasible. Therefore, a non-viral gene delivery method for T cell transduction was developed using the piggyBac (PB) transposon. In order to adapt the PB system to allow for purification and expansion of antigen-expressing T cells, the construct was designed to also encode a cell surface marker, truncated human CD19 (tCD19), for selection of modified T cells based on CD19 expression.

Figure 3A:
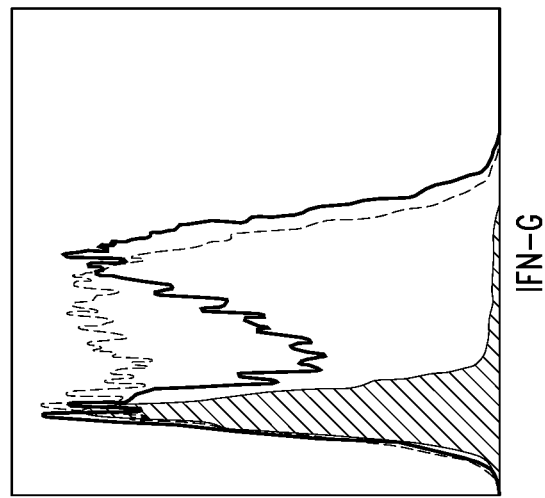
FIGS. 3A to 3C show the stable non-viral expression of antigen in primary human T cells by piggyBac transposon. Protein expression in T cells was assessed using flow cytometry. (A) Primary human peripheral blood mononuclear cells (PBMCs) were nucleofected with plasmids encoding the piggyBac transposase and a piggyBac transposon encoding truncated CD19 translationally linked to the CMV NLV epitope. T cells were stained for CD19 7 days following anti-CD3/CD28 stimulation. (B) CD19$^+$ T cells were enriched by CD19 microbeads and stained for CD19 on day 13 of a rapid expansion protocol. (C) Interferon production by CMV NLV-specific CD8$^+$ T cells when co-cultured with T cells stably expressing the NLV epitope (dashed line compared to untransfected (grey) or untransfected T cells pulsed with NLV peptide (solid line).
Figure 3B:
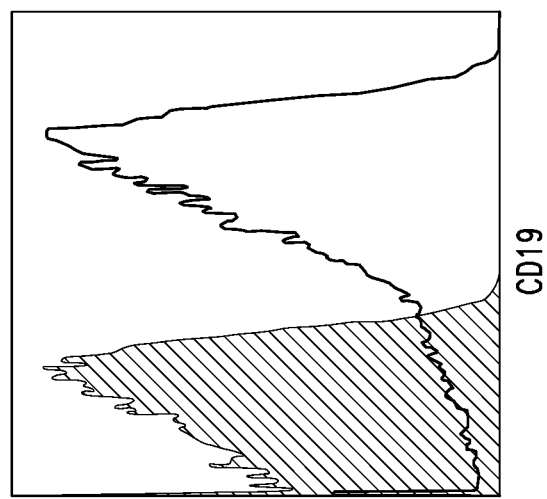
Figure 3C:
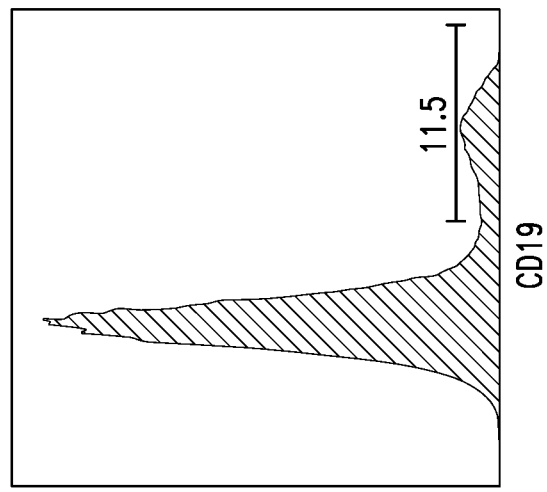

In preliminary experiments to test feasibility, the tCD19 was translationally linked to a minigene encoding the HLA-A2 restricted CMV pp65 epitope NLV and the resulting construct was flanked by PB transposon repeats. The tCD19-CMV construct was electroporated into human peripheral blood mononuclear cells (PBMCs), and the cells were stimulated with CD3 and CD28 in the presence of IL-15, according to the methods described in Nakazawa, et al. (*J. Immunother.* 32(8):826-869 (2009)). After 7 days of culture, between 5% and 30% of T cells stably expressed tCD19 (FIG. 3A), indicating stable integration of the construct. In order to obtain large numbers of T cells expressing the CMV antigen, modified cells were enriched by CD19 magnetic selection and the enriched cells were expanded using a rapid expansion protocol used to expand therapeutic T cell products, resulting in 100-500-fold expansion over 13 days. Over 80% of the expanded T cells expressed the tCD19 marker (FIG. 3B). The resulting cells efficiently presented the NLV antigen, as demonstrated by their ability to activate NLV-specific CD8+ T cells obtained from a CMV positive donor to a level equivalent to that of T cells pulsed with the NLV peptide (FIG. 3C). Using this procedure, greater than $10^9$ antigen expressing T cells can be obtained in 20 days from less than or equal to $5 \times 10^6$ PBMCs obtained from a 10 cc blood draw, demonstrating the feasibility of this approach for preparing Tvax cells and testing Tvax for the ability to elicit neoantigen-specific T cell responses.

Example 10

RNA Electroporation into Monocyte-Derived Dendritic Cells Efficiently Expands Memory CD8+ and CD4+ T Cells from Peripheral Blood A successful vaccine trial requires accurate prediction of immunogenic antigens and manufacture of the vaccine, as well as reliable tools for identifying and quantitating antigen-specific T cell responses present prior to vaccination or elicited in response to the vaccine. For a T cell-based neoantigen vaccine, Tvax cells could be used to screen for immunogenic neoantigens; however, their efficiency for direct presentation of class II antigens is lower than that of dendritic cells (DCs) or activated B cells, which directly present antigens on both class I and class II MHC to both CD4+ and CD8+ T cells and express costimulatory molecules to optimally stimulate T cells in vitro.

Accordingly, DC expression of electroporated mRNA was used to screen for immunogenic neoantigens. For screening, in-vitro-transcribed mRNA encoding candidate antigens was expressed in autologous monocyte-derived DCs obtained from peripheral blood. Intracellular expression from mRNA has been used to screen large numbers of candidate antigens that have been assembled into minigenes (Tran et al., Science 344: 641, 2014), and has the advantage of avoiding experimental artifacts from extracellular peptides that bind MHC but are not processed (Carreno et al., Science 348: 803, 2015). As an alternative, primary B cells may be used, and they can be efficiently expanded greater than 100-fold from even small clinical samples through co-culture with CD40L (Liebig et al., Journal of Visualized Experiments 32: e1373, 2009).

Figure 4A:
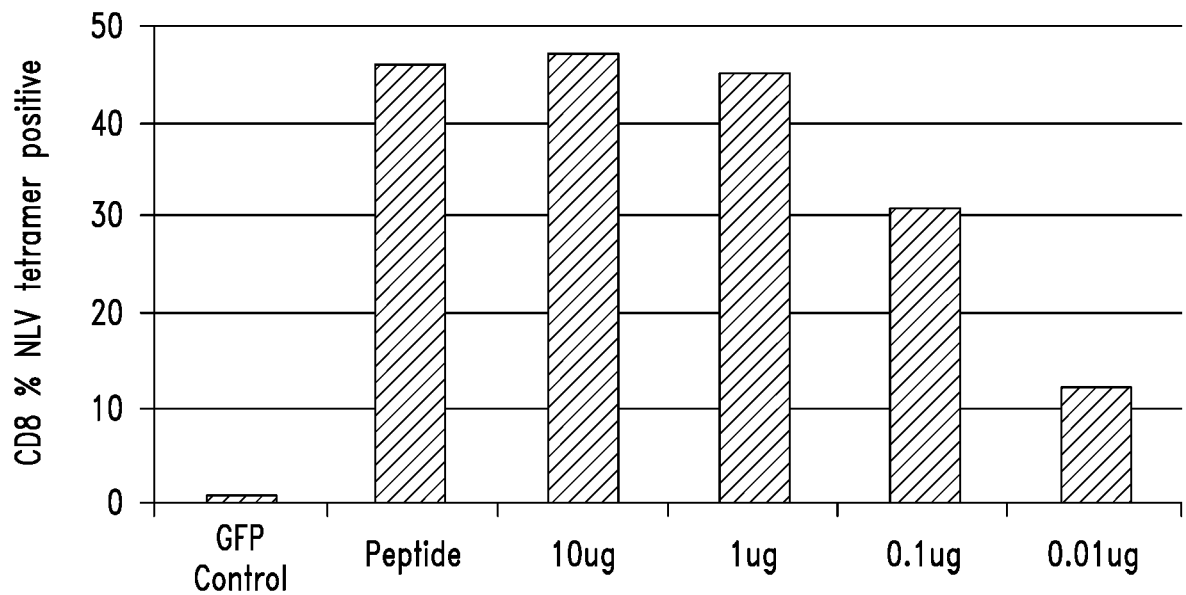
FIGS. 4A to 4B show that small amounts of RNA efficiently expand CD8$^+$ and CD4$^+$ memory responses. CD8$^+$ or CD4$^+$ T cells from a CMV-positive donor were stimulated with decreasing amounts of mRNA encoding the CMV pp65 gene. Unmodified cells and unmodified cells pulsed with CMV pp65 peptide served as negative controls and positive controls, respectively. (A) CD8$^+$ T cells were stained with tetramer containing the immunodominant NLV peptide complexed with major histocompatibility complex (MHC). (B) CD4$^+$ T cells were incubated with autologous B cells pulsed with peptides encompassing the pp65 gene in the presence of brefeldin A and stained for intracellular IFN-γ.
Figure 4B:
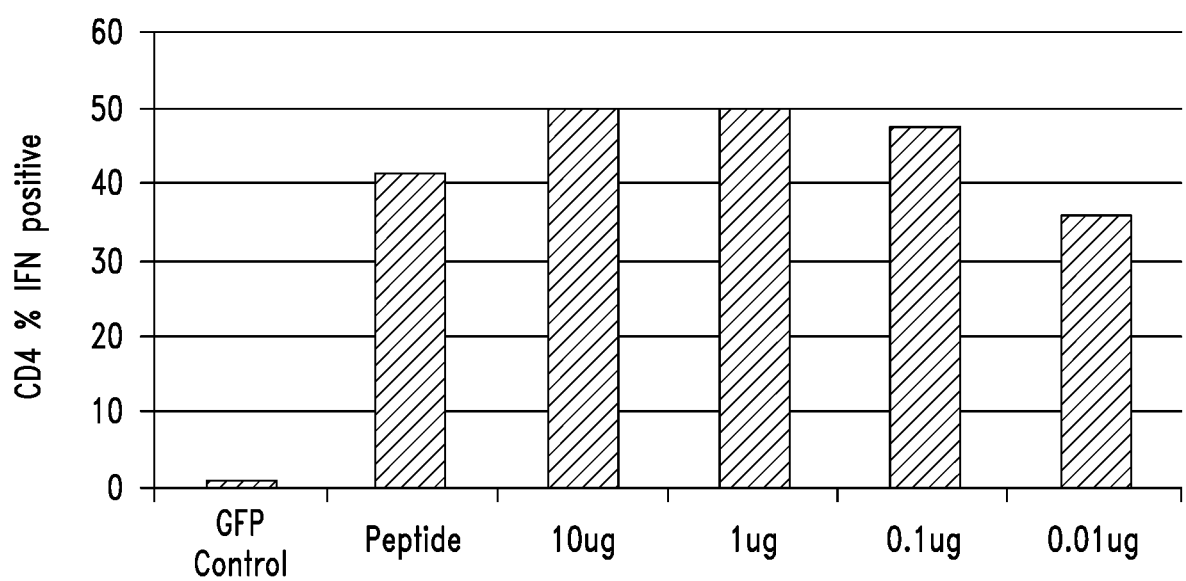

Viral antigen mRNAs were assembled into minigenes and inserted into DCs, illustrating the feasibility of using large pools of potential antigens to expand rare, antigen-specific cells. An expression construct was created by fusing (a) the T7 promoter, (b) the CMV pp65 gene or a minigene containing CMV epitopes, and (c) sequences targeting the fusion protein to the endocytic pathway to enhance class I and class II MHC presentation (Kreiter, et al., J Immunol 180: 309, 2008). Decreasing amounts of mRNA in-vitro transcribed from the construct were electroporated into DCs and used to stimulate PBMCs from a CMV-positive donor. Cells responding to the immunodominant CMV pp65 CD8+ epitope were efficiently expanded 10 days after stimulation with as little as 0.01 ug of mRNA encoding the antigen in target DCs (FIG. 4A). Similarly, CMV pp65 CD4+ responses were efficiently expanded by as little as 0.01 ug of an mRNA construct encoding pp65 (FIG. 4B). These data show that robust viral memory responses to strong antigens can be expanded, at least in the absence of exhaustion that may characterize cancer-specific T cells. These data demonstrate that expressing small amounts of RNA encoding antigenic epitopes as part of a pool can efficiently expand memory CD4+ and CD8+ responses to antigens in that pool. This system can be used to expand rare neoantigen-reactive T cells that can be found in the peripheral blood in clinical samples of melanoma (Snyder et al., New Engl. J. Med. Medicine 371: 2189, 2014) and lung cancer patients (Rizvi et al., Science 348: 124, 2015) in order to assess naïve or memory responses to candidate neoantigens predicted by a bioinformatics platform.

Example 11

Identification of Candidate Neoantigens from Clinical Samples in Non-Small Cell Lung Cancer (NSCLC) and Melanoma Blood and tumor samples were obtained from non-small cell lung cancer (NSCLC) patients (4) and melanoma patients (2). DNA was isolated from archival fixed tissue, and exome capture was performed using SureSelect (Agilent Technologies) followed by paired-end 100 sequencing. The union of missense mutations from MuTect (Cibulskis et al., Nature Biotechnology 31: 213, 2013), VarScan (Koboldt et al., Bioinformatics 25: 2283, 2009; Koboldt et al., Genome Research 22: 568, 2012), and Strelka (Saunders et al., Bioinformatics 28: 1811, 2012) were filtered for expression above 0.5 transcripts per million using the trimmed mean expression of 50 similar tumors from the Cancer Genome Atlas dataset (top and bottom deciles removed). Frame-shift mutations not subject to nonsense-mediated decay were identified using the union of VarScan and Strelka. Using this approach, 265 missense mutations and 8 frame-shift mutations that were not subject to nonsense mediate decay were identified. See FIG. 10, top schematic.

Figure 10:
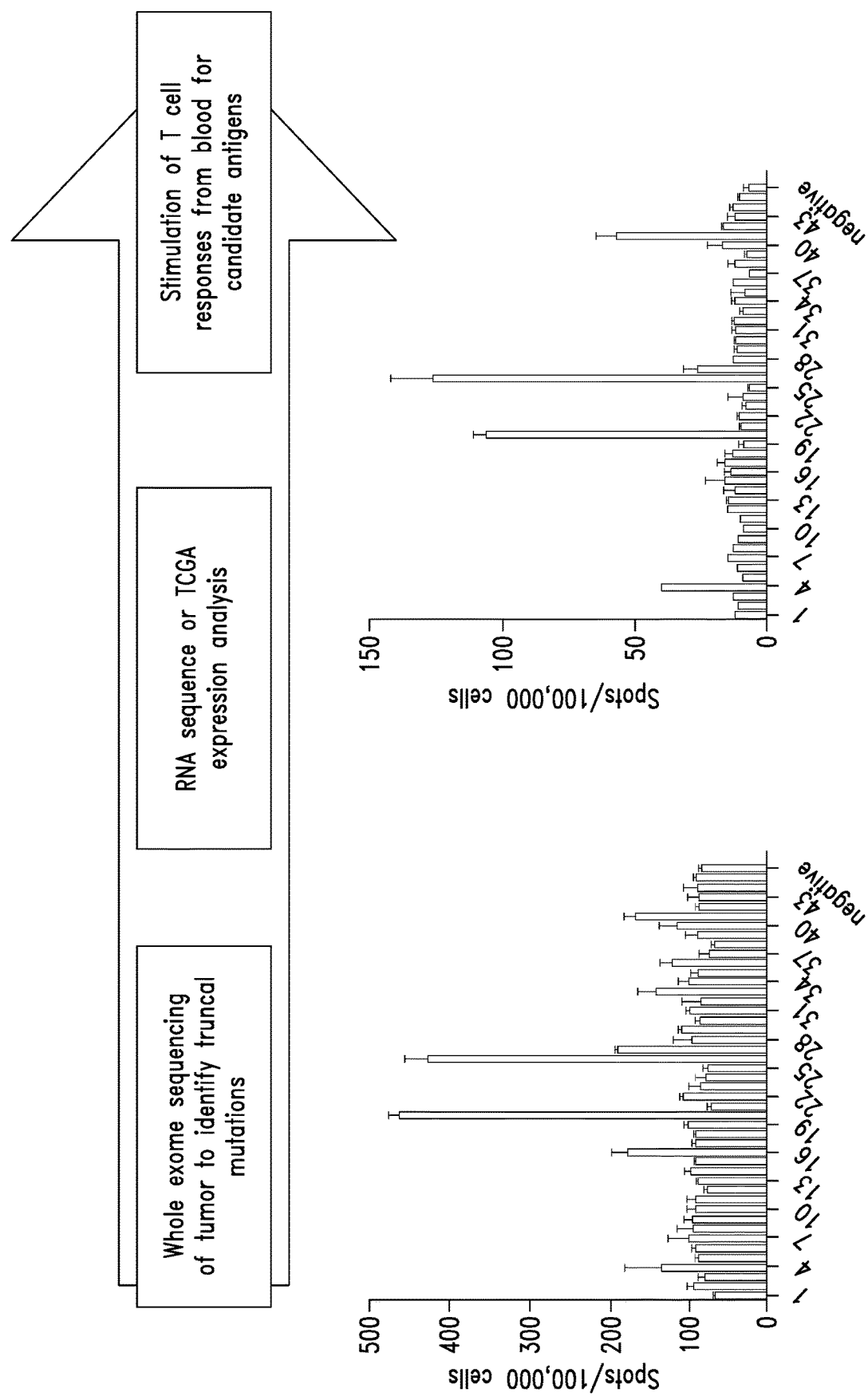
FIG. 10 illustrates an exemplary method for identifying candidate neoantigens from patient tumors (top) and data showing T cell response (Elispot cytokine release assay) from peripheral blood from a lung cancer patient following two rounds of stimulation with candidate neoantigens (bottom left and right).

The identified mutations were encoded in minigenes such that the amino acid sequences included the 13 flanking amino acids on either side of the mutation to encompass potential CD8+ and CD4+ epitopes. The 27 resulting amino acid minigenes were then assembled into 26 tandem minigene molecules that were synthesized and cloned in parallel into an in-vitro transcription construct described above in Example 3, sequence verified, and transcribed into mRNA. To determine whether there were pre-existing neoantigen CD8+ and CD4+ memory T cell responses in the patient, the mRNAs were used to stimulate T cells using transfected autologous DCs as antigen presenting cells. Exemplary data is shown in FIG. 10, bottom left and right panels.

In particular, exome capture and cDNA capture were performed on tumor tissue from two melanoma patients and one lung cancer patient who had previously attained complete tumor regression following treatment with adoptively transferred, in vitro-expanded tumor infiltrating lymphocytes (TILs). Leukapheresis products were also obtained from the three patients prior to and after TIL infusion, and tumor reactive TIL populations and single cell tumor suspensions were obtained. Exome sequences of the tumor samples were identified. Candidate-expressed neoantigens were incorporated into in-vitro transcription products for DC transfection and analysis of potential neoantigen-reactive T cells.

The results of these experiments are useful in validating candidate neoantigens that can be expressed as minigenes for vaccine construction.

Example 12

Identification and Characterization of Immunogenic Neoantigens

Computational analysis of sequence variants was used to predict neoantigen binding to patient-specific MHC alleles and to select candidate neoantigens for incorporation into $T_{VAX}$ cells. Samples were obtained from 4 NSCLC patients and 2 melanoma patients and subjected to genomic analysis. Expressed, protein-coding variants were identified as described above in Example 11. HLA typing was determined from exome data using OptiType (Szolek et al., Bioinformatics 30(23): 3310-3316 (2014)) and missense and frame shift mutations were analyzed for formation of novel peptides predicted to bind autologous MHC alleles using NetMHCpan (Trolle et al., *Bioinformatics* 31(13):2174-2181 (2015)).

An assay for detecting rare neoantigen-reactive cells in clinical samples from NSCLC and melanoma patients was developed. Specifically, all expressed protein coding mutations were systematically evaluated in order to determine whether antigens with T cell responses would have been predicted by our bioinformatic workflow. Candidate neoantigens were assembled into tandem minigenes as described above in Example 11. Autologous T cells from the blood were stimulated with autologous DC transfected (mRNA) to express 20-mer peptides from a pool comprising approximately 50 of the top candidate neoantigens in order to expand rare neoantigen-reactive T cell populations. The resulting expanded T cells were then tested for reactivity to specific individual neoantigens by incubation with autologous DC or B cells electroporated with mRNA expressing those neoantigens or pulsed with synthetic peptides, followed by measuring interferon release. In a validation experiment, $T_{VAX}$ presenting an exemplary neoantigen (TERF1) from a lung cancer patient activated cancer-specific T cells from the same patient (FIG. 11, bottom right); these data are discussed further in Example 14. TILs are analyzed in the same way. This assay platform can be used for immune monitoring in human studies, as well as for investigating whether T cell responses in patients can be successfully predicted bioinformatically.

A method for determining the number of computationally predicted neoepitopes that can prime autologous naïve T cells in vitro is developed. It is likely that only a fraction of potentially immunogenic neoantigens that could respond to vaccination will have pre-existing memory responses in cancer patients. For example, in a published trial, the majority (4 of 7) of neoantigen vaccine responses were not detected prior to vaccination (Carreno et al., *Science* 348 (6236):803-808 (2015)). In order to identify antigens without memory responses that are nonetheless capable of being processed, being presented, and eliciting a T cell response, a system for priming naïve T cell responses in vitro using antigens expressed in DCs is used (Bleakley et al., *Blood* 115(23):4923-4933 (2010)). Briefly, this system involves expressing pools of mRNA encoding candidate epitopes in autologous DCs, and culturing purified naïve (CD45RA+/CD62L+) T cells in the presence of IL-12 and IL-15, followed by screening of these T cells against antigens expressed in autologous B cells or DCs. By systematically evaluating immunogenic neoantigens in both the memory and naïve T cell repertoire, these experiments will allow for bioinformatic epitope prediction and for rationally determining the number and selection criteria for neoantigens to target with a vaccine.

Example 13

Method of Treating NSCLC

Correlative longitudinal studies of treatment with neoantigen-reactive T cells in NSCLC patients undergoing immune checkpoint molecule inhibitor therapy are conducted. Research core needle biopsies are obtained from NSCLC patients prior to initiation of immune checkpoint blockade therapy. If existing neoantigen-specific T cell responses can be identified in the blood of these patients, the unique T cell receptor beta (TCRB) sequences associated with these antigen specific T cells are identified (Adaptive Biotechnologies). Because global sequencing of TCRB is a highly sensitive and quantitative measure of TCR frequency, this technique is used to enumerate neoantigen-specific T cells in the tumor and longitudinal blood samples of these patients during immune checkpoint inhibition therapy. Tetramer reagents are made for CD8+ antigen specific T cells, allowing for longitudinal analysis of cell phenotype. The phenotype and localization of neoantigen-specific T cells is then observed during lung cancer immunotherapy. Combined with knowledge of tumor gene expression and the microenvironment, these observations could suggest predictive biomarkers for response, or mechanisms of resistance to treatment.

Example 14

Activation of Neoantigen-Specific T Cells by Autologous $T_{VAX}$

In this proof-of-principle experiment, T cells from a human lung cancer patient were modified using the piggy bac transposon system to express a neoantigen and used to activate endogenous T cells specific for the neoantigen. The plasmid pJV53 was created by cloning linear fragments encoding an ER targeting signal peptide (SEQ ID NO.: 1) derived from murine Igκ chain with a sequence encoding the TERF1 mutation identified in a human lung cancer patient and the C-terminal domain of human class I MHC linked to a T2A skip sequence and truncated human CD19 into the vector PB713B (System Biosciences, Palo Alto, Calif., USA) containing piggy bac transposon sequences. The plasmid containing the piggy bac transposase pb200pa-1 was obtained from System Biosciences. The method of Nakazawa et al. (*J. Immunother.* 32(8):826 (2009)) was followed to introduce the TERF1 transposon into the cells. Briefly, cryopreserved human PBMC were rested overnight in medium containing 5 ng/ml recombinant human IL-15, and then nucleofected with 5 ug transposon pJV53 and 5 ug transposase pb200pa-1 plasmid DNA in solution V using a 2b nucleofector (Lonza, Basel, SU) according to manufacturer's instructions using program U-014. Cells were rested in CTL with 5 ng/ml IL-15 for 24 hours and then stimulated with 3/28 human dynabeads for 7 days in CTL with 5 ng/ml IL-15. On day +7 of stimulation, modified cells were enriched using the surface marker truncated CD19 using CD19 microbeads (Miltenyi Bio) according to the manufacturer's instructions, and then expanded by a rapid expansion protocol as described previously. Cells were assayed for antigen presentation at day +21 of rapid expansion.

Next, cryopreserved peripheral blood mononuclear cells were thawed and rested overnight in CTL (RPMI (Gibco) supplemented with 10% human serum, beta-mercaptoethanol, penicillin and streptomycin, and 1-glutamine) supplemented with 2 ng/ml recombinant human IL-7 (PeproTech). The following morning, cells were washed and stimulated at $10^6$ cells in the presence of $T_{vax}$. Recombinant human IL-2 (PeproTech) was added to a final concentration of 10 U/ml on day +3, and half media changes with supplemental IL-2 were performed on days +3, +6, and +9. On day +21, antigen-specific T cells were stained for intracellular cytokines (Miltenyi Biotech) following the manufacturer's instructions, using autologous B cells as antigen presenting cells pulsed with 10 ug/ml 21-mer TERF1 mutant peptide. CD4+ IFNγ-secreting cells were sorted on a FACS Aria2. Sorted cells were rested in CTL supplemented with 10 ng/ml human IL-15 for 5 days, then expanded using a rapid expansion protocol described previously (Riddell et al., *Science* 257(5067): 238-242 (1993)). Cells were used or cryopreserved at day 13 or 14 of this expansion. Cryopreserved cells were thawed and rested overnight in CTL supplemented with 10 ug/ml human IL-2 prior to assays.

Figure 11:
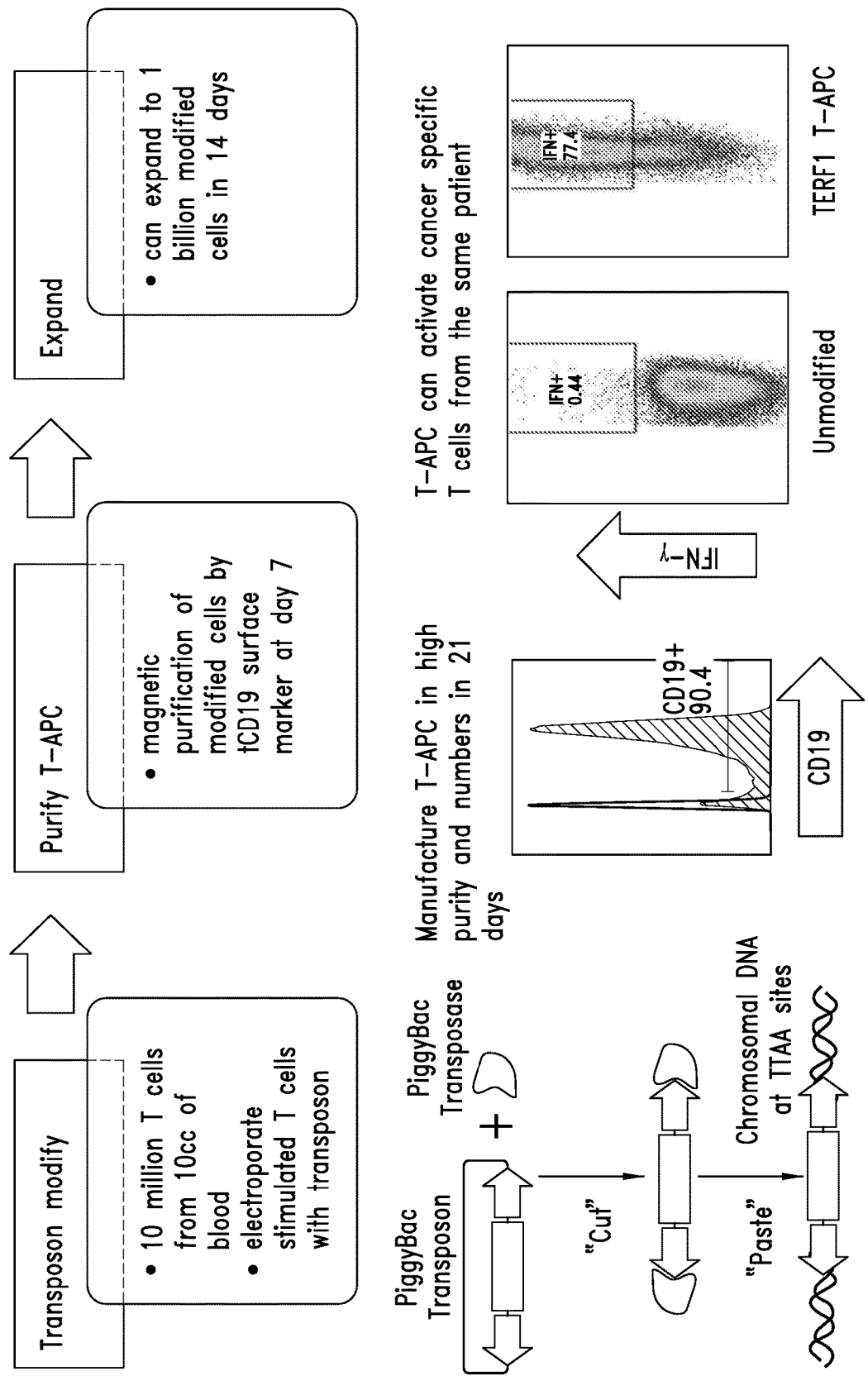
FIG. 11 shows an exemplary scheme for modifying T cells to express a neoantigen to form a T cell vaccine according to the present disclosure. At bottom right, flow cytometry data from a proof-of-principle experiment is provided showing activation of T cells from a lung cancer patient by autologous TERF1 $T_{VAX}$.

As shown in FIG. 11 (bottom right panel), vaccination with autologous $T_{TERF1}$ cells produced a robust interferon-γ release by cancer-specific T cells from the patient. These data show that autologous $T_{VAX}$ presenting human neoantigens can induce an immune response in the patient, indicating that personalized $T_{VAX}$ having therapeutic efficacy and reduced risk of immunogenicity can be efficiently developed.

Example 15

Identification and Testing of Neoantigens from Cancer Patients

Blood and tumor samples were obtained from lung cancer and melanoma cancer patients as described in Example 11. Candidate mutations were identified by whole exome sequencing using the publically available algorithms Mutect and Strelka. Mutations identified by both of these algorithms were filtered by variant allele frequency and ranked by expression from similar tumors in the cancer genome atlas, or by RNA seq of the tumor when this was available. The top ~46 mutations from each patient were chosen for screening.

PBMC from a given patient were rested overnight in IL-7 and stimulated with 1 ug/ml of each candidate (crude) peptide in a mix (~92 peptides encompassing the ~46 candidate mutations per patient sample, corresponding to SEQ ID NOs.: 15-512) with IL-2 being added at day +3. Autologous B cells were isolated using immunomagnetic beads targeting CD19 (Milltenyi) and incubated in a 1:1 ratio with NIH 3T3 cells expressing CD40L for 7 days in B cell medium as described by Tran et al. (*Science* 344(6184): 641-645 (2014)) supplemented with 200 U/ml human IL-4 (PeproTech). B cells were subsequently harvested and re-stimulated with 3T3 cd40L every 4 days. B cells were used as antigen-presenting cells in assays at day +3 of stimulation 2 or 3. On day +14, cells were re-stimulated with pairs of peptides representing individual mutations at 10 ug/ml and reactivity was read out by Elispot.

Figure 12A:
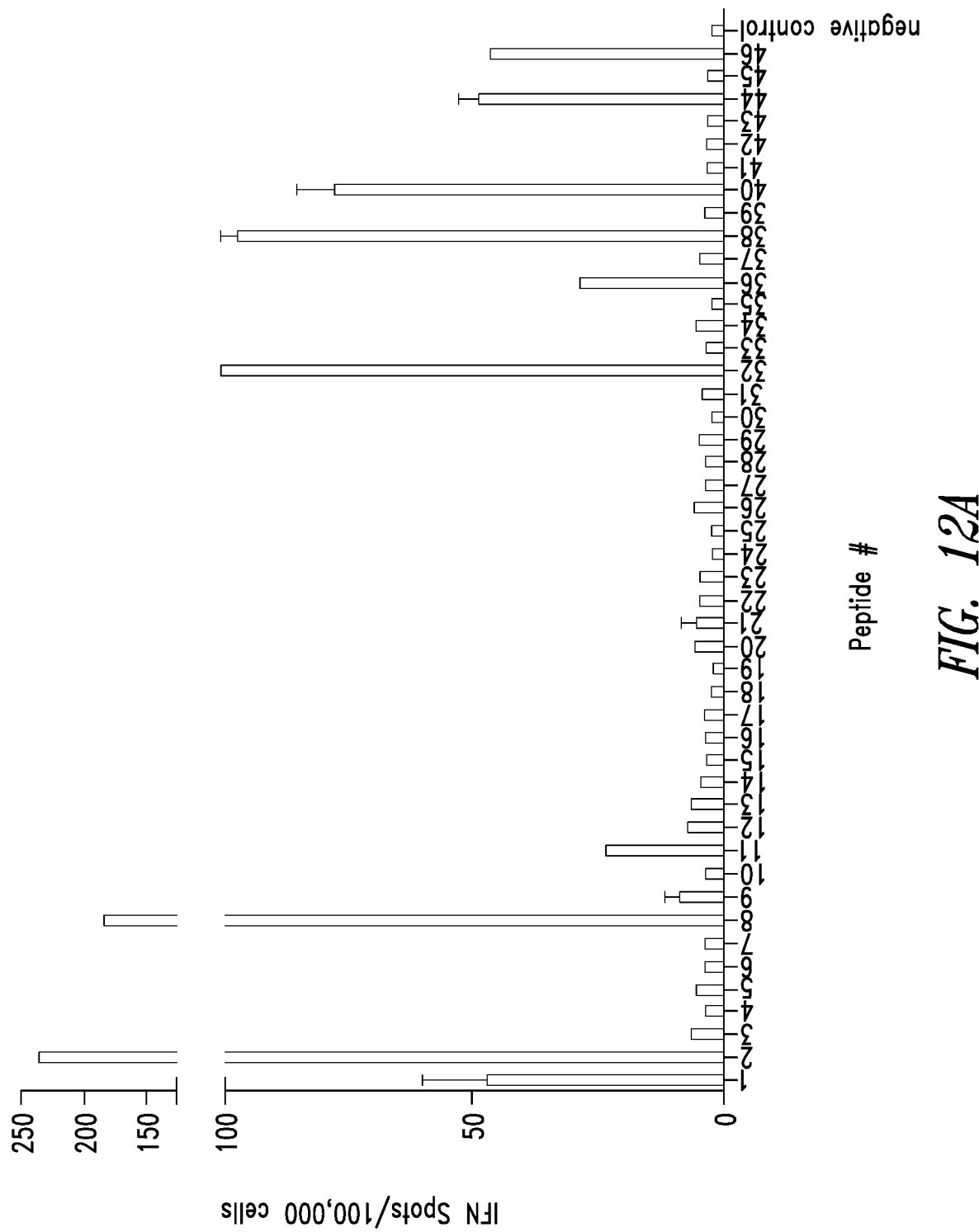
FIGS. 12A-12D show interferon-release data (Elispot assay) from peripheral blood from cancer patients following stimulation with 20-mer candidate neoantigen peptides, and subsequent validation of candidates. (A) Cytokine release by blood from a melanoma patient following stimulation with pooled candidate neoantigen peptides. (B) Cytokine release by blood from a lung cancer patient following stimulation with pooled candidate neoantigen peptides. (C) Verification of specific T cell response against individual peptides in the melanoma patient sample shown in (A). (D) Verification of specific T cell response against individual peptides in the lung cancer patient sample shown in (B).
Figure 12B:
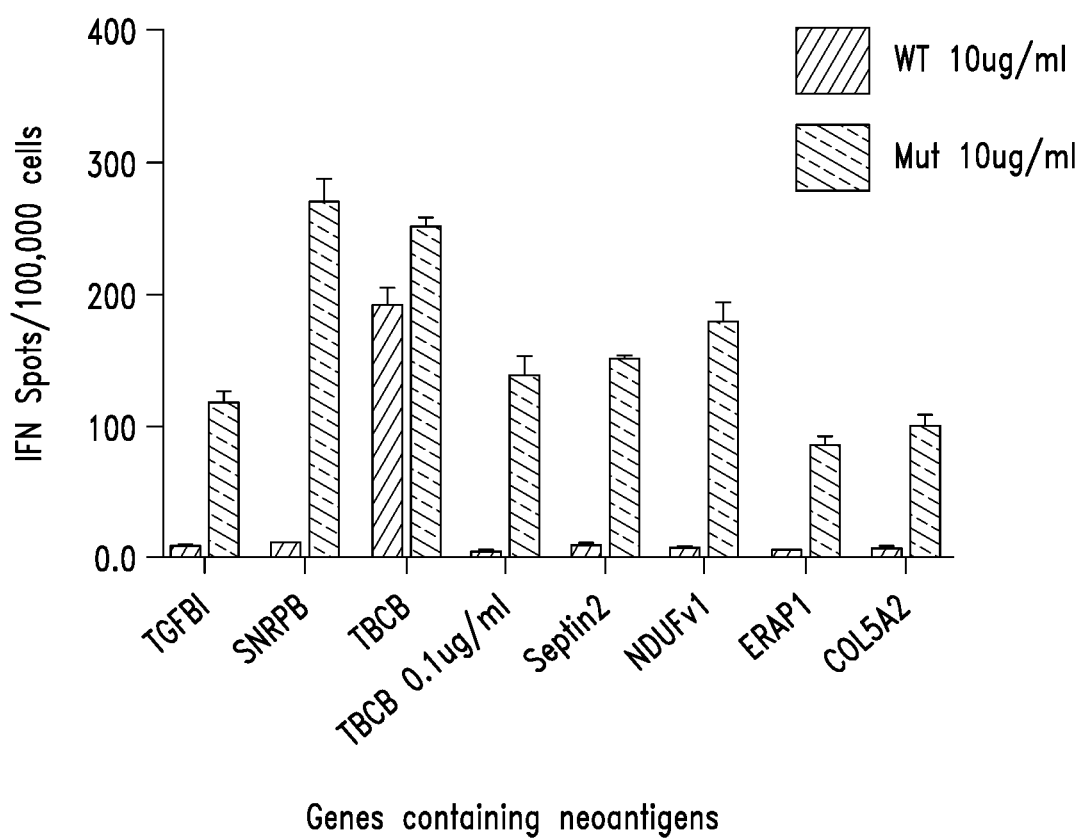
Figure 12C:
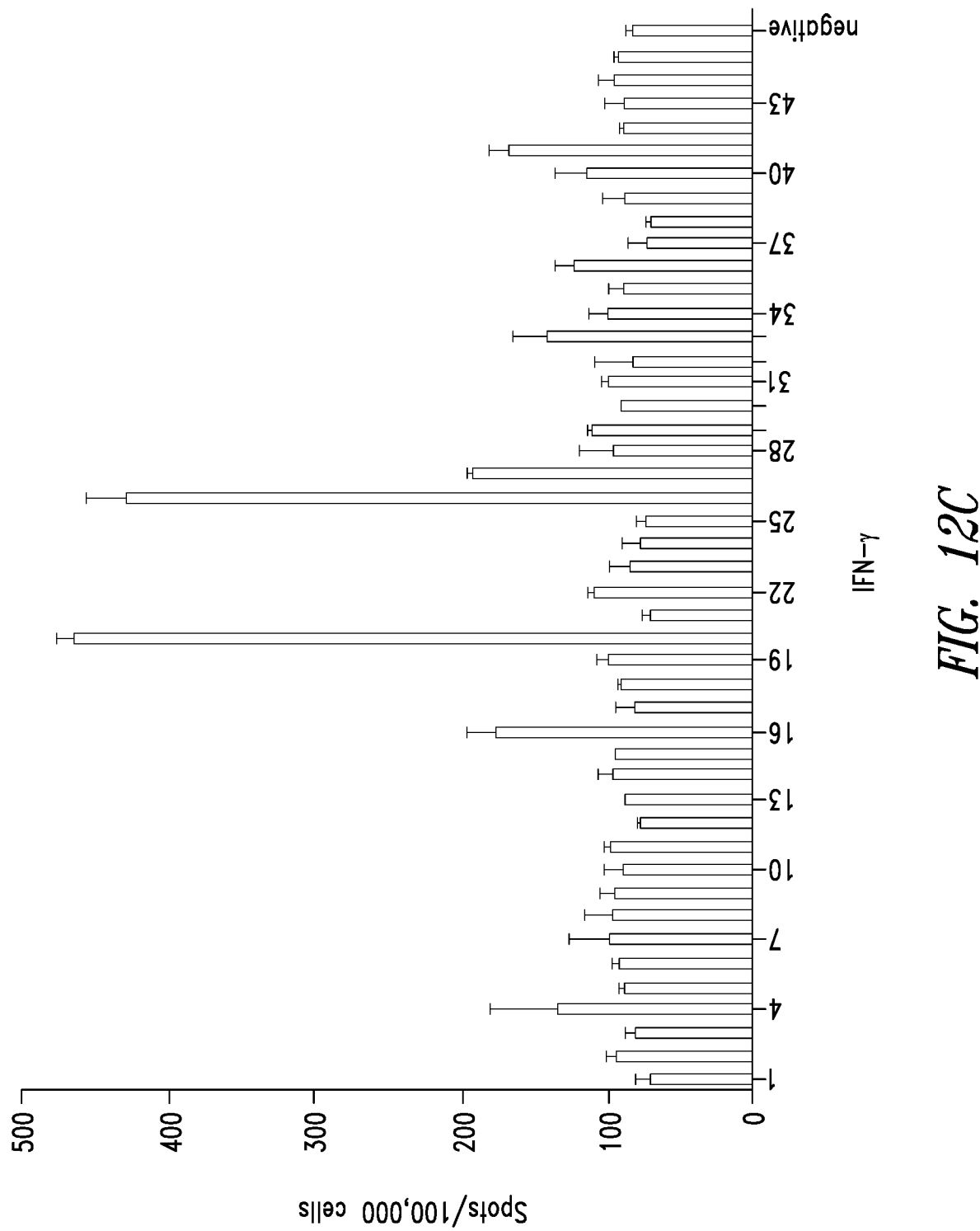
Figure 12D:
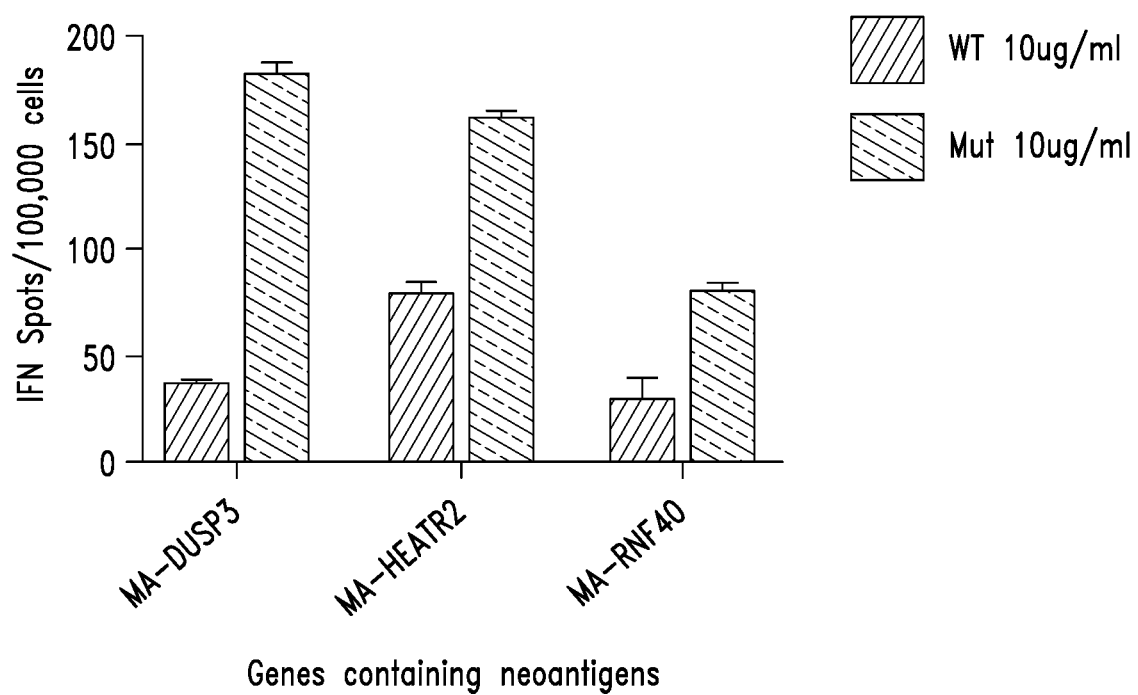
Figure 13A:
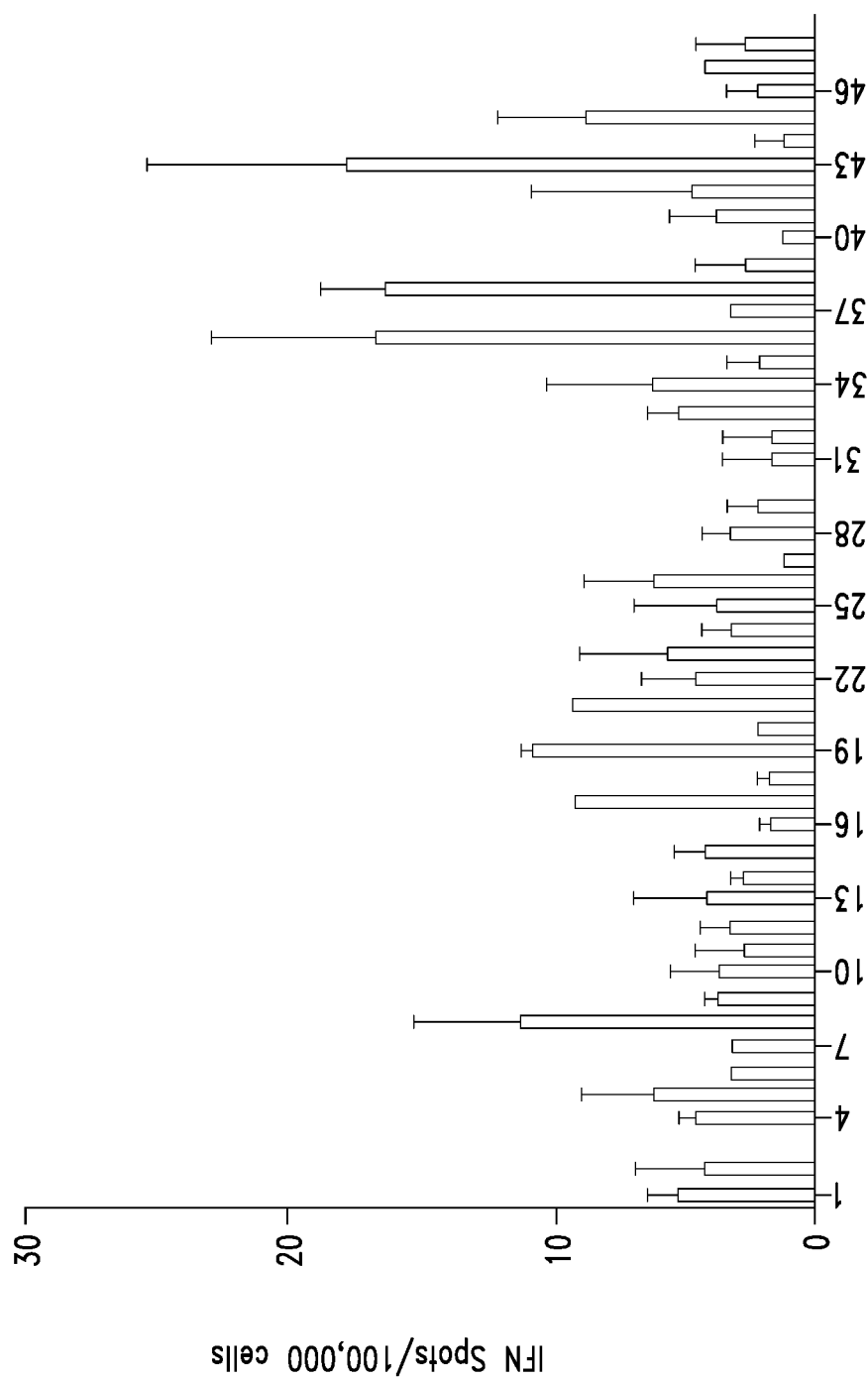
FIGS. 13A-C show interferon-release data (Elispot) from blood samples from three additional lung cancer patients.
Figure 13B:
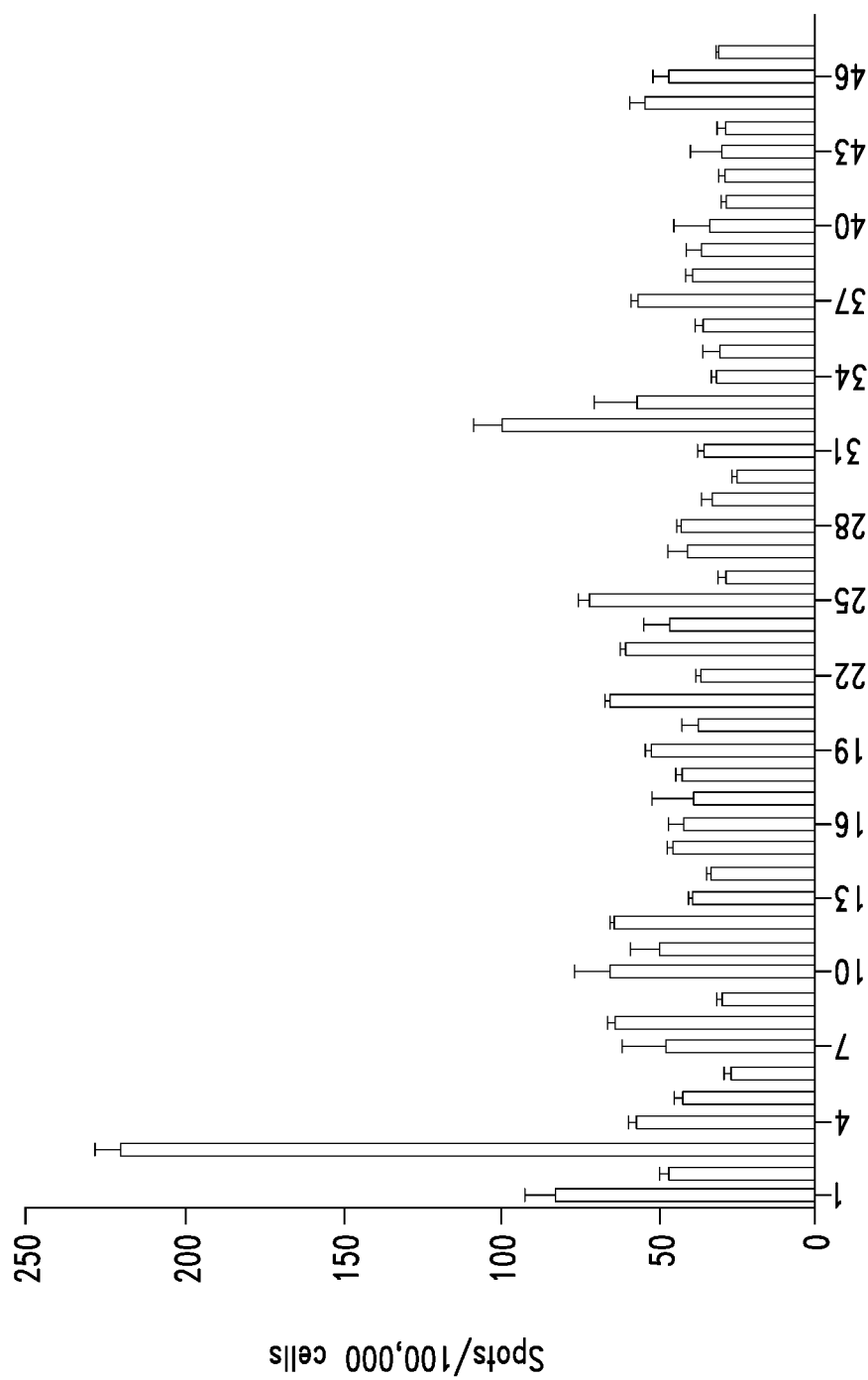
Figure 13C:
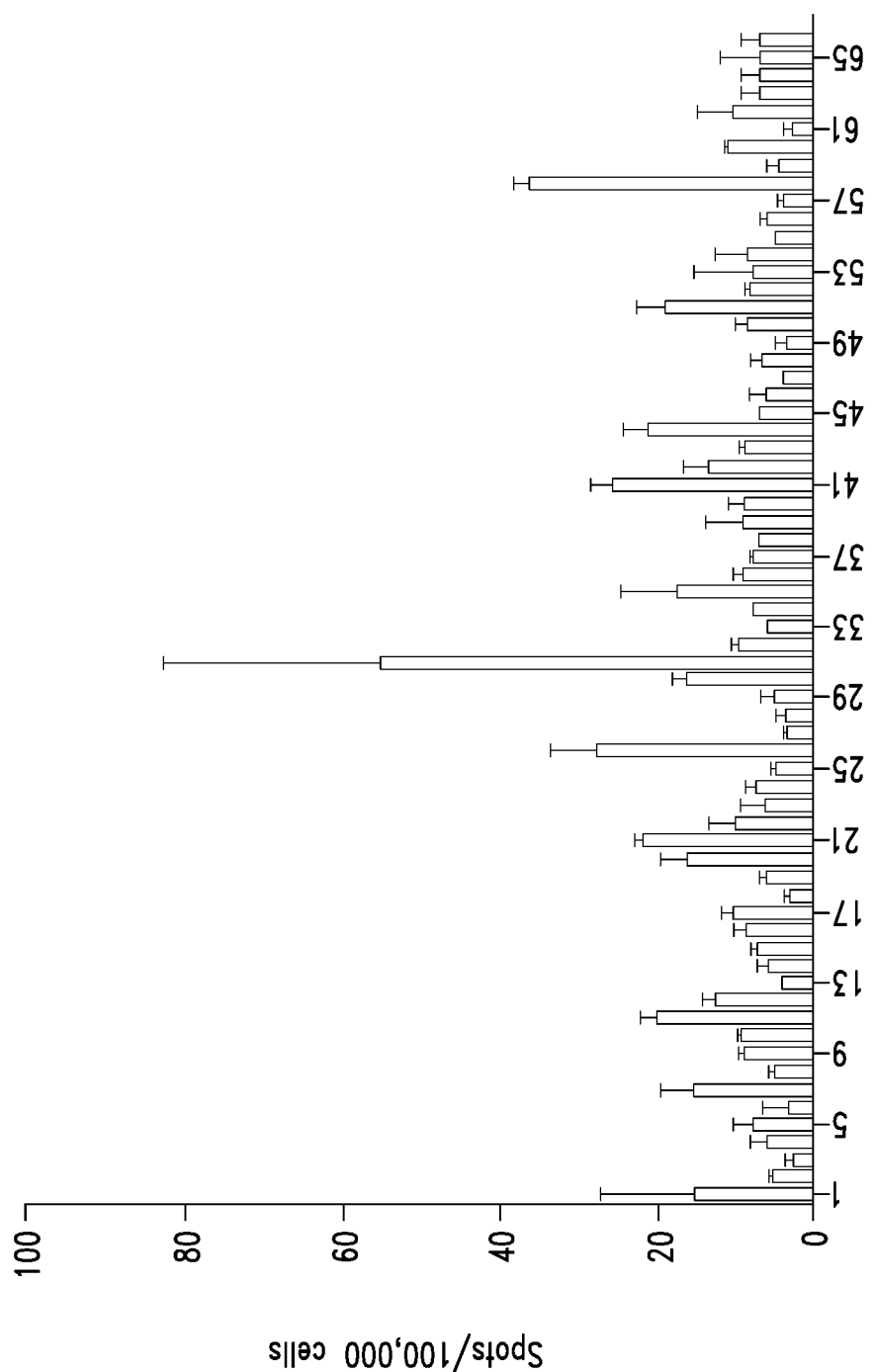

Exemplary data from initial screening of 5 patients is shown in FIGS. 12A, 12C, and 13A-13C. For patients X198 (melanoma) and MA 511 (lung cancer), 80% pure 27-mer peptides containing the mutant peptide (or wildtype counterpart) were used in the Elispot assay to confirm that the T cell response was to the purified peptide and specific for the mutant. FIGS. 12B and 12D, respectively. This was the case for 7 mutations identified in patient X198 and 3 mutations identified in patient MA 511.

All of the U.S. patents, U.S. patent application publications, U.S. patent applications, foreign patents, foreign patent applications and non-patent publications referred to in this specification, and/or listed in the Application Data Sheet, are incorporated herein by reference, in their entirety. The various embodiments described above can be combined to provide further embodiments. Aspects of the embodiments can be modified, if necessary to employ concepts of the various patents, applications and publications to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

What is claimed is:

1. A T cell comprising:
   a heterologous polynucleotide encoding a fusion protein, wherein the encoded fusion protein comprises:
   (i)(a) a tumor neoantigen, wherein the tumor neoantigen comprises a peptide that binds a human Class I Major Histocompatibility Complex (MHC) molecule; and
   (i)(b) an antigen peptide or tumor neoantigen peptide, wherein the antigen peptide or tumor neoantigen peptide binds a human Class II MHC molecule; and
   (ii) a polynucleotide encoding an immunogenicity enhancer.

2. The T cell of claim 1, wherein the encoded fusion protein comprises (i)(a) the tumor neoantigen comprising a peptide that binds a human Class I MHC molecule and (i)(b) a tumor neoantigen that binds a human Class II MHC molecule.

3. The T cell of claim 1, wherein the T cell encodes a plurality of tumor neoantigens.

4. The T cell of claim 1, wherein the immunogenicity enhancer comprises an interleukin-12 (IL-12), a granulocyte-macrophage colony-stimulating factor (GM-CSF), an inducible cell death factor, a bacterial flagellin, a CD80, a CD137L, a CD40L, a secreted interleukin-2 (IL-2), a secreted IL-2 that binds T cells independent of CD25, a secreted interleukin-15 (IL-15), a secreted IL-15-IL-15Rα complex, a secreted interferon-β (IFNβ), a secreted interferon-α1 (IFN-α1), a secreted interleukin-7 (IL-7), or any combination thereof.

5. The T cell of claim 4, wherein the immunogenicity enhancer comprises:
   (a) a fusion protein that localizes to the cell surface of the T cell and comprises the IL-12;
   (b) a fusion protein that localizes to the cell surface of the T cell and comprises the IL-12, and the GM-CSF;
   (c) the IL-12 and the GM-CSF;
   (d) the inducible cell death factor, wherein the inducible cell death factor is comprised of a receptor interacting serine/threonine kinase 3 (RIPK3);
   (e) a fusion protein comprising the inducible cell death factor and a multimerization domain, wherein the inducible cell death factor comprises a RIPK3 kinase domain and the multimerization domain comprises a FK506-binding protein or multimerizing portion thereof;
   (f) the bacterial flagellin, wherein the bacterial flagellin is comprised of a *Salmonella* phase 1 flagellin;
   (g) a fusion protein that localizes to the cell surface of the T cell and comprises the bacterial flagellin; or
   (h) the GM-CSF.

6. The T cell of claim 4, wherein the immunogenicity enhancer comprises CD80, CD137L, IFN-β, IL-12, GM-CSF, or any combination thereof.

7. The T cell of claim 1, further comprising a heterologous polynucleotide encoding a costimulatory molecule.

8. The T cell of claim 7, wherein the costimulatory molecule comprises a CD80, a CD86, a B7RP1, a CD137L, an OX40L, a CD70, a CD30L, a CD154, an ICAM-1, a CD2BP2, a LIGHT, a KLRD1, a ligand that specifically binds to a CD83, an agonist of CD137 (4-1BB), an agonist of CD134 (OX-40), an agonist of CD27, an agonist of CD28, an agonist of CD40, an agonist of CD122, an agonist of GITR, an agonist of ICOS, or any combination thereof.

9. A composition comprising the T cell of claim 1 and a pharmaceutically acceptable carrier, diluent, or excipient.

10. The T cell of claim 1, wherein:
    (i) the T cell is a naïve, central memory, naïve and central memory, effector memory, or combination thereof;
    (ii) the T cell is a CD4+ T cell, a CD8+ T cell, or both;
    (iii) the T cell is a human T cell; or
    (iv) any combination of (i)-(iii).

11. The T cell of claim 1, wherein the polynucleotide encoding the fusion protein is comprised in a transposon expression construct that comprises one or more minigenes each encoding a tumor neoantigen.

12. The T cell of claim 1, wherein the fusion protein comprises an antigen from KRAS, B-Raf, SF31, MYD88, DDX3X, MAPK1, GNB1, p53, raf, ras, myc, pRb, PTEN, CD95, α-fetoprotein (AFP), B7H4, BTLA, CD3, CD19, CD20, CD25, CD22, CD28, CD30, CD40, CD44v6, CD52, CD56, CD79b, CD80, CD81, CD86, CD134 (OX40), CD137 (4-1BB), CD151, CD276, CA125, CEA, CEACAM6, 5 c-Met, CT-7, CTLA-4, EGFR, EGFRvIII, ErbB2, ErbB3, ErbB4, EphA2, FLT1, FLT4, Frizzled, O-acetyl-GD2, GD2, GHRHR, GHR, GITR, gp130, HVEM, IGF1R, IL6R, KDR, L1CAM, Lewis A, Lewis Y, LTβR, LIFRβ, LRP5, MAGE, mesothelin, MUC1, NY-ESO-1, OSMRβ, PD1, PD-L1, PD-L2, PSMA, PTCH1, RANK, Robo1, ROR1, TERT, TGFBR2, TGFBR1, TLR7, TLR9, TNFRSF4, 10 TNFR1, TNFR2, tyrosinase, TWEAK-R, or WT-1.

13. The T cell of claim 1, wherein the immunogenicity enhancer, when expressed by the T cell, is capable of improving an immune response against the tumor neoantigen or tumor neoantigens as compared to the T cell encoding the tumor neoantigen or tumor neoantigens without the immunogenicity enhancer, wherein the immune response comprises direct and/or indirect activation of T cells, wherein indirect activation is mediated by dendritic cells.

14. The T cell of claim 1, wherein the fusion protein comprises a peptide linker disposed between and connecting:
    (1) two tumor neoantigens; and/or
    (2) a tumor neoantigen comprising the peptide that binds a human Class I MHC molecule and an antigen peptide or tumor neoantigen peptide that binds a human Class II MHC molecule.

15. A human T cell comprising:
    a heterologous polynucleotide encoding a fusion protein, wherein the encoded fusion protein comprises:
    (i)(a) cancer-associated neoantigen, wherein the cancer-associated neoantigen comprises a peptide that binds a human Class I Major Histocompatibility Complex (MHC) molecule; and
    (i)(b) an antigen peptide or cancer-associated neoantigen peptide, wherein the antigen peptide or neoantigen peptide binds a human Class II MHC molecule; and
    (ii) a polynucleotide encoding an immunogenicity enhancer.

16. The human T cell of claim 15, wherein the T cell encodes a plurality of cancer-associated neoantigens.

17. The human T cell of claim 15, wherein the immunogenicity enhancer comprises CD80, CD137L, IFN-β, IL-12, GM-CSF, or any combination thereof.

18. The human T cell of claim 15, wherein the fusion protein comprises a peptide linker disposed between and connecting:
    (1) two cancer-associated neoantigens; and/or
    (2) a cancer-associated neoantigen comprising a peptide that binds a human Class I MHC molecule and an antigen peptide or cancer-associated neoantigen peptide that binds a human Class II MHC molecule.

19. A human T cell comprising:
a heterologous polynucleotide encoding a fusion protein, wherein the encoded fusion protein comprises:
- (i)(a) cancer-associated neoantigen, wherein the cancer-associated neoantigen comprises a peptide that binds a human Class II Major Histocompatibility Complex (MHC) molecule; and
- (i)(b) an antigen peptide or cancer-associated neoantigen peptide, wherein the antigen peptide or cancer-associated neoantigen peptide binds a human Class I MHC molecule; and
- (ii) a polynucleotide encoding an immunogenicity enhancer.

20. The human T cell of claim 19, wherein the immunogenicity enhancer comprises CD80, CD137L, IFN-β, IL-12, GM-CSF, or any combination thereof.

21. The human T cell of claim 19, wherein the encoded fusion protein comprises a peptide linker disposed between and connecting:
- (1) two cancer-associated neoantigens; and/or
- (2) (2)(a) a cancer-associated neoantigen comprising a peptide that binds a human Class II MHC molecule and (2)(b) an antigen peptide or cancer-associated neoantigen peptide that binds a human Class I MHC molecule.

22. The human T cell of claim 19, wherein the T cell encodes a plurality of cancer-associated neoantigens.

* * * * *

UNITED STATES PATENT AND TRADEMARK OFFICE
CERTIFICATE OF CORRECTION

PATENT NO. : 11,723,962 B2
APPLICATION NO. : 16/098808
DATED : August 15, 2023
INVENTOR(S) : Stanley R. Riddell et al.

It is certified that error appears in the above-identified patent and that said Letters Patent is hereby corrected as shown below:

In the Claims

Column 285, Claim 1, Line 3:
The wording "a heterologous" should read: -- (i) a heterologous --.

Column 287, Claim 19, Line 4:
"a heterologous" should read: -- (i) a heterologous --.

Signed and Sealed this
Thirteenth Day of May, 2025

Coke Morgan Stewart
*Acting Director of the United States Patent and Trademark Office*

SEQUENCE LISTING

```
<160> NUMBER OF SEQ ID NOS: 514

<210> SEQ ID NO 1
<211> LENGTH: 21
<212> TYPE: PRT
<213> ORGANISM: Artificial Sequence
<220> FEATURE:
<223> OTHER INFORMATION: Signal peptide

<400> SEQUENCE: 1

Met Glu Thr Asp Thr Leu Leu Leu Trp Val Leu Leu Leu Trp Val Pro
1               5                   10                  15

Gly Ser Thr Gly Asp
            20

<210> SEQ ID NO 2
<211> LENGTH: 13
<212> TYPE: PRT
<213> ORGANISM: Artificial Sequence
<220> FEATURE:
<223> OTHER INFORMATION: HA tag

<400> SEQUENCE: 2

Tyr Pro Tyr Asp Val Pro Asp Tyr Ala Gly Ala Gly Ser
1               5                   10

<210> SEQ ID NO 3
```

```
<211> LENGTH: 1800
<212> TYPE: DNA
<213> ORGANISM: Artificial Sequence
<220> FEATURE:
<223> OTHER INFORMATION: Bacterial flagellin (membrane-tethered)

<400> SEQUENCE: 3
atggaaaccg acaccctgct gctgtgggtg ctgctgctgt gggtgccagg cagcacaggc      60
gactaccctt cgacgtgcc agactacgct ggcgctggct ctatggccca agtgatcaac     120
accaacagcc tgagcctgct gacccagaac aacctcgtga agtcccagag cgccctgggc     180
accgctatcg agagactgtc tagcggcctg agaatcaaca cgccaaggga cgatgccgct     240
ggccaggcta tcgccaacag attcaccgcc aacatcaagg gcctgaccca ggccagcaga     300
aacgccaacg acggcatctc tatcgcccag accacagagg gggccctgaa cgagatcaac     360
aacaacctgc agagagtgcg cgagctggcc gtgcagagcg ccacatctac aaacagccag     420
tccgacctgg acagcatcca ggccgagatc acccagagac tgaatgagat cgacagagtg     480
tccggccaga cccagttcaa cggcgtgaag gtgctggccc aggacaacac cctgaccatc     540
caagtgggcg ccaacgatgg cgagacaatc gacatcgacc tgaagcagat caactcccag     600
accctgggcc tggacaccct gaacgtgcag cagaagtaca aggtgtccga caccgccgcc     660
accgtgacag gctacgccga tacaacaatc gccctggacg actccacctt caaggcctct     720
gctacaggcc tgggcggcac cgaccagaag attgacggcg atctgaagtt cgacgacacc     780
accggcaagt actacgccaa agtgaccgtg accggcggca caggcaagga cggctactat     840
gaggtgtccg tggacaagac caacggcgaa gtgaccctgg ctgcggcgc tacatctcca     900
ctgacaggcg gactgcctgc caccgccaca gaggacgtga agaatgtgca ggtggccaac     960
gccgacctga cagaggctaa ggccgctctg acagccgctg cgtgaccgg aacagccagc    1020
gtcgtgaaga tgagctacac cgacaacaac ggcaagacca tcgacggcgg cctggccgtg    1080
aaagtgggcg acgattacta cagcgccaca cagaacaagg atggcagcat cagcatcgac    1140
accacaaagt acaccgccga cgatggcacc agcaagaccg ccctgaacaa gctgggcgga    1200
gccgatggca agaccgaggt ggtgtctatc ggcggcaaga catacgccgc ctctaaggcc    1260
gagggccaca acttcaaggc tcagcctgat ctggccgagg ccgctgccac acaacagag    1320
aaccccctgc agaagatcga cgccgccctg gctcaggtgg acacactgag aagcgatctg    1380
ggcgctgtgc agaacaggtt caactccgcc atcaccaacc tgggcaacac cgtgaacaac    1440
ctgaacagcg cccgcagcag aatcgaggac agcgactacg ctaccgaggt gtccaacatg    1500
agcaaggccc agatcctgca gcaggccggc acatctgtgc tggcacaggc caatcaggtg    1560
ccccagaacg tgctgtccct gctgagagcc gtgcccgacc ctagactgca ggtggacgag    1620
cagaagctga tctccgaaga ggacctgaac gccgtgggcc aggacacaca ggaagtgatc    1680
gtggtgcccc acagcctgcc cttcaaggtg gtcgtgatca cgccatcct ggccctggtg    1740
gtgctgacca tcatcagtct gatcatcctg atcatgctgt ggcagaaaaa gcccaggtga    1800

<210> SEQ ID NO 4
<211> LENGTH: 498
<212> TYPE: PRT
<213> ORGANISM: Artificial Sequence
<220> FEATURE:
<223> OTHER INFORMATION: Bacterial flagellin (membrane-tethered)

<400> SEQUENCE: 4

Met Ala Gln Val Ile Asn Thr Asn Ser Leu Ser Leu Leu Thr Gln Asn
```

```
1               5                   10                  15
Asn Leu Val Lys Ser Gln Ser Ala Leu Gly Thr Ala Ile Glu Arg Leu
                20                  25                  30

Ser Ser Gly Leu Arg Ile Asn Ser Ala Lys Asp Asp Ala Ala Gly Gln
                35                  40                  45

Ala Ile Ala Asn Arg Phe Thr Ala Asn Ile Lys Gly Leu Thr Gln Ala
        50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Thr Ser Thr Asn Ser Gln Ser Asp Leu Asp Ser Ile
                100                 105                 110

Gln Ala Glu Ile Thr Gln Arg Leu Asn Glu Ile Asp Arg Val Ser Gly
                115                 120                 125

Gln Thr Gln Phe Asn Gly Val Lys Val Leu Ala Gln Asp Asn Thr Leu
                130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
                180                 185                 190

Asp Thr Thr Ile Ala Leu Asp Asp Ser Thr Phe Lys Ala Ser Ala Thr
                195                 200                 205

Gly Leu Gly Gly Thr Asp Gln Lys Ile Asp Gly Asp Leu Lys Phe Asp
        210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
                260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
        290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asp Thr Thr Lys Tyr Thr Ala
        340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
        370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
                420                 425                 430
```

```
Phe Asn Ser Ala Ile Thr Asn Leu Gly Asn Thr Val Asn Asn Leu Asn
            435                 440                 445

Ser Ala Arg Ser Arg Ile Glu Asp Ser Asp Tyr Ala Thr Glu Val Ser
    450                 455                 460

Asn Met Ser Lys Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg Ala
                485                 490                 495

Val Pro

<210> SEQ ID NO 5
<211> LENGTH: 67
<212> TYPE: PRT
<213> ORGANISM: Artificial Sequence
<220> FEATURE:
<223> OTHER INFORMATION: PDGF transmembrane and cytoplasmic peptide

<400> SEQUENCE: 5

Asp Pro Arg Leu Gln Val Asp Glu Gln Lys Leu Ile Ser Glu Glu Asp
1               5                   10                  15

Leu Asn Ala Val Gly Gln Asp Thr Gln Glu Val Ile Val Val Pro His
            20                  25                  30

Ser Leu Pro Phe Lys Val Val Val Ile Ser Ala Ile Leu Ala Leu Val
        35                  40                  45

Val Leu Thr Ile Ile Ser Leu Ile Ile Leu Ile Met Leu Trp Gln Lys
    50                  55                  60

Lys Pro Arg
65

<210> SEQ ID NO 6
<211> LENGTH: 7184
<212> TYPE: DNA
<213> ORGANISM: Homo sapiens

<400> SEQUENCE: 6
tttcgctttc attttgggcc gagctggagg cggcggggcc gtcccggaac ggctgcggcc      60
gggcaccccg ggagttaatc cgaaagcgcc gcaagccccg cgggccggcc gcaccgcacg     120
tgtcaccgag aagctgatgt agagagagac acagaaggag acagaaagca agagaccaga     180
gtcccgggaa agtcctgccg cgcctcggga caattataaa aatgtggccc cctgggtcag     240
cctcccagcc accgccctca cctgccgcgg ccacaggtct gcatccagcg gctcgccctg     300
tgtccctgca gtgccggctc agcatgtgtc cagcgcgcag tgagtactca gcccgccagg     360
tctttggctc gctcgggtgc ggaggggcgg ctgcttggga agagtgggta gaaactcaag     420
tctgcctaag gagagactgg aacagcagca gccgtctcct gcaaagagga ataagaatag     480
gggtctcacc gtgtgctaaa tagggcatgt ctcttttcat ctcgaaacag cctgatgagc     540
tatcattatg cccacttcgt agaggagaaa ctgaggccca gcgtgggaga tttcctgctt     600
tcctgcctag ggtccctcag ctacaaacag aaggcagatc ctagccagtt ctaaagtcag     660
gcttggccgg gtgcaatggc tcacgcctgt aatcccagca ctttgggagg ccaaggcgga     720
cagatctcct gaggtcagga gttcaagacc agcctgacca acatggtgaa accccgtctc     780
tactaacaaa tacacaaatt agccgagtgt ggtggtgggt gcctgtaatc ccatctactc     840
gggagtctaa ggcagggaaa attgcttgaa ctcgaggtg gaggttgcag tgagccaaaa     900
tcgtgccact gcactccagt ctgggccaca gagtgagact ccgtcttaaa aaaacaaaaa     960
```

-continued

```
aagtcaggct ttctcactcc actgttttta aaacactggg tcccaagtct gactcagcca      1020
cttcaccacc tggtctgggt ttccctgatc aaaaacatgt aggctttctc tgggtgagtg      1080
ttgggttcaa caccettgtc caagctcatc tctagaccct cacagggagc tggcttctag      1140
ccctagaata gagtggcgct ttgtaataac tcgagtcatc tctcaggtgt tgaaggaaaa      1200
gtgttggaaa tggggttgagg gaggtgggtg ccaagcatga atggatgggt gaaggtggcc      1260
agaatggagg gaaggtggtg caggcaggcc atccaggctg aagctcctcc acctgctcct      1320
cttccttcca ggcctcctcc ttgtggctac cctggtcctc ctggaccacc tcagtttggc      1380
cagaaacctc cccgtggcca ctccagaccc aggaatgttc ccatgccttc accactccca      1440
aaacctgctg agggccgtca gcaacatgct ccagaaggtg agcctttcct gtcctctcca      1500
ctgtggacct gcaccctccc tgaggaaggg gcctctgatc ctcccctctg gtacctgatg      1560
gaactgcaga gaaattgtgg aagttcatta gcagctgtca acagcaggag agggaacttt      1620
acaaatggcc caagtgttaa agagtcctag tgaaattgtg tctccagaga agcaagagt       1680 agtaataaat tataatgatg ttggttttgg ctatgtctac actgagtaaa gtggatattt      1740
gcagtgttcc tgtagcctgc caacagagat agaattgtgt caggtccaca tggtttctct      1800
ggcaccacac cactgatcaa tcccggaaat agttacttgg gtgcatactc tgtgttgggg      1860
ggcaggggta caaagatgaa atagccttgt ccctcctgct gcccaccagc ttctacttgg      1920
tgacacagtt ccttcttgga gcaacacatc tcagggagga ctatgacagt gcacatgcag      1980
ccttcatttt ctaggaagaa gttacctaat tttatttaca gcttcgttct tttaggtttc      2040
atattttaat gtaaaaaaca ttgccgttaa aaactgctcc agtagctact gctgcaaagg      2100
ctaaaggcta atgttttaaa agatgtcctc tgcctttctg ctctctagga attttttctt      2160
gagtattttc tagcttgttg ccttaggaat atcttaaaat aagctcaatg ccaccaagcc      2220 ttccttaaagg gctcctttcc cctttcaatc tttcataatg tgctgtgcat tgctcctcac      2280
aattcaatta atcttaattg gacaggggc tcaagtgaaa actgctttgt ttcccgaaga      2340
aaggttcaaa atgggtaact tttaggtgct ccaattcata tagattttt tgtgcaaaag       2400 ctgacacccc tactcccaga tatagtccta agggtcaaaa gattatagaa atcaatttaa      2460
tgttttgtac atcatttgtc aaatttgctg tagtagaaaa caaatgaggt agatgcaagt      2520
gattcaccgg ccatatccag ggcacaggtt tgtagaattt gggctatatg tttattttt       2580 agtttgatgc cattcaaaaa ccaaacattt caattaagat ttcaaaattc tagcttctct      2640
tgaaaagatc tgaagaacaa cactggactc acacctccaa atctaactct ttataacctg      2700
ctcagaatag tggggttgcc caggtctgtt taaacacctc cgggaatagt gtattcattt      2760
cctactgctg ctgtcacaaa tgtagtgggt ttaaatgaca caaatttatt atcttacagc      2820
tctgggcatc agaagtccaa aatgggtcct actgggctaa agtcaatgtg tcagcagagc      2880 tgtagcccectt tctggaggct cttggggaga atctgttgcc ttgctttgtc aggtctagag    2940
gctgcccaca ttccttgact tgtggcccct tccattgtcc ataccagcaa tgtctggttg      3000
agtctttctc atgctgctcc ctctggactg accttctacc cgcttctact tttgaggaca      3060
ctgcttacac tggattcacc cagataatcc aggatcatct ctctactctt agatcagctg      3120
attagcaaat tgaatgtcat ctgcaccttc attcctctttt ggcaggtcac atagctcatt     3180
accgggttcc agggattggg aggtggatgt ctttggaggt ggagaattgg tctagctacc      3240
acagaaaggg attttactac ttgtgcccaa acgtattctg aattttcagg ccttgcttct      3300
```

```
tggctcatgc tgttacctct gtctgaaatt tccctcctcc attgtcgaca ctttactcct    3360
cttaatgtgg gtgtcccaac tctaggaagc tttgcttccc ttcctgcccc tcctcagaag    3420
cttcatgccc ttctcaccat gtctcaccta ctgatgcctc ctggtcattt gggcaattgt    3480
ctgtctcagc agctaaactt gcaatccagg agggtataca tggtcctctt ctctgtcatg    3540
ttcttagtac ctaatggagt gcctgccacc cattaggctg ttgaatggaa aaatgatcgt    3600
aatcttcaat catacagtcc tttacttcct aagatacatt tcataatttt acccaacggt    3660
gctttccaac acactaagat gacatctctg tgtatgtgtg tgcgtgtgtg cactgcaaat    3720
taaatctcag cttgtcttaa gggtttgcat gtttgttata tccatcagac tgtgaccttat   3780 acagttcccc ctttagaagt tatacttgaa ataggtattc atagaataca gtcactttag    3840
caaaagaaga aacaattttc accagaagca agtgtcacag tgaggtgtgg aggctggtta    3900
gcacaggctg ttgacatgat ttattgtgtt tacataatga aaaaatatgt aatccagaga    3960
aacatgcccc aagcttaggg agaggagggt gagagacaga atgtaaggaa tctattttct    4020
tttgtattat gaagaaccag aatttcctgc aagtcaaagt gacagaggtc aagggcagcc    4080
agccggagcc ttcctggcac cctggcttac cagccttgtg gggtgccagg tgcattatca    4140
atgttataaa ctgagtttct ccttcatttt ttataggcca gacaaactct gaatttttac    4200
ccttgcactt ctgaagagat tgatcatgaa gatatcacaa aagataaaac cagcacagtg    4260
gaggcctgtt taccattgga attaaccaag gtataaagga ttttcctccc agagcatgca    4320
gtgtggttaa aaactgtgca tcaaatctca cctgcttcta aaaattcacg tttctggtat    4380
ccatcattat gggattttaa ctggtcctac ttcagaagtt agatttggga gaaaaattat    4440
ttttaaaaaa tggttttttt tgcaacaatg tgaatacact taacacttaa aaatagttca    4500
gatgctaaat attatgatat gtgttttac cataataaaa aaatttgag acctgaagag      4560 tcagaaagat ttatactaag aattaatact ttgatatatg attttttccc tctagaatga    4620
gagttgccta aattccagag agacctcttt cataactgta agtcaaaaaa tgaaaagttt    4680
cagcctgtat gatgaattca tatcactgat gtctgattat ttttccctct agaatgggag   4740
ttgcctggcc tccagaaaga cctcttttat gatggtaaga cacacagctc tttcctcaaa    4800
tgcaatgggg gaaatgtttt tagcccatct caatggatac ttccccatct tgtcatgtca    4860 cccaggcccct gtgccttagt agtatttatg aagacttgaa gatgtaccag gtggagttca   4920
agaccatgaa tgcaaagctt ctgatggatc ctaagaggca gatctttcta gatcaaaaca    4980
tgctggcagt tattgatgag ctgatgcagg taagacttca ttctatcagt gagagcacct    5040 tttttcatgct aaagataacc agccagggtc tttgataaag agatataaaa agaggtctgg   5100 aggccttttta aaggcctgac agacctacat tttcaagaag acagccttga gggtgccgtc    5160
tatagggagc acaaatgtga gcagatcaca ttatgaaaag cagactccaa agtattcact    5220
ctgtggtatc ccccacactc ggcaaatgtt tttgtgcatt ttcttatgtc agcctcaaaa    5280
caaccatatg ggatctgcac aaaggaggga accaaacctt aggagagtta aaccacttgt    5340
ctgaggctct gcctcttaaa atccttcaag aggatttcac tacacttacc ttctcactca    5400
cctctaaagg ctccaggacg tgctccagga tgtgcatgca aggggccagt ttgcatatct    5460
gcaaatattg ctgggaaaca agcaagattg gtgcctgatt atgacccatt gtgaaccaaa    5520
atgtgaacca aataaaagaa tgacctatca tctgggcat ctataatgtt attcataggc      5580
aagaacttgc tttgttatgt tctgaatcac cataacacag atgctaatat aaaacaaata    5640
tttatataag cgagggtgac tgctttggtg acgaggacat gggataaaaa tatggtggca    5700
```

```
gaaatcattg tctgaaaagt aattgtttta cttttattct tttcgtgtgt gtgtgtgtgt    5760
gtgtgtgtgt gtgtgtgtgt gtgcatgtgc cagatttctt gtttgaaagg caatgagctt    5820
catccaagta tcaaagaatg ttagcatcta gagagctgta gttgctattt cattttagg     5880 accaagagtt gggtgatttg ggtgctagaa tcaattctac cagtaaccag acaactattc    5940
ccaagtcact taaccccctct gtgcctcagt ttcctccagt ataaaatggg gtgactttat   6000
tctagctttc ttttagactt tttgtgagga agatatgaaa gtatttattc atcaagggtg    6060
caaatgtaag gttttatatt ctgttatcaa atcaaagtgc taaacttggg aaattcattg    6120
ccaggtttat ctgacacaaa tggcatgtct tcagtaaaca ggcctgttac tgatagtgag    6180
ttctgatcaa tagcaatcca tcacctccct gtgctaaaca gaagtgggct ttttaatgta    6240
acatatataa aattaattag atattgcagc agatgtcatt ttaaaggaac tgtttctttc    6300
taagacacaa ctcccactga tgattttttc taaatagttt taagggtctt ttcagagctc    6360
attgaagatg gatgtgcttg gaaaatgagt atttcttttc tcattctgcc tggtgatctg    6420
gctgagagta gatttggatt gggtttagga gtggcataag ggactgagtt gcaggctctg    6480
agacatgtac tggcttcact cattttatg aatgaatatt tgaattttgg aataccatgt     6540
aagtcatgct tactgttcat tctcctaggc cctgaatttc aacagtgaga ctgtgccaca    6600
aaaatcctcc cttgaagaac cggattttta taaaactaaa atcaagctct gcatacttct    6660
tcatgctttc agaattcggg cagtgactat tgatagagtg atgagctatc tgaatgcttc    6720
ctaaaaagcg aggtccctcc aaaccgttgt cattttata aaactttgaa atgaggaaac     6780
tttgatagga tgtggattaa gaactaggga gggggaaaga aggatgggac tattacatcc    6840
acatgatacc tctgatcaag tattttgac atttactgtg gataaattgt ttttaagttt     6900
tcatgaatga attgctaaga agggaaaata tccatcctga aggtgttttt cattcacttt    6960
aatagaaggg caaatattta taagctattt ctgtaccaaa gtgtttgtgg aaacaaacat    7020
gtaagcataa cttattttaa aatatttatt tatataactt ggtaatcatg aaagcatctg    7080
agctaactta tatttattta tgttatattt attaaattat ttatcaagtg tatttgaaaa    7140 atattttaa gtgttctaaa aataaaagta ttgaattaaa gtga                      7184
```

<210> SEQ ID NO 7
<211> LENGTH: 1450
<212> TYPE: DNA
<213> ORGANISM: Homo sapiens

<400> SEQUENCE: 7

```
tttcgctttc attttgggcc gagctggagg cggcggggcc gtcccggaac ggctgcggcc      60
gggcaccccg ggagttaatc cgaaagcgcc gcaagcccg cgggccggcc gcaccgcacg      120
tgtcaccgag aagctgatgt agagagagac acagaaggag acagaaagca agagaccaga     180
gtcccgggaa agtcctgccg cgcctcggga caattataaa aatgtggccc cctgggtcag    240
cctcccagcc accgccctca cctgccgcgg ccacaggtct gcatccagcg gctcgccctg    300
tgtccctgca gtgccggctc agcatgtgtc cagcgcgcag cctcctcctt gtggctaccc    360
tggtcctcct ggaccacctc agtttggcca gaaacctccc cgtggccact ccagacccag    420
gaatgttccc atgccttcac cactcccaaa acctgctgag ggccgtcagc aacatgctcc    480
agaaggccag acaaactcta gaattttacc cttgcacttc tgaagagatt gatcatgaag    540
atatcacaaa agataaaacc agcacagtgg aggcctgttt accattggaa ttaaccaaga    600
```

```
atgagagttg cctaaattcc agagagacct ctttcataac taatgggagt tgcctggcct    660
ccagaaagac ctcttttatg atggccctgt gccttagtag tatttatgaa gacttgaaga    720
tgtaccaggt ggagttcaag accatgaatg caaagcttct gatggatcct aagaggcaga    780
tctttctaga tcaaaacatg ctggcagtta ttgatgagct gatgcaggcc ctgaatttca    840
acagtgagac tgtgccacaa aaatcctccc ttgaagaacc ggatttttat aaaactaaaa    900
tcaagctctg catacttctt catgctttca gaattcgggc agtgactatt gatagagtga    960
tgagctatct gaatgcttcc taaaaagcga ggtccctcca aaccgttgtc attttttataa  1020 aactttgaaa tgaggaaact ttgataggat gtggattaag aactagggag ggggaaagaa   1080
ggatgggact attacatcca catgatacct ctgatcaagt attttttgaca tttactgtgg   1140 ataaattgtt tttaagtttt catgaatgaa ttgctaagaa gggaaaatat ccatcctgaa   1200 ggtgttttc attcactta atagaagggc aaatatttat aagctatttc tgtaccaaag     1260
tgtttgtgga aacaaacatg taagcataac ttattttaaa atatttatttt atataacttg   1320 gtaatcatga aagcatctga gctaacttat atttatttat gttatattta ttaaattatt   1380
tatcaagtgt atttgaaaaa tatttttaag tgttctaaaa ataaaagtat tgaattaaag   1440
tgaaaaaaaa                                                          1450

<210> SEQ ID NO 8
<211> LENGTH: 253
<212> TYPE: PRT
<213> ORGANISM: Homo sapiens

<400> SEQUENCE: 8

Met Trp Pro Pro Gly Ser Ala Ser Gln Pro Pro Ser Pro Ala Ala
 1               5                  10                  15

Ala Thr Gly Leu His Pro Ala Ala Arg Pro Val Ser Leu Gln Cys Arg
             20                  25                  30

Leu Ser Met Cys Pro Ala Arg Ser Leu Leu Val Ala Thr Leu Val
         35                  40                  45

Leu Leu Asp His Leu Ser Leu Ala Arg Asn Leu Pro Val Ala Thr Pro
     50                  55                  60

Asp Pro Gly Met Phe Pro Cys Leu His His Ser Gln Asn Leu Leu Arg
 65                  70                  75                  80

Ala Val Ser Asn Met Leu Gln Lys Ala Arg Gln Thr Leu Glu Phe Tyr
                 85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220
```

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250

<210> SEQ ID NO 9
<211> LENGTH: 15691
<212> TYPE: DNA
<213> ORGANISM: Homo sapiens

<400> SEQUENCE: 9

| | | | | | |
|---|---|---|---|---|---|
| ctgtttcagg | gccattggac | tctccgtcct | gcccagagca | aggtaagcac | ttcccaagcc | 60 |
| cctacctccc | tcccctccct | gtgggcctgc | agctgtccag | gtgtagaaac | cgttagtgtg | 120 |
| ctaccccagc | agctggcagg | agggagttgg | tggattcctg | gaagcatccc | tggtgagtca | 180 |
| tctgctggaa | cattagtgaa | aacttagtac | tctagggacc | gatgtacagt | gtccatttta | 240 |
| aaagccacct | aataataact | gtatagcaag | atctgtgtgt | atgcatagtt | tgtggaaatg | 300 |
| tttgttttat | cttattttga | agtggtgtgt | attgatgtat | aaaagtatat | tcctaaatgt | 360 |
| taatgcccat | cagttaaagg | attgtataga | gctaaagtga | gtggtgcctg | ccttactatt | 420 |
| gaaattttta | aaaagccttt | cgtgcattcc | ttaaagtaat | tggattcata | attataataa | 480 |
| tgttacaaat | cagacttgct | cccatatttg | tgatggtctt | ggtcgtcagt | tgtgatatca | 540 |
| accaaaatga | cagctgggat | ccccattctt | gtggattaac | taactttggc | cccagttaaa | 600 |
| aaatgaaaag | ctattattgc | ttcctaaaga | gttttttaaat | ctgtgagaag | ggggaaaaaa | 660 |
| aggtttttt | acttgcccag | gtaaaattgt | gtgcaacaac | aatgtcattt | taacaaaggg | 720 |
| attactaaac | cccaggtgat | gacccacttt | tcaaacaag | gaattgcaag | atactagatg | 780 |
| gaatgtgggt | aacctcttag | agtttagttt | actggaatct | gaaattgtat | gatttccgta | 840 |
| cattccttca | tgctactaat | aagtcatgga | atccctctgt | gctggactct | gggggtaaag | 900 |
| tgcaaaacaa | gatagacatg | atccatggca | taagagagtt | cactcagtgt | ggcagagaag | 960 |
| acaaacagta | aagaagagac | tgtattgttg | ccattgtagt | aaatgctgtg | gaaggagggg | 1020 |
| agcaaatagt | gggtcctgac | ttcatctagg | caccatgaca | cttcacgtga | attatgtcac | 1080 |
| taactcctta | ccacagtagc | atgcccattt | tatagatcag | gagtgtgggg | cttaaagggg | 1140 |
| ccaagtgact | cacccagagt | cacacagttc | tagaagtctg | cctggccctc | aaactaggga | 1200 |
| tctttgcatg | tgccacccat | gccatctgtg | actatatctt | tttattcttt | aataataact | 1260 |
| cccttttcta | attaaaggta | acaaacaaaa | cttaaaaaag | agatgcccac | ccaagcgtca | 1320 |
| ttggcatgct | gatgttggca | ccagtgttgg | gaagccctta | gcatactcca | ggaagtagga | 1380 |
| gtgtgtaacg | tggggtccct | tgtccttca | tgcaagggtt | tcaagagttt | agaaaaccta | 1440 |
| tgaaattgca | cacacaaaaa | tgtgttttaa | tcatcaagac | tctcagactt | accatgctga | 1500 |
| gaaatgtggg | ctgagggata | gcgctcccta | gtatcagctg | atgggccaga | gagccaaagg | 1560 |
| aggagaccca | ccaccatcac | ctctcctgga | cagtgctctg | tggtttcaaa | tgtaggtgat | 1620 |
| actaaaatgg | gagttgcttc | ttagaaccat | ggccggggtt | cccttgaccc | tgaagtgcag | 1680 |
| ttcacctgag | attgtcaaat | gcatctgagg | catgcagagg | aagtgctggg | cacacagcta | 1740 |
| gtgggaatac | ctcagcgtaa | gtggccagga | gatgccagga | atctccacta | tttcccttcc | 1800 |
| agtgtgccag | cctctgggtt | ttacaggcgc | atgtaattgc | agtacctctg | tgcacatttc | 1860 |
| cctactgcct | agaatgactt | tcttgactat | ccatgatata | taaaacacag | ataccgaatt | 1920 |

```
gttcccttac ctcttcctct aggttcaagt taatatgtta ttggttgcct tctataatat    1980
gttatctcat tgccttccc aacaagcctt tgagataagt attaggtcca ttttatagac     2040
aaagagactg aggctcagcg agtaacttgg ccaacaagtt gctcccactg ctcaacagca    2100
aatgagcggt gggaccaaaa ttcaagcctg tgtctgttta acttcaagcc tgtgaatgta    2160
ctaaccggtg ccctgtgcca gctagtactt tgctacagtc ataacctaga ctgaagtgat    2220
agccatgccc ctaaaactcc atgctgtggt gacagcactg agcagtgtcc aagaaggctt    2280
gacttctagg cctgtctctg ccactcacaa actttataag ggaataaagt acatagcaag    2340
gtccgcctag agttagtagc agttctgaca aagctgtaat ttgtcaatat tccgtcaccc    2400
aacccaggaa tgctcatttt taaggtattt gactgaaaca gttgagcatt gcccttcata    2460
tagtttaaaa cagtggtttc agaaccactt tcctccagac catgggtgct ctgcaaggtg    2520
aatggagttg tttcagaatg tttcaataat catccctacc tcattcgtaa gtggcatgta    2580
atttttgcaa tcggaagatt ttcataaacc ctggatacta acctagactg gtttctatat    2640
cagatggtgg cttatttaac ataaaattat gcatttact atttcatggt ggatatatca     2700
atatgttgtg gtcttttccc aatgaacact tgattttca ggggttctgg accctgaaca     2760
tgggttaaac cagtggttct caaggtgtgg tcttagcgcc agcagcatct gcttcccctg    2820
gaaactttct agaaatgcat attctcaggc cctcatgcct gctgaatcag acactctggg    2880
ggtgggactc agccgtctgt tgtagcagtg cttccaggtt atcctgacag tcactcaaat    2940
tttagaacca ctaggttctc tatatgggag agagtagtct ttgaacttgg aaaacaagag    3000
aagctaaacc cctacagcaa gggctggtga ccaggtcgtt gccagaacct gaaagttcgc    3060
ctctgtatta ccgttcctgt ccctaaccca agtccttcag ttctgggtgc tccagcacac    3120
actgctttgt gctgcagtga tacaaatgta tggctcatct ccccagctgg cggggaggca    3180
tttaacacac tgacttaata aatatttatt gagtaaaagt atttgctcct aggaagcggg    3240
atccaggtaa gccctttttt tctctctcaa ctgcttctag cccagtgctc tttatgtagt    3300
aagcactaaa taaacaactg ctagatgttg atccagaaag tcacattcct tctctaagct    3360
ttaagtttct catcttaaaa ataagaggat tgtatcagat ggcttgcctt aggtctcttt    3420
cagctccaga gccccaaata ccctatggtt ctctatttag agatgttctt ccccacagac    3480
tgccatagaa ctcctgtaat ttacttagta tttgcttgac agtatggaga agaaggggga    3540
gaatcaagat tttatttaaa aaaaagtag ctagaatgtg tatatggttc acaaaggtaa     3600
caagaattat tgacattctt tcttctcttt tttcttcctc ttccttctct tttcctcctt    3660
ctcttccccc tgcttctctc ccttcttata gatgtgtcac cagcagttgg tcatctcttg    3720
gttttccctg gtttttctgg catctcccct cgtggccata tgggaactga agaaagatgg    3780
taaccagcct ctcattattc tctgtggagg ccccacttct aagccaggac tcttgggcag    3840
ccactggtgg gaaatcaaac tgaaatgggc aaccatgcac tgggtcctct agagaaagcc    3900
atcactctgg gaaaatgcaa tgccatatct ctctttctcta ctttgatggt atctatattg    3960
tttggttttc acattggatg acattggtac actatggtgg ggaaagacat atgatatatg    4020
atatggtggg gaaagacata tgacatatga tattttccaa tattactaaa aactgtttca    4080
cacaattaaa attccaaagt agaggatttg caaagtataa caactgtgtt cgtttctcat    4140
tccaccacat gatactgccc cctcagttgg cactgtgatg acttacctct gaccaagcac    4200
tttggaggaa gcataggatt cagactcaca ttgacttggg ttcaagtcct aggtctgtca    4260
atgactggtt atgtgacttt aagctgggtc acctctaatc ctgaatttcc tcaactgtaa    4320
```

```
actggatgtt acaaagtgga tgcctaccac gtgggttatt tagtgggtta atgaatgcag    4380
aatacaactc gacagatagt aaagtgaaag taaatgtcag ctagtattac tattttggtt    4440
gtttaaaata tctttcatga ttcaagagat acttttatt atcccaatga tcagtaaaaa     4500
ttattagtag actaatagaa tagttaatgg taaaataagg agttctgccc atccttctag    4560
tatctcacac tcagtaaatg tgcattctga ccgttggctg tacctgaaag accctcagat    4620
ttttatcact gaagccaaca tcataatgtt ggcgattact atctttaatt gtataataat    4680
aatagttaat gtttattgag tgcactgtct cacttaattc tcacaagagc catatgaagt    4740
agagactgtc tgtatcccat tttacagatg ttggaaactg aggccagaga gattaagtaa    4800
cttgcccaat gtcacatacc tggtaagggt ggaacaggga cttgatccca attctgtctt    4860
gcttcaaagc tggtgcactt aaatttgtga aacgttttt acaaggacat gaagtaattt      4920
tttcccaggt ctttggagag ctgaataaga ggaaatggac ataaattaag gatgaaaata    4980
tttcagctga tgatcagaaa taatcttttg atattctaga aagtaccatc ttgaaatggg    5040
tacctgaaag aaatctggga ccactcctct cttctcaaga attttaggaa gacagaatcc    5100
agccacccct tctccatgag aatttgagag atttagacac tctcttaagt aaaggcaaag    5160
gcctgagcca ggggtatatg gcagatccct tccaaccctg ggattgttag cgagctcagg    5220
aaccttggtc ctggcatatt tgacccctta gtgacttctg atttggtaaa ccacagaaat    5280
tccagaaaat cagtgtgaga actctccga ggtgtgactt aggagggcag acgatgcagt      5340
gaggctaagt gccaggttct tgatgctcct cttcagcttt cctcctgcag ctgttttccc    5400
tgctgttgag caaacatctt ctagggcttc cgagcctcag ttgggacagg aaagtaacca    5460
tgctcttcag gtgtcagggg gacaaaaaaa aaaccaagaa aaagccaaaa gtgccacatg    5520
gttttacatc agcacagcta atcatttccc cagagttgga ccccaaatgc ttttgacctc    5580 ttattttgt tatccattca gtccttataa tccaattgat gtaaagtgaa aactttatat      5640
tctacaatgc tttacatcca gaggccaata acgagaacca ccatttataa agcatgtaag    5700
ggcactgtgt atgagcttat ataatccaca tatccacctt ctaaagcaag gctaatatt      5760 tttctcattt taaagatgat gacactgagg cttacagtag ttgaatgtct tgccaaaggc    5820
cacaagactg gagcaagggc tagagctgct tctaaatcca ggcctctgcc actccaaaat    5880
gcaggctctc aaccactgtg actcataaac ttgagcaggc atcagcacca tctgagagc     5940 ttaagaacca tataactaaa tccatcccaa ggtttctgat tcagcagctg agaatttgca    6000
tttctgatct attccaaggt gatgctgctg atggtgtttc atcgatcatg ctttgggaac    6060
tactacatta aacaattcta ttcaattaat aatttatgca tggattaaaa aaatgaatga    6120
agctttgcta tgcacactc tgaaatacta tactaagcca ttcctcaaag gccagtttag      6180
acactagcat taggcatccc ttgcaaagcc aagagacaa aaggtctgag ctgtagccct      6240
tgtacttctg acttgctgtg accatgctta gatcgttggc ctcagtacgc ttcttcatta    6300
aatgggaaga ctaagctcta ctggactgct tcataagagt gtaagatagc taaaaataat    6360
aataataata ataataatgc agagagaatg aaaatctcca ctggtgattt aaaacagagg    6420
gaacgaaatc cttaaatatc catggaaaat tgttaagaga gtttctctgt acagttggct    6480
gactcctcag tctataagta acgataacta acaccgaatt tactgtgtgg cagacactgt    6540
gctaagtact ttacgtgctt ttttttttt tcatttaatc ctcagtcaaa tgtaaggcag      6600
atactgttat tattatcatt ttacagatga ggaaactgag gctcatgata atgaaatacc    6660
```

```
ttgttccaaa tcccccagct ggttagtgga gacaggatga cagtcttggt tcgttgttct    6720
cgacaccctg agcttttaac cactatgtta ctctgctgaa tattgtgccc tgccgtattc    6780
tctatgaaac tgaaattgtg ctggaagttt ctctccccca gcctttggc aaagagtctt     6840
gtgctgtttg cagttttggg tatattaagg tgtttccaat ctgctaaata atcaaaggtt    6900
actattaaag gcagccttcc agtcaatgag tcgatggcag ctataaaact ctttgtttct    6960
cttttccatg accttgagcc caagcagggt ctcatgcctt gagatcatct cagcaagcat    7020
ttgccaaata cttgttgtaa acaaggttgt gtttaggcaa tggggatgcc cgaagggtta    7080
ataaaacaca gtcccagagt tcctggagct tacagcctgg ttctccactt tatgtgcatt    7140
ccagtttatg tcgtagaatt ggattggtat ccggatgccc ctgagaaat ggtggtcctc      7200
acctgtgaca cccctgaaga gatggtatc acctggacct tggaccagag cagtgaggtc      7260
ttaggctctg gcaaaaccct gaccatccaa gtcaaagagt ttggagatgc tggccagtac    7320
acctgtcaca aggaggcga ggttctaagc cattcgctcc tgctgcttca caaaaggaa       7380
gatggaattt ggtccactga tattttaaag gaccagaaag gtaattctat acccttggat    7440
agtatcaatt ttctctttcg ctcataagag ttaaaaacaa caacaacaac aaattgaaaa    7500
gccaagtcat ggtgagtgta atgaattaac atcaagtctc ttattgatgt taattgatgt    7560
taacctccat tttcctttgc tttcctggac cctttgggtt atcaaccatc aaaatctcat    7620
attaagggag tttcatgatc agtctgaatg cttagcctca tgttttcttt aaataatggt    7680
gatattattt aatggctaat ggaaattaac cgatagtgta tcactctgca ctggggtgat    7740
agccttcaaa aaatgaatgc ctctgccagg catgttaggt gtgtagtgta ctctgcagaa    7800
tcaacacccc actgggatac tcccaatcct tatggagcta cccaagaggc aacgcatgga    7860
agaacttcac cctgtaccat ctggtgatct gtgattcatc acaatcaaaa cctttctgca    7920
aaaaactcct aaatattgaa ttttgtttt tttcaaatcc agaacccaaa aataagacct      7980
ttctaagatg cgaggccaag aattattctg gacgtttcac ctgctggtgg ctgacgacaa    8040
tcagtactga tttgacattc agtgtcaaaa gcagcagagg gtgagtgaaa ctgctctggt    8100
ttctcagcat ttttctagaa ctatttcatt aagaaattaa gggcaacctc tcagtgacct    8160
atcagttaat gataatggga aaagcaaagt caaacccgtg ttttttcaac cgcccttcct    8220
tgtctacatt gaagaaagaa catggagatt ttagccgatt gcttgaataa atgtatgtgt    8280
tggggcagga tattattggg aactgagaat agtctctgct gtgtttgaac ccactcatcc    8340
aaattgcctg gccatgcttc ctgaagcctc atagcaccaa agaaagggat aaacggagaa    8400
ttcaaagcta caaatgactt gctgaaattg caccttgagt caaaaataaa aacaagagct    8460
ccagggcgta gatcttaggg gccctgaagc agactccaaa actcgatgag gcctcccgaa    8520
attttcccag ggccacctca actccttta cttctgctga caccactaat ctgaagttcg      8580
ctgttggtcc aatgcacctg gactttccgt aagaaagcaa cttccataaa tacaagacct    8640
atgtgttaac ccccatgtgg cttactttaa tcatcaccga agcaaacccc aggtgatcat    8700
cctgacttta ccattatttc actgagtaaa ttaagcattg gggtctcact ttttcatctt    8760
taaaaggaaa atgcttacta agaaatgtt tctccaagtg cataaagaca taatcagcag      8820
aggaatggtt aaataaaaca tggtacacta tactcttgct taatgtgcag tcattgaagt    8880
ggataaccca acccatatgt tttgtcatgg agagctcccc ataatatgtt cagggggaa      8940
aaggatggtt acataatcat atgtatacaa tttgatccta gttcataaaa ataaaatcta    9000
tatgtataag taaaatatat atagtggata tatataatgt agagatgtat ataacatgga    9060
```

```
ttatatatat aatgtgtgta tacatatgtg tgtgtgtgtg tgtgtgtata tatatatata    9120
tatataaaat gtgtatacaa ttatcttgaa tattcattga aaaagttctg gccaggcaca    9180
gtggctcaca cctgaaatcc taactctttg ggaggctgag acagaatgat tgcttgaggc    9240
caggagttca agaccagcct aggcaacaca gtgagacccc atctcagaaa atattaaaaa    9300
taaaaaaatt aggtgggtgt ggtggcacac acctgtagtc ccagctactt gggaggcaga    9360
gggaggggat cacttgagcc taggagtttg aggctacagt ggggtctgat tccaccactt    9420
cactccagcc tgggtggcag agcaaaaccc tgtctcttaa aaaaaaaag agagagagag     9480
agagaaagaa aaagaaaaag gaaggtctgg aaggatacaa caagctatta ttagtactta    9540
aacctgtgga gagcagttaa ggatgaagga gacatacact tctttccttt atatggatct    9600
ttatcatctt tacttttata attagtgtgt actgatttgt gtattgatttt tataattaaa   9660
atgggaaaaa atgaatttaa gttttttaaca aggggggttta ataatcagag attctagatc  9720
taaaacaaac aaaaacttcc atattcattt agtccagaga catgtaagtg ctcttgaatt    9780
taagcttttt ctcctgggga gggcagtttc ttaccctctg ggtagaaatc agcccagttg    9840
gagaaactgt gtcctcagac aacagttgag gccttacctg ccttactggc tacaatcact    9900
aggaactctc tccccaatgt gtaacacagg ctaatttctg tctttgactt cagctcttct    9960
gacccccaag gggtgacgtg cggagctgct acactctctg cagagagagt cagagggggac  10020
aacaaggagt atgagtactc agtggagtgc caggaggaca gtgcctgccc agctgctgag   10080
gagagtctgc ccattgaggt catggtggat gccgttcaca agctcaagta tgaaaactac   10140
accagcagct tcttcatcag ggacatcagt gagttttgga tgattatatg tgctccataa   10200
ggaaagatac tatttgtcac gtgttcacaa tgccccatgc actgtggggt aggtggttga   10260
caagcatcat ctcttttatt ctgcatccaa aaacaaaata cgatgtagat actgttatct   10320
gcattttaag gaagaggaaa ttgagtctta gaaaagttaa gcaacttgcc ccagatctca   10380
gatcttacag ctagccgttc aaatccagat ccactccact acagctgctc tttactgcac   10440
tttgattcag ctgccagata gtttccatga tgaatcccag agcctaatca agcataaat   10500
tcatattcag aaccagggct tccttactaa tgcaattat tcccaaccaa tccttcctta   10560
gcatttgaaa agggacttct ttcttagaat ataaaccctt ccaaaatgga catctttttt   10620
tttaattggc agatagggat ttcaccataa gtcatttcct ttactattta ttcattgacc   10680
aggcagcatg ataaagtgta atagaaccag agaacttgct tcaaaactta tggagggttt   10740
gtacttggtg ggtggggtct agttcacata gggtggccaa ggaaggcctc tctgaggagg   10800
tgacatttag ctgacaccaa aaggaaagat gtcagttgtg ttaagagcag agggaagcat   10860
atgtgcgaag cacctgctag gagccgtgat cttgtgtgg agcagtgcca ggcctacaga   10920
gcccaaccac acaccctagc atgtctctgc ctcctcttat ctagaagacc taattgagga   10980
aggagtcttt gtgaaactca ctgctgtatc cttcatgcac agtccagtgg ctggaacata   11040
atgggcgctc agtattcatg gaataaacaa gcaaattgag catagagaca attgactgta   11100
actgctccaa gacatgtccg caccaaaagc tatgaaaaga caaaagaaag ggcagtaaat   11160
agaaaatcta tcatctcatc cccagggaga ggctcagctt agttccatgt tcagtgcaaa   11220
gtgagggatt agcacagaca gggtggtcct tcaatgcatg gcccataacc attaaagcag   11280
aggtcttctc actgtgcggt cccatctgat tgttcagtga tgaggattct gagcatctct   11340
cagatcctgc aatacatgtg gatctgagat gtggccattg ataatgactg ccttcccgag   11400
```

```
gcaccagcgt gagcacctgc ggcagaggtg cctcacattt gccagccagg tgctcacaga    11460
agttaagtaa ctatccagtg gactcacagc tgatcaaagg tgcaagtgag atcataagcc    11520
aaaaccactg aactccaaag ccttattagg aaaataaagc atgtttatcc tcttccacag    11580
tcaaacctga cccacccaag aacttgcagc tgaagccatt aaagaattct cggcaggtgg    11640
aggtcagctg ggagtaccct gacacctgga gtactccaca ttcctacttc tccctgacat    11700
tctgcgttca ggtccagggc aagagcaaga gagaaaaggt aagaagtgat tcaggtgcag    11760
tatattcctt ggtcagtttt acggaggccc accataaagt gagaagatga atgatgataa    11820
taacaatgac atccatgtat cacttaacaa cagggataca ttctgagaaa ttcatcttta    11880
ggcagctata tcattgtgca acatatatg gtgtacccac acaaacctag atggtatagc     11940
ctactacgct tctaggcttt atggtatagc ctattgctcc taggctgcaa acctgtacag    12000
catgttcctg tactgaatac tgtaggcaat tacaacacaa tggtttgtat atctaaacag    12060
aaaagatata gcaaaatac aatattataa caatatagga ccactggtca tatatgtgat     12120
ccttctttga ctgaaatgtt attatgtgat gcataattac ttttcttagc acttttctat    12180
gtgtctagag ctgtgccaag ggttttccat gtttatttca cttaatctac aaaattaacg    12240
caacaaaggt agctgatgtt attcttgttt ttttaccccc tttttgtgg aaaagaggct     12300 ttccttttt ccagaaactg tggcaaggta agtaaagct gtagctgatg caggaatttt      12360
gtgtaggtgt tagcagcact gccctcacta cgtgctcatt ggacagtagc ccaaccccaa    12420
gaaaaggatg gttggtagcc agtagtatta tcatcatttc acaagtgatt gaagactcag    12480
agaggttaag tgactttacc aaggtcaccc agctaggaaa tgcataacc aagacataaa     12540 ctcaatctgc cagacagaaa ggccatgcac ctaaccactc cactacctct gatgttggtc    12600
attgatcttg gcactcagaa ttagtcctga tagaggagac ctgggctcca gaagcctaaa    12660
attgttgttt caactgagtg catgtaatga atgatagaac aggcaagaga tatcgccccc    12720
aaaatggata gctcctggct gttccagata ttataaaatt attttactaa acagaatgtc    12780
tacacttata gaggctaaga tattggcttc ccagcttcct caccttacag cagaattcct    12840
ttgcctgttg caaggttcca gaggcccttt tgtaccgccc cagactcctt tcaccccact    12900
tttaaaatca ctggacaaag ccctaattca gcatagcatt tagcatgtgg tagaaattca    12960
gtgagctagt tactctctgg gaaataatt aggtagggag gctatcctgg aatagatatt     13020
tacctaaata ttattttaca tcttggcaag tactttccct atttaagatc tgtatgacta    13080
ataggtgata ttgagtgctt cctatgtgct aaagacttgc taagagtttg acgtgatttt    13140
taccttgaac tataattcta tgaagtaggc attattgtta tccctattta aagtgagga    13200 aacagacaca gagaacctaa gacattttcc tgaagttaca cagctattaa gtagcagtgc    13260
cagaatttga aggcaagttt tctgatgaaa tgatcaggat atggtatttc tcaatatctc    13320
agggatggct agagcaaatc tgtctctctc tcaccatcag ctcaggactg ggtgagtggc    13380 catgggtct tgaggcaagg caattgtgct agaaagatga aagctgggcc aaacgatttc     13440
tccctcaagg gcttacaaag tacaaaagct gcacctacat gtggagtgtc tgccagtagg    13500
tggtgcaagt tctatgcaca cccctgtgaa ttgcaagcac agtgccctaa gaccaagatg    13560 ggcttgttt gggagagtat gcattgcaga aacaggctca gcttaccctg tgactatgtt     13620
gccaaggggt cttcacagct ttccttctct tttgcagaaa gatagagtct tcacggacaa    13680
gacctcagcc acggtcatct gccgcaaaaa tgccagcatt agcgtgcggg cccaggaccg    13740
ctactatagc tcatcttgga gcgaatgggc atctgtgccc tgcagttagg tgagcaggcc    13800
```

```
ctcaaaggcc agcccaggcc tgcactctca gtgcacctgg atgcagggat atgattgggg    13860
gctgtgttgg agaggaaagg gggatggagt ggccagcacc cagttgccag aatcagaaac    13920
atacatttat tcactaacag atatttattt ggtgcctttg ttatgtagga cactgtgctg    13980
gccacaggga tattgcagga aagaaaacag accggggttc tggcctccta agagaaaggg    14040
caaagaaaag agagaggtag ccaggaggca gagcatggag gacttgcaag cttgcaggac    14100
tcagaatctt gttctggggg ccccgggccc tgaaacccac tgaagggttt tcagcaagga    14160
agtaacacaa tcagatatta ttttaagaaa accctcaaga aagcctctgg caagcatggt    14220
gccagccaaa ttccaggcca cataaggaag gcctgggcct tctggcatga aatccctgaa    14280
acccagttgc ccaggatcat atgttgtgag aaataagaag agacattgct gttacaatgt    14340
caccccacat caacttttgg cattctcttc caggttctga tccaggatga aaatttggag    14400
gaaaagtgga agatattaag caaaatgttt aaagacacaa cggaatagac ccaaaaagat    14460
aatttctatc tgatttgctt taaaacgttt ttttaggatc acaatgatat ctttgctgta    14520
tttgtatagt tagatgctaa atgctcattg aaacaatcag ctaatttatg tatagatttt    14580
ccagctctca agttgccatg ggccttcatg ctatttaaat atttaagtaa tttatgtatt    14640
tattagtata ttactgttat ttaacgtttg tctgccagga tgtatggaat gtttcatact    14700
cttatgacct gatccatcag gatcagtccc tattatgcaa aatgtgaatt taattttatt    14760
tgtactgaca acttttcaag caaggctgca agtacatcag ttttatgaca atcaggaaga    14820
atgcagtgtt ctgataccag tgccatcata cacttgtgat ggatgggaac gcaagagata    14880
cttacatgga aacctgacaa tgcaaacctg ttgagaagat ccaggagaac aagatgctag    14940
ttcccatgtc tgtgaagact tcctggagat ggtgttgata aagcaattta gggccactta    15000
cacttctaag caagtttaat ctttggatgc ctgaatttta aagggctag aaaaaaatga    15060 ttgaccagcc tgggaaacat aacaagaccc cgtctctaca aaaaaaattt aaaattagcc    15120
aggcgtggtg gctcatgctt gtggtcccag ctgttcagga ggatgaggca ggaggatctc    15180
ttgagcccag gaggtcaagg ctatggtgag ccgtgattgt gccactgcat accagcctag    15240
gtgacagaat gagaccctgt ctcaaaaaaa aaaatgattg aaattaaaat tcagctttag    15300
cttccatggc agtcctcacc cccacctctc taaaagacac aggaggatga cacagaaaca    15360
ccgtaagtgt ctggaaggca aaaagatctt aagattcaag agagaggaca agtagttatg    15420
gctaaggaca tgaaattgtc agaatggcag gtggcttctt aacagccctg tgagaagcag    15480
acagatgcaa agaaaatctg gaatcccttt ctcattagca tgaatgaacc tgatacacaa    15540
ttatgaccag aaaatatggc tccatgaagg tgctactttt aagtaatgta tgtgcgctct    15600
gtaaagtgat tacatttgtt tcctgtttgt ttatttattt atttattttt gcattctgag    15660
gctgaactaa taaaaactct tctttgtaat c                                   15691
```

<210> SEQ ID NO 10
<211> LENGTH: 2347
<212> TYPE: DNA
<213> ORGANISM: Homo sapiens

<400> SEQUENCE: 10

```
ctgtttcagg gccattggac tctccgtcct gcccagagca agatgtgtca ccagcagttg      60
gtcatctctt ggtttttccct ggttttttctg gcatctcccc tcgtggccat atgggaactg     120
aagaaagatg tttatgtcgt agaattggat tggtatccgg atgcccctgg agaaatggtg     180
```

```
gtcctcacct gtgacacccc tgaagaagat ggtatcacct ggaccttgga ccagagcagt    240
gaggtcttag gctctggcaa aaccctgacc atccaagtca aagagtttgg agatgctggc    300
cagtacacct gtcacaaagg aggcgaggtt ctaagccatt cgctcctgct gcttcacaaa    360
aaggaagatg gaatttggtc cactgatatt ttaaaggacc agaaagaacc caaaaataag    420
acctttctaa gatgcgaggc caagaattat tctggacgtt tcacctgctg gtggctgacg    480
acaatcagta ctgatttgac attcagtgtc aaaagcagca gaggctcttc tgacccccaa    540
ggggtgacgt gcggagctgc tacactctct gcagagagag tcagagggga caacaaggag    600
tatgagtact cagtggagtg ccaggaggac agtgcctgcc cagctgctga ggagagtctg    660
cccattgagg tcatggtgga tgccgttcac aagctcaagt atgaaaacta caccagcagc    720
ttcttcatca gggacatcat caaacctgac ccacccaaga acttgcagct gaagccatta    780
aagaattctc ggcaggtgga ggtcagctgg gagtaccctg acacctggag tactccacat    840
tcctacttct ccctgacatt ctgcgttcag gtccagggca agagcaagag agaaaagaaa    900
gatagagtct tcacggacaa gacctcagcc acggtcatct gccgcaaaaa tgccagcatt    960
agcgtgcggg cccaggaccg ctactatagc tcatccttgga gcgaatgggc atctgtgccc   1020
tgcagttagg ttctgatcca ggatgaaaat ttggaggaaa agtggaagat attaagcaaa   1080
atgtttaaag acacaacgga atagacccaa aaagataatt tctatctgat ttgctttaaa   1140
acgttttttt aggatcacaa tgatatcttt gctgtatttg tatagttaga tgctaaatgc   1200
tcattgaaac aatcagctaa tttatgtata gattttccag ctctcaagtt gccatgggcc   1260
ttcatgctat ttaaatattt aagtaattta tgtatttatt agtatattac tgttatttaa   1320
cgtttgtctg ccaggatgta tggaatgttt catactctta tgacctgatc catcaggatc   1380
agtccctatt atgcaaaatg tgaatttaat tttatttgta ctgacaactt ttcaagcaag   1440
gctgcaagta catcagtttt atgacaatca ggaagaatgc agtgttctga taccagtgcc   1500
atcatacact tgtgatggat gggaacgcaa gagatactta catggaaacc tgacaatgca   1560
aacctgttga aagatccag gagaacaaga tgctagttcc catgtctgtg aagacttcct   1620
ggagatggtt tgataaagc aatttagggc cacttacact tctaagcaag tttaatcttt   1680
ggatgcctga attttaaaag ggctagaaaa aaatgattga ccagcctggg aaacataaca   1740 agacccgtc tctacaaaaa aaatttaaaa ttagccaggc gtggtggctc atgcttgtgg   1800
tcccagctgt tcaggaggat gaggcaggag gatctcttga gcccaggagg tcaaggctat   1860
ggtgagccgt gattgtgcca ctgcatacca gcctaggtga cagaatgaga ccctgtctca   1920
aaaaaaaaaa tgattgaaat taaaattcag ctttagcttc catggcagtc ctcaccccca   1980
cctctctaaa agacacagga ggatgacaca gaaacaccgt aagtgtctgg aaggcaaaaa   2040
gatcttaaga ttcaagagag aggacaagta gttatggcta aggacatgaa attgtcagaa   2100
tggcaggtgg cttcttaaca gccctgtgag aagcagacag atgcaaagaa atctggaat   2160 cccttttctca ttagcatgaa tgaacctgat acacaattat gaccagaaaa tatggctcca   2220
tgaaggtgct acttttaagt aatgtatgtg cgctctgtaa agtgattaca tttgtttcct   2280
gtttgtttat ttatttattt attttttgcat tctgaggctg aactaataaa aactcttctt   2340
tgtaatc                                                              2347
```

<210> SEQ ID NO 11
<211> LENGTH: 328
<212> TYPE: PRT
<213> ORGANISM: Homo sapiens

<400> SEQUENCE: 11

| | | | | | | | | | | | | | | |
|---|---|---|---|---|---|---|---|---|---|---|---|---|---|---|
|Met|Cys|His|Gln|Gln|Leu|Val|Ile|Ser|Trp|Phe|Ser|Leu|Val|Phe|Leu|
|1| | | |5| | | | |10| | | | |15| |

| | | | | | | | | | | | | | | |
|---|---|---|---|---|---|---|---|---|---|---|---|---|---|---|
|Ala|Ser|Pro|Leu|Val|Ala|Ile|Trp|Glu|Leu|Lys|Lys|Asp|Val|Tyr|Val|
| | | |20| | | | |25| | | | |30| | |

| | | | | | | | | | | | | | | |
|---|---|---|---|---|---|---|---|---|---|---|---|---|---|---|
|Val|Glu|Leu|Asp|Trp|Tyr|Pro|Asp|Ala|Pro|Gly|Glu|Met|Val|Val|Leu|
| | | |35| | | | |40| | | | |45| | |

| | | | | | | | | | | | | | | |
|---|---|---|---|---|---|---|---|---|---|---|---|---|---|---|
|Thr|Cys|Asp|Thr|Pro|Glu|Glu|Asp|Gly|Ile|Thr|Trp|Thr|Leu|Asp|Gln|
| |50| | | | |55| | | | |60| | | | |

| | | | | | | | | | | | | | | |
|---|---|---|---|---|---|---|---|---|---|---|---|---|---|---|
|Ser|Ser|Glu|Val|Leu|Gly|Ser|Gly|Lys|Thr|Leu|Thr|Ile|Gln|Val|Lys|
|65| | | | |70| | | | |75| | | | |80|

| | | | | | | | | | | | | | | |
|---|---|---|---|---|---|---|---|---|---|---|---|---|---|---|
|Glu|Phe|Gly|Asp|Ala|Gly|Gln|Tyr|Thr|Cys|His|Lys|Gly|Gly|Glu|Val|
| | | | |85| | | | |90| | | | |95| |

| | | | | | | | | | | | | | | |
|---|---|---|---|---|---|---|---|---|---|---|---|---|---|---|
|Leu|Ser|His|Ser|Leu|Leu|Leu|Leu|His|Lys|Lys|Glu|Asp|Gly|Ile|Trp|
| | | |100| | | | |105| | | | |110| | |

| | | | | | | | | | | | | | | |
|---|---|---|---|---|---|---|---|---|---|---|---|---|---|---|
|Ser|Thr|Asp|Ile|Leu|Lys|Asp|Gln|Lys|Glu|Pro|Lys|Asn|Lys|Thr|Phe|
| | | |115| | | | |120| | | | |125| | |

| | | | | | | | | | | | | | |
|---|---|---|---|---|---|---|---|---|---|---|---|---|---|
|Leu|Arg|Cys|Glu|Ala|Lys|Asn|Tyr|Ser|Gly|Arg|Phe|Thr|Cys|Trp|Trp|
| |130| | | | |135| | | | |140| | | |

| | | | | | | | | | | | | | | |
|---|---|---|---|---|---|---|---|---|---|---|---|---|---|---|
|Leu|Thr|Thr|Ile|Ser|Thr|Asp|Leu|Thr|Phe|Ser|Val|Lys|Ser|Ser|Arg|
|145| | | | |150| | | | |155| | | | |160|

| | | | | | | | | | | | | | | |
|---|---|---|---|---|---|---|---|---|---|---|---|---|---|---|
|Gly|Ser|Ser|Asp|Pro|Gln|Gly|Val|Thr|Cys|Gly|Ala|Ala|Thr|Leu|Ser|
| | | | |165| | | | |170| | | | |175| |

| | | | | | | | | | | | | | | |
|---|---|---|---|---|---|---|---|---|---|---|---|---|---|---|
|Ala|Glu|Arg|Val|Arg|Gly|Asp|Asn|Lys|Glu|Tyr|Glu|Tyr|Ser|Val|Glu|
| | | |180| | | | |185| | | | |190| | |

| | | | | | | | | | | | | | | |
|---|---|---|---|---|---|---|---|---|---|---|---|---|---|---|
|Cys|Gln|Glu|Asp|Ser|Ala|Cys|Pro|Ala|Ala|Glu|Glu|Ser|Leu|Pro|Ile|
| | | |195| | | | |200| | | | |205| | |

| | | | | | | | | | | | | | | |
|---|---|---|---|---|---|---|---|---|---|---|---|---|---|---|
|Glu|Val|Met|Val|Asp|Ala|Val|His|Lys|Leu|Lys|Tyr|Glu|Asn|Tyr|Thr|
| | | |210| | | | |215| | | | |220| | |

| | | | | | | | | | | | | | | |
|---|---|---|---|---|---|---|---|---|---|---|---|---|---|---|
|Ser|Ser|Phe|Phe|Ile|Arg|Asp|Ile|Ile|Lys|Pro|Asp|Pro|Pro|Lys|Asn|
|225| | | | |230| | | | |235| | | | |240|

| | | | | | | | | | | | | | | |
|---|---|---|---|---|---|---|---|---|---|---|---|---|---|---|
|Leu|Gln|Leu|Lys|Pro|Leu|Lys|Asn|Ser|Arg|Gln|Val|Glu|Val|Ser|Trp|
| | | |245| | | | |250| | | | |255| | |

| | | | | | | | | | | | | | | |
|---|---|---|---|---|---|---|---|---|---|---|---|---|---|---|
|Glu|Tyr|Pro|Asp|Thr|Trp|Ser|Thr|Pro|His|Ser|Tyr|Phe|Ser|Leu|Thr|
| | | |260| | | | |265| | | | |270| | |

| | | | | | | | | | | | | | | |
|---|---|---|---|---|---|---|---|---|---|---|---|---|---|---|
|Phe|Cys|Val|Gln|Val|Gln|Gly|Lys|Ser|Lys|Arg|Glu|Lys|Lys|Asp|Arg|
| | | |275| | | | |280| | | | |285| | |

| | | | | | | | | | | | | | | |
|---|---|---|---|---|---|---|---|---|---|---|---|---|---|---|
|Val|Phe|Thr|Asp|Lys|Thr|Ser|Ala|Thr|Val|Ile|Cys|Arg|Lys|Asn|Ala|
| | | |290| | | | |295| | | | |300| | |

| | | | | | | | | | | | | | | |
|---|---|---|---|---|---|---|---|---|---|---|---|---|---|---|
|Ser|Ile|Ser|Val|Arg|Ala|Gln|Asp|Arg|Tyr|Tyr|Ser|Ser|Ser|Trp|Ser|
|305| | | | |310| | | | |315| | | | |320|

| | | | | | |
|---|---|---|---|---|---|
|Glu|Trp|Ala|Ser|Val|Pro|Cys|Ser|
| | | | |325| | | |

<210> SEQ ID NO 12
<211> LENGTH: 2379
<212> TYPE: DNA
<213> ORGANISM: Homo sapiens

<400> SEQUENCE: 12

```
acacagagag aaaggctaaa gttctctgga ggatgtggct gcagagcctg ctgctcttgg      60
gcactgtggc ctgcagcatc tctgcacccg cccgctcgcc cagccccagc acgcagccct     120
gggagcatgt gaatgccatc caggaggccc ggcgtctcct gaacctgagt agagacactg     180
```

```
ctgctgagat ggtaagtgag agaatgtggg cctgtgccta ggccacccag ctggcccctg    240
actggccacg cctgtcagct tgataacatg acatttcct tttctacaga atgaaacagt    300
agaagtcatc tcagaaatgt ttgacctcca ggtaagatgc ttctctctga catagctttc    360
cagaagcccc tgccctgggg tggaggtggg gactccattt tagatggcac cacacagggt    420
tgtccacttt ctctccagtc agctggctgc aggaggaggg ggtagcaact gggtgctcaa    480
gaggctgctg gccgtgcccc tatggcagtc acatgagctc ctttatcagc tgagcggcca    540
tgggcagacc tagcattcaa tggccaggag tcaccagggg acaggtggta agtgggggt     600 cacttcatga gacaggagct gtgggtttgg ggcgctcact gtgccccgag accaagtcct    660
gttgagacag tgctgactac agagaggcac agaggggttt caggaacaac ccttgcccac    720
ccagcaggtc caggtgaggc ccacccccc tctccctgaa tgatggggtg agagtcacct    780
ccttccctaa ggctgggctc ctctccaggt gccgctgagg gtggcctggg cggggcagtg    840
agaagggcag gttcgtgcct gccatggaca gggcagggtc tatgactgga cccagcctgt    900
gcccctccca agccctactc ctgggggctg ggggcagcag caaaaaggag tggtggagag    960
ttcttgtacc actgtgggca cttggccact gctcaccgac gaacgacatt tccacagga    1020 gccgacctgc ctacagaccc gcctggagct gtacaagcag ggcctgcggg gcagcctcac    1080
caagctcaag ggcccccttga ccatgatggc cagccactac aagcagcact gcctccaac    1140 cccggtgagt gcctacggca gggcctccag caggaatgtc ttaatctagg gggtggggtc    1200
gacatgggga gagatctatg gctgtggctg ttcaggaccc cagggggttt ctgtgccaac    1260
agttatgtaa tgattagccc tccagagagg aggcagacag cccatttcat cccaaggagt    1320
cagagccaca gagcgctgaa gcccacagtg ctccccagca ggagctgctc ctatcctggt    1380
cattattgtc attatggtta atgaggtcag aggtgagggc aaacccaagg aaacttgggg    1440
cctgcccaag gcccagagga agtgcccagg cccaagtgcc accttctggc aggactttcc    1500
tctggcccca catggggtgc ttgaattgca gaggatcaag gaagggaggc tacttggaat    1560
ggacaaggac ctcaggcact ccttcctgcg ggaagggagc aaagtttgtg gccttgactc    1620
cactccttct gggtgcccag agacgacctc agcccagctg ccctgctctg ccctgggacc    1680
aaaaaggcag gcgtttgact gcccagaagg ccaacctcag gctggcactt aagtcaggcc    1740
cttgactctg gctgccactg gcagagctat gcactccttg gggaacacgt gggtggcagc    1800
agcgtcacct gacccaggtc agtgggtgtg tcctggagtg ggcctcctgg cctctgagtt    1860
ctaagaggca gtagagaaac atgctggtgc ttccttcccc cacgttaccc acttgcctgg    1920
actcaagtgt ttttattttt tcttttttta aaggaaactt cctgtgcaac ccagattatc    1980
acctttgaaa gtttcaaaga gaacctgaag gactttctgc ttgtcatccc ctttgactgc    2040
tgggagccag tccaggagtg agaccggcca gatgaggctg gccaagccgg ggagctgctc    2100
tctcatgaaa caagagctag aaactcagga tggtcatctt ggagggacca aggggtgggc    2160
cacagccatg gtgggagtgg cctggacctg cctgggcca cactgaccct gatacaggca     2220
tggcagaaga atgggaatat tttatactga cagaaatcag taatatttat atatttatat    2280
ttttaaaata tttatttatt tatttattta agttcatatt ccatttttat tcaagatgtt    2340
ttaccgtaat aattattatt aaaaatatgc ttctacttg                           2379
```

<210> SEQ ID NO 13
<211> LENGTH: 800
<212> TYPE: DNA

<213> ORGANISM: Homo sapiens

<400> SEQUENCE: 13

```
acacagagag aaaggctaaa gttctctgga ggatgtggct gcagagcctg ctgctcttgg      60
gcactgtggc ctgcagcatc tctgcacccg cccgctcgcc cagccccagc acgcagccct     120
gggagcatgt gaatgccatc caggaggccc ggcgtctcct gaacctgagt agagacactg     180
ctgctgagat gaatgaaaca gtagaagtca tctcagaaat gtttgacctc caggagccga     240
cctgcctaca gacccgcctg gagctgtaca agcagggcct gcggggcagc ctcaccaagc     300
tcaagggccc cttgaccatg atggccagcc actacaagca gcactgccct ccaaccccgg     360
aaacttcctg tgcaacccag attatcacct ttgaaagttt caagagaaac ctgaaggact     420
ttctgcttgt catccccttt gactgctggg agccagtcca ggagtgagac cggccagatg     480
aggctggcca agccggggag ctgctctctc atgaaacaag agctagaaac tcaggatggt     540
catcttggag ggaccaaggg gtgggccaca gccatggtgg gagtggcctg gacctgccct     600
gggccacact gaccctgata caggcatggc agaagaatgg gaatatttta tactgacaga     660
aatcagtaat atttatatat ttatattttt aaaatattta tttatttatt tatttaagtt     720
catattccat atttattcaa gatgttttac cgtaataatt attattaaaa atatgcttct     780
acttgaaaaa aaaaaaaaaa                                                 800
```

<210> SEQ ID NO 14
<211> LENGTH: 144
<212> TYPE: PRT
<213> ORGANISM: Homo sapiens

<400> SEQUENCE: 14

```
Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
130                 135                 140
```

<210> SEQ ID NO 15
<211> LENGTH: 19
<212> TYPE: PRT
<213> ORGANISM: Artificial Sequence
<220> FEATURE:
<223> OTHER INFORMATION: synthetic peptide

<400> SEQUENCE: 15

```
Arg Val Asn His Val Thr Leu Ser Gln Pro Lys Ile Val Lys Trp Asp
1               5                   10                  15
```

Arg Asp Thr

<210> SEQ ID NO 16
<211> LENGTH: 20
<212> TYPE: PRT
<213> ORGANISM: Artificial Sequence
<220> FEATURE:
<223> OTHER INFORMATION: synthetic peptide

<400> SEQUENCE: 16

Ser Ala Ser Val Leu Leu Leu Leu Leu Leu Arg Arg Thr Glu Gln
1               5                   10                  15

Pro Cys Gly Ala
            20

<210> SEQ ID NO 17
<211> LENGTH: 20
<212> TYPE: PRT
<213> ORGANISM: Artificial Sequence
<220> FEATURE:
<223> OTHER INFORMATION: synthetic peptide

<400> SEQUENCE: 17

Leu Leu Leu Leu Arg Arg Thr Glu Gln Pro Cys Gly Ala Glu Leu Thr
1               5                   10                  15

Phe Glu Leu Pro
            20

<210> SEQ ID NO 18
<211> LENGTH: 20
<212> TYPE: PRT
<213> ORGANISM: Artificial Sequence
<220> FEATURE:
<223> OTHER INFORMATION: synthetic peptide

<400> SEQUENCE: 18

Pro Thr Gly Asp Phe Asp Ser Lys Pro Ser Trp Ala Asp Leu Val Glu
1               5                   10                  15

Glu Glu Gly Glu
            20

<210> SEQ ID NO 19
<211> LENGTH: 20
<212> TYPE: PRT
<213> ORGANISM: Artificial Sequence
<220> FEATURE:
<223> OTHER INFORMATION: synthetic peptide

<400> SEQUENCE: 19

Lys Pro Ser Trp Ala Asp Leu Val Glu Glu Gly Glu Asp Asp Lys
1               5                   10                  15

Cys Val Thr Ser
            20

<210> SEQ ID NO 20
<211> LENGTH: 20
<212> TYPE: PRT
<213> ORGANISM: Artificial Sequence
<220> FEATURE:
<223> OTHER INFORMATION: synthetic peptide

<400> SEQUENCE: 20

Glu Arg Ser Gly Ala Gly Thr Glu Asp Ser Ala Cys Ile Thr Trp Ala
1               5                   10                  15

Tyr Tyr Ser Thr
            20

<210> SEQ ID NO 21
<211> LENGTH: 20
<212> TYPE: PRT
<213> ORGANISM: Artificial Sequence
<220> FEATURE:
<223> OTHER INFORMATION: synthetic peptide

<400> SEQUENCE: 21

Glu Asp Ser Ala Cys Ile Thr Trp Ala Tyr Tyr Ser Thr Val Asp Gln
1               5                   10                  15

Val Lys Asp Leu
            20

<210> SEQ ID NO 22
<211> LENGTH: 20
<212> TYPE: PRT
<213> ORGANISM: Artificial Sequence
<220> FEATURE:
<223> OTHER INFORMATION: synthetic peptide

<400> SEQUENCE: 22

Thr Cys Glu Phe Tyr Met Ala Tyr Ala Asp Tyr His Asp Phe Met Glu
1               5                   10                  15

Ile Thr Glu Lys
            20

<210> SEQ ID NO 23
<211> LENGTH: 20
<212> TYPE: PRT
<213> ORGANISM: Artificial Sequence
<220> FEATURE:
<223> OTHER INFORMATION: synthetic peptide

<400> SEQUENCE: 23

Tyr Ala Asp Tyr His Asp Phe Met Glu Ile Thr Glu Lys Met Val Ser
1               5                   10                  15

Gly Met Val Lys
            20

<210> SEQ ID NO 24
<211> LENGTH: 20
<212> TYPE: PRT
<213> ORGANISM: Artificial Sequence
<220> FEATURE:
<223> OTHER INFORMATION: synthetic peptide

<400> SEQUENCE: 24

Gln Thr Arg Tyr His Phe Leu Ile Leu Leu Phe Ser Thr Asp Gly Asp
1               5                   10                  15

Ile Ser Leu Thr
            20

<210> SEQ ID NO 25
<211> LENGTH: 20
<212> TYPE: PRT
<213> ORGANISM: Artificial Sequence
<220> FEATURE:
<223> OTHER INFORMATION: synthetic peptide

<400> SEQUENCE: 25

Ile Leu Leu Phe Ser Thr Asp Gly Asp Ile Ser Leu Thr Leu Asn Met

```
                1               5                   10                  15

Asn Glu Glu Glu
            20

<210> SEQ ID NO 26
<211> LENGTH: 20
<212> TYPE: PRT
<213> ORGANISM: Artificial Sequence
<220> FEATURE:
<223> OTHER INFORMATION: synthetic peptide

<400> SEQUENCE: 26

Leu Phe Ser Met Ala Thr Leu Leu Arg Thr Ser Phe Ser Tyr Pro Gly
1               5                   10                  15

Val Ile Pro Arg
            20

<210> SEQ ID NO 27
<211> LENGTH: 20
<212> TYPE: PRT
<213> ORGANISM: Artificial Sequence
<220> FEATURE:
<223> OTHER INFORMATION: synthetic peptide

<400> SEQUENCE: 27

Leu Arg Thr Ser Phe Ser Tyr Pro Gly Val Ile Pro Arg Ala Leu Pro
1               5                   10                  15

Asp Glu Ala Ala
            20

<210> SEQ ID NO 28
<211> LENGTH: 20
<212> TYPE: PRT
<213> ORGANISM: Artificial Sequence
<220> FEATURE:
<223> OTHER INFORMATION: synthetic peptide

<400> SEQUENCE: 28

Pro Gln Thr Asp Phe Ile Ile Val Leu Ala Asp Gly Gln Leu Ser Glu
1               5                   10                  15

Met Gly Pro Tyr
            20

<210> SEQ ID NO 29
<211> LENGTH: 20
<212> TYPE: PRT
<213> ORGANISM: Artificial Sequence
<220> FEATURE:
<223> OTHER INFORMATION: synthetic peptide

<400> SEQUENCE: 29

Val Leu Ala Asp Gly Gln Leu Ser Glu Met Gly Pro Tyr Pro Ala Leu
1               5                   10                  15

Leu Gln Arg Asn
            20

<210> SEQ ID NO 30
<211> LENGTH: 20
<212> TYPE: PRT
<213> ORGANISM: Artificial Sequence
<220> FEATURE:
<223> OTHER INFORMATION: synthetic peptide

<400> SEQUENCE: 30
```

```
Val Ser Lys Val Glu Ile Leu Gln His Val Ile Asp Tyr Val Arg Asp
1               5                   10                  15

Leu Gln Leu Glu
            20
```

<210> SEQ ID NO 31
<211> LENGTH: 20
<212> TYPE: PRT
<213> ORGANISM: Artificial Sequence
<220> FEATURE:
<223> OTHER INFORMATION: synthetic peptide

<400> SEQUENCE: 31

```
Gln His Val Ile Asp Tyr Val Arg Asp Leu Gln Leu Glu Leu Asn Ser
1               5                   10                  15

Glu Ser Glu Val
            20
```

<210> SEQ ID NO 32
<211> LENGTH: 20
<212> TYPE: PRT
<213> ORGANISM: Artificial Sequence
<220> FEATURE:
<223> OTHER INFORMATION: synthetic peptide

<400> SEQUENCE: 32

```
Lys Glu Val Ala Glu Ala Tyr Glu Val Leu Ser Asp Lys Asn Lys Arg
1               5                   10                  15

Glu Ile Tyr Asp
            20
```

<210> SEQ ID NO 33
<211> LENGTH: 20
<212> TYPE: PRT
<213> ORGANISM: Artificial Sequence
<220> FEATURE:
<223> OTHER INFORMATION: synthetic peptide

<400> SEQUENCE: 33

```
Glu Val Leu Ser Asp Lys Asn Lys Arg Glu Ile Tyr Asp Arg Tyr Gly
1               5                   10                  15

Arg Glu Gly Leu
            20
```

<210> SEQ ID NO 34
<211> LENGTH: 20
<212> TYPE: PRT
<213> ORGANISM: Artificial Sequence
<220> FEATURE:
<223> OTHER INFORMATION: synthetic peptide

<400> SEQUENCE: 34

```
Arg Lys Phe Ser Ser Phe Phe Lys Ser Leu Val Ile Glu Val Asp Lys
1               5                   10                  15

Glu Leu Tyr Gly
            20
```

<210> SEQ ID NO 35
<211> LENGTH: 20
<212> TYPE: PRT
<213> ORGANISM: Artificial Sequence
<220> FEATURE:
<223> OTHER INFORMATION: synthetic peptide

<400> SEQUENCE: 35

```
Lys Ser Leu Val Ile Glu Val Asp Lys Glu Leu Tyr Gly Pro Asp Asn
1               5                   10                  15

His Leu Val Glu
            20

<210> SEQ ID NO 36
<211> LENGTH: 20
<212> TYPE: PRT
<213> ORGANISM: Artificial Sequence
<220> FEATURE:
<223> OTHER INFORMATION: synthetic peptide

<400> SEQUENCE: 36

Phe Gly Thr Arg Asp Ala Leu His Leu Gly Phe Pro Arg Lys Pro Arg
1               5                   10                  15

Pro Lys Leu His
            20

<210> SEQ ID NO 37
<211> LENGTH: 20
<212> TYPE: PRT
<213> ORGANISM: Artificial Sequence
<220> FEATURE:
<223> OTHER INFORMATION: synthetic peptide

<400> SEQUENCE: 37

His Leu Gly Phe Pro Arg Lys Pro Arg Pro Lys Leu His His Ser Leu
1               5                   10                  15

Ser Phe Ser Gly
            20

<210> SEQ ID NO 38
<211> LENGTH: 20
<212> TYPE: PRT
<213> ORGANISM: Artificial Sequence
<220> FEATURE:
<223> OTHER INFORMATION: synthetic peptide

<400> SEQUENCE: 38

Ile Gly Glu Ser Thr Ser His Val Pro Pro Thr Thr Leu Lys Asp Ile
1               5                   10                  15

Val Ala Lys Glu
            20

<210> SEQ ID NO 39
<211> LENGTH: 20
<212> TYPE: PRT
<213> ORGANISM: Artificial Sequence
<220> FEATURE:
<223> OTHER INFORMATION: synthetic peptide

<400> SEQUENCE: 39

Val Pro Pro Thr Thr Leu Lys Asp Ile Val Ala Lys Glu Thr Glu Thr
1               5                   10                  15

Asp Ile Asp Arg
            20

<210> SEQ ID NO 40
<211> LENGTH: 20
<212> TYPE: PRT
<213> ORGANISM: Artificial Sequence
<220> FEATURE:
<223> OTHER INFORMATION: synthetic peptide
```

```
<400> SEQUENCE: 40

Glu Asp Glu Ile Lys Gly Cys Leu Asp Phe Leu Arg Thr Leu Tyr Ser
1               5                   10                  15

Val Phe Gly Phe
            20

<210> SEQ ID NO 41
<211> LENGTH: 20
<212> TYPE: PRT
<213> ORGANISM: Artificial Sequence
<220> FEATURE:
<223> OTHER INFORMATION: synthetic peptide

<400> SEQUENCE: 41

Leu Asp Phe Leu Arg Thr Leu Tyr Ser Val Phe Gly Phe Ser Phe Lys
1               5                   10                  15

Leu Asn Leu Ser
            20

<210> SEQ ID NO 42
<211> LENGTH: 20
<212> TYPE: PRT
<213> ORGANISM: Artificial Sequence
<220> FEATURE:
<223> OTHER INFORMATION: synthetic peptide

<400> SEQUENCE: 42

Glu Thr Leu Thr Glu Cys Trp Asp His Asp Pro Glu Ala Leu Leu Thr
1               5                   10                  15

Ala Gln Cys Val
            20

<210> SEQ ID NO 43
<211> LENGTH: 20
<212> TYPE: PRT
<213> ORGANISM: Artificial Sequence
<220> FEATURE:
<223> OTHER INFORMATION: synthetic peptide

<400> SEQUENCE: 43

Asp His Asp Pro Glu Ala Leu Leu Thr Ala Gln Cys Val Ala Glu Arg
1               5                   10                  15

Phe Ser Glu Leu
            20

<210> SEQ ID NO 44
<211> LENGTH: 20
<212> TYPE: PRT
<213> ORGANISM: Artificial Sequence
<220> FEATURE:
<223> OTHER INFORMATION: synthetic peptide

<400> SEQUENCE: 44

Pro Val Glu Ala Ala Lys Glu Thr Thr Glu Val Pro Glu Asp Leu Thr
1               5                   10                  15

Pro Thr Pro Thr
            20

<210> SEQ ID NO 45
<211> LENGTH: 20
<212> TYPE: PRT
<213> ORGANISM: Artificial Sequence
<220> FEATURE:
<223> OTHER INFORMATION: synthetic peptide
```

```
<400> SEQUENCE: 45

Thr Thr Glu Val Pro Glu Asp Leu Thr Pro Thr Pro Thr Glu Ala Ala
1               5                   10                  15

Pro Met Pro Glu
            20

<210> SEQ ID NO 46
<211> LENGTH: 20
<212> TYPE: PRT
<213> ORGANISM: Artificial Sequence
<220> FEATURE:
<223> OTHER INFORMATION: synthetic peptide

<400> SEQUENCE: 46

Leu Val Pro Ser Glu Glu Asp Phe Gln Gly Ile Thr Pro Trp Ala Gln
1               5                   10                  15

Gly Pro Ser Ser
            20

<210> SEQ ID NO 47
<211> LENGTH: 20
<212> TYPE: PRT
<213> ORGANISM: Artificial Sequence
<220> FEATURE:
<223> OTHER INFORMATION: synthetic peptide

<400> SEQUENCE: 47

Phe Gln Gly Ile Thr Pro Trp Ala Gln Gly Pro Ser Ser Arg Gly Arg
1               5                   10                  15

Glu Pro Glu Ala
            20

<210> SEQ ID NO 48
<211> LENGTH: 20
<212> TYPE: PRT
<213> ORGANISM: Artificial Sequence
<220> FEATURE:
<223> OTHER INFORMATION: synthetic peptide

<400> SEQUENCE: 48

Val Met Thr Pro Val Pro Leu Phe Ser Lys Gln Arg Ser Cys Cys Arg
1               5                   10                  15

Pro Phe Cys Glu
            20

<210> SEQ ID NO 49
<211> LENGTH: 20
<212> TYPE: PRT
<213> ORGANISM: Artificial Sequence
<220> FEATURE:
<223> OTHER INFORMATION: synthetic peptide

<400> SEQUENCE: 49

Phe Ser Lys Gln Arg Ser Cys Cys Arg Pro Phe Cys Glu Val Tyr Val
1               5                   10                  15

Gly Asp Glu Arg
            20

<210> SEQ ID NO 50
<211> LENGTH: 20
<212> TYPE: PRT
<213> ORGANISM: Artificial Sequence
<220> FEATURE:
```

<223> OTHER INFORMATION: synthetic peptide

<400> SEQUENCE: 50

Thr Ile His Tyr Asn Tyr Met Cys Asn Ser Ser Cys Met Cys Gly Met
1               5                   10                  15

Asn Arg Arg Pro
            20

<210> SEQ ID NO 51
<211> LENGTH: 20
<212> TYPE: PRT
<213> ORGANISM: Artificial Sequence
<220> FEATURE:
<223> OTHER INFORMATION: synthetic peptide

<400> SEQUENCE: 51

Cys Asn Ser Ser Cys Met Cys Gly Met Asn Arg Arg Pro Ile Leu Thr
1               5                   10                  15

Ile Ile Thr Leu
            20

<210> SEQ ID NO 52
<211> LENGTH: 20
<212> TYPE: PRT
<213> ORGANISM: Artificial Sequence
<220> FEATURE:
<223> OTHER INFORMATION: synthetic peptide

<400> SEQUENCE: 52

Pro Pro Ser Arg Leu Pro Ser Pro Asp Pro Ala Ala Ser Cys Ser Pro
1               5                   10                  15

Ser Thr Val Asp
            20

<210> SEQ ID NO 53
<211> LENGTH: 20
<212> TYPE: PRT
<213> ORGANISM: Artificial Sequence
<220> FEATURE:
<223> OTHER INFORMATION: synthetic peptide

<400> SEQUENCE: 53

Pro Asp Pro Ala Ala Ser Cys Ser Pro Ser Thr Val Asp Ser Ala Ser
1               5                   10                  15

Pro Ala Arg Lys
            20

<210> SEQ ID NO 54
<211> LENGTH: 20
<212> TYPE: PRT
<213> ORGANISM: Artificial Sequence
<220> FEATURE:
<223> OTHER INFORMATION: synthetic peptide

<400> SEQUENCE: 54

Cys Asn Glu Val Thr Pro Arg Ile Tyr Val Gly Asn Ala Phe Val Ala
1               5                   10                  15

Gln Asp Ile Pro
            20

<210> SEQ ID NO 55
<211> LENGTH: 20
<212> TYPE: PRT
<213> ORGANISM: Artificial Sequence

```
<220> FEATURE:
<223> OTHER INFORMATION: synthetic peptide

<400> SEQUENCE: 55

Ile Tyr Val Gly Asn Ala Phe Val Ala Gln Asp Ile Pro Lys Leu Gln
1               5                   10                  15

Lys Leu Gly Ile
            20

<210> SEQ ID NO 56
<211> LENGTH: 20
<212> TYPE: PRT
<213> ORGANISM: Artificial Sequence
<220> FEATURE:
<223> OTHER INFORMATION: synthetic peptide

<400> SEQUENCE: 56

Pro Arg Lys Asp Ser Leu Leu Lys Pro Gly Leu Arg Ala Phe Val Gly
1               5                   10                  15

Gly Ala Ala Ala
            20

<210> SEQ ID NO 57
<211> LENGTH: 20
<212> TYPE: PRT
<213> ORGANISM: Artificial Sequence
<220> FEATURE:
<223> OTHER INFORMATION: synthetic peptide

<400> SEQUENCE: 57

Lys Pro Gly Leu Arg Ala Phe Val Gly Gly Ala Ala Ala Val Ser Thr
1               5                   10                  15

Gln Ala Met His
            20

<210> SEQ ID NO 58
<211> LENGTH: 20
<212> TYPE: PRT
<213> ORGANISM: Artificial Sequence
<220> FEATURE:
<223> OTHER INFORMATION: synthetic peptide

<400> SEQUENCE: 58

His Leu Ser Glu Glu Met Ala Arg Thr Phe Asn Cys Val Val Gly
1               5                   10                  15

Ala Val Leu Val
            20

<210> SEQ ID NO 59
<211> LENGTH: 20
<212> TYPE: PRT
<213> ORGANISM: Artificial Sequence
<220> FEATURE:
<223> OTHER INFORMATION: synthetic peptide

<400> SEQUENCE: 59

Ala Arg Thr Phe Asn Cys Val Val Gly Ala Val Leu Val Val Ser Lys
1               5                   10                  15

Glu Gln Thr Glu
            20

<210> SEQ ID NO 60
<211> LENGTH: 20
<212> TYPE: PRT
```

```
<213> ORGANISM: Artificial Sequence
<220> FEATURE:
<223> OTHER INFORMATION: synthetic peptide

<400> SEQUENCE: 60

Gly Ala Leu Gly Pro Arg Gly Glu Lys Gly Pro Ile Gly Thr Pro Gly
1               5                   10                  15

Ile Gly Gly Pro
            20

<210> SEQ ID NO 61
<211> LENGTH: 20
<212> TYPE: PRT
<213> ORGANISM: Artificial Sequence
<220> FEATURE:
<223> OTHER INFORMATION: synthetic peptide

<400> SEQUENCE: 61

Glu Lys Gly Pro Ile Gly Thr Pro Gly Ile Gly Gly Pro Pro Gly Glu
1               5                   10                  15

Pro Gly Leu Pro
            20

<210> SEQ ID NO 62
<211> LENGTH: 20
<212> TYPE: PRT
<213> ORGANISM: Artificial Sequence
<220> FEATURE:
<223> OTHER INFORMATION: synthetic peptide

<400> SEQUENCE: 62

Lys Asn Ala Gln Gly Ile Ile Asn Pro Ile Glu Ala Lys His Arg Lys
1               5                   10                  15

Gly Lys Gly Ala
            20

<210> SEQ ID NO 63
<211> LENGTH: 20
<212> TYPE: PRT
<213> ORGANISM: Artificial Sequence
<220> FEATURE:
<223> OTHER INFORMATION: synthetic peptide

<400> SEQUENCE: 63

Asn Pro Ile Glu Ala Lys His Arg Lys Gly Lys Gly Ala Val Gly Ala
1               5                   10                  15

Tyr Gly Ser Glu
            20

<210> SEQ ID NO 64
<211> LENGTH: 20
<212> TYPE: PRT
<213> ORGANISM: Artificial Sequence
<220> FEATURE:
<223> OTHER INFORMATION: synthetic peptide

<400> SEQUENCE: 64

Arg Lys Asp Phe Gln Tyr Glu Ala Met Gln Glu Arg Arg Lys Ala Glu
1               5                   10                  15

Asn Met Ala Gln
            20

<210> SEQ ID NO 65
<211> LENGTH: 20
```

```
<212> TYPE: PRT
<213> ORGANISM: Artificial Sequence
<220> FEATURE:
<223> OTHER INFORMATION: synthetic peptide

<400> SEQUENCE: 65

Ala Met Gln Glu Arg Arg Lys Ala Glu Asn Met Ala Gln Arg Gly Ile
1               5                   10                  15

Gly Val Ala Ala
            20

<210> SEQ ID NO 66
<211> LENGTH: 20
<212> TYPE: PRT
<213> ORGANISM: Artificial Sequence
<220> FEATURE:
<223> OTHER INFORMATION: synthetic peptide

<400> SEQUENCE: 66

His Gln His Trp Lys Val Arg Val Ala Ala Ile Glu Ala Ala Gly Ala
1               5                   10                  15

Val Ile His Phe
            20

<210> SEQ ID NO 67
<211> LENGTH: 20
<212> TYPE: PRT
<213> ORGANISM: Artificial Sequence
<220> FEATURE:
<223> OTHER INFORMATION: synthetic peptide

<400> SEQUENCE: 67

Val Ala Ala Ile Glu Ala Ala Gly Ala Val Ile His Phe Gly Asn Gly
1               5                   10                  15

Lys Ser Val Asp
            20

<210> SEQ ID NO 68
<211> LENGTH: 20
<212> TYPE: PRT
<213> ORGANISM: Artificial Sequence
<220> FEATURE:
<223> OTHER INFORMATION: synthetic peptide

<400> SEQUENCE: 68

Ile Thr Leu Ser Arg Lys Gly Ile Val Lys Leu Asn Ile Asn Phe Gln
1               5                   10                  15

Glu Phe Asn Tyr
            20

<210> SEQ ID NO 69
<211> LENGTH: 20
<212> TYPE: PRT
<213> ORGANISM: Artificial Sequence
<220> FEATURE:
<223> OTHER INFORMATION: synthetic peptide

<400> SEQUENCE: 69

Ile Val Lys Leu Asn Ile Asn Phe Gln Glu Phe Asn Tyr Arg Thr Ile
1               5                   10                  15

Glu Glu Ser Ala
            20

<210> SEQ ID NO 70
```

```
<211> LENGTH: 20
<212> TYPE: PRT
<213> ORGANISM: Artificial Sequence
<220> FEATURE:
<223> OTHER INFORMATION: synthetic peptide

<400> SEQUENCE: 70

Pro Gly Ser Leu Ala Ser His Val Lys Asn Leu Asp Glu Lys Gly Leu
1               5                   10                  15

Asp Leu Leu Ser
            20

<210> SEQ ID NO 71
<211> LENGTH: 20
<212> TYPE: PRT
<213> ORGANISM: Artificial Sequence
<220> FEATURE:
<223> OTHER INFORMATION: synthetic peptide

<400> SEQUENCE: 71

Val Lys Asn Leu Asp Glu Lys Gly Leu Asp Leu Leu Ser Lys Met Leu
1               5                   10                  15

Ile Tyr Asp Pro
            20

<210> SEQ ID NO 72
<211> LENGTH: 20
<212> TYPE: PRT
<213> ORGANISM: Artificial Sequence
<220> FEATURE:
<223> OTHER INFORMATION: synthetic peptide

<400> SEQUENCE: 72

Met Gly Val Phe Ala Lys Ala Phe Leu Ser Thr Leu Phe Thr Pro Leu
1               5                   10                  15

Asn Phe Val Met
            20

<210> SEQ ID NO 73
<211> LENGTH: 20
<212> TYPE: PRT
<213> ORGANISM: Artificial Sequence
<220> FEATURE:
<223> OTHER INFORMATION: synthetic peptide

<400> SEQUENCE: 73

Phe Leu Ser Thr Leu Phe Thr Pro Leu Asn Phe Val Met Glu Lys Val
1               5                   10                  15

Glu Ser Ile Leu
            20

<210> SEQ ID NO 74
<211> LENGTH: 20
<212> TYPE: PRT
<213> ORGANISM: Artificial Sequence
<220> FEATURE:
<223> OTHER INFORMATION: synthetic peptide

<400> SEQUENCE: 74

Ser Pro Val Thr Pro Val Thr Pro Gly Thr Pro Gly Asn Ser Met His
1               5                   10                  15

Phe Glu Asn Ile
            20
```

-continued

```
<210> SEQ ID NO 75
<211> LENGTH: 20
<212> TYPE: PRT
<213> ORGANISM: Artificial Sequence
<220> FEATURE:
<223> OTHER INFORMATION: synthetic peptide

<400> SEQUENCE: 75

Pro Gly Thr Pro Gly Asn Ser Met His Phe Glu Asn Ile Ser Ser Pro
1               5                   10                  15

Glu Ser Ser Pro
            20

<210> SEQ ID NO 76
<211> LENGTH: 20
<212> TYPE: PRT
<213> ORGANISM: Artificial Sequence
<220> FEATURE:
<223> OTHER INFORMATION: synthetic peptide

<400> SEQUENCE: 76

Trp Thr Gln Trp Ile Glu Gly Asp Glu Leu His Leu Glu Ile Arg Val
1               5                   10                  15

Glu Gly Val Val
            20

<210> SEQ ID NO 77
<211> LENGTH: 20
<212> TYPE: PRT
<213> ORGANISM: Artificial Sequence
<220> FEATURE:
<223> OTHER INFORMATION: synthetic peptide

<400> SEQUENCE: 77

Asp Glu Leu His Leu Glu Ile Arg Val Glu Gly Val Val Cys Lys Gln
1               5                   10                  15

Val Phe Lys Lys
            20

<210> SEQ ID NO 78
<211> LENGTH: 20
<212> TYPE: PRT
<213> ORGANISM: Artificial Sequence
<220> FEATURE:
<223> OTHER INFORMATION: synthetic peptide

<400> SEQUENCE: 78

Phe Gly Thr His Glu Thr Ala Phe Leu Gly Pro Lys Asp Val Phe Pro
1               5                   10                  15

Tyr Ser Glu Asn
            20

<210> SEQ ID NO 79
<211> LENGTH: 20
<212> TYPE: PRT
<213> ORGANISM: Artificial Sequence
<220> FEATURE:
<223> OTHER INFORMATION: synthetic peptide

<400> SEQUENCE: 79

Phe Leu Gly Pro Lys Asp Val Phe Pro Tyr Ser Glu Asn Lys Glu Lys
1               5                   10                  15

Tyr Gly Lys Pro
            20
```

<210> SEQ ID NO 80
<211> LENGTH: 20
<212> TYPE: PRT
<213> ORGANISM: Artificial Sequence
<220> FEATURE:
<223> OTHER INFORMATION: synthetic peptide

<400> SEQUENCE: 80

Pro Ser Gly Thr Pro Gly Asp Pro Lys Arg Thr Ile Gly His Phe Leu
1               5                   10                  15

Ala Ser Thr Glu
            20

<210> SEQ ID NO 81
<211> LENGTH: 20
<212> TYPE: PRT
<213> ORGANISM: Artificial Sequence
<220> FEATURE:
<223> OTHER INFORMATION: synthetic peptide

<400> SEQUENCE: 81

Pro Lys Arg Thr Ile Gly His Phe Leu Ala Ser Thr Glu Ala Phe Ser
1               5                   10                  15

Arg Phe Glu Thr
            20

<210> SEQ ID NO 82
<211> LENGTH: 20
<212> TYPE: PRT
<213> ORGANISM: Artificial Sequence
<220> FEATURE:
<223> OTHER INFORMATION: synthetic peptide

<400> SEQUENCE: 82

Lys Cys Glu Arg Arg Arg Cys Leu Arg Ile Val Glu Arg Arg Arg Gly
1               5                   10                  15

Cys Gly Val Cys
            20

<210> SEQ ID NO 83
<211> LENGTH: 20
<212> TYPE: PRT
<213> ORGANISM: Artificial Sequence
<220> FEATURE:
<223> OTHER INFORMATION: synthetic peptide

<400> SEQUENCE: 83

Leu Arg Ile Val Glu Arg Arg Arg Gly Cys Gly Val Cys Arg Gly Cys
1               5                   10                  15

Gln Thr Gln Glu
            20

<210> SEQ ID NO 84
<211> LENGTH: 20
<212> TYPE: PRT
<213> ORGANISM: Artificial Sequence
<220> FEATURE:
<223> OTHER INFORMATION: synthetic peptide

<400> SEQUENCE: 84

Asp Leu Ala Thr Pro Arg Thr Pro Glu Glu Ala Gln Arg Gly Asp Ser
1               5                   10                  15

Leu Val Gly Ala
            20

```
<210> SEQ ID NO 85
<211> LENGTH: 20
<212> TYPE: PRT
<213> ORGANISM: Artificial Sequence
<220> FEATURE:
<223> OTHER INFORMATION: synthetic peptide

<400> SEQUENCE: 85

Pro Glu Glu Ala Gln Arg Gly Asp Ser Leu Val Gly Ala Gly Pro Ala
1               5                   10                  15

Ser Arg Leu Leu
            20

<210> SEQ ID NO 86
<211> LENGTH: 20
<212> TYPE: PRT
<213> ORGANISM: Artificial Sequence
<220> FEATURE:
<223> OTHER INFORMATION: synthetic peptide

<400> SEQUENCE: 86

Phe Thr Lys Ser Met Ser Ser Leu Gln Asp Asp Arg Asp Met Val Ile
1               5                   10                  15

Asp Glu Ala Lys
            20

<210> SEQ ID NO 87
<211> LENGTH: 20
<212> TYPE: PRT
<213> ORGANISM: Artificial Sequence
<220> FEATURE:
<223> OTHER INFORMATION: synthetic peptide

<400> SEQUENCE: 87

Leu Gln Asp Asp Arg Asp Met Val Ile Asp Glu Ala Lys Lys Trp Glu
1               5                   10                  15

Arg Lys Phe Ser
            20

<210> SEQ ID NO 88
<211> LENGTH: 20
<212> TYPE: PRT
<213> ORGANISM: Artificial Sequence
<220> FEATURE:
<223> OTHER INFORMATION: synthetic peptide

<400> SEQUENCE: 88

Gly Tyr Val Val Arg Gln Thr Leu Ser Thr Glu Leu Ser Ser Ala Pro
1               5                   10                  15

Lys Asn Val Thr
            20

<210> SEQ ID NO 89
<211> LENGTH: 20
<212> TYPE: PRT
<213> ORGANISM: Artificial Sequence
<220> FEATURE:
<223> OTHER INFORMATION: synthetic peptide

<400> SEQUENCE: 89

Leu Ser Thr Glu Leu Ser Ser Ala Pro Lys Asn Val Thr Ser Met Ile
1               5                   10                  15

Asn Leu Lys Thr
```

-continued

20

<210> SEQ ID NO 90
<211> LENGTH: 20
<212> TYPE: PRT
<213> ORGANISM: Artificial Sequence
<220> FEATURE:
<223> OTHER INFORMATION: synthetic peptide

<400> SEQUENCE: 90

Glu Thr Pro Leu Thr Pro Gly Leu Ala Asn Glu Ser Gly Asp Pro Gln
1               5                   10                  15

Ala Glu Val Thr
            20

<210> SEQ ID NO 91
<211> LENGTH: 20
<212> TYPE: PRT
<213> ORGANISM: Artificial Sequence
<220> FEATURE:
<223> OTHER INFORMATION: synthetic peptide

<400> SEQUENCE: 91

Leu Ala Asn Glu Ser Gly Asp Pro Gln Ala Glu Val Thr Ser Leu Leu
1               5                   10                  15

Leu Pro Ala His
            20

<210> SEQ ID NO 92
<211> LENGTH: 20
<212> TYPE: PRT
<213> ORGANISM: Artificial Sequence
<220> FEATURE:
<223> OTHER INFORMATION: synthetic peptide

<400> SEQUENCE: 92

Gln Gly Gly Phe Gly Cys Gly Asn Gln Leu Pro Lys Thr His Gly Gly
1               5                   10                  15

Ser Glu Thr Lys
            20

<210> SEQ ID NO 93
<211> LENGTH: 20
<212> TYPE: PRT
<213> ORGANISM: Artificial Sequence
<220> FEATURE:
<223> OTHER INFORMATION: synthetic peptide

<400> SEQUENCE: 93

Asn Gln Leu Pro Lys Thr His Gly Gly Ser Glu Thr Lys Lys Gln Arg
1               5                   10                  15

Ser Lys Arg Thr
            20

<210> SEQ ID NO 94
<211> LENGTH: 20
<212> TYPE: PRT
<213> ORGANISM: Artificial Sequence
<220> FEATURE:
<223> OTHER INFORMATION: synthetic peptide

<400> SEQUENCE: 94

Gly Thr Gln Gly Lys Leu Glu Ala Ala Gly Ser Phe Asn Cys Asp Asp
1               5                   10                  15

Asp Ala Glu Ser
        20

<210> SEQ ID NO 95
<211> LENGTH: 20
<212> TYPE: PRT
<213> ORGANISM: Artificial Sequence
<220> FEATURE:
<223> OTHER INFORMATION: synthetic peptide

<400> SEQUENCE: 95

Ala Ala Gly Ser Phe Asn Cys Asp Asp Ala Glu Ser Cys Pro Ile
1               5                   10                  15

Cys Leu Asn Ala
        20

<210> SEQ ID NO 96
<211> LENGTH: 20
<212> TYPE: PRT
<213> ORGANISM: Artificial Sequence
<220> FEATURE:
<223> OTHER INFORMATION: synthetic peptide

<400> SEQUENCE: 96

Leu Lys Ser Leu Leu Gln Trp Val Thr Ser Arg Gln Met Gln Phe Glu
1               5                   10                  15

Gly Gly Phe Gln
        20

<210> SEQ ID NO 97
<211> LENGTH: 20
<212> TYPE: PRT
<213> ORGANISM: Artificial Sequence
<220> FEATURE:
<223> OTHER INFORMATION: synthetic peptide

<400> SEQUENCE: 97

Val Thr Ser Arg Gln Met Gln Phe Glu Gly Gly Phe Gln Gly Arg Cys
1               5                   10                  15

Asn Lys Leu Val
        20

<210> SEQ ID NO 98
<211> LENGTH: 20
<212> TYPE: PRT
<213> ORGANISM: Artificial Sequence
<220> FEATURE:
<223> OTHER INFORMATION: synthetic peptide

<400> SEQUENCE: 98

Gln Gly Leu Val Val Gly Ile Asp Leu Lys Asn Gln Met Met Leu Leu
1               5                   10                  15

Gln Gly Gly Glu
        20

<210> SEQ ID NO 99
<211> LENGTH: 20
<212> TYPE: PRT
<213> ORGANISM: Artificial Sequence
<220> FEATURE:
<223> OTHER INFORMATION: synthetic peptide

<400> SEQUENCE: 99

Asp Leu Lys Asn Gln Met Met Leu Leu Gln Gly Gly Glu Ala Leu Pro
1               5                   10                  15

Phe Ser His Leu
            20

<210> SEQ ID NO 100
<211> LENGTH: 20
<212> TYPE: PRT
<213> ORGANISM: Artificial Sequence
<220> FEATURE:
<223> OTHER INFORMATION: synthetic peptide

<400> SEQUENCE: 100

Ser Pro Thr Pro Glu Pro Gly Val Gly Ala Gly Asp Leu Ser Gly Pro
1               5                   10                  15

Thr Ser Ala Pro
            20

<210> SEQ ID NO 101
<211> LENGTH: 20
<212> TYPE: PRT
<213> ORGANISM: Artificial Sequence
<220> FEATURE:
<223> OTHER INFORMATION: synthetic peptide

<400> SEQUENCE: 101

Val Gly Ala Gly Asp Leu Ser Gly Pro Thr Ser Ala Pro Val Pro Ser
1               5                   10                  15

Gly Ser Gln Ser
            20

<210> SEQ ID NO 102
<211> LENGTH: 20
<212> TYPE: PRT
<213> ORGANISM: Artificial Sequence
<220> FEATURE:
<223> OTHER INFORMATION: synthetic peptide

<400> SEQUENCE: 102

His Asn Gln Leu Lys His Thr Trp Gln Lys Ala Asn Asp Leu Phe Leu
1               5                   10                  15

Glu Ser Gln Arg
            20

<210> SEQ ID NO 103
<211> LENGTH: 20
<212> TYPE: PRT
<213> ORGANISM: Artificial Sequence
<220> FEATURE:
<223> OTHER INFORMATION: synthetic peptide

<400> SEQUENCE: 103

Trp Gln Lys Ala Asn Asp Leu Phe Leu Glu Ser Gln Arg Leu Leu Met
1               5                   10                  15

Arg Asp Met Gln
            20

<210> SEQ ID NO 104
<211> LENGTH: 20
<212> TYPE: PRT
<213> ORGANISM: Artificial Sequence
<220> FEATURE:
<223> OTHER INFORMATION: synthetic peptide

<400> SEQUENCE: 104

Gly Arg Lys Asn Leu Tyr Thr Ala Met Pro Leu Pro Ile Leu Arg Asp

```
                1               5                  10                 15
Lys Val Glu Leu
            20

<210> SEQ ID NO 105
<211> LENGTH: 20
<212> TYPE: PRT
<213> ORGANISM: Artificial Sequence
<220> FEATURE:
<223> OTHER INFORMATION: synthetic peptide

<400> SEQUENCE: 105

Ala Met Pro Leu Pro Ile Leu Arg Asp Lys Val Glu Leu Glu Val Thr
1               5                  10                 15

Leu Pro Gly Glu
            20

<210> SEQ ID NO 106
<211> LENGTH: 20
<212> TYPE: PRT
<213> ORGANISM: Artificial Sequence
<220> FEATURE:
<223> OTHER INFORMATION: synthetic peptide

<400> SEQUENCE: 106

Gln Thr Thr Thr Ala Asp Gln Leu Leu Glu Phe Phe Lys Leu Val Gly
1               5                  10                 15

Glu Val Lys Phe
            20

<210> SEQ ID NO 107
<211> LENGTH: 20
<212> TYPE: PRT
<213> ORGANISM: Artificial Sequence
<220> FEATURE:
<223> OTHER INFORMATION: synthetic peptide

<400> SEQUENCE: 107

Leu Leu Glu Phe Phe Lys Leu Val Gly Glu Val Lys Phe Val Arg Met
1               5                  10                 15

Ala Gly Asp Glu
            20

<210> SEQ ID NO 108
<211> LENGTH: 20
<212> TYPE: PRT
<213> ORGANISM: Artificial Sequence
<220> FEATURE:
<223> OTHER INFORMATION: synthetic peptide

<400> SEQUENCE: 108

Leu Ala Glu Gln Arg Phe Pro Gly Arg Val Leu Pro Ser Tyr Leu Asp
1               5                  10                 15

Leu Leu Leu His
            20

<210> SEQ ID NO 109
<211> LENGTH: 20
<212> TYPE: PRT
<213> ORGANISM: Artificial Sequence
<220> FEATURE:
<223> OTHER INFORMATION: synthetic peptide

<400> SEQUENCE: 109
```

Gly Arg Val Leu Pro Ser Tyr Leu Asp Leu Leu Leu His Met Asn Asn
1               5                   10                  15

Ala Arg Tyr Leu
            20

<210> SEQ ID NO 110
<211> LENGTH: 20
<212> TYPE: PRT
<213> ORGANISM: Artificial Sequence
<220> FEATURE:
<223> OTHER INFORMATION: synthetic peptide

<400> SEQUENCE: 110

Met Pro His Pro Gly Met Ser Gln Met Gln Leu Ala His Tyr Gly Pro
1               5                   10                  15

His Gly Leu Gly
            20

<210> SEQ ID NO 111
<211> LENGTH: 20
<212> TYPE: PRT
<213> ORGANISM: Artificial Sequence
<220> FEATURE:
<223> OTHER INFORMATION: synthetic peptide

<400> SEQUENCE: 111

Gln Met Gln Leu Ala His Tyr Gly Pro His Gly Leu Gly His Pro His
1               5                   10                  15

Ala Gly Pro Pro
            20

<210> SEQ ID NO 112
<211> LENGTH: 20
<212> TYPE: PRT
<213> ORGANISM: Artificial Sequence
<220> FEATURE:
<223> OTHER INFORMATION: synthetic peptide

<400> SEQUENCE: 112

His Gly Met Trp Gln Thr Ile Ser Val Glu Glu Leu Ala Gln Asn Leu
1               5                   10                  15

Val Ile Lys Val
            20

<210> SEQ ID NO 113
<211> LENGTH: 20
<212> TYPE: PRT
<213> ORGANISM: Artificial Sequence
<220> FEATURE:
<223> OTHER INFORMATION: synthetic peptide

<400> SEQUENCE: 113

Ser Val Glu Glu Leu Ala Gln Asn Leu Val Ile Lys Val Asn Arg Asp
1               5                   10                  15

Ala Val Met Lys
            20

<210> SEQ ID NO 114
<211> LENGTH: 20
<212> TYPE: PRT
<213> ORGANISM: Artificial Sequence
<220> FEATURE:
<223> OTHER INFORMATION: synthetic peptide

<400> SEQUENCE: 114

Gly Thr Pro Leu Val Ala Ala Pro Ser Leu Asn Ala Thr Ile Val Val
1               5                   10                  15

Thr Thr Val Tyr
            20

<210> SEQ ID NO 115
<211> LENGTH: 20
<212> TYPE: PRT
<213> ORGANISM: Artificial Sequence
<220> FEATURE:
<223> OTHER INFORMATION: synthetic peptide

<400> SEQUENCE: 115

Pro Ser Leu Asn Ala Thr Ile Val Val Thr Thr Val Tyr Gln Glu Pro
1               5                   10                  15

Ile Met Ser Gln
            20

<210> SEQ ID NO 116
<211> LENGTH: 20
<212> TYPE: PRT
<213> ORGANISM: Artificial Sequence
<220> FEATURE:
<223> OTHER INFORMATION: synthetic peptide

<400> SEQUENCE: 116

Asp Thr Phe Ser Gly Phe Lys Val Asp Ile Trp Ser Ala Val Val Thr
1               5                   10                  15

Leu Tyr Asn Ile
            20

<210> SEQ ID NO 117
<211> LENGTH: 20
<212> TYPE: PRT
<213> ORGANISM: Artificial Sequence
<220> FEATURE:
<223> OTHER INFORMATION: synthetic peptide

<400> SEQUENCE: 117

Val Asp Ile Trp Ser Ala Val Val Thr Leu Tyr Asn Ile Thr Thr Gly
1               5                   10                  15

Leu Tyr Pro Phe
            20

<210> SEQ ID NO 118
<211> LENGTH: 20
<212> TYPE: PRT
<213> ORGANISM: Artificial Sequence
<220> FEATURE:
<223> OTHER INFORMATION: synthetic peptide

<400> SEQUENCE: 118

Glu Glu Ile Arg Asp His Phe Met Glu Met Leu Asp His Ser Ile Gln
1               5                   10                  15

Ile Glu Asp Leu
            20

<210> SEQ ID NO 119
<211> LENGTH: 20
<212> TYPE: PRT
<213> ORGANISM: Artificial Sequence
<220> FEATURE:
<223> OTHER INFORMATION: synthetic peptide

```
<400> SEQUENCE: 119

Met Glu Met Leu Asp His Ser Ile Gln Ile Glu Asp Leu Glu Ile Ala
1               5                   10                  15

Glu Glu Thr Asn
            20

<210> SEQ ID NO 120
<211> LENGTH: 20
<212> TYPE: PRT
<213> ORGANISM: Artificial Sequence
<220> FEATURE:
<223> OTHER INFORMATION: synthetic peptide

<400> SEQUENCE: 120

Cys Lys Asp Ile Lys Lys Cys Asn Asn Glu Thr Ser Trp Ile Ile Leu
1               5                   10                  15

Ala Asn Asn Val
            20

<210> SEQ ID NO 121
<211> LENGTH: 20
<212> TYPE: PRT
<213> ORGANISM: Artificial Sequence
<220> FEATURE:
<223> OTHER INFORMATION: synthetic peptide

<400> SEQUENCE: 121

Asn Asn Glu Thr Ser Trp Ile Ile Leu Ala Asn Asn Val Ser Asn Ile
1               5                   10                  15

Ile Thr Glu Ile
            20

<210> SEQ ID NO 122
<211> LENGTH: 20
<212> TYPE: PRT
<213> ORGANISM: Artificial Sequence
<220> FEATURE:
<223> OTHER INFORMATION: synthetic peptide

<400> SEQUENCE: 122

Glu Phe Val Asn Gln Pro Tyr Leu Leu Tyr Ser Val His Ile Lys Ser
1               5                   10                  15

Thr Lys Pro Ser
            20

<210> SEQ ID NO 123
<211> LENGTH: 20
<212> TYPE: PRT
<213> ORGANISM: Artificial Sequence
<220> FEATURE:
<223> OTHER INFORMATION: synthetic peptide

<400> SEQUENCE: 123

Leu Leu Tyr Ser Val His Ile Lys Ser Thr Lys Pro Ser Leu Ser Pro
1               5                   10                  15

Ser Lys Pro Gln
            20

<210> SEQ ID NO 124
<211> LENGTH: 20
<212> TYPE: PRT
<213> ORGANISM: Artificial Sequence
<220> FEATURE:
<223> OTHER INFORMATION: synthetic peptide
```

```
<400> SEQUENCE: 124

Ser Pro Leu Ile Thr Val His Leu Lys His Arg Leu Thr Leu Lys Gln
1               5                   10                  15

His Ser Glu Ala
            20

<210> SEQ ID NO 125
<211> LENGTH: 20
<212> TYPE: PRT
<213> ORGANISM: Artificial Sequence
<220> FEATURE:
<223> OTHER INFORMATION: synthetic peptide

<400> SEQUENCE: 125

Leu Lys His Arg Leu Thr Leu Lys Gln His Ser Glu Ala Thr Asn Ser
1               5                   10                  15

Ser Asn Arg Val
            20

<210> SEQ ID NO 126
<211> LENGTH: 20
<212> TYPE: PRT
<213> ORGANISM: Artificial Sequence
<220> FEATURE:
<223> OTHER INFORMATION: synthetic peptide

<400> SEQUENCE: 126

Glu Arg Gln Ser Leu Ala Gln Ala Ala Ala Gln Glu Ala Val Thr Leu
1               5                   10                  15

Leu Asp Ala Gly
            20

<210> SEQ ID NO 127
<211> LENGTH: 20
<212> TYPE: PRT
<213> ORGANISM: Artificial Sequence
<220> FEATURE:
<223> OTHER INFORMATION: synthetic peptide

<400> SEQUENCE: 127

Ala Ala Ala Gln Glu Ala Val Thr Leu Leu Asp Ala Gly Gln Pro Arg
1               5                   10                  15

Gln Ala Leu Gly
            20

<210> SEQ ID NO 128
<211> LENGTH: 20
<212> TYPE: PRT
<213> ORGANISM: Artificial Sequence
<220> FEATURE:
<223> OTHER INFORMATION: synthetic peptide

<400> SEQUENCE: 128

Ser Arg Val Thr Arg Gln Lys Glu Lys Gly Lys Ser Pro Glu His Leu
1               5                   10                  15

Lys Asp Lys Gly
            20

<210> SEQ ID NO 129
<211> LENGTH: 20
<212> TYPE: PRT
<213> ORGANISM: Artificial Sequence
<220> FEATURE:
```

<223> OTHER INFORMATION: synthetic peptide

<400> SEQUENCE: 129

Glu Lys Gly Lys Ser Pro Glu His Leu Lys Asp Lys Gly Gln Asp Ala
1               5                   10                  15

Arg Glu Arg Arg
            20

<210> SEQ ID NO 130
<211> LENGTH: 20
<212> TYPE: PRT
<213> ORGANISM: Artificial Sequence
<220> FEATURE:
<223> OTHER INFORMATION: synthetic peptide

<400> SEQUENCE: 130

Gly Ala Pro Leu Leu Ser Cys Leu Leu Ala Leu Leu Ala Val Cys Pro
1               5                   10                  15

Gly Gly Arg Pro
            20

<210> SEQ ID NO 131
<211> LENGTH: 20
<212> TYPE: PRT
<213> ORGANISM: Artificial Sequence
<220> FEATURE:
<223> OTHER INFORMATION: synthetic peptide

<400> SEQUENCE: 131

Leu Leu Ala Leu Leu Ala Val Cys Pro Gly Gly Arg Pro Gln Thr Val
1               5                   10                  15

Leu Thr Asp Asp
            20

<210> SEQ ID NO 132
<211> LENGTH: 20
<212> TYPE: PRT
<213> ORGANISM: Artificial Sequence
<220> FEATURE:
<223> OTHER INFORMATION: synthetic peptide

<400> SEQUENCE: 132

Leu Gly Val Thr Gln Ile Leu Leu Gly Val Val Ser Cys Phe Leu Gly
1               5                   10                  15

Val Cys Leu Ser
            20

<210> SEQ ID NO 133
<211> LENGTH: 20
<212> TYPE: PRT
<213> ORGANISM: Artificial Sequence
<220> FEATURE:
<223> OTHER INFORMATION: synthetic peptide

<400> SEQUENCE: 133

Leu Gly Val Val Ser Cys Phe Leu Gly Val Cys Leu Ser Leu Gly Pro
1               5                   10                  15

Trp Thr Val Leu
            20

<210> SEQ ID NO 134
<211> LENGTH: 20
<212> TYPE: PRT
<213> ORGANISM: Artificial Sequence

```
<220> FEATURE:
<223> OTHER INFORMATION: synthetic peptide

<400> SEQUENCE: 134

Ser Ser Ser Asn Gln Gln Asp Pro Gly Glu Pro Gly Glu Glu Glu Val
1               5                   10                  15

Gln Glu Glu Asp
            20

<210> SEQ ID NO 135
<211> LENGTH: 20
<212> TYPE: PRT
<213> ORGANISM: Artificial Sequence
<220> FEATURE:
<223> OTHER INFORMATION: synthetic peptide

<400> SEQUENCE: 135

Pro Gly Glu Pro Gly Glu Glu Glu Val Gln Glu Glu Asp His Asp Val
1               5                   10                  15

Thr Gln Thr Glu
            20

<210> SEQ ID NO 136
<211> LENGTH: 20
<212> TYPE: PRT
<213> ORGANISM: Artificial Sequence
<220> FEATURE:
<223> OTHER INFORMATION: synthetic peptide

<400> SEQUENCE: 136

Met Pro Glu Met Ser Ile Lys Pro Gln Lys Ile Ser Ile Thr Asp Val
1               5                   10                  15

Gly Leu His Leu
            20

<210> SEQ ID NO 137
<211> LENGTH: 20
<212> TYPE: PRT
<213> ORGANISM: Artificial Sequence
<220> FEATURE:
<223> OTHER INFORMATION: synthetic peptide

<400> SEQUENCE: 137

Pro Gln Lys Ile Ser Ile Thr Asp Val Gly Leu His Leu Lys Gly Pro
1               5                   10                  15

Lys Met Lys Gly
            20

<210> SEQ ID NO 138
<211> LENGTH: 20
<212> TYPE: PRT
<213> ORGANISM: Artificial Sequence
<220> FEATURE:
<223> OTHER INFORMATION: synthetic peptide

<400> SEQUENCE: 138

Met Lys Cys Val Leu Val Ala Thr Glu Gly Ala Glu Val Val Phe Tyr
1               5                   10                  15

Trp Thr Asp Gln
            20

<210> SEQ ID NO 139
<211> LENGTH: 20
<212> TYPE: PRT
```

```
<213> ORGANISM: Artificial Sequence
<220> FEATURE:
<223> OTHER INFORMATION: synthetic peptide

<400> SEQUENCE: 139

Thr Glu Gly Ala Glu Val Val Phe Tyr Trp Thr Asp Gln Gln Phe Glu
1               5                   10                  15

Glu Ser Leu Arg
            20

<210> SEQ ID NO 140
<211> LENGTH: 18
<212> TYPE: PRT
<213> ORGANISM: Artificial Sequence
<220> FEATURE:
<223> OTHER INFORMATION: synthetic peptide

<400> SEQUENCE: 140

Met Ala Asp Glu Arg Lys Ser Tyr Ser Glu His Asp Asp Glu Arg Val
1               5                   10                  15

Asn Phe

<210> SEQ ID NO 141
<211> LENGTH: 18
<212> TYPE: PRT
<213> ORGANISM: Artificial Sequence
<220> FEATURE:
<223> OTHER INFORMATION: synthetic peptide

<400> SEQUENCE: 141

Met Ala Asp Glu Arg Lys Ser Tyr Ser Glu His Asp Asp Glu Arg Val
1               5                   10                  15

Asn Phe

<210> SEQ ID NO 142
<211> LENGTH: 20
<212> TYPE: PRT
<213> ORGANISM: Artificial Sequence
<220> FEATURE:
<223> OTHER INFORMATION: synthetic peptide

<400> SEQUENCE: 142

Gln Ser Glu Arg Cys Ala Asn Gly Leu Gly Asn Asp Asn Tyr Ser Asn
1               5                   10                  15

Thr Leu Asn Thr
            20

<210> SEQ ID NO 143
<211> LENGTH: 20
<212> TYPE: PRT
<213> ORGANISM: Artificial Sequence
<220> FEATURE:
<223> OTHER INFORMATION: synthetic peptide

<400> SEQUENCE: 143

Gly Leu Gly Asn Asp Asn Tyr Ser Asn Thr Leu Asn Thr Asp Tyr Ser
1               5                   10                  15

Phe Leu Glu Ile
            20

<210> SEQ ID NO 144
<211> LENGTH: 20
<212> TYPE: PRT
<213> ORGANISM: Artificial Sequence
```

-continued

```
<220> FEATURE:
<223> OTHER INFORMATION: synthetic peptide

<400> SEQUENCE: 144

Ile Lys Leu Arg Leu Gly Glu Lys Glu Ile Leu Glu Lys Val Val Lys
1               5                   10                  15

Ser Ala Ala Val
            20

<210> SEQ ID NO 145
<211> LENGTH: 20
<212> TYPE: PRT
<213> ORGANISM: Artificial Sequence
<220> FEATURE:
<223> OTHER INFORMATION: synthetic peptide

<400> SEQUENCE: 145

Lys Glu Ile Leu Glu Lys Val Val Lys Ser Ala Ala Val Asn Arg Glu
1               5                   10                  15

Tyr Tyr Arg Gln
            20

<210> SEQ ID NO 146
<211> LENGTH: 20
<212> TYPE: PRT
<213> ORGANISM: Artificial Sequence
<220> FEATURE:
<223> OTHER INFORMATION: synthetic peptide

<400> SEQUENCE: 146

Ala Asp Ala Gly Tyr Ala Ile Leu Glu Lys Lys Gly Ala Ile Ala Glu
1               5                   10                  15

Arg Gln His Thr
            20

<210> SEQ ID NO 147
<211> LENGTH: 20
<212> TYPE: PRT
<213> ORGANISM: Artificial Sequence
<220> FEATURE:
<223> OTHER INFORMATION: synthetic peptide

<400> SEQUENCE: 147

Leu Glu Lys Lys Gly Ala Ile Ala Glu Arg Gln His Thr Ser Met Asp
1               5                   10                  15

Leu Pro Lys Leu
            20

<210> SEQ ID NO 148
<211> LENGTH: 20
<212> TYPE: PRT
<213> ORGANISM: Artificial Sequence
<220> FEATURE:
<223> OTHER INFORMATION: synthetic peptide

<400> SEQUENCE: 148

Val Gly Met Val Phe Ser Ala Phe Cys Trp His Ile Glu Tyr His Trp
1               5                   10                  15

Ser Tyr Ser Ile
            20

<210> SEQ ID NO 149
<211> LENGTH: 20
<212> TYPE: PRT
```

```
<213> ORGANISM: Artificial Sequence
<220> FEATURE:
<223> OTHER INFORMATION: synthetic peptide

<400> SEQUENCE: 149

Phe Cys Trp His Ile Glu Tyr His Trp Ser Tyr Ser Ile Asn Tyr Leu
1               5                   10                  15

His Trp Gly Glu
            20

<210> SEQ ID NO 150
<211> LENGTH: 20
<212> TYPE: PRT
<213> ORGANISM: Artificial Sequence
<220> FEATURE:
<223> OTHER INFORMATION: synthetic peptide

<400> SEQUENCE: 150

Arg Ile Leu Glu Lys Lys Gly Ser Ala Ala Leu Lys Asp Ile Lys Arg
1               5                   10                  15

Gln Leu His Leu
            20

<210> SEQ ID NO 151
<211> LENGTH: 20
<212> TYPE: PRT
<213> ORGANISM: Artificial Sequence
<220> FEATURE:
<223> OTHER INFORMATION: synthetic peptide

<400> SEQUENCE: 151

Ser Ala Ala Leu Lys Asp Ile Lys Arg Gln Leu His Leu Glu Arg Lys
1               5                   10                  15

Arg Ala Asp Lys
            20

<210> SEQ ID NO 152
<211> LENGTH: 20
<212> TYPE: PRT
<213> ORGANISM: Artificial Sequence
<220> FEATURE:
<223> OTHER INFORMATION: synthetic peptide

<400> SEQUENCE: 152

Pro Gly Tyr Gln Gly Val Asn Cys Glu Tyr Glu Val Asp Asp Cys Gln
1               5                   10                  15

Asn Gln Pro Cys
            20

<210> SEQ ID NO 153
<211> LENGTH: 20
<212> TYPE: PRT
<213> ORGANISM: Artificial Sequence
<220> FEATURE:
<223> OTHER INFORMATION: synthetic peptide

<400> SEQUENCE: 153

Cys Glu Tyr Glu Val Asp Asp Cys Gln Asn Gln Pro Cys Gln Asn Gly
1               5                   10                  15

Gly Thr Cys Ile
            20

<210> SEQ ID NO 154
<211> LENGTH: 20
```

```
<212> TYPE: PRT
<213> ORGANISM: Artificial Sequence
<220> FEATURE:
<223> OTHER INFORMATION: synthetic peptide

<400> SEQUENCE: 154

Val Val Gly Ser Lys Asp Met Ser Thr Trp Val Phe Gly Thr Glu Arg
1               5                   10                  15

Trp Asp Asn Leu
            20

<210> SEQ ID NO 155
<211> LENGTH: 20
<212> TYPE: PRT
<213> ORGANISM: Artificial Sequence
<220> FEATURE:
<223> OTHER INFORMATION: synthetic peptide

<400> SEQUENCE: 155

Ser Thr Trp Val Phe Gly Thr Glu Arg Trp Asp Asn Leu Ile Tyr Tyr
1               5                   10                  15

Ala Leu Gly Gly
            20

<210> SEQ ID NO 156
<211> LENGTH: 20
<212> TYPE: PRT
<213> ORGANISM: Artificial Sequence
<220> FEATURE:
<223> OTHER INFORMATION: synthetic peptide

<400> SEQUENCE: 156

Leu Glu Glu Ser Glu Arg Asp Arg Arg Glu Glu Ser Arg Gln His Gly
1               5                   10                  15

Arg Asn Trp Gly
            20

<210> SEQ ID NO 157
<211> LENGTH: 20
<212> TYPE: PRT
<213> ORGANISM: Artificial Sequence
<220> FEATURE:
<223> OTHER INFORMATION: synthetic peptide

<400> SEQUENCE: 157

Arg Arg Glu Glu Ser Arg Gln His Gly Arg Asn Trp Gly Gly Pro Asp
1               5                   10                  15

Phe Glu Arg Val
            20

<210> SEQ ID NO 158
<211> LENGTH: 20
<212> TYPE: PRT
<213> ORGANISM: Artificial Sequence
<220> FEATURE:
<223> OTHER INFORMATION: synthetic peptide

<400> SEQUENCE: 158

Arg Arg Leu Ser Leu Gln Pro Arg Ser His Ser Val Pro His Ser Pro
1               5                   10                  15

Ser Gln Gly Ser
            20

<210> SEQ ID NO 159
```

```
<211> LENGTH: 20
<212> TYPE: PRT
<213> ORGANISM: Artificial Sequence
<220> FEATURE:
<223> OTHER INFORMATION: synthetic peptide

<400> SEQUENCE: 159

Arg Ser His Ser Val Pro His Ser Pro Ser Gln Gly Ser Tyr Ser Arg
1               5                   10                  15

Ala Arg Ile Tyr
            20

<210> SEQ ID NO 160
<211> LENGTH: 20
<212> TYPE: PRT
<213> ORGANISM: Artificial Sequence
<220> FEATURE:
<223> OTHER INFORMATION: synthetic peptide

<400> SEQUENCE: 160

Val Leu Pro Pro Val Tyr Asn Gln Gln Asn Glu Asp Thr Phe Ile Ile
1               5                   10                  15

Arg Ile Ser Val
            20

<210> SEQ ID NO 161
<211> LENGTH: 20
<212> TYPE: PRT
<213> ORGANISM: Artificial Sequence
<220> FEATURE:
<223> OTHER INFORMATION: synthetic peptide

<400> SEQUENCE: 161

Gln Gln Asn Glu Asp Thr Phe Ile Ile Arg Ile Ser Val Glu Asp Asn
1               5                   10                  15

Asn Gly Asn Met
            20

<210> SEQ ID NO 162
<211> LENGTH: 20
<212> TYPE: PRT
<213> ORGANISM: Artificial Sequence
<220> FEATURE:
<223> OTHER INFORMATION: synthetic peptide

<400> SEQUENCE: 162

Leu Arg Tyr Leu Ala Glu Leu Cys Gly Val Gly Ala Val Ile Pro Gly
1               5                   10                  15

Thr Cys Gly Gly
            20

<210> SEQ ID NO 163
<211> LENGTH: 20
<212> TYPE: PRT
<213> ORGANISM: Artificial Sequence
<220> FEATURE:
<223> OTHER INFORMATION: synthetic peptide

<400> SEQUENCE: 163

Cys Gly Val Gly Ala Val Ile Pro Gly Thr Cys Gly Gly Pro Arg
1               5                   10                  15

Ala Ala Phe Pro
            20
```

```
<210> SEQ ID NO 164
<211> LENGTH: 20
<212> TYPE: PRT
<213> ORGANISM: Artificial Sequence
<220> FEATURE:
<223> OTHER INFORMATION: synthetic peptide

<400> SEQUENCE: 164

Gln Asp Phe Thr Thr Leu Arg Asp His Cys Leu Ser Met Val Arg Thr
1               5                   10                  15

Phe Lys Asp Glu
            20

<210> SEQ ID NO 165
<211> LENGTH: 20
<212> TYPE: PRT
<213> ORGANISM: Artificial Sequence
<220> FEATURE:
<223> OTHER INFORMATION: synthetic peptide

<400> SEQUENCE: 165

Asp His Cys Leu Ser Met Val Arg Thr Phe Lys Asp Glu Thr Phe Pro
1               5                   10                  15

Ala Ala Asp Ser
            20

<210> SEQ ID NO 166
<211> LENGTH: 20
<212> TYPE: PRT
<213> ORGANISM: Artificial Sequence
<220> FEATURE:
<223> OTHER INFORMATION: synthetic peptide

<400> SEQUENCE: 166

Ala Pro Glu Gly Glu Pro Gly Ala Pro Gln Ala Leu Gly Tyr Ala Pro
1               5                   10                  15

Ser Thr Ser Val
            20

<210> SEQ ID NO 167
<211> LENGTH: 20
<212> TYPE: PRT
<213> ORGANISM: Artificial Sequence
<220> FEATURE:
<223> OTHER INFORMATION: synthetic peptide

<400> SEQUENCE: 167

Ala Pro Gln Ala Leu Gly Tyr Ala Pro Ser Thr Ser Val Ser Leu Thr
1               5                   10                  15

Thr Ala Val Gln
            20

<210> SEQ ID NO 168
<211> LENGTH: 20
<212> TYPE: PRT
<213> ORGANISM: Artificial Sequence
<220> FEATURE:
<223> OTHER INFORMATION: synthetic peptide

<400> SEQUENCE: 168

Ser Glu Arg Gly Glu Pro Ser Asn Glu Pro Ser Thr Glu Ala Asn Lys
1               5                   10                  15

Thr Gln Glu Gln
            20
```

<210> SEQ ID NO 169
<211> LENGTH: 20
<212> TYPE: PRT
<213> ORGANISM: Artificial Sequence
<220> FEATURE:
<223> OTHER INFORMATION: synthetic peptide

<400> SEQUENCE: 169

Asn Glu Pro Ser Thr Glu Ala Asn Lys Thr Gln Glu Gln Ser Asp Val
1               5                   10                  15

Lys Leu Pro Lys
            20

<210> SEQ ID NO 170
<211> LENGTH: 20
<212> TYPE: PRT
<213> ORGANISM: Artificial Sequence
<220> FEATURE:
<223> OTHER INFORMATION: synthetic peptide

<400> SEQUENCE: 170

Asn Gly Leu Arg Gly Val Glu Leu Glu Ala Ser Pro Ala Leu Ser Gly
1               5                   10                  15

Asn Pro Glu Glu
            20

<210> SEQ ID NO 171
<211> LENGTH: 20
<212> TYPE: PRT
<213> ORGANISM: Artificial Sequence
<220> FEATURE:
<223> OTHER INFORMATION: synthetic peptide

<400> SEQUENCE: 171

Leu Glu Ala Ser Pro Ala Leu Ser Gly Asn Pro Glu Glu Thr Asp Lys
1               5                   10                  15

Leu Leu Lys Arg
            20

<210> SEQ ID NO 172
<211> LENGTH: 20
<212> TYPE: PRT
<213> ORGANISM: Artificial Sequence
<220> FEATURE:
<223> OTHER INFORMATION: synthetic peptide

<400> SEQUENCE: 172

Leu Gln Tyr Thr Leu Glu Asp Met Arg Ala Thr Leu Thr Gln His Val
1               5                   10                  15

Asp Glu Ile Lys
            20

<210> SEQ ID NO 173
<211> LENGTH: 20
<212> TYPE: PRT
<213> ORGANISM: Artificial Sequence
<220> FEATURE:
<223> OTHER INFORMATION: synthetic peptide

<400> SEQUENCE: 173

Met Arg Ala Thr Leu Thr Gln His Val Asp Glu Ile Lys Glu Leu Tyr
1               5                   10                  15

Ser Glu Ser Asp
            20

<210> SEQ ID NO 174
<211> LENGTH: 20
<212> TYPE: PRT
<213> ORGANISM: Artificial Sequence
<220> FEATURE:
<223> OTHER INFORMATION: synthetic peptide

<400> SEQUENCE: 174

Ser Gly Glu Glu His Asp Met Trp Val Phe Arg Leu Cys Phe Leu Trp
1               5                   10                  15

Leu Glu Asn Ser
            20

<210> SEQ ID NO 175
<211> LENGTH: 20
<212> TYPE: PRT
<213> ORGANISM: Artificial Sequence
<220> FEATURE:
<223> OTHER INFORMATION: synthetic peptide

<400> SEQUENCE: 175

Trp Val Phe Arg Leu Cys Phe Leu Trp Leu Glu Asn Ser Gly Val Ser
1               5                   10                  15

Glu Val Asn Gly
            20

<210> SEQ ID NO 176
<211> LENGTH: 20
<212> TYPE: PRT
<213> ORGANISM: Artificial Sequence
<220> FEATURE:
<223> OTHER INFORMATION: synthetic peptide

<400> SEQUENCE: 176

Val Arg Leu Ala Leu Gly Asn Gly Leu Arg Gly Asp Val Leu Arg Gln
1               5                   10                  15

Phe Val Lys Arg
            20

<210> SEQ ID NO 177
<211> LENGTH: 20
<212> TYPE: PRT
<213> ORGANISM: Artificial Sequence
<220> FEATURE:
<223> OTHER INFORMATION: synthetic peptide

<400> SEQUENCE: 177

Gly Leu Arg Gly Asp Val Leu Arg Gln Phe Val Lys Arg Phe Gly Asp
1               5                   10                  15

Ile Cys Ile Tyr
            20

<210> SEQ ID NO 178
<211> LENGTH: 20
<212> TYPE: PRT
<213> ORGANISM: Artificial Sequence
<220> FEATURE:
<223> OTHER INFORMATION: synthetic peptide

<400> SEQUENCE: 178

Gly Val Lys Gly Leu Pro Leu Asn Ile Gln Val Asp Thr Cys Ser Tyr
1               5                   10                  15

Asn Asn Arg Ser

```
                    20

<210> SEQ ID NO 179
<211> LENGTH: 20
<212> TYPE: PRT
<213> ORGANISM: Artificial Sequence
<220> FEATURE:
<223> OTHER INFORMATION: synthetic peptide

<400> SEQUENCE: 179

Asn Ile Gln Val Asp Thr Cys Ser Tyr Asn Asn Arg Ser Asn Lys Pro
1               5                   10                  15

Val His Arg Ala
            20

<210> SEQ ID NO 180
<211> LENGTH: 20
<212> TYPE: PRT
<213> ORGANISM: Artificial Sequence
<220> FEATURE:
<223> OTHER INFORMATION: synthetic peptide

<400> SEQUENCE: 180

Arg Thr Asn Ser Val Pro Thr Ser Gln Cys Gly Val Ser Phe Leu Ala
1               5                   10                  15

Ala Ala Thr Val
            20

<210> SEQ ID NO 181
<211> LENGTH: 20
<212> TYPE: PRT
<213> ORGANISM: Artificial Sequence
<220> FEATURE:
<223> OTHER INFORMATION: synthetic peptide

<400> SEQUENCE: 181

Ser Gln Cys Gly Val Ser Phe Leu Ala Ala Ala Thr Val Ser Thr Ser
1               5                   10                  15

Pro Val Leu Leu
            20

<210> SEQ ID NO 182
<211> LENGTH: 20
<212> TYPE: PRT
<213> ORGANISM: Artificial Sequence
<220> FEATURE:
<223> OTHER INFORMATION: synthetic peptide

<400> SEQUENCE: 182

Lys Phe Ser Glu Asp His Leu Asn Ile Thr Cys Ser Ala Ser Ala Arg
1               5                   10                  15

Pro Ala Pro Met
            20

<210> SEQ ID NO 183
<211> LENGTH: 20
<212> TYPE: PRT
<213> ORGANISM: Artificial Sequence
<220> FEATURE:
<223> OTHER INFORMATION: synthetic peptide

<400> SEQUENCE: 183

Asn Ile Thr Cys Ser Ala Ser Ala Arg Pro Ala Pro Met Val Phe Trp
1               5                   10                  15
```

```
Lys Val Pro Arg
         20

<210> SEQ ID NO 184
<211> LENGTH: 20
<212> TYPE: PRT
<213> ORGANISM: Artificial Sequence
<220> FEATURE:
<223> OTHER INFORMATION: synthetic peptide

<400> SEQUENCE: 184

Ala Ala Ala Ala Gly Ser Ala Pro Ser Gln Ala Gly Pro Val Ser Ala
1               5                   10                  15

Pro Ser Ser Ala
         20

<210> SEQ ID NO 185
<211> LENGTH: 20
<212> TYPE: PRT
<213> ORGANISM: Artificial Sequence
<220> FEATURE:
<223> OTHER INFORMATION: synthetic peptide

<400> SEQUENCE: 185

Pro Ser Gln Ala Gly Pro Val Ser Ala Pro Ser Ser Ala Ala Ser Gly
1               5                   10                  15

Ala Ser Ser Pro
         20

<210> SEQ ID NO 186
<211> LENGTH: 20
<212> TYPE: PRT
<213> ORGANISM: Artificial Sequence
<220> FEATURE:
<223> OTHER INFORMATION: synthetic peptide

<400> SEQUENCE: 186

Gln Leu Pro Leu Ser Arg Ile Lys Phe Thr Gly Lys Glu Phe Glu Asp
1               5                   10                  15

Ser Gln Leu Val
         20

<210> SEQ ID NO 187
<211> LENGTH: 20
<212> TYPE: PRT
<213> ORGANISM: Artificial Sequence
<220> FEATURE:
<223> OTHER INFORMATION: synthetic peptide

<400> SEQUENCE: 187

Lys Phe Thr Gly Lys Glu Phe Glu Asp Ser Gln Leu Val Ser His Leu
1               5                   10                  15

Met Ser Cys Lys
         20

<210> SEQ ID NO 188
<211> LENGTH: 20
<212> TYPE: PRT
<213> ORGANISM: Artificial Sequence
<220> FEATURE:
<223> OTHER INFORMATION: synthetic peptide

<400> SEQUENCE: 188

Val Glu Gln Glu Asp Ala Gly Asp Tyr Thr Cys Asp Thr Cys His Thr
1               5                   10                  15
```

Gln Ser Met Ala
            20

<210> SEQ ID NO 189
<211> LENGTH: 20
<212> TYPE: PRT
<213> ORGANISM: Artificial Sequence
<220> FEATURE:
<223> OTHER INFORMATION: synthetic peptide

<400> SEQUENCE: 189

Asp Tyr Thr Cys Asp Thr Cys His Thr Gln Ser Met Ala Ser Leu Ser
1               5                   10                  15

Val Arg Val Pro
            20

<210> SEQ ID NO 190
<211> LENGTH: 20
<212> TYPE: PRT
<213> ORGANISM: Artificial Sequence
<220> FEATURE:
<223> OTHER INFORMATION: synthetic peptide

<400> SEQUENCE: 190

Leu Pro Gly Gln Gln Glu Lys Glu Ala Ser Ala Ser Pro Tyr Pro Ala
1               5                   10                  15

Lys Lys Ser Phe
            20

<210> SEQ ID NO 191
<211> LENGTH: 20
<212> TYPE: PRT
<213> ORGANISM: Artificial Sequence
<220> FEATURE:
<223> OTHER INFORMATION: synthetic peptide

<400> SEQUENCE: 191

Glu Ala Ser Ala Ser Pro Tyr Pro Ala Lys Lys Ser Phe Ile Cys Lys
1               5                   10                  15

Ala Cys Asp Lys
            20

<210> SEQ ID NO 192
<211> LENGTH: 20
<212> TYPE: PRT
<213> ORGANISM: Artificial Sequence
<220> FEATURE:
<223> OTHER INFORMATION: synthetic peptide

<400> SEQUENCE: 192

Leu Leu Phe Phe Ser Leu Ser Gly Leu Ser Ile Ile Cys Asp Met Ser
1               5                   10                  15

Val Glu Arg Tyr
            20

<210> SEQ ID NO 193
<211> LENGTH: 20
<212> TYPE: PRT
<213> ORGANISM: Artificial Sequence
<220> FEATURE:
<223> OTHER INFORMATION: synthetic peptide

<400> SEQUENCE: 193

Gly Leu Ser Ile Ile Cys Asp Met Ser Val Glu Arg Tyr Leu Ala Ile

Asn His Ala Tyr
        20

<210> SEQ ID NO 194
<211> LENGTH: 20
<212> TYPE: PRT
<213> ORGANISM: Artificial Sequence
<220> FEATURE:
<223> OTHER INFORMATION: synthetic peptide

<400> SEQUENCE: 194

Thr Glu Ala Lys Ser Lys Leu Thr Pro Thr Leu Tyr Val Trp Lys Tyr
1               5                   10                  15

Ser Thr Ser Leu
        20

<210> SEQ ID NO 195
<211> LENGTH: 20
<212> TYPE: PRT
<213> ORGANISM: Artificial Sequence
<220> FEATURE:
<223> OTHER INFORMATION: synthetic peptide

<400> SEQUENCE: 195

Thr Pro Thr Leu Tyr Val Trp Lys Tyr Ser Thr Ser Leu Tyr Ala Ser
1               5                   10                  15

Pro Ser Met Val
        20

<210> SEQ ID NO 196
<211> LENGTH: 20
<212> TYPE: PRT
<213> ORGANISM: Artificial Sequence
<220> FEATURE:
<223> OTHER INFORMATION: synthetic peptide

<400> SEQUENCE: 196

Glu Ser Trp Val Gln Thr Val Leu Pro Leu Val Met Asp Thr Gln Leu
1               5                   10                  15

Leu Gly Gln Arg
        20

<210> SEQ ID NO 197
<211> LENGTH: 20
<212> TYPE: PRT
<213> ORGANISM: Artificial Sequence
<220> FEATURE:
<223> OTHER INFORMATION: synthetic peptide

<400> SEQUENCE: 197

Leu Pro Leu Val Met Asp Thr Gln Leu Leu Gly Gln Arg Leu Lys Pro
1               5                   10                  15

Arg Asp Pro Cys
        20

<210> SEQ ID NO 198
<211> LENGTH: 20
<212> TYPE: PRT
<213> ORGANISM: Artificial Sequence
<220> FEATURE:
<223> OTHER INFORMATION: synthetic peptide

<400> SEQUENCE: 198

```
Val Arg Asp Gly Arg Ala Ser Val His Ser Met Ile Ser Gln Lys Val
1               5                   10                  15

Thr Ile Ala Gly
            20

<210> SEQ ID NO 199
<211> LENGTH: 20
<212> TYPE: PRT
<213> ORGANISM: Artificial Sequence
<220> FEATURE:
<223> OTHER INFORMATION: synthetic peptide

<400> SEQUENCE: 199

Val His Ser Met Ile Ser Gln Lys Val Thr Ile Ala Gly Phe Asp Leu
1               5                   10                  15

Asn Ser Tyr Arg
            20

<210> SEQ ID NO 200
<211> LENGTH: 20
<212> TYPE: PRT
<213> ORGANISM: Artificial Sequence
<220> FEATURE:
<223> OTHER INFORMATION: synthetic peptide

<400> SEQUENCE: 200

Glu Gly Asp Cys Trp Ile Cys Met Glu Leu Met Ser Thr Leu Phe Asp
1               5                   10                  15

Lys Phe Tyr Lys
            20

<210> SEQ ID NO 201
<211> LENGTH: 20
<212> TYPE: PRT
<213> ORGANISM: Artificial Sequence
<220> FEATURE:
<223> OTHER INFORMATION: synthetic peptide

<400> SEQUENCE: 201

Met Glu Leu Met Ser Thr Leu Phe Asp Lys Phe Tyr Lys Tyr Val Tyr
1               5                   10                  15

Ser Val Leu Asp
            20

<210> SEQ ID NO 202
<211> LENGTH: 20
<212> TYPE: PRT
<213> ORGANISM: Artificial Sequence
<220> FEATURE:
<223> OTHER INFORMATION: synthetic peptide

<400> SEQUENCE: 202

Glu Phe Asn Cys Pro Val Thr Phe Cys Lys Lys Gly Phe Arg Tyr Phe
1               5                   10                  15

Lys Asn Leu Ile
            20

<210> SEQ ID NO 203
<211> LENGTH: 20
<212> TYPE: PRT
<213> ORGANISM: Artificial Sequence
<220> FEATURE:
<223> OTHER INFORMATION: synthetic peptide

<400> SEQUENCE: 203
```

```
Phe Cys Lys Lys Gly Phe Arg Tyr Phe Lys Asn Leu Ile Ala His Val
1               5                   10                  15

Lys Gly His Lys
            20

<210> SEQ ID NO 204
<211> LENGTH: 20
<212> TYPE: PRT
<213> ORGANISM: Artificial Sequence
<220> FEATURE:
<223> OTHER INFORMATION: synthetic peptide

<400> SEQUENCE: 204

Ile His Arg Asp Leu Ala Ala Arg Asn Cys Leu Val Gly Lys Asn His
1               5                   10                  15

Val Val Lys Val
            20

<210> SEQ ID NO 205
<211> LENGTH: 20
<212> TYPE: PRT
<213> ORGANISM: Artificial Sequence
<220> FEATURE:
<223> OTHER INFORMATION: synthetic peptide

<400> SEQUENCE: 205

Arg Asn Cys Leu Val Gly Lys Asn His Val Val Lys Val Ala Asp Phe
1               5                   10                  15

Gly Leu Ser Arg
            20

<210> SEQ ID NO 206
<211> LENGTH: 20
<212> TYPE: PRT
<213> ORGANISM: Artificial Sequence
<220> FEATURE:
<223> OTHER INFORMATION: synthetic peptide

<400> SEQUENCE: 206

Asn Lys Ala Gly Ser Phe Phe Trp Asn Leu Arg Gln Phe Ile Thr Leu
1               5                   10                  15

Val Ser Thr Ser
            20

<210> SEQ ID NO 207
<211> LENGTH: 20
<212> TYPE: PRT
<213> ORGANISM: Artificial Sequence
<220> FEATURE:
<223> OTHER INFORMATION: synthetic peptide

<400> SEQUENCE: 207

Trp Asn Leu Arg Gln Phe Ile Thr Leu Val Ser Thr Ser Arg Thr Met
1               5                   10                  15

Arg Leu Cys Cys
            20

<210> SEQ ID NO 208
<211> LENGTH: 20
<212> TYPE: PRT
<213> ORGANISM: Artificial Sequence
<220> FEATURE:
<223> OTHER INFORMATION: synthetic peptide
```

-continued

<400> SEQUENCE: 208

Glu Asn Gln Asp Val Ile Ser Glu Ile Leu Asn Ser His Val Asn Ile
1               5                   10                  15

Met Pro Met Asp
            20

<210> SEQ ID NO 209
<211> LENGTH: 20
<212> TYPE: PRT
<213> ORGANISM: Artificial Sequence
<220> FEATURE:
<223> OTHER INFORMATION: synthetic peptide

<400> SEQUENCE: 209

Glu Ile Leu Asn Ser His Val Asn Ile Met Pro Met Asp Ile Lys Gly
1               5                   10                  15

Ile Ala Arg Thr
            20

<210> SEQ ID NO 210
<211> LENGTH: 20
<212> TYPE: PRT
<213> ORGANISM: Artificial Sequence
<220> FEATURE:
<223> OTHER INFORMATION: synthetic peptide

<400> SEQUENCE: 210

Ile Leu Ser Ser Gly Val Phe Tyr Phe Ser Trp Pro Asn Asn Gly Ser
1               5                   10                  15

Arg Phe Asp Leu
            20

<210> SEQ ID NO 211
<211> LENGTH: 20
<212> TYPE: PRT
<213> ORGANISM: Artificial Sequence
<220> FEATURE:
<223> OTHER INFORMATION: synthetic peptide

<400> SEQUENCE: 211

Tyr Phe Ser Trp Pro Asn Asn Gly Ser Arg Phe Asp Leu Thr Val Arg
1               5                   10                  15

Thr Gln Lys Gln
            20

<210> SEQ ID NO 212
<211> LENGTH: 20
<212> TYPE: PRT
<213> ORGANISM: Artificial Sequence
<220> FEATURE:
<223> OTHER INFORMATION: synthetic peptide

<400> SEQUENCE: 212

Met Trp Leu Arg Ala Phe Ile Leu Ala Thr Leu Ala Ala Ser Ala Ala
1               5                   10                  15

Trp Gly His Pro
            20

<210> SEQ ID NO 213
<211> LENGTH: 20
<212> TYPE: PRT
<213> ORGANISM: Artificial Sequence
<220> FEATURE:
<223> OTHER INFORMATION: synthetic peptide

```
<400> SEQUENCE: 213

Phe Ile Leu Ala Thr Leu Ala Ala Ser Ala Ala Trp Gly His Pro Ser
1               5                   10                  15

Ser Pro Pro Val
            20

<210> SEQ ID NO 214
<211> LENGTH: 20
<212> TYPE: PRT
<213> ORGANISM: Artificial Sequence
<220> FEATURE:
<223> OTHER INFORMATION: synthetic peptide

<400> SEQUENCE: 214

Thr Ile Leu Gln Ala Phe Ser Leu Glu Ser Pro Cys Pro Leu Asp Thr
1               5                   10                  15

Leu Ser Leu Lys
            20

<210> SEQ ID NO 215
<211> LENGTH: 20
<212> TYPE: PRT
<213> ORGANISM: Artificial Sequence
<220> FEATURE:
<223> OTHER INFORMATION: synthetic peptide

<400> SEQUENCE: 215

Leu Glu Ser Pro Cys Pro Leu Asp Thr Leu Ser Leu Lys Pro Thr Val
1               5                   10                  15

Ser Gly Leu Phe
            20

<210> SEQ ID NO 216
<211> LENGTH: 20
<212> TYPE: PRT
<213> ORGANISM: Artificial Sequence
<220> FEATURE:
<223> OTHER INFORMATION: synthetic peptide

<400> SEQUENCE: 216

Asp Ile Leu Trp Arg Gln Asp Ile Asp Leu Gly Val Ser Gln Glu Val
1               5                   10                  15

Phe Asp Phe Ser
            20

<210> SEQ ID NO 217
<211> LENGTH: 20
<212> TYPE: PRT
<213> ORGANISM: Artificial Sequence
<220> FEATURE:
<223> OTHER INFORMATION: synthetic peptide

<400> SEQUENCE: 217

Ile Asp Leu Gly Val Ser Gln Glu Val Phe Asp Phe Ser Gln Arg Arg
1               5                   10                  15

Lys Glu Tyr Glu
            20

<210> SEQ ID NO 218
<211> LENGTH: 20
<212> TYPE: PRT
<213> ORGANISM: Artificial Sequence
<220> FEATURE:
```

<223> OTHER INFORMATION: synthetic peptide

<400> SEQUENCE: 218

Arg Thr Val Val Asp Ser Glu Gly Arg Thr Glu Thr Thr Ile Thr Arg
1               5                   10                  15

His Glu Ala Asp
            20

<210> SEQ ID NO 219
<211> LENGTH: 20
<212> TYPE: PRT
<213> ORGANISM: Artificial Sequence
<220> FEATURE:
<223> OTHER INFORMATION: synthetic peptide

<400> SEQUENCE: 219

Gly Arg Thr Glu Thr Thr Ile Thr Arg His Glu Ala Asp Ser Ser Pro
1               5                   10                  15

Arg Gly Asp Pro
            20

<210> SEQ ID NO 220
<211> LENGTH: 20
<212> TYPE: PRT
<213> ORGANISM: Artificial Sequence
<220> FEATURE:
<223> OTHER INFORMATION: synthetic peptide

<400> SEQUENCE: 220

Pro Lys Phe Gly Phe Gly Ala Lys Ser Pro Lys Ala Asp Thr Lys Ser
1               5                   10                  15

Pro Ser Leu Asp
            20

<210> SEQ ID NO 221
<211> LENGTH: 20
<212> TYPE: PRT
<213> ORGANISM: Artificial Sequence
<220> FEATURE:
<223> OTHER INFORMATION: synthetic peptide

<400> SEQUENCE: 221

Lys Ser Pro Lys Ala Asp Thr Lys Ser Pro Ser Leu Asp Val Thr Val
1               5                   10                  15

Pro Glu Ala Glu
            20

<210> SEQ ID NO 222
<211> LENGTH: 20
<212> TYPE: PRT
<213> ORGANISM: Artificial Sequence
<220> FEATURE:
<223> OTHER INFORMATION: synthetic peptide

<400> SEQUENCE: 222

Glu Leu Gln Gln Glu Glu Glu Gln Leu Leu Arg Glu Glu Pro Glu Lys
1               5                   10                  15

Arg Arg Arg Gln
            20

<210> SEQ ID NO 223
<211> LENGTH: 20
<212> TYPE: PRT
<213> ORGANISM: Artificial Sequence

```
<220> FEATURE:
<223> OTHER INFORMATION: synthetic peptide

<400> SEQUENCE: 223

Gln Leu Leu Arg Glu Glu Pro Glu Lys Arg Arg Arg Gln Glu Leu Glu
1               5                   10                  15
Arg Gln Tyr Arg
            20

<210> SEQ ID NO 224
<211> LENGTH: 20
<212> TYPE: PRT
<213> ORGANISM: Artificial Sequence
<220> FEATURE:
<223> OTHER INFORMATION: synthetic peptide

<400> SEQUENCE: 224

Met Ser Gln Glu Arg Phe Thr Gln Asp Thr Gln Pro His Cys Ile Tyr
1               5                   10                  15
Ser Pro Arg Glu
            20

<210> SEQ ID NO 225
<211> LENGTH: 20
<212> TYPE: PRT
<213> ORGANISM: Artificial Sequence
<220> FEATURE:
<223> OTHER INFORMATION: synthetic peptide

<400> SEQUENCE: 225

Gln Asp Thr Gln Pro His Cys Ile Tyr Ser Pro Arg Glu Met Thr Arg
1               5                   10                  15
Trp Val Arg Gly
            20

<210> SEQ ID NO 226
<211> LENGTH: 20
<212> TYPE: PRT
<213> ORGANISM: Artificial Sequence
<220> FEATURE:
<223> OTHER INFORMATION: synthetic peptide

<400> SEQUENCE: 226

Gly Glu Glu Leu Asp Lys Leu Trp Arg Glu Phe Leu His Gln Lys Glu
1               5                   10                  15
Lys Val His Glu
            20

<210> SEQ ID NO 227
<211> LENGTH: 20
<212> TYPE: PRT
<213> ORGANISM: Artificial Sequence
<220> FEATURE:
<223> OTHER INFORMATION: synthetic peptide

<400> SEQUENCE: 227

Trp Arg Glu Phe Leu His Gln Lys Glu Lys Val His Glu Tyr Asn Val
1               5                   10                  15
Leu Leu Glu Thr
            20

<210> SEQ ID NO 228
<211> LENGTH: 20
<212> TYPE: PRT
```

```
<213> ORGANISM: Artificial Sequence
<220> FEATURE:
<223> OTHER INFORMATION: synthetic peptide

<400> SEQUENCE: 228

Phe Gly Glu Ile Ser Gly Thr Ile Ala Ile Glu Met Asp Glu Gly Thr
1               5                   10                  15

Tyr Ile His Ala
            20

<210> SEQ ID NO 229
<211> LENGTH: 20
<212> TYPE: PRT
<213> ORGANISM: Artificial Sequence
<220> FEATURE:
<223> OTHER INFORMATION: synthetic peptide

<400> SEQUENCE: 229

Ile Ala Ile Glu Met Asp Glu Gly Thr Tyr Ile His Ala Leu Asp Asn
1               5                   10                  15

Gly Leu Phe Thr
            20

<210> SEQ ID NO 230
<211> LENGTH: 20
<212> TYPE: PRT
<213> ORGANISM: Artificial Sequence
<220> FEATURE:
<223> OTHER INFORMATION: synthetic peptide

<400> SEQUENCE: 230

Ile Asp Tyr Ile Arg Phe Leu Gln His Ser Asn Gln Lys Pro Lys Gln
1               5                   10                  15

Glu Asn Leu Ser
            20

<210> SEQ ID NO 231
<211> LENGTH: 20
<212> TYPE: PRT
<213> ORGANISM: Artificial Sequence
<220> FEATURE:
<223> OTHER INFORMATION: synthetic peptide

<400> SEQUENCE: 231

Gln His Ser Asn Gln Lys Pro Lys Gln Glu Asn Leu Ser Leu Arg Thr
1               5                   10                  15

Ala Val His Lys
            20

<210> SEQ ID NO 232
<211> LENGTH: 20
<212> TYPE: PRT
<213> ORGANISM: Artificial Sequence
<220> FEATURE:
<223> OTHER INFORMATION: synthetic peptide

<400> SEQUENCE: 232

Ile Ile His Arg Asp Leu Lys Cys Asp Asn Ile Phe Ile Ile Gly Pro
1               5                   10                  15

Thr Gly Ser Val
            20

<210> SEQ ID NO 233
<211> LENGTH: 20
```

```
<212> TYPE: PRT
<213> ORGANISM: Artificial Sequence
<220> FEATURE:
<223> OTHER INFORMATION: synthetic peptide

<400> SEQUENCE: 233

Cys Asp Asn Ile Phe Ile Ile Gly Pro Thr Gly Ser Val Lys Ile Gly
1               5                   10                  15

Asp Leu Gly Leu
            20

<210> SEQ ID NO 234
<211> LENGTH: 20
<212> TYPE: PRT
<213> ORGANISM: Artificial Sequence
<220> FEATURE:
<223> OTHER INFORMATION: synthetic peptide

<400> SEQUENCE: 234

Val Glu Val Glu Val Thr Thr Ala Pro Gly Ile Tyr Ser Leu Thr Glu
1               5                   10                  15

Met Leu Asp Phe
            20

<210> SEQ ID NO 235
<211> LENGTH: 20
<212> TYPE: PRT
<213> ORGANISM: Artificial Sequence
<220> FEATURE:
<223> OTHER INFORMATION: synthetic peptide

<400> SEQUENCE: 235

Ala Pro Gly Ile Tyr Ser Leu Thr Glu Met Leu Asp Phe Gly Thr Leu
1               5                   10                  15

Arg Thr Gln Asp
            20

<210> SEQ ID NO 236
<211> LENGTH: 20
<212> TYPE: PRT
<213> ORGANISM: Artificial Sequence
<220> FEATURE:
<223> OTHER INFORMATION: synthetic peptide

<400> SEQUENCE: 236

Glu Asp Thr Phe Leu Ser Glu Ser Asp Ser Glu Glu Lys Ser Ser
1               5                   10                  15

Ser Lys Arg Arg
            20

<210> SEQ ID NO 237
<211> LENGTH: 20
<212> TYPE: PRT
<213> ORGANISM: Artificial Sequence
<220> FEATURE:
<223> OTHER INFORMATION: synthetic peptide

<400> SEQUENCE: 237

Ser Asp Ser Glu Glu Lys Ser Ser Ser Lys Arg Arg Gly Arg Gly
1               5                   10                  15

Ser Gln Lys Asp
            20

<210> SEQ ID NO 238
```

```
<211> LENGTH: 20
<212> TYPE: PRT
<213> ORGANISM: Artificial Sequence
<220> FEATURE:
<223> OTHER INFORMATION: synthetic peptide

<400> SEQUENCE: 238

Leu Ala Pro Ser Asp Pro Phe Ser Leu Lys Thr Ile Glu Tyr Val Arg
1               5                   10                  15

Glu Phe Leu Gly
            20

<210> SEQ ID NO 239
<211> LENGTH: 20
<212> TYPE: PRT
<213> ORGANISM: Artificial Sequence
<220> FEATURE:
<223> OTHER INFORMATION: synthetic peptide

<400> SEQUENCE: 239

Ser Leu Lys Thr Ile Glu Tyr Val Arg Glu Phe Leu Gly Arg His Ser
1               5                   10                  15

Glu Arg Phe Asp
            20

<210> SEQ ID NO 240
<211> LENGTH: 20
<212> TYPE: PRT
<213> ORGANISM: Artificial Sequence
<220> FEATURE:
<223> OTHER INFORMATION: synthetic peptide

<400> SEQUENCE: 240

Leu Pro Glu Lys Cys Ala Val Asp Lys Ile Ile Asp Ser Val Pro Gln
1               5                   10                  15

Leu Ser Gly Ser
            20

<210> SEQ ID NO 241
<211> LENGTH: 20
<212> TYPE: PRT
<213> ORGANISM: Artificial Sequence
<220> FEATURE:
<223> OTHER INFORMATION: synthetic peptide

<400> SEQUENCE: 241

Asp Lys Ile Ile Asp Ser Val Pro Gln Leu Ser Gly Ser Leu Asp Tyr
1               5                   10                  15

Asn Val Val His
            20

<210> SEQ ID NO 242
<211> LENGTH: 20
<212> TYPE: PRT
<213> ORGANISM: Artificial Sequence
<220> FEATURE:
<223> OTHER INFORMATION: synthetic peptide

<400> SEQUENCE: 242

Arg Val Glu Tyr Leu Asp Asp Arg Asn Thr Phe Arg His Gly Val Val
1               5                   10                  15

Val Pro Tyr Glu
            20
```

```
<210> SEQ ID NO 243
<211> LENGTH: 20
<212> TYPE: PRT
<213> ORGANISM: Artificial Sequence
<220> FEATURE:
<223> OTHER INFORMATION: synthetic peptide

<400> SEQUENCE: 243

Arg Asn Thr Phe Arg His Gly Val Val Val Pro Tyr Glu Pro Pro Glu
1               5                   10                  15

Val Gly Ser Asp
            20

<210> SEQ ID NO 244
<211> LENGTH: 20
<212> TYPE: PRT
<213> ORGANISM: Artificial Sequence
<220> FEATURE:
<223> OTHER INFORMATION: synthetic peptide

<400> SEQUENCE: 244

Asp Pro Cys Leu Ser Lys Lys Pro Leu Glu Glu Lys Pro Pro Gln Pro
1               5                   10                  15

Tyr Ser Ala Arg
            20

<210> SEQ ID NO 245
<211> LENGTH: 20
<212> TYPE: PRT
<213> ORGANISM: Artificial Sequence
<220> FEATURE:
<223> OTHER INFORMATION: synthetic peptide

<400> SEQUENCE: 245

Pro Leu Glu Glu Lys Pro Pro Gln Pro Tyr Ser Ala Arg Glu Ser Leu
1               5                   10                  15

Ser Glu Val Gln
            20

<210> SEQ ID NO 246
<211> LENGTH: 20
<212> TYPE: PRT
<213> ORGANISM: Artificial Sequence
<220> FEATURE:
<223> OTHER INFORMATION: synthetic peptide

<400> SEQUENCE: 246

Leu Gln Gln Thr Ala Leu Gln Glu Asp Gln Glu Asn Ile Tyr Pro Glu
1               5                   10                  15

Lys Ala Ala Pro
            20

<210> SEQ ID NO 247
<211> LENGTH: 20
<212> TYPE: PRT
<213> ORGANISM: Artificial Sequence
<220> FEATURE:
<223> OTHER INFORMATION: synthetic peptide

<400> SEQUENCE: 247

Glu Asp Gln Glu Asn Ile Tyr Pro Glu Lys Ala Ala Pro Val Gln Gln
1               5                   10                  15

Pro Arg Thr Arg
            20
```

-continued

```
<210> SEQ ID NO 248
<211> LENGTH: 20
<212> TYPE: PRT
<213> ORGANISM: Artificial Sequence
<220> FEATURE:
<223> OTHER INFORMATION: synthetic peptide

<400> SEQUENCE: 248

Pro Gly Phe Pro Pro Ala Pro Ala Asn Leu Ser Thr Pro Leu Val Ser
1               5                   10                  15

Ser Gly Val Gln
            20

<210> SEQ ID NO 249
<211> LENGTH: 20
<212> TYPE: PRT
<213> ORGANISM: Artificial Sequence
<220> FEATURE:
<223> OTHER INFORMATION: synthetic peptide

<400> SEQUENCE: 249

Ala Asn Leu Ser Thr Pro Leu Val Ser Ser Gly Val Gln Thr Ala His
1               5                   10                  15

Ser Asn Thr Ile
            20

<210> SEQ ID NO 250
<211> LENGTH: 20
<212> TYPE: PRT
<213> ORGANISM: Artificial Sequence
<220> FEATURE:
<223> OTHER INFORMATION: synthetic peptide

<400> SEQUENCE: 250

Arg Gln Gly Leu Lys Tyr Cys Leu Pro Leu Thr Phe Cys Leu His Thr
1               5                   10                  15

Gly Leu Ser Gln
            20

<210> SEQ ID NO 251
<211> LENGTH: 20
<212> TYPE: PRT
<213> ORGANISM: Artificial Sequence
<220> FEATURE:
<223> OTHER INFORMATION: synthetic peptide

<400> SEQUENCE: 251

Leu Pro Leu Thr Phe Cys Leu His Thr Gly Leu Ser Gln Tyr Ile Ala
1               5                   10                  15

Val Glu Ala Ala
            20

<210> SEQ ID NO 252
<211> LENGTH: 20
<212> TYPE: PRT
<213> ORGANISM: Artificial Sequence
<220> FEATURE:
<223> OTHER INFORMATION: synthetic peptide

<400> SEQUENCE: 252

Met Val Leu His Lys His Gly Glu Lys Leu Tyr Thr Gly Pro Arg Glu
1               5                   10                  15

Val Val Thr Glu
            20
```

```
<210> SEQ ID NO 253
<211> LENGTH: 20
<212> TYPE: PRT
<213> ORGANISM: Artificial Sequence
<220> FEATURE:
<223> OTHER INFORMATION: synthetic peptide

<400> SEQUENCE: 253

Glu Lys Leu Tyr Thr Gly Pro Arg Glu Val Val Thr Glu His Leu Ile
1               5                   10                  15

Asn Lys Val Arg
            20

<210> SEQ ID NO 254
<211> LENGTH: 20
<212> TYPE: PRT
<213> ORGANISM: Artificial Sequence
<220> FEATURE:
<223> OTHER INFORMATION: synthetic peptide

<400> SEQUENCE: 254

Ala Pro Ala Cys Asp His Phe Gly Asn Ala Lys Cys Asn Cys Tyr Cys
1               5                   10                  15

Asn Glu Cys Phe
            20

<210> SEQ ID NO 255
<211> LENGTH: 20
<212> TYPE: PRT
<213> ORGANISM: Artificial Sequence
<220> FEATURE:
<223> OTHER INFORMATION: synthetic peptide

<400> SEQUENCE: 255

Gly Asn Ala Lys Cys Asn Cys Tyr Cys Asn Glu Cys Phe Gln Phe Lys
1               5                   10                  15

Gln Met Tyr Gly
            20

<210> SEQ ID NO 256
<211> LENGTH: 20
<212> TYPE: PRT
<213> ORGANISM: Artificial Sequence
<220> FEATURE:
<223> OTHER INFORMATION: synthetic peptide

<400> SEQUENCE: 256

Arg Ala Met Glu Glu Trp Arg Gln Phe His Cys Asp Leu Tyr Asp Leu
1               5                   10                  15

Thr Gln Trp Ile
            20

<210> SEQ ID NO 257
<211> LENGTH: 20
<212> TYPE: PRT
<213> ORGANISM: Artificial Sequence
<220> FEATURE:
<223> OTHER INFORMATION: synthetic peptide

<400> SEQUENCE: 257

Gln Phe His Cys Asp Leu Tyr Asp Leu Thr Gln Trp Ile Thr Glu Ala
1               5                   10                  15

Glu Glu Leu Leu
```

```
                20

<210> SEQ ID NO 258
<211> LENGTH: 20
<212> TYPE: PRT
<213> ORGANISM: Artificial Sequence
<220> FEATURE:
<223> OTHER INFORMATION: synthetic peptide

<400> SEQUENCE: 258

His Ala Ser Met Tyr Tyr Pro Tyr Leu Cys Glu Ile Met His Phe Asp
1               5                   10                  15

Leu Ile Pro Glu
            20

<210> SEQ ID NO 259
<211> LENGTH: 20
<212> TYPE: PRT
<213> ORGANISM: Artificial Sequence
<220> FEATURE:
<223> OTHER INFORMATION: synthetic peptide

<400> SEQUENCE: 259

Tyr Leu Cys Glu Ile Met His Phe Asp Leu Ile Pro Glu Leu Arg Ala
1               5                   10                  15

Val Leu Arg Lys
            20

<210> SEQ ID NO 260
<211> LENGTH: 20
<212> TYPE: PRT
<213> ORGANISM: Artificial Sequence
<220> FEATURE:
<223> OTHER INFORMATION: synthetic peptide

<400> SEQUENCE: 260

Pro Glu Pro Glu Pro Val Glu Ala Asn Ser Glu Glu Ser Tyr Ser Val
1               5                   10                  15

Phe Ser Glu Asn
            20

<210> SEQ ID NO 261
<211> LENGTH: 20
<212> TYPE: PRT
<213> ORGANISM: Artificial Sequence
<220> FEATURE:
<223> OTHER INFORMATION: synthetic peptide

<400> SEQUENCE: 261

Ala Asn Ser Glu Glu Ser Tyr Ser Val Phe Ser Glu Asn Thr Glu Asp
1               5                   10                  15

Leu Gln Glu Gln
            20

<210> SEQ ID NO 262
<211> LENGTH: 20
<212> TYPE: PRT
<213> ORGANISM: Artificial Sequence
<220> FEATURE:
<223> OTHER INFORMATION: synthetic peptide

<400> SEQUENCE: 262

His Gln Val Asn Gly Cys Pro Ala Asp Ala Glu Lys Asp Leu Leu Ile
1               5                   10                  15
```

Thr Thr Asp Ser
        20

<210> SEQ ID NO 263
<211> LENGTH: 20
<212> TYPE: PRT
<213> ORGANISM: Artificial Sequence
<220> FEATURE:
<223> OTHER INFORMATION: synthetic peptide

<400> SEQUENCE: 263

Ala Asp Ala Glu Lys Asp Leu Leu Ile Thr Thr Asp Ser Asp Gly Thr
1               5                   10                  15

Tyr Arg Arg Pro
        20

<210> SEQ ID NO 264
<211> LENGTH: 20
<212> TYPE: PRT
<213> ORGANISM: Artificial Sequence
<220> FEATURE:
<223> OTHER INFORMATION: synthetic peptide

<400> SEQUENCE: 264

Arg Leu Leu Leu Val Leu Ser Gly Val Val Met Val Phe Asn Thr Ser
1               5                   10                  15

Ala Phe Gly Ala
        20

<210> SEQ ID NO 265
<211> LENGTH: 20
<212> TYPE: PRT
<213> ORGANISM: Artificial Sequence
<220> FEATURE:
<223> OTHER INFORMATION: synthetic peptide

<400> SEQUENCE: 265

Gly Val Val Met Val Phe Asn Thr Ser Ala Phe Gly Ala Tyr Phe Lys
1               5                   10                  15

Leu Thr Gln Gly
        20

<210> SEQ ID NO 266
<211> LENGTH: 20
<212> TYPE: PRT
<213> ORGANISM: Artificial Sequence
<220> FEATURE:
<223> OTHER INFORMATION: synthetic peptide

<400> SEQUENCE: 266

Ser Leu Ala Leu Asp Ala Leu Pro Pro Glu Leu Leu Val Leu Val Leu
1               5                   10                  15

Ser His Val Pro
        20

<210> SEQ ID NO 267
<211> LENGTH: 20
<212> TYPE: PRT
<213> ORGANISM: Artificial Sequence
<220> FEATURE:
<223> OTHER INFORMATION: synthetic peptide

<400> SEQUENCE: 267

Pro Pro Glu Leu Leu Val Leu Val Leu Ser His Val Pro Pro Arg Ser
1               5                   10                  15

Leu Val Thr Arg
        20

<210> SEQ ID NO 268
<211> LENGTH: 20
<212> TYPE: PRT
<213> ORGANISM: Artificial Sequence
<220> FEATURE:
<223> OTHER INFORMATION: synthetic peptide

<400> SEQUENCE: 268

Leu Pro Ser Asn Glu Asp Lys Glu Phe Pro Leu Cys Ser Leu Ala
1               5                   10                  15

Arg Tyr Cys Leu
        20

<210> SEQ ID NO 269
<211> LENGTH: 20
<212> TYPE: PRT
<213> ORGANISM: Artificial Sequence
<220> FEATURE:
<223> OTHER INFORMATION: synthetic peptide

<400> SEQUENCE: 269

Glu Glu Phe Pro Leu Cys Ser Leu Ala Arg Tyr Cys Leu Arg Ala Pro
1               5                   10                  15

Phe Gly Arg Asn
        20

<210> SEQ ID NO 270
<211> LENGTH: 20
<212> TYPE: PRT
<213> ORGANISM: Artificial Sequence
<220> FEATURE:
<223> OTHER INFORMATION: synthetic peptide

<400> SEQUENCE: 270

Ala Ser Asp Pro Ala Gly Gly Gly Pro Asn His His Ala Ser Gln Leu
1               5                   10                  15

Ser Gly Asp Ser
        20

<210> SEQ ID NO 271
<211> LENGTH: 20
<212> TYPE: PRT
<213> ORGANISM: Artificial Sequence
<220> FEATURE:
<223> OTHER INFORMATION: synthetic peptide

<400> SEQUENCE: 271

Gly Pro Asn His His Ala Ser Gln Leu Ser Gly Asp Ser Ala Leu Pro
1               5                   10                  15

Leu Tyr Ser Leu
        20

<210> SEQ ID NO 272
<211> LENGTH: 20
<212> TYPE: PRT
<213> ORGANISM: Artificial Sequence
<220> FEATURE:
<223> OTHER INFORMATION: synthetic peptide

<400> SEQUENCE: 272

Asn Val Asp Ile Cys Gln Leu Leu His Lys Phe Gly Ala Tyr Leu Leu

```
                1               5                  10                 15

Ala Thr Asp Tyr
            20

<210> SEQ ID NO 273
<211> LENGTH: 20
<212> TYPE: PRT
<213> ORGANISM: Artificial Sequence
<220> FEATURE:
<223> OTHER INFORMATION: synthetic peptide

<400> SEQUENCE: 273

Leu His Lys Phe Gly Ala Tyr Leu Leu Ala Thr Asp Tyr Gln Gly Asn
1               5                  10                 15

Thr Ala Leu His
            20

<210> SEQ ID NO 274
<211> LENGTH: 20
<212> TYPE: PRT
<213> ORGANISM: Artificial Sequence
<220> FEATURE:
<223> OTHER INFORMATION: synthetic peptide

<400> SEQUENCE: 274

Leu Gln Arg Ser Cys Ser Cys Asn Gly Thr Ala Thr Arg Leu Ser Gly
1               5                  10                 15

Gln Ser Tyr Val
            20

<210> SEQ ID NO 275
<211> LENGTH: 20
<212> TYPE: PRT
<213> ORGANISM: Artificial Sequence
<220> FEATURE:
<223> OTHER INFORMATION: synthetic peptide

<400> SEQUENCE: 275

Asn Gly Thr Ala Thr Arg Leu Ser Gly Gln Ser Tyr Val Arg Tyr Arg
1               5                  10                 15

Ala Pro Ala Ala
            20

<210> SEQ ID NO 276
<211> LENGTH: 20
<212> TYPE: PRT
<213> ORGANISM: Artificial Sequence
<220> FEATURE:
<223> OTHER INFORMATION: synthetic peptide

<400> SEQUENCE: 276

Thr Leu Arg Arg Leu His Asn Arg Arg Thr Leu Ser Met Leu Phe Pro
1               5                  10                 15

Met Lys Ser Ser
            20

<210> SEQ ID NO 277
<211> LENGTH: 20
<212> TYPE: PRT
<213> ORGANISM: Artificial Sequence
<220> FEATURE:
<223> OTHER INFORMATION: synthetic peptide

<400> SEQUENCE: 277
```

-continued

Arg Arg Thr Leu Ser Met Leu Phe Pro Met Lys Ser Ser Gln Gly Ser
1               5                   10                  15

Val Glu Glu Gln
            20

<210> SEQ ID NO 278
<211> LENGTH: 20
<212> TYPE: PRT
<213> ORGANISM: Artificial Sequence
<220> FEATURE:
<223> OTHER INFORMATION: synthetic peptide

<400> SEQUENCE: 278

Ser Asn Tyr Lys Ile Lys Tyr Phe Gly Phe Asp Asp Leu Gly Glu Ser
1               5                   10                  15

Glu Asp Asp Glu
            20

<210> SEQ ID NO 279
<211> LENGTH: 20
<212> TYPE: PRT
<213> ORGANISM: Artificial Sequence
<220> FEATURE:
<223> OTHER INFORMATION: synthetic peptide

<400> SEQUENCE: 279

Phe Gly Phe Asp Asp Leu Gly Glu Ser Glu Asp Glu Asp Asp Asp
1               5                   10                  15

Cys Gln Val Glu
            20

<210> SEQ ID NO 280
<211> LENGTH: 20
<212> TYPE: PRT
<213> ORGANISM: Artificial Sequence
<220> FEATURE:
<223> OTHER INFORMATION: synthetic peptide

<400> SEQUENCE: 280

Ala Arg Trp Leu Ala Leu Phe Leu Ser Leu Lys Ala Ser Cys Arg Leu
1               5                   10                  15

His Gln Leu Arg
            20

<210> SEQ ID NO 281
<211> LENGTH: 20
<212> TYPE: PRT
<213> ORGANISM: Artificial Sequence
<220> FEATURE:
<223> OTHER INFORMATION: synthetic peptide

<400> SEQUENCE: 281

Leu Ser Leu Lys Ala Ser Cys Arg Leu His Gln Leu Arg Ser Trp Gly
1               5                   10                  15

Ala Pro Glu Gly
            20

<210> SEQ ID NO 282
<211> LENGTH: 20
<212> TYPE: PRT
<213> ORGANISM: Artificial Sequence
<220> FEATURE:
<223> OTHER INFORMATION: synthetic peptide

<400> SEQUENCE: 282

Ser Gln Val Asp Gly Gln Tyr Phe Val Cys Asn Met Asp Asn Phe Lys
1               5                   10                  15

Phe Ser Ala Glu
            20

<210> SEQ ID NO 283
<211> LENGTH: 20
<212> TYPE: PRT
<213> ORGANISM: Artificial Sequence
<220> FEATURE:
<223> OTHER INFORMATION: synthetic peptide

<400> SEQUENCE: 283

Phe Val Cys Asn Met Asp Asn Phe Lys Phe Ser Ala Glu Leu Ile Gln
1               5                   10                  15

His Ile Pro Leu
            20

<210> SEQ ID NO 284
<211> LENGTH: 20
<212> TYPE: PRT
<213> ORGANISM: Artificial Sequence
<220> FEATURE:
<223> OTHER INFORMATION: synthetic peptide

<400> SEQUENCE: 284

Leu Phe Lys Val Ser Asp Asp Glu Tyr Lys Val Thr Ile Pro Pro Gln
1               5                   10                  15

Leu Leu Leu Ala
            20

<210> SEQ ID NO 285
<211> LENGTH: 20
<212> TYPE: PRT
<213> ORGANISM: Artificial Sequence
<220> FEATURE:
<223> OTHER INFORMATION: synthetic peptide

<400> SEQUENCE: 285

Glu Tyr Lys Val Thr Ile Pro Pro Gln Leu Leu Leu Ala Thr Gln Arg
1               5                   10                  15

Phe Leu Ser Arg
            20

<210> SEQ ID NO 286
<211> LENGTH: 20
<212> TYPE: PRT
<213> ORGANISM: Artificial Sequence
<220> FEATURE:
<223> OTHER INFORMATION: synthetic peptide

<400> SEQUENCE: 286

Leu Gln Glu Glu Ile Thr Ser Leu Gln Ser Ser Val Gln Lys Tyr Glu
1               5                   10                  15

Glu Lys Asn Thr
            20

<210> SEQ ID NO 287
<211> LENGTH: 20
<212> TYPE: PRT
<213> ORGANISM: Artificial Sequence
<220> FEATURE:
<223> OTHER INFORMATION: synthetic peptide

<400> SEQUENCE: 287

Leu Gln Ser Ser Val Gln Lys Tyr Glu Glu Lys Asn Thr Lys Ile Lys
1               5                   10                  15

Gln Leu Leu Val
            20

<210> SEQ ID NO 288
<211> LENGTH: 20
<212> TYPE: PRT
<213> ORGANISM: Artificial Sequence
<220> FEATURE:
<223> OTHER INFORMATION: synthetic peptide

<400> SEQUENCE: 288

Pro Gly Gly Met Val Asn Arg Asp Glu Tyr Leu Leu Gly Leu Pro Ile
1               5                   10                  15

Asp Lys Tyr Val
            20

<210> SEQ ID NO 289
<211> LENGTH: 20
<212> TYPE: PRT
<213> ORGANISM: Artificial Sequence
<220> FEATURE:
<223> OTHER INFORMATION: synthetic peptide

<400> SEQUENCE: 289

Asp Glu Tyr Leu Leu Gly Leu Pro Ile Asp Lys Tyr Val Phe Glu Lys
1               5                   10                  15

Met Glu Glu Lys
            20

<210> SEQ ID NO 290
<211> LENGTH: 20
<212> TYPE: PRT
<213> ORGANISM: Artificial Sequence
<220> FEATURE:
<223> OTHER INFORMATION: synthetic peptide

<400> SEQUENCE: 290

Met Ala Ala Leu Gly Val Gln Ser Ile Asn Trp Gln Lys Ala Phe Asn
1               5                   10                  15

Arg Gln Ala His
            20

<210> SEQ ID NO 291
<211> LENGTH: 20
<212> TYPE: PRT
<213> ORGANISM: Artificial Sequence
<220> FEATURE:
<223> OTHER INFORMATION: synthetic peptide

<400> SEQUENCE: 291

Gln Ser Ile Asn Trp Gln Lys Ala Phe Asn Arg Gln Ala His His Thr
1               5                   10                  15

Asp Lys Phe Ser
            20

<210> SEQ ID NO 292
<211> LENGTH: 20
<212> TYPE: PRT
<213> ORGANISM: Artificial Sequence
<220> FEATURE:
<223> OTHER INFORMATION: synthetic peptide

<400> SEQUENCE: 292

Leu Lys Gln Trp Arg Gln Arg Met Leu Phe Gly Ile Phe Ser Trp Gly
1               5                   10                  15

Leu Leu Phe Leu
            20

<210> SEQ ID NO 293
<211> LENGTH: 20
<212> TYPE: PRT
<213> ORGANISM: Artificial Sequence
<220> FEATURE:
<223> OTHER INFORMATION: synthetic peptide

<400> SEQUENCE: 293

Met Leu Phe Gly Ile Phe Ser Trp Gly Leu Leu Phe Leu Leu Ile Phe
1               5                   10                  15

Ile Tyr Phe Thr
            20

<210> SEQ ID NO 294
<211> LENGTH: 20
<212> TYPE: PRT
<213> ORGANISM: Artificial Sequence
<220> FEATURE:
<223> OTHER INFORMATION: synthetic peptide

<400> SEQUENCE: 294

Ile Ala Leu Gln Arg Thr Gly Asp Pro Ala Asn Leu Asn Leu Leu Arg
1               5                   10                  15

Pro His Leu Glu
            20

<210> SEQ ID NO 295
<211> LENGTH: 20
<212> TYPE: PRT
<213> ORGANISM: Artificial Sequence
<220> FEATURE:
<223> OTHER INFORMATION: synthetic peptide

<400> SEQUENCE: 295

Asp Pro Ala Asn Leu Asn Leu Leu Arg Pro His Leu Glu Leu Leu Ala
1               5                   10                  15

Asn Ile Asp Pro
            20

<210> SEQ ID NO 296
<211> LENGTH: 20
<212> TYPE: PRT
<213> ORGANISM: Artificial Sequence
<220> FEATURE:
<223> OTHER INFORMATION: synthetic peptide

<400> SEQUENCE: 296

Met Glu Ile Ser Thr Cys Glu Thr Glu Ala Ser Glu Gln Cys Asp Tyr
1               5                   10                  15

Val Leu Val Ala
            20

<210> SEQ ID NO 297
<211> LENGTH: 20
<212> TYPE: PRT
<213> ORGANISM: Artificial Sequence
<220> FEATURE:

<223> OTHER INFORMATION: synthetic peptide

<400> SEQUENCE: 297

Thr Glu Ala Ser Glu Gln Cys Asp Tyr Val Leu Val Ala Gln Arg His
1               5                   10                  15

Thr Gln Arg Asp
            20

<210> SEQ ID NO 298
<211> LENGTH: 20
<212> TYPE: PRT
<213> ORGANISM: Artificial Sequence
<220> FEATURE:
<223> OTHER INFORMATION: synthetic peptide

<400> SEQUENCE: 298

Ser Ser Gln Leu Leu Asn Gly Leu Lys Thr Ala Ala Thr Asn Val Trp
1               5                   10                  15

Glu Thr Arg Ile
            20

<210> SEQ ID NO 299
<211> LENGTH: 20
<212> TYPE: PRT
<213> ORGANISM: Artificial Sequence
<220> FEATURE:
<223> OTHER INFORMATION: synthetic peptide

<400> SEQUENCE: 299

Leu Lys Thr Ala Ala Thr Asn Val Trp Glu Thr Arg Ile Lys Leu Leu
1               5                   10                  15

Cys Cys Cys Ile
            20

<210> SEQ ID NO 300
<211> LENGTH: 20
<212> TYPE: PRT
<213> ORGANISM: Artificial Sequence
<220> FEATURE:
<223> OTHER INFORMATION: synthetic peptide

<400> SEQUENCE: 300

Met Leu Leu Glu Leu Arg Glu Lys Ala Glu Ser Glu Lys Pro Thr Ile
1               5                   10                  15

Ile Asn Lys Phe
            20

<210> SEQ ID NO 301
<211> LENGTH: 20
<212> TYPE: PRT
<213> ORGANISM: Artificial Sequence
<220> FEATURE:
<223> OTHER INFORMATION: synthetic peptide

<400> SEQUENCE: 301

Lys Ala Glu Ser Glu Lys Pro Thr Ile Ile Asn Lys Phe Glu Leu Arg
1               5                   10                  15

Glu Ala Glu Met
            20

<210> SEQ ID NO 302
<211> LENGTH: 20
<212> TYPE: PRT
<213> ORGANISM: Artificial Sequence

```
<220> FEATURE:
<223> OTHER INFORMATION: synthetic peptide

<400> SEQUENCE: 302

Val Thr Asp Lys Gly Ser Phe Glu Lys Ala Ser Glu Leu Gln Val Gln
1               5                   10                  15

Leu Arg Arg Ala
            20

<210> SEQ ID NO 303
<211> LENGTH: 20
<212> TYPE: PRT
<213> ORGANISM: Artificial Sequence
<220> FEATURE:
<223> OTHER INFORMATION: synthetic peptide

<400> SEQUENCE: 303

Glu Lys Ala Ser Glu Leu Gln Val Gln Leu Arg Arg Ala Arg Gln Thr
1               5                   10                  15

Asp Asp Val Pro
            20

<210> SEQ ID NO 304
<211> LENGTH: 20
<212> TYPE: PRT
<213> ORGANISM: Artificial Sequence
<220> FEATURE:
<223> OTHER INFORMATION: synthetic peptide

<400> SEQUENCE: 304

Thr Val Lys Val Ser Asn Asn Ala Glu Asp Pro Lys Asp Phe Met Leu
1               5                   10                  15

Ser Gly Glu Arg
            20

<210> SEQ ID NO 305
<211> LENGTH: 20
<212> TYPE: PRT
<213> ORGANISM: Artificial Sequence
<220> FEATURE:
<223> OTHER INFORMATION: synthetic peptide

<400> SEQUENCE: 305

Ala Glu Asp Pro Lys Asp Phe Met Leu Ser Gly Glu Arg Val Leu Gln
1               5                   10                  15

Thr Glu Arg Ser
            20

<210> SEQ ID NO 306
<211> LENGTH: 20
<212> TYPE: PRT
<213> ORGANISM: Artificial Sequence
<220> FEATURE:
<223> OTHER INFORMATION: synthetic peptide

<400> SEQUENCE: 306

Val Asn Glu Trp Phe Ser Arg Ser Asp Glu Leu Leu Gly Phe Asp Asp
1               5                   10                  15

Ser His Asp Gly
            20

<210> SEQ ID NO 307
<211> LENGTH: 20
<212> TYPE: PRT
```

-continued

<213> ORGANISM: Artificial Sequence
<220> FEATURE:
<223> OTHER INFORMATION: synthetic peptide

<400> SEQUENCE: 307

Ser Asp Glu Leu Leu Gly Phe Asp Asp Ser His Asp Gly Glu Ser Glu
1               5                   10                  15

Ser Asn Ala Lys
            20

<210> SEQ ID NO 308
<211> LENGTH: 20
<212> TYPE: PRT
<213> ORGANISM: Artificial Sequence
<220> FEATURE:
<223> OTHER INFORMATION: synthetic peptide

<400> SEQUENCE: 308

Arg Arg Met Arg Asp Arg Glu Ala Lys Arg Leu Gln Arg Ile Gln Glu
1               5                   10                  15

Thr Asp Glu Gln
            20

<210> SEQ ID NO 309
<211> LENGTH: 20
<212> TYPE: PRT
<213> ORGANISM: Artificial Sequence
<220> FEATURE:
<223> OTHER INFORMATION: synthetic peptide

<400> SEQUENCE: 309

Ala Lys Arg Leu Gln Arg Ile Gln Glu Thr Asp Glu Gln Arg Ala Arg
1               5                   10                  15

Arg Leu Gln Arg
            20

<210> SEQ ID NO 310
<211> LENGTH: 20
<212> TYPE: PRT
<213> ORGANISM: Artificial Sequence
<220> FEATURE:
<223> OTHER INFORMATION: synthetic peptide

<400> SEQUENCE: 310

Lys Lys Gly Ala Pro His Asp Leu Lys Cys Val Thr Asn Ser Leu Gln
1               5                   10                  15

Val Trp Asn Cys
            20

<210> SEQ ID NO 311
<211> LENGTH: 20
<212> TYPE: PRT
<213> ORGANISM: Artificial Sequence
<220> FEATURE:
<223> OTHER INFORMATION: synthetic peptide

<400> SEQUENCE: 311

Leu Lys Cys Val Thr Asn Ser Leu Gln Val Trp Asn Cys Ser Trp Lys
1               5                   10                  15

Ala Pro Ser Gly
            20

<210> SEQ ID NO 312
<211> LENGTH: 20

```
<212> TYPE: PRT
<213> ORGANISM: Artificial Sequence
<220> FEATURE:
<223> OTHER INFORMATION: synthetic peptide

<400> SEQUENCE: 312

Ser Pro Ser Ser Thr Ser Thr Ser Ser Ser Ser Ser His Leu Ala
1               5                   10                  15

Ser Ser Pro Thr
            20

<210> SEQ ID NO 313
<211> LENGTH: 20
<212> TYPE: PRT
<213> ORGANISM: Artificial Sequence
<220> FEATURE:
<223> OTHER INFORMATION: synthetic peptide

<400> SEQUENCE: 313

Ser Ser Ser Ser Ser Ser His Leu Ala Ser Ser Pro Thr Val Ile Thr
1               5                   10                  15

Ser Val Ser Ser
            20

<210> SEQ ID NO 314
<211> LENGTH: 18
<212> TYPE: PRT
<213> ORGANISM: Artificial Sequence
<220> FEATURE:
<223> OTHER INFORMATION: synthetic peptide

<400> SEQUENCE: 314

Met Leu Gly Ser Lys Ala Val Met Leu Leu Leu Leu Leu Pro Trp Thr
1               5                   10                  15

Ala Gln

<210> SEQ ID NO 315
<211> LENGTH: 18
<212> TYPE: PRT
<213> ORGANISM: Artificial Sequence
<220> FEATURE:
<223> OTHER INFORMATION: synthetic peptide

<400> SEQUENCE: 315

Met Leu Gly Ser Lys Ala Val Met Leu Leu Leu Leu Leu Pro Trp Thr
1               5                   10                  15

Ala Gln

<210> SEQ ID NO 316
<211> LENGTH: 20
<212> TYPE: PRT
<213> ORGANISM: Artificial Sequence
<220> FEATURE:
<223> OTHER INFORMATION: synthetic peptide

<400> SEQUENCE: 316

Cys Ala Asp Phe His Thr Tyr Leu Ser Arg Cys Asn Ser Met Lys Val
1               5                   10                  15

Glu Gly Gly Thr
            20

<210> SEQ ID NO 317
<211> LENGTH: 20
<212> TYPE: PRT
```

-continued

```
<213> ORGANISM: Artificial Sequence
<220> FEATURE:
<223> OTHER INFORMATION: synthetic peptide

<400> SEQUENCE: 317

Leu Ser Arg Cys Asn Ser Met Lys Val Glu Gly Gly Thr Trp Ala Val
1               5                   10                  15

Tyr Glu Arg Pro
            20

<210> SEQ ID NO 318
<211> LENGTH: 20
<212> TYPE: PRT
<213> ORGANISM: Artificial Sequence
<220> FEATURE:
<223> OTHER INFORMATION: synthetic peptide

<400> SEQUENCE: 318

Gln Asp Tyr Gln Ala Glu Gln Asp Ala Leu Arg Ala Lys Pro Asn Gln
1               5                   10                  15

Glu Val Ala Asp
            20

<210> SEQ ID NO 319
<211> LENGTH: 20
<212> TYPE: PRT
<213> ORGANISM: Artificial Sequence
<220> FEATURE:
<223> OTHER INFORMATION: synthetic peptide

<400> SEQUENCE: 319

Asp Ala Leu Arg Ala Lys Pro Asn Gln Glu Val Ala Asp Arg Glu Trp
1               5                   10                  15

Arg Arg Lys Glu
            20

<210> SEQ ID NO 320
<211> LENGTH: 20
<212> TYPE: PRT
<213> ORGANISM: Artificial Sequence
<220> FEATURE:
<223> OTHER INFORMATION: synthetic peptide

<400> SEQUENCE: 320

Arg Leu Ile Gln Ala Gly Arg Leu Met Pro Gln Asp Gln Phe Lys Gly
1               5                   10                  15

Phe Gln Arg Leu
            20

<210> SEQ ID NO 321
<211> LENGTH: 20
<212> TYPE: PRT
<213> ORGANISM: Artificial Sequence
<220> FEATURE:
<223> OTHER INFORMATION: synthetic peptide

<400> SEQUENCE: 321

Leu Met Pro Gln Asp Gln Phe Lys Gly Phe Gln Arg Leu Lys Ala Ala
1               5                   10                  15

His Ala Ala Leu
            20

<210> SEQ ID NO 322
<211> LENGTH: 20
```

```
<212> TYPE: PRT
<213> ORGANISM: Artificial Sequence
<220> FEATURE:
<223> OTHER INFORMATION: synthetic peptide

<400> SEQUENCE: 322

Leu Tyr Ile Leu Asp Ala Thr Asn Pro Arg His Ser Asn Cys Leu Arg
1               5                   10                  15

Phe Val His Glu
            20

<210> SEQ ID NO 323
<211> LENGTH: 20
<212> TYPE: PRT
<213> ORGANISM: Artificial Sequence
<220> FEATURE:
<223> OTHER INFORMATION: synthetic peptide

<400> SEQUENCE: 323

Asn Pro Arg His Ser Asn Cys Leu Arg Phe Val His Glu Ala Pro Ser
1               5                   10                  15

Gln Glu Gln Lys
            20

<210> SEQ ID NO 324
<211> LENGTH: 20
<212> TYPE: PRT
<213> ORGANISM: Artificial Sequence
<220> FEATURE:
<223> OTHER INFORMATION: synthetic peptide

<400> SEQUENCE: 324

Cys Cys Phe Cys His Glu Glu Gly Asp Gly Ala Thr Asp Arg Pro Ala
1               5                   10                  15

Arg Leu Leu Asn
            20

<210> SEQ ID NO 325
<211> LENGTH: 20
<212> TYPE: PRT
<213> ORGANISM: Artificial Sequence
<220> FEATURE:
<223> OTHER INFORMATION: synthetic peptide

<400> SEQUENCE: 325

Gly Asp Gly Ala Thr Asp Arg Pro Ala Arg Leu Leu Asn Leu Asp Leu
1               5                   10                  15

Asp Leu Trp Val
            20

<210> SEQ ID NO 326
<211> LENGTH: 20
<212> TYPE: PRT
<213> ORGANISM: Artificial Sequence
<220> FEATURE:
<223> OTHER INFORMATION: synthetic peptide

<400> SEQUENCE: 326

Pro Leu Pro Pro Leu Gly Cys Leu Leu Gly Glu Thr Arg Tyr Ala Cys
1               5                   10                  15

Gly Cys Cys Pro
            20

<210> SEQ ID NO 327
```

```
<211> LENGTH: 20
<212> TYPE: PRT
<213> ORGANISM: Artificial Sequence
<220> FEATURE:
<223> OTHER INFORMATION: synthetic peptide

<400> SEQUENCE: 327

Leu Leu Gly Glu Thr Arg Tyr Ala Cys Gly Cys Pro Met Cys Ala
1               5                   10                  15

Arg Gly Glu Gly
            20

<210> SEQ ID NO 328
<211> LENGTH: 20
<212> TYPE: PRT
<213> ORGANISM: Artificial Sequence
<220> FEATURE:
<223> OTHER INFORMATION: synthetic peptide

<400> SEQUENCE: 328

Gly Val Leu Leu Gly Arg Trp Asp Asn Asn Tyr Gly Asp Ser Val Ser
1               5                   10                  15

Pro Met Ser Trp
            20

<210> SEQ ID NO 329
<211> LENGTH: 20
<212> TYPE: PRT
<213> ORGANISM: Artificial Sequence
<220> FEATURE:
<223> OTHER INFORMATION: synthetic peptide

<400> SEQUENCE: 329

Asp Asn Asn Tyr Gly Asp Ser Val Ser Pro Met Ser Trp Ile Gly Ser
1               5                   10                  15

Val Asp Ile Leu
            20

<210> SEQ ID NO 330
<211> LENGTH: 20
<212> TYPE: PRT
<213> ORGANISM: Artificial Sequence
<220> FEATURE:
<223> OTHER INFORMATION: synthetic peptide

<400> SEQUENCE: 330

Ser Phe Pro Leu Lys Gly Ile Thr Glu Gln Gln Lys Glu Cys Leu Glu
1               5                   10                  15

Ile Val Lys Met
            20

<210> SEQ ID NO 331
<211> LENGTH: 20
<212> TYPE: PRT
<213> ORGANISM: Artificial Sequence
<220> FEATURE:
<223> OTHER INFORMATION: synthetic peptide

<400> SEQUENCE: 331

Thr Glu Gln Gln Lys Glu Cys Leu Glu Ile Val Lys Met Val Met Ile
1               5                   10                  15

Ser Leu Glu Gly
            20
```

```
<210> SEQ ID NO 332
<211> LENGTH: 20
<212> TYPE: PRT
<213> ORGANISM: Artificial Sequence
<220> FEATURE:
<223> OTHER INFORMATION: synthetic peptide

<400> SEQUENCE: 332

Arg Leu Leu Tyr Gly Phe Leu Ile Lys Ala Asn Asn Ser Arg Phe Gln
1               5                   10                  15

Ser Ile Leu Arg
            20

<210> SEQ ID NO 333
<211> LENGTH: 20
<212> TYPE: PRT
<213> ORGANISM: Artificial Sequence
<220> FEATURE:
<223> OTHER INFORMATION: synthetic peptide

<400> SEQUENCE: 333

Ile Lys Ala Asn Asn Ser Arg Phe Gln Ser Ile Leu Arg Gln Asp Leu
1               5                   10                  15

Arg Ser Tyr Leu
            20

<210> SEQ ID NO 334
<211> LENGTH: 20
<212> TYPE: PRT
<213> ORGANISM: Artificial Sequence
<220> FEATURE:
<223> OTHER INFORMATION: synthetic peptide

<400> SEQUENCE: 334

Val Pro Ala Gly Ser Ala Ala Val Phe Pro Cys Ile Ala Leu Gly Tyr
1               5                   10                  15

Pro Thr Pro Asp
            20

<210> SEQ ID NO 335
<211> LENGTH: 20
<212> TYPE: PRT
<213> ORGANISM: Artificial Sequence
<220> FEATURE:
<223> OTHER INFORMATION: synthetic peptide

<400> SEQUENCE: 335

Val Phe Pro Cys Ile Ala Leu Gly Tyr Pro Thr Pro Asp Ile Ser Trp
1               5                   10                  15

Ser Lys Leu Asp
            20

<210> SEQ ID NO 336
<211> LENGTH: 20
<212> TYPE: PRT
<213> ORGANISM: Artificial Sequence
<220> FEATURE:
<223> OTHER INFORMATION: synthetic peptide

<400> SEQUENCE: 336

Cys Ala Arg Phe Ser Tyr Leu Trp Leu Lys Phe Ser Leu Phe Ile Tyr
1               5                   10                  15

Ser Thr Val Phe
            20
```

<210> SEQ ID NO 337
<211> LENGTH: 20
<212> TYPE: PRT
<213> ORGANISM: Artificial Sequence
<220> FEATURE:
<223> OTHER INFORMATION: synthetic peptide

<400> SEQUENCE: 337

Trp Leu Lys Phe Ser Leu Phe Ile Tyr Ser Thr Val Phe Trp Leu Ile
1               5                   10                  15

Gly Ala Leu Val
            20

<210> SEQ ID NO 338
<211> LENGTH: 20
<212> TYPE: PRT
<213> ORGANISM: Artificial Sequence
<220> FEATURE:
<223> OTHER INFORMATION: synthetic peptide

<400> SEQUENCE: 338

Cys Lys Thr Thr Ile Glu Ala Ile His Gly Leu Met Ser Glu Val Ile
1               5                   10                  15

Lys Asp Lys Leu
            20

<210> SEQ ID NO 339
<211> LENGTH: 20
<212> TYPE: PRT
<213> ORGANISM: Artificial Sequence
<220> FEATURE:
<223> OTHER INFORMATION: synthetic peptide

<400> SEQUENCE: 339

Ile His Gly Leu Met Ser Glu Val Ile Lys Asp Lys Leu Phe Asn Gln
1               5                   10                  15

Ile Asn Ile Ser
            20

<210> SEQ ID NO 340
<211> LENGTH: 20
<212> TYPE: PRT
<213> ORGANISM: Artificial Sequence
<220> FEATURE:
<223> OTHER INFORMATION: synthetic peptide

<400> SEQUENCE: 340

Ala Ala Thr Ser Ala Leu Val Lys Ala Ala Ser Ala Ala His Arg Glu
1               5                   10                  15

Leu Val Ala Gln
            20

<210> SEQ ID NO 341
<211> LENGTH: 20
<212> TYPE: PRT
<213> ORGANISM: Artificial Sequence
<220> FEATURE:
<223> OTHER INFORMATION: synthetic peptide

<400> SEQUENCE: 341

Lys Ala Ala Ser Ala Ala His Arg Glu Leu Val Ala Gln Gly Lys Val
1               5                   10                  15

Gly Ala Ile Pro
            20

```
<210> SEQ ID NO 342
<211> LENGTH: 20
<212> TYPE: PRT
<213> ORGANISM: Artificial Sequence
<220> FEATURE:
<223> OTHER INFORMATION: synthetic peptide

<400> SEQUENCE: 342

Trp Cys Val Ser Pro Lys Gly Pro Trp Thr Cys Val Gly Glu Met Asn
1               5                   10                  15

Arg Asn Gln Gly
            20

<210> SEQ ID NO 343
<211> LENGTH: 20
<212> TYPE: PRT
<213> ORGANISM: Artificial Sequence
<220> FEATURE:
<223> OTHER INFORMATION: synthetic peptide

<400> SEQUENCE: 343

Pro Trp Thr Cys Val Gly Glu Met Asn Arg Asn Gln Gly Glu Gln
1               5                   10                  15

Arg Gly Gly Gly
            20

<210> SEQ ID NO 344
<211> LENGTH: 20
<212> TYPE: PRT
<213> ORGANISM: Artificial Sequence
<220> FEATURE:
<223> OTHER INFORMATION: synthetic peptide

<400> SEQUENCE: 344

Gly Leu Gly Gln Ala Pro Ala Gly Gly Leu Thr Glu Gln Gln Leu Met
1               5                   10                  15

Glu Gln Leu Glu
            20

<210> SEQ ID NO 345
<211> LENGTH: 20
<212> TYPE: PRT
<213> ORGANISM: Artificial Sequence
<220> FEATURE:
<223> OTHER INFORMATION: synthetic peptide

<400> SEQUENCE: 345

Gly Gly Leu Thr Glu Gln Gln Leu Met Glu Gln Leu Glu His Cys Glu
1               5                   10                  15

Leu Ala Pro Pro
            20

<210> SEQ ID NO 346
<211> LENGTH: 20
<212> TYPE: PRT
<213> ORGANISM: Artificial Sequence
<220> FEATURE:
<223> OTHER INFORMATION: synthetic peptide

<400> SEQUENCE: 346

Leu Pro Lys Thr Cys Asp Ile Ser Phe Ser Asp Pro Asp Tyr Leu Leu
1               5                   10                  15

Asn Phe Lys Leu
```

20

<210> SEQ ID NO 347
<211> LENGTH: 20
<212> TYPE: PRT
<213> ORGANISM: Artificial Sequence
<220> FEATURE:
<223> OTHER INFORMATION: synthetic peptide

<400> SEQUENCE: 347

Ser Phe Ser Asp Pro Asp Tyr Leu Leu Asn Phe Lys Leu Val Ile Cys
1               5                   10                  15

Pro Asp Glu Gly
            20

<210> SEQ ID NO 348
<211> LENGTH: 20
<212> TYPE: PRT
<213> ORGANISM: Artificial Sequence
<220> FEATURE:
<223> OTHER INFORMATION: synthetic peptide

<400> SEQUENCE: 348

Asn Ser Asp Pro Gly Ile Ala Val Gly Phe Asp Glu Phe Val Ser Val
1               5                   10                  15

Asp Phe Ser Gly
            20

<210> SEQ ID NO 349
<211> LENGTH: 20
<212> TYPE: PRT
<213> ORGANISM: Artificial Sequence
<220> FEATURE:
<223> OTHER INFORMATION: synthetic peptide

<400> SEQUENCE: 349

Val Gly Phe Asp Glu Phe Val Ser Val Asp Phe Ser Gly Thr Phe Tyr
1               5                   10                  15

Val Asn Thr Asp
            20

<210> SEQ ID NO 350
<211> LENGTH: 20
<212> TYPE: PRT
<213> ORGANISM: Artificial Sequence
<220> FEATURE:
<223> OTHER INFORMATION: synthetic peptide

<400> SEQUENCE: 350

Gly Arg Val Pro Tyr Pro Arg Ile Pro Leu Lys Asp Val Phe Pro Arg
1               5                   10                  15

Val Glu Lys Gly
            20

<210> SEQ ID NO 351
<211> LENGTH: 20
<212> TYPE: PRT
<213> ORGANISM: Artificial Sequence
<220> FEATURE:
<223> OTHER INFORMATION: synthetic peptide

<400> SEQUENCE: 351

Ile Pro Leu Lys Asp Val Phe Pro Arg Val Glu Lys Gly Tyr Lys Met
1               5                   10                  15

Asp Ala Pro Asp
        20

<210> SEQ ID NO 352
<211> LENGTH: 20
<212> TYPE: PRT
<213> ORGANISM: Artificial Sequence
<220> FEATURE:
<223> OTHER INFORMATION: synthetic peptide

<400> SEQUENCE: 352

Asp Arg Ser Phe Ser Gln Lys Ser Asn Leu Ile Thr His Pro Lys Ser
1               5                   10                  15

His Ile Arg Asp
        20

<210> SEQ ID NO 353
<211> LENGTH: 20
<212> TYPE: PRT
<213> ORGANISM: Artificial Sequence
<220> FEATURE:
<223> OTHER INFORMATION: synthetic peptide

<400> SEQUENCE: 353

Ser Asn Leu Ile Thr His Pro Lys Ser His Ile Arg Asp Gly Ala Phe
1               5                   10                  15

Cys Cys Ala Ile
        20

<210> SEQ ID NO 354
<211> LENGTH: 20
<212> TYPE: PRT
<213> ORGANISM: Artificial Sequence
<220> FEATURE:
<223> OTHER INFORMATION: synthetic peptide

<400> SEQUENCE: 354

Glu Ser Ser Glu Ala Pro Gln Asp Pro Leu Asn Trp Phe Val Ile Leu
1               5                   10                  15

Val Pro His Ser
        20

<210> SEQ ID NO 355
<211> LENGTH: 20
<212> TYPE: PRT
<213> ORGANISM: Artificial Sequence
<220> FEATURE:
<223> OTHER INFORMATION: synthetic peptide

<400> SEQUENCE: 355

Asp Pro Leu Asn Trp Phe Val Ile Leu Val Pro His Ser Leu Arg Gln
1               5                   10                  15

Ala Gln Ala Ser
        20

<210> SEQ ID NO 356
<211> LENGTH: 20
<212> TYPE: PRT
<213> ORGANISM: Artificial Sequence
<220> FEATURE:
<223> OTHER INFORMATION: synthetic peptide

<400> SEQUENCE: 356

Ile Cys Ala Tyr Ala Asn Ser Tyr His Ser Tyr Val Ile Val Phe Val
1               5                   10                  15

Val Pro Asn Gln
            20

<210> SEQ ID NO 357
<211> LENGTH: 20
<212> TYPE: PRT
<213> ORGANISM: Artificial Sequence
<220> FEATURE:
<223> OTHER INFORMATION: synthetic peptide

<400> SEQUENCE: 357

Tyr His Ser Tyr Val Ile Val Phe Val Val Pro Asn Gln Lys Glu Leu
1               5                   10                  15

Thr Glu Leu Ala
            20

<210> SEQ ID NO 358
<211> LENGTH: 20
<212> TYPE: PRT
<213> ORGANISM: Artificial Sequence
<220> FEATURE:
<223> OTHER INFORMATION: synthetic peptide

<400> SEQUENCE: 358

Gly Gly Asn Asp His Glu Ile Phe Thr Asp Pro Arg Thr Val Gly Tyr
1               5                   10                  15

Ser Val Thr Ala
            20

<210> SEQ ID NO 359
<211> LENGTH: 20
<212> TYPE: PRT
<213> ORGANISM: Artificial Sequence
<220> FEATURE:
<223> OTHER INFORMATION: synthetic peptide

<400> SEQUENCE: 359

Phe Thr Asp Pro Arg Thr Val Gly Tyr Ser Val Thr Ala Pro Glu Asp
1               5                   10                  15

Thr Arg Arg Ile
            20

<210> SEQ ID NO 360
<211> LENGTH: 20
<212> TYPE: PRT
<213> ORGANISM: Artificial Sequence
<220> FEATURE:
<223> OTHER INFORMATION: synthetic peptide

<400> SEQUENCE: 360

Asp Glu Arg Glu Ser Thr Asp Asp Glu Ser Asn Pro Leu Val Arg Ala
1               5                   10                  15

Gly Ile Trp Thr
            20

<210> SEQ ID NO 361
<211> LENGTH: 20
<212> TYPE: PRT
<213> ORGANISM: Artificial Sequence
<220> FEATURE:
<223> OTHER INFORMATION: synthetic peptide

<400> SEQUENCE: 361

Asp Glu Ser Asn Pro Leu Val Arg Ala Gly Ile Trp Thr Lys Thr His

```
1               5                   10                  15

Thr Ile Trp Tyr
            20

<210> SEQ ID NO 362
<211> LENGTH: 20
<212> TYPE: PRT
<213> ORGANISM: Artificial Sequence
<220> FEATURE:
<223> OTHER INFORMATION: synthetic peptide

<400> SEQUENCE: 362

Lys Val Leu Pro Val Tyr Met Asn Cys Leu Leu Lys Asn Tyr Val Leu
1               5                   10                  15

Leu Ser Arg Pro
            20

<210> SEQ ID NO 363
<211> LENGTH: 20
<212> TYPE: PRT
<213> ORGANISM: Artificial Sequence
<220> FEATURE:
<223> OTHER INFORMATION: synthetic peptide

<400> SEQUENCE: 363

Asn Cys Leu Leu Lys Asn Tyr Val Leu Leu Ser Arg Pro Glu Ile Ser
1               5                   10                  15

Thr Asp Glu Arg
            20

<210> SEQ ID NO 364
<211> LENGTH: 20
<212> TYPE: PRT
<213> ORGANISM: Artificial Sequence
<220> FEATURE:
<223> OTHER INFORMATION: synthetic peptide

<400> SEQUENCE: 364

Ser Gln Lys Ile Thr Gly Val Phe Glu Leu Met Arg Glu Phe Thr His
1               5                   10                  15

Met Glu Tyr Asp
            20

<210> SEQ ID NO 365
<211> LENGTH: 20
<212> TYPE: PRT
<213> ORGANISM: Artificial Sequence
<220> FEATURE:
<223> OTHER INFORMATION: synthetic peptide

<400> SEQUENCE: 365

Phe Glu Leu Met Arg Glu Phe Thr His Met Glu Tyr Asp Leu Glu Lys
1               5                   10                  15

Arg Gly Ile Thr
            20

<210> SEQ ID NO 366
<211> LENGTH: 20
<212> TYPE: PRT
<213> ORGANISM: Artificial Sequence
<220> FEATURE:
<223> OTHER INFORMATION: synthetic peptide

<400> SEQUENCE: 366
```

```
Gln Lys Glu Glu Ala Glu His Lys Lys Lys Met Ala Trp Leu Glu Ser
1               5                   10                  15

Asn Asn Tyr Gln
            20

<210> SEQ ID NO 367
<211> LENGTH: 20
<212> TYPE: PRT
<213> ORGANISM: Artificial Sequence
<220> FEATURE:
<223> OTHER INFORMATION: synthetic peptide

<400> SEQUENCE: 367

Lys Lys Lys Met Ala Trp Leu Glu Ser Asn Asn Tyr Gln Ser Phe Cys
1               5                   10                  15

Leu Pro Ser Glu
            20

<210> SEQ ID NO 368
<211> LENGTH: 20
<212> TYPE: PRT
<213> ORGANISM: Artificial Sequence
<220> FEATURE:
<223> OTHER INFORMATION: synthetic peptide

<400> SEQUENCE: 368

Val Pro Ser Lys Ser Lys Ala Ala Ala Ser Ala Thr Arg Val Trp Thr
1               5                   10                  15

Glu Gln Glu Thr
            20

<210> SEQ ID NO 369
<211> LENGTH: 20
<212> TYPE: PRT
<213> ORGANISM: Artificial Sequence
<220> FEATURE:
<223> OTHER INFORMATION: synthetic peptide

<400> SEQUENCE: 369

Ala Ala Ser Ala Thr Arg Val Trp Thr Glu Gln Glu Thr Leu Leu Leu
1               5                   10                  15

Leu Glu Ala Leu
            20

<210> SEQ ID NO 370
<211> LENGTH: 20
<212> TYPE: PRT
<213> ORGANISM: Artificial Sequence
<220> FEATURE:
<223> OTHER INFORMATION: synthetic peptide

<400> SEQUENCE: 370

Pro Thr Ile Met Asp Ile Val Val Ile Ala Gly Val Ile Pro Ala Val
1               5                   10                  15

Ala Ile Val Leu
            20

<210> SEQ ID NO 371
<211> LENGTH: 20
<212> TYPE: PRT
<213> ORGANISM: Artificial Sequence
<220> FEATURE:
<223> OTHER INFORMATION: synthetic peptide

<400> SEQUENCE: 371
```

```
Val Ile Ala Gly Val Ile Pro Ala Val Ala Ile Val Leu Val Ser Leu
1               5                   10                  15

Leu Phe Val Met
            20

<210> SEQ ID NO 372
<211> LENGTH: 20
<212> TYPE: PRT
<213> ORGANISM: Artificial Sequence
<220> FEATURE:
<223> OTHER INFORMATION: synthetic peptide

<400> SEQUENCE: 372

Pro Thr Pro Ser Thr Asp Ala Glu Tyr Pro Ala Asn Gly Cys Gly Ala
1               5                   10                  15

Asp Arg Ile Tyr
            20

<210> SEQ ID NO 373
<211> LENGTH: 20
<212> TYPE: PRT
<213> ORGANISM: Artificial Sequence
<220> FEATURE:
<223> OTHER INFORMATION: synthetic peptide

<400> SEQUENCE: 373

Glu Tyr Pro Ala Asn Gly Cys Gly Ala Asp Arg Ile Tyr Asp Leu Asn
1               5                   10                  15

Ile Pro Ala Phe
            20

<210> SEQ ID NO 374
<211> LENGTH: 20
<212> TYPE: PRT
<213> ORGANISM: Artificial Sequence
<220> FEATURE:
<223> OTHER INFORMATION: synthetic peptide

<400> SEQUENCE: 374

Ser Val Leu Gly Phe Val Leu Tyr Ala Leu Ala Gly Ala Met Gly Phe
1               5                   10                  15

Phe Thr His Tyr
            20

<210> SEQ ID NO 375
<211> LENGTH: 20
<212> TYPE: PRT
<213> ORGANISM: Artificial Sequence
<220> FEATURE:
<223> OTHER INFORMATION: synthetic peptide

<400> SEQUENCE: 375

Tyr Ala Leu Ala Gly Ala Met Gly Phe Phe Thr His Tyr Leu Leu Pro
1               5                   10                  15

Gln Leu Arg Lys
            20

<210> SEQ ID NO 376
<211> LENGTH: 20
<212> TYPE: PRT
<213> ORGANISM: Artificial Sequence
<220> FEATURE:
<223> OTHER INFORMATION: synthetic peptide
```

-continued

<400> SEQUENCE: 376

Leu Ser Leu Phe Val Leu Gly Leu Phe Leu Trp Phe Met Lys Arg
1               5                   10                  15

Glu Arg Gln Glu
            20

<210> SEQ ID NO 377
<211> LENGTH: 20
<212> TYPE: PRT
<213> ORGANISM: Artificial Sequence
<220> FEATURE:
<223> OTHER INFORMATION: synthetic peptide

<400> SEQUENCE: 377

Gly Leu Phe Leu Trp Phe Met Lys Arg Glu Arg Gln Glu Glu Tyr Ile
1               5                   10                  15

Glu Glu Lys Lys
            20

<210> SEQ ID NO 378
<211> LENGTH: 20
<212> TYPE: PRT
<213> ORGANISM: Artificial Sequence
<220> FEATURE:
<223> OTHER INFORMATION: synthetic peptide

<400> SEQUENCE: 378

Arg Leu Ser Pro Gly Glu Ala Leu Pro Pro Val Ser Gln Gly Gly Thr
1               5                   10                  15

Gly Lys Ala Pro
            20

<210> SEQ ID NO 379
<211> LENGTH: 20
<212> TYPE: PRT
<213> ORGANISM: Artificial Sequence
<220> FEATURE:
<223> OTHER INFORMATION: synthetic peptide

<400> SEQUENCE: 379

Leu Pro Pro Val Ser Gln Gly Gly Thr Gly Lys Ala Pro Glu Leu Pro
1               5                   10                  15

Ser Gly Ser Gly
            20

<210> SEQ ID NO 380
<211> LENGTH: 20
<212> TYPE: PRT
<213> ORGANISM: Artificial Sequence
<220> FEATURE:
<223> OTHER INFORMATION: synthetic peptide

<400> SEQUENCE: 380

Ala Leu His Pro Arg Gly Ile Arg Glu Lys Ala Leu His Glu His Leu
1               5                   10                  15

Asn Lys His Arg
            20

<210> SEQ ID NO 381
<211> LENGTH: 20
<212> TYPE: PRT
<213> ORGANISM: Artificial Sequence
<220> FEATURE:
<223> OTHER INFORMATION: synthetic peptide

<400> SEQUENCE: 381

Arg Glu Lys Ala Leu His Glu His Leu Asn Lys His Arg Asp Phe Leu
1               5                   10                  15

Gln Glu Val Cys
            20

<210> SEQ ID NO 382
<211> LENGTH: 20
<212> TYPE: PRT
<213> ORGANISM: Artificial Sequence
<220> FEATURE:
<223> OTHER INFORMATION: synthetic peptide

<400> SEQUENCE: 382

Lys Glu Glu Val Asn Asp Lys Arg Tyr Leu Arg Cys Pro Ser Ala Met
1               5                   10                  15

Thr Val Met His
            20

<210> SEQ ID NO 383
<211> LENGTH: 20
<212> TYPE: PRT
<213> ORGANISM: Artificial Sequence
<220> FEATURE:
<223> OTHER INFORMATION: synthetic peptide

<400> SEQUENCE: 383

Arg Tyr Leu Arg Cys Pro Ser Ala Met Thr Val Met His Leu Arg Lys
1               5                   10                  15

Phe Leu Arg Ser
            20

<210> SEQ ID NO 384
<211> LENGTH: 18
<212> TYPE: PRT
<213> ORGANISM: Artificial Sequence
<220> FEATURE:
<223> OTHER INFORMATION: synthetic peptide

<400> SEQUENCE: 384

Met Ala His Ile Ala Ile Asn Gln Tyr Leu Gln Gln Val Tyr Glu Ala
1               5                   10                  15

Ile Asp

<210> SEQ ID NO 385
<211> LENGTH: 20
<212> TYPE: PRT
<213> ORGANISM: Artificial Sequence
<220> FEATURE:
<223> OTHER INFORMATION: synthetic peptide

<400> SEQUENCE: 385

Gly Arg Arg Lys Leu Lys Leu Trp Lys His Ser Glu Lys Gln Pro Glu
1               5                   10                  15

Thr Asn Val Ala
            20

<210> SEQ ID NO 386
<211> LENGTH: 20
<212> TYPE: PRT
<213> ORGANISM: Artificial Sequence
<220> FEATURE:
<223> OTHER INFORMATION: synthetic peptide

<400> SEQUENCE: 386

Trp Lys His Ser Glu Lys Gln Pro Glu Thr Asn Val Ala Glu Gly Arg
1               5                   10                  15

Arg Val Phe Glu
            20

<210> SEQ ID NO 387
<211> LENGTH: 20
<212> TYPE: PRT
<213> ORGANISM: Artificial Sequence
<220> FEATURE:
<223> OTHER INFORMATION: synthetic peptide

<400> SEQUENCE: 387

Glu Ile Thr Lys Lys Tyr Ala Lys Gly Val Ile Pro Ser Ile Leu Phe
1               5                   10                  15

Leu Gln Asp Asp
            20

<210> SEQ ID NO 388
<211> LENGTH: 20
<212> TYPE: PRT
<213> ORGANISM: Artificial Sequence
<220> FEATURE:
<223> OTHER INFORMATION: synthetic peptide

<400> SEQUENCE: 388

Lys Gly Val Ile Pro Ser Ile Leu Phe Leu Gln Asp Asp Glu Asp Asp
1               5                   10                  15

Asp Glu Leu Ala
            20

<210> SEQ ID NO 389
<211> LENGTH: 20
<212> TYPE: PRT
<213> ORGANISM: Artificial Sequence
<220> FEATURE:
<223> OTHER INFORMATION: synthetic peptide

<400> SEQUENCE: 389

Arg Val Ser Arg Pro Ala Pro Gly Asp Ser Arg Glu Gly Gly Trp Ser
1               5                   10                  15

Glu Pro Arg Leu
            20

<210> SEQ ID NO 390
<211> LENGTH: 20
<212> TYPE: PRT
<213> ORGANISM: Artificial Sequence
<220> FEATURE:
<223> OTHER INFORMATION: synthetic peptide

<400> SEQUENCE: 390

Gly Asp Ser Arg Glu Gly Gly Trp Ser Glu Pro Arg Leu Asp Thr Gln
1               5                   10                  15

Glu Glu Pro Pro
            20

<210> SEQ ID NO 391
<211> LENGTH: 20
<212> TYPE: PRT
<213> ORGANISM: Artificial Sequence
<220> FEATURE:

<223> OTHER INFORMATION: synthetic peptide

<400> SEQUENCE: 391

Val Tyr Asn Asp Ser Arg Val Ser Pro Val Ser Glu Asn His Val Ala
1               5                   10                  15

Ser Ser Glu Gly
            20

<210> SEQ ID NO 392
<211> LENGTH: 20
<212> TYPE: PRT
<213> ORGANISM: Artificial Sequence
<220> FEATURE:
<223> OTHER INFORMATION: synthetic peptide

<400> SEQUENCE: 392

Ser Pro Val Ser Glu Asn His Val Ala Ser Ser Glu Gly Tyr Val Leu
1               5                   10                  15

Phe Tyr Gln Leu
            20

<210> SEQ ID NO 393
<211> LENGTH: 20
<212> TYPE: PRT
<213> ORGANISM: Artificial Sequence
<220> FEATURE:
<223> OTHER INFORMATION: synthetic peptide

<400> SEQUENCE: 393

Leu Asp Ser Glu Ala Ser Val Arg Leu Thr Ala Glu Gln Pro Arg Phe
1               5                   10                  15

Phe Leu His Gly
            20

<210> SEQ ID NO 394
<211> LENGTH: 20
<212> TYPE: PRT
<213> ORGANISM: Artificial Sequence
<220> FEATURE:
<223> OTHER INFORMATION: synthetic peptide

<400> SEQUENCE: 394

Arg Leu Thr Ala Glu Gln Pro Arg Phe Phe Leu His Gly Val Thr Leu
1               5                   10                  15

Val Pro Ile Glu
            20

<210> SEQ ID NO 395
<211> LENGTH: 20
<212> TYPE: PRT
<213> ORGANISM: Artificial Sequence
<220> FEATURE:
<223> OTHER INFORMATION: synthetic peptide

<400> SEQUENCE: 395

Met Thr Glu Tyr Lys Leu Val Val Val Gly Ala Val Gly Val Gly Lys
1               5                   10                  15

Ser Ala Leu Thr
            20

<210> SEQ ID NO 396
<211> LENGTH: 20
<212> TYPE: PRT
<213> ORGANISM: Artificial Sequence

```
<220> FEATURE:
<223> OTHER INFORMATION: synthetic peptide

<400> SEQUENCE: 396

Leu Val Val Val Gly Ala Val Gly Val Gly Lys Ser Ala Leu Thr Ile
1               5                   10                  15

Gln Leu Ile Gln
            20

<210> SEQ ID NO 397
<211> LENGTH: 20
<212> TYPE: PRT
<213> ORGANISM: Artificial Sequence
<220> FEATURE:
<223> OTHER INFORMATION: synthetic peptide

<400> SEQUENCE: 397

His Ser Thr Tyr Ser Ser Thr Pro Gly Arg Arg Lys Pro Lys Val His
1               5                   10                  15

Arg Pro Arg Ser
            20

<210> SEQ ID NO 398
<211> LENGTH: 20
<212> TYPE: PRT
<213> ORGANISM: Artificial Sequence
<220> FEATURE:
<223> OTHER INFORMATION: synthetic peptide

<400> SEQUENCE: 398

Pro Gly Arg Arg Lys Pro Lys Val His Arg Pro Arg Ser Pro Ile Leu
1               5                   10                  15

Glu Glu Lys Asp
            20

<210> SEQ ID NO 399
<211> LENGTH: 20
<212> TYPE: PRT
<213> ORGANISM: Artificial Sequence
<220> FEATURE:
<223> OTHER INFORMATION: synthetic peptide

<400> SEQUENCE: 399

Gln Glu Leu Gln Pro Leu Tyr Leu Asn Leu His Ala Tyr Leu Arg Arg
1               5                   10                  15

Ala Leu His Arg
            20

<210> SEQ ID NO 400
<211> LENGTH: 20
<212> TYPE: PRT
<213> ORGANISM: Artificial Sequence
<220> FEATURE:
<223> OTHER INFORMATION: synthetic peptide

<400> SEQUENCE: 400

Leu Asn Leu His Ala Tyr Leu Arg Arg Ala Leu His Arg His Tyr Gly
1               5                   10                  15

Ala Gln His Ile
            20

<210> SEQ ID NO 401
<211> LENGTH: 20
<212> TYPE: PRT
```

<210> SEQ ID NO 401
<211> LENGTH: 20
<212> TYPE: PRT
<213> ORGANISM: Artificial Sequence
<220> FEATURE:
<223> OTHER INFORMATION: synthetic peptide

<400> SEQUENCE: 401

Phe Thr Asp Cys Gly Ile His Ala Arg Glu Trp Val Ser Thr Ala Phe
1               5                   10                  15

Cys Gln Trp Phe
            20

<210> SEQ ID NO 402
<211> LENGTH: 20
<212> TYPE: PRT
<213> ORGANISM: Artificial Sequence
<220> FEATURE:
<223> OTHER INFORMATION: synthetic peptide

<400> SEQUENCE: 402

Ala Arg Glu Trp Val Ser Thr Ala Phe Cys Gln Trp Phe Val Tyr Gln
1               5                   10                  15

Ala Thr Lys Thr
            20

<210> SEQ ID NO 403
<211> LENGTH: 20
<212> TYPE: PRT
<213> ORGANISM: Artificial Sequence
<220> FEATURE:
<223> OTHER INFORMATION: synthetic peptide

<400> SEQUENCE: 403

Glu Glu Ser Val Arg Gly Tyr Asp Trp Ser Pro Arg Asp Ser Arg Arg
1               5                   10                  15

Ser Pro Asp Gln
            20

<210> SEQ ID NO 404
<211> LENGTH: 20
<212> TYPE: PRT
<213> ORGANISM: Artificial Sequence
<220> FEATURE:
<223> OTHER INFORMATION: synthetic peptide

<400> SEQUENCE: 404

Asp Trp Ser Pro Arg Asp Ser Arg Arg Ser Pro Asp Gln Gly Arg Gln
1               5                   10                  15

Gln Ala Glu Arg
            20

<210> SEQ ID NO 405
<211> LENGTH: 20
<212> TYPE: PRT
<213> ORGANISM: Artificial Sequence
<220> FEATURE:
<223> OTHER INFORMATION: synthetic peptide

<400> SEQUENCE: 405

Arg Ala Thr Pro Val Thr Arg Val Gly Ser Ala Ala Pro Leu Arg Ser
1               5                   10                  15

Pro Ser Glu Thr
            20

<210> SEQ ID NO 406
<211> LENGTH: 20

```
<212> TYPE: PRT
<213> ORGANISM: Artificial Sequence
<220> FEATURE:
<223> OTHER INFORMATION: synthetic peptide

<400> SEQUENCE: 406

Val Gly Ser Ala Ala Pro Leu Arg Ser Pro Ser Glu Thr Gly Arg Gln
1               5                   10                  15

Ala Gly Arg Glu
            20

<210> SEQ ID NO 407
<211> LENGTH: 20
<212> TYPE: PRT
<213> ORGANISM: Artificial Sequence
<220> FEATURE:
<223> OTHER INFORMATION: synthetic peptide

<400> SEQUENCE: 407

Ala Ala Ala Pro Pro Gly Ser Met Pro Thr Ala Pro Glu Ser Glu Pro
1               5                   10                  15

Glu Ala Pro Ile
            20

<210> SEQ ID NO 408
<211> LENGTH: 20
<212> TYPE: PRT
<213> ORGANISM: Artificial Sequence
<220> FEATURE:
<223> OTHER INFORMATION: synthetic peptide

<400> SEQUENCE: 408

Met Pro Thr Ala Pro Glu Ser Glu Pro Glu Ala Pro Ile Ser His Pro
1               5                   10                  15

Pro Pro Pro Thr
            20

<210> SEQ ID NO 409
<211> LENGTH: 20
<212> TYPE: PRT
<213> ORGANISM: Artificial Sequence
<220> FEATURE:
<223> OTHER INFORMATION: synthetic peptide

<400> SEQUENCE: 409

Asp Thr Gly Pro Met Arg Phe Tyr Tyr Val Val Gly Trp Val Ile Pro
1               5                   10                  15

Ala Ile Val Thr
            20

<210> SEQ ID NO 410
<211> LENGTH: 20
<212> TYPE: PRT
<213> ORGANISM: Artificial Sequence
<220> FEATURE:
<223> OTHER INFORMATION: synthetic peptide

<400> SEQUENCE: 410

Tyr Tyr Val Val Gly Trp Val Ile Pro Ala Ile Val Thr Gly Leu Ala
1               5                   10                  15

Val Gly Leu Asp
            20

<210> SEQ ID NO 411
```

```
<211> LENGTH: 20
<212> TYPE: PRT
<213> ORGANISM: Artificial Sequence
<220> FEATURE:
<223> OTHER INFORMATION: synthetic peptide

<400> SEQUENCE: 411

Lys Leu Asp Leu Glu Glu Lys Leu Phe Gly Gln His Leu Ser Thr Glu
1               5                   10                  15

Val Ile Phe Lys
            20

<210> SEQ ID NO 412
<211> LENGTH: 20
<212> TYPE: PRT
<213> ORGANISM: Artificial Sequence
<220> FEATURE:
<223> OTHER INFORMATION: synthetic peptide

<400> SEQUENCE: 412

Leu Phe Gly Gln His Leu Ser Thr Glu Val Ile Phe Lys Ala Leu Thr
1               5                   10                  15

Gly Phe Arg Asn
            20

<210> SEQ ID NO 413
<211> LENGTH: 20
<212> TYPE: PRT
<213> ORGANISM: Artificial Sequence
<220> FEATURE:
<223> OTHER INFORMATION: synthetic peptide

<400> SEQUENCE: 413

Lys Asp Val Ile Leu Leu Gly Asp Phe Asn Ala Asp Cys Thr Ser Leu
1               5                   10                  15

Thr Lys Lys Arg
            20

<210> SEQ ID NO 414
<211> LENGTH: 20
<212> TYPE: PRT
<213> ORGANISM: Artificial Sequence
<220> FEATURE:
<223> OTHER INFORMATION: synthetic peptide

<400> SEQUENCE: 414

Asp Phe Asn Ala Asp Cys Thr Ser Leu Thr Lys Lys Arg Leu Asp Lys
1               5                   10                  15

Leu Glu Leu Arg
            20

<210> SEQ ID NO 415
<211> LENGTH: 20
<212> TYPE: PRT
<213> ORGANISM: Artificial Sequence
<220> FEATURE:
<223> OTHER INFORMATION: synthetic peptide

<400> SEQUENCE: 415

Asp Lys Leu Lys Ala Cys Glu Val Ser Lys Asn Lys Asp Arg Lys Glu
1               5                   10                  15

Gln Ser Glu Thr
            20
```

```
<210> SEQ ID NO 416
<211> LENGTH: 20
<212> TYPE: PRT
<213> ORGANISM: Artificial Sequence
<220> FEATURE:
<223> OTHER INFORMATION: synthetic peptide

<400> SEQUENCE: 416

Val Ser Lys Asn Lys Asp Arg Lys Glu Gln Ser Glu Thr Val Ser Leu
1               5                   10                  15

Ser Glu Asp Glu
            20

<210> SEQ ID NO 417
<211> LENGTH: 20
<212> TYPE: PRT
<213> ORGANISM: Artificial Sequence
<220> FEATURE:
<223> OTHER INFORMATION: synthetic peptide

<400> SEQUENCE: 417

Asn Lys Ile Thr Arg Asp Phe Lys Pro Gly Asp Arg Val Leu Val Glu
1               5                   10                  15

Val Val Thr Thr
            20

<210> SEQ ID NO 418
<211> LENGTH: 20
<212> TYPE: PRT
<213> ORGANISM: Artificial Sequence
<220> FEATURE:
<223> OTHER INFORMATION: synthetic peptide

<400> SEQUENCE: 418

Lys Pro Gly Asp Arg Val Leu Val Glu Val Val Thr Thr Met Thr Ser
1               5                   10                  15

Ala Asp Val Met
            20

<210> SEQ ID NO 419
<211> LENGTH: 20
<212> TYPE: PRT
<213> ORGANISM: Artificial Sequence
<220> FEATURE:
<223> OTHER INFORMATION: synthetic peptide

<400> SEQUENCE: 419

Ile Val Val Ser Asp Pro Glu Asp Ile Thr Asp Cys Pro Met Thr Pro
1               5                   10                  15

Asp Thr Pro Asn
            20

<210> SEQ ID NO 420
<211> LENGTH: 20
<212> TYPE: PRT
<213> ORGANISM: Artificial Sequence
<220> FEATURE:
<223> OTHER INFORMATION: synthetic peptide

<400> SEQUENCE: 420

Asp Ile Thr Asp Cys Pro Met Thr Pro Asp Thr Pro Asn Asn Asp Pro
1               5                   10                  15

Arg Cys Ser Thr
            20
```

<210> SEQ ID NO 421
<211> LENGTH: 20
<212> TYPE: PRT
<213> ORGANISM: Artificial Sequence
<220> FEATURE:
<223> OTHER INFORMATION: synthetic peptide

<400> SEQUENCE: 421

Val Gly Ser Thr Thr Thr Gln Leu Tyr Thr Asp Arg Thr Lys Lys Leu
1               5                   10                  15

Arg Pro Glu Met
            20

<210> SEQ ID NO 422
<211> LENGTH: 20
<212> TYPE: PRT
<213> ORGANISM: Artificial Sequence
<220> FEATURE:
<223> OTHER INFORMATION: synthetic peptide

<400> SEQUENCE: 422

Leu Tyr Thr Asp Arg Thr Lys Lys Leu Arg Pro Glu Met Glu Gly Pro
1               5                   10                  15

Gly Ser Phe Thr
            20

<210> SEQ ID NO 423
<211> LENGTH: 20
<212> TYPE: PRT
<213> ORGANISM: Artificial Sequence
<220> FEATURE:
<223> OTHER INFORMATION: synthetic peptide

<400> SEQUENCE: 423

Cys Asp Cys Asp Glu Phe Arg Lys Ile Lys Pro Lys Asn Phe Lys Gln
1               5                   10                  15

Ala Glu Arg Glu
            20

<210> SEQ ID NO 424
<211> LENGTH: 20
<212> TYPE: PRT
<213> ORGANISM: Artificial Sequence
<220> FEATURE:
<223> OTHER INFORMATION: synthetic peptide

<400> SEQUENCE: 424

Lys Ile Lys Pro Lys Asn Phe Lys Gln Ala Glu Arg Glu Glu Lys Arg
1               5                   10                  15

Val Leu Gly Leu
            20

<210> SEQ ID NO 425
<211> LENGTH: 20
<212> TYPE: PRT
<213> ORGANISM: Artificial Sequence
<220> FEATURE:
<223> OTHER INFORMATION: synthetic peptide

<400> SEQUENCE: 425

Gln Gln Ser Glu Ala Tyr Lys Met Cys Thr Glu Lys Ile Arg Glu Lys
1               5                   10                  15

Lys Ile Lys Lys
            20

```
<210> SEQ ID NO 426
<211> LENGTH: 20
<212> TYPE: PRT
<213> ORGANISM: Artificial Sequence
<220> FEATURE:
<223> OTHER INFORMATION: synthetic peptide

<400> SEQUENCE: 426

Met Cys Thr Glu Lys Ile Arg Glu Lys Lys Ile Lys Lys Glu Asp Ser
1               5                   10                  15

Ser Ser Gly Leu
            20

<210> SEQ ID NO 427
<211> LENGTH: 20
<212> TYPE: PRT
<213> ORGANISM: Artificial Sequence
<220> FEATURE:
<223> OTHER INFORMATION: synthetic peptide

<400> SEQUENCE: 427

His Glu Lys Arg Leu Arg Val His Ala His Ser Thr Thr Asn Ser Ala
1               5                   10                  15

Arg Phe Val Gln
            20

<210> SEQ ID NO 428
<211> LENGTH: 20
<212> TYPE: PRT
<213> ORGANISM: Artificial Sequence
<220> FEATURE:
<223> OTHER INFORMATION: synthetic peptide

<400> SEQUENCE: 428

His Ala His Ser Thr Thr Asn Ser Ala Arg Phe Val Gln Arg Pro Leu
1               5                   10                  15

Leu Phe Ala Ser
            20

<210> SEQ ID NO 429
<211> LENGTH: 20
<212> TYPE: PRT
<213> ORGANISM: Artificial Sequence
<220> FEATURE:
<223> OTHER INFORMATION: synthetic peptide

<400> SEQUENCE: 429

Glu Asn Thr Asp Pro Gly Tyr Asn Cys Leu Pro Cys Pro Leu Arg Phe
1               5                   10                  15

Thr Gly Ser Gln
            20

<210> SEQ ID NO 430
<211> LENGTH: 20
<212> TYPE: PRT
<213> ORGANISM: Artificial Sequence
<220> FEATURE:
<223> OTHER INFORMATION: synthetic peptide

<400> SEQUENCE: 430

Asn Cys Leu Pro Cys Pro Leu Arg Phe Thr Gly Ser Gln Pro Phe Gly
1               5                   10                  15

Gln Gly Val Glu
```

-continued

```
            20

<210> SEQ ID NO 431
<211> LENGTH: 20
<212> TYPE: PRT
<213> ORGANISM: Artificial Sequence
<220> FEATURE:
<223> OTHER INFORMATION: synthetic peptide

<400> SEQUENCE: 431

Trp Ser Gly Cys Phe Gly Lys Met Ala Gly Ser Gly Val Cys Gln Ala
1               5                   10                  15

Thr Ser Thr Ala
            20

<210> SEQ ID NO 432
<211> LENGTH: 20
<212> TYPE: PRT
<213> ORGANISM: Artificial Sequence
<220> FEATURE:
<223> OTHER INFORMATION: synthetic peptide

<400> SEQUENCE: 432

Met Ala Gly Ser Gly Val Cys Gln Ala Thr Ser Thr Ala Ser Thr Phe
1               5                   10                  15

Val Lys Pro Ile
            20

<210> SEQ ID NO 433
<211> LENGTH: 20
<212> TYPE: PRT
<213> ORGANISM: Artificial Sequence
<220> FEATURE:
<223> OTHER INFORMATION: synthetic peptide

<400> SEQUENCE: 433

Lys Gly Glu Lys Gly Glu Pro Gly Ser Ile Phe Ser Pro Asn Gly Gly
1               5                   10                  15

Ala Leu Gly Pro
            20

<210> SEQ ID NO 434
<211> LENGTH: 20
<212> TYPE: PRT
<213> ORGANISM: Artificial Sequence
<220> FEATURE:
<223> OTHER INFORMATION: synthetic peptide

<400> SEQUENCE: 434

Gly Ser Ile Phe Ser Pro Asn Gly Gly Ala Leu Gly Pro Ala Gln Lys
1               5                   10                  15

Gly Ala Lys Gly
            20

<210> SEQ ID NO 435
<211> LENGTH: 20
<212> TYPE: PRT
<213> ORGANISM: Artificial Sequence
<220> FEATURE:
<223> OTHER INFORMATION: synthetic peptide

<400> SEQUENCE: 435

Gln Arg Leu Ala Glu Glu Lys Ala Gln Ala Ser Ser Ile Leu Val Gly
1               5                   10                  15
```

Ser Arg Cys Glu
          20

<210> SEQ ID NO 436
<211> LENGTH: 20
<212> TYPE: PRT
<213> ORGANISM: Artificial Sequence
<220> FEATURE:
<223> OTHER INFORMATION: synthetic peptide

<400> SEQUENCE: 436

Ala Gln Ala Ser Ser Ile Leu Val Gly Ser Arg Cys Glu Val Arg Ala
1               5                   10                  15

Ala Gly Gln Ser
          20

<210> SEQ ID NO 437
<211> LENGTH: 20
<212> TYPE: PRT
<213> ORGANISM: Artificial Sequence
<220> FEATURE:
<223> OTHER INFORMATION: synthetic peptide

<400> SEQUENCE: 437

Asp Asn Thr Ala Glu Trp Asp His Leu Lys Ile Ser Ile Ser Met Cys
1               5                   10                  15

Leu Ser Leu Gly
          20

<210> SEQ ID NO 438
<211> LENGTH: 20
<212> TYPE: PRT
<213> ORGANISM: Artificial Sequence
<220> FEATURE:
<223> OTHER INFORMATION: synthetic peptide

<400> SEQUENCE: 438

His Leu Lys Ile Ser Ile Ser Met Cys Leu Ser Leu Gly Leu Val Gly
1               5                   10                  15

Leu Ser Phe Cys
          20

<210> SEQ ID NO 439
<211> LENGTH: 20
<212> TYPE: PRT
<213> ORGANISM: Artificial Sequence
<220> FEATURE:
<223> OTHER INFORMATION: synthetic peptide

<400> SEQUENCE: 439

Pro Ala Leu Gly Leu Leu Gly Asp Pro Phe Arg Pro Leu Ser Gln Gln
1               5                   10                  15

Val Asn Leu Thr
          20

<210> SEQ ID NO 440
<211> LENGTH: 20
<212> TYPE: PRT
<213> ORGANISM: Artificial Sequence
<220> FEATURE:
<223> OTHER INFORMATION: synthetic peptide

<400> SEQUENCE: 440

Asp Pro Phe Arg Pro Leu Ser Gln Gln Val Asn Leu Thr Asp Gly Arg
1               5                   10                  15

Trp His Arg Val
            20

<210> SEQ ID NO 441
<211> LENGTH: 20
<212> TYPE: PRT
<213> ORGANISM: Artificial Sequence
<220> FEATURE:
<223> OTHER INFORMATION: synthetic peptide

<400> SEQUENCE: 441

Glu Arg Gly Val Lys Leu Arg Leu Thr Val Val Asp Thr Ser Gly Tyr
1               5                   10                  15

Gly Asp Ala Ile
            20

<210> SEQ ID NO 442
<211> LENGTH: 20
<212> TYPE: PRT
<213> ORGANISM: Artificial Sequence
<220> FEATURE:
<223> OTHER INFORMATION: synthetic peptide

<400> SEQUENCE: 442

Leu Thr Val Val Asp Thr Ser Gly Tyr Gly Asp Ala Ile Asn Cys Arg
1               5                   10                  15

Asp Cys Phe Lys
            20

<210> SEQ ID NO 443
<211> LENGTH: 20
<212> TYPE: PRT
<213> ORGANISM: Artificial Sequence
<220> FEATURE:
<223> OTHER INFORMATION: synthetic peptide

<400> SEQUENCE: 443

Gly Pro Asp Val Asp Leu Gln Gly Pro Glu Ala Lys Ile Glu Phe Pro
1               5                   10                  15

Lys Phe Ser Met
            20

<210> SEQ ID NO 444
<211> LENGTH: 20
<212> TYPE: PRT
<213> ORGANISM: Artificial Sequence
<220> FEATURE:
<223> OTHER INFORMATION: synthetic peptide

<400> SEQUENCE: 444

Gly Pro Glu Ala Lys Ile Glu Phe Pro Lys Phe Ser Met Pro Lys Ile
1               5                   10                  15

Gly Ile Pro Gly
            20

<210> SEQ ID NO 445
<211> LENGTH: 20
<212> TYPE: PRT
<213> ORGANISM: Artificial Sequence
<220> FEATURE:
<223> OTHER INFORMATION: synthetic peptide

<400> SEQUENCE: 445

Val Thr Leu Ser Lys Pro Val Pro Glu Ser Glu Phe Ser Phe Ser Pro

```
Leu Gln Ala Pro
        20

<210> SEQ ID NO 446
<211> LENGTH: 20
<212> TYPE: PRT
<213> ORGANISM: Artificial Sequence
<220> FEATURE:
<223> OTHER INFORMATION: synthetic peptide

<400> SEQUENCE: 446

Pro Glu Ser Glu Phe Ser Phe Ser Pro Leu Gln Ala Pro Thr Pro Leu
1               5                   10                  15

Ala Ser His Thr
        20

<210> SEQ ID NO 447
<211> LENGTH: 20
<212> TYPE: PRT
<213> ORGANISM: Artificial Sequence
<220> FEATURE:
<223> OTHER INFORMATION: synthetic peptide

<400> SEQUENCE: 447

Leu Lys Gly Asp Ser Gly Pro Lys Gly Glu Lys Gly His Leu Gly Leu
1               5                   10                  15

Ile Gly Leu Ile
        20

<210> SEQ ID NO 448
<211> LENGTH: 20
<212> TYPE: PRT
<213> ORGANISM: Artificial Sequence
<220> FEATURE:
<223> OTHER INFORMATION: synthetic peptide

<400> SEQUENCE: 448

Lys Gly Glu Lys Gly His Leu Gly Leu Ile Gly Leu Ile Gly Pro Pro
1               5                   10                  15

Gly Glu Gln Gly
        20

<210> SEQ ID NO 449
<211> LENGTH: 20
<212> TYPE: PRT
<213> ORGANISM: Artificial Sequence
<220> FEATURE:
<223> OTHER INFORMATION: synthetic peptide

<400> SEQUENCE: 449

Asp Gly Asp Lys Gly Glu Ile Gly Glu Pro Gly Gln Lys Glu Ser Lys
1               5                   10                  15

Gly Asp Lys Gly
        20

<210> SEQ ID NO 450
<211> LENGTH: 20
<212> TYPE: PRT
<213> ORGANISM: Artificial Sequence
<220> FEATURE:
<223> OTHER INFORMATION: synthetic peptide

<400> SEQUENCE: 450
```

Gly Glu Pro Gly Gln Lys Glu Ser Lys Gly Asp Lys Gly Glu Gln Gly
1               5                   10                  15

Pro Pro Gly Pro
            20

<210> SEQ ID NO 451
<211> LENGTH: 20
<212> TYPE: PRT
<213> ORGANISM: Artificial Sequence
<220> FEATURE:
<223> OTHER INFORMATION: synthetic peptide

<400> SEQUENCE: 451

Leu Gly Pro Lys Gly Glu Pro Gly Ile Pro Gly Asp Gln Asp Leu Gln
1               5                   10                  15

Gly Pro Pro Gly
            20

<210> SEQ ID NO 452
<211> LENGTH: 20
<212> TYPE: PRT
<213> ORGANISM: Artificial Sequence
<220> FEATURE:
<223> OTHER INFORMATION: synthetic peptide

<400> SEQUENCE: 452

Gly Ile Pro Gly Asp Gln Asp Leu Gln Gly Pro Pro Gly Ile Pro Gly
1               5                   10                  15

Ile Gly Gly Pro
            20

<210> SEQ ID NO 453
<211> LENGTH: 20
<212> TYPE: PRT
<213> ORGANISM: Artificial Sequence
<220> FEATURE:
<223> OTHER INFORMATION: synthetic peptide

<400> SEQUENCE: 453

Lys Gly Ala Lys Gly Ser Ser Gly Pro Thr Gly Pro Lys Ser Glu Ala
1               5                   10                  15

Gly His Pro Gly
            20

<210> SEQ ID NO 454
<211> LENGTH: 20
<212> TYPE: PRT
<213> ORGANISM: Artificial Sequence
<220> FEATURE:
<223> OTHER INFORMATION: synthetic peptide

<400> SEQUENCE: 454

Gly Pro Thr Gly Pro Lys Ser Glu Ala Gly His Pro Gly Pro Pro Gly
1               5                   10                  15

Pro Pro Gly Pro
            20

<210> SEQ ID NO 455
<211> LENGTH: 20
<212> TYPE: PRT
<213> ORGANISM: Artificial Sequence
<220> FEATURE:
<223> OTHER INFORMATION: synthetic peptide

<400> SEQUENCE: 455

```
Phe Leu Ile Arg Asp Ser Glu Ser Ser Pro Ser Asp Phe Phe Val Ser
1               5                   10                  15

Leu Lys Ala Ser
            20

<210> SEQ ID NO 456
<211> LENGTH: 20
<212> TYPE: PRT
<213> ORGANISM: Artificial Sequence
<220> FEATURE:
<223> OTHER INFORMATION: synthetic peptide

<400> SEQUENCE: 456

Ser Ser Pro Ser Asp Phe Phe Val Ser Leu Lys Ala Ser Gly Lys Asn
1               5                   10                  15

Lys His Phe Lys
            20

<210> SEQ ID NO 457
<211> LENGTH: 20
<212> TYPE: PRT
<213> ORGANISM: Artificial Sequence
<220> FEATURE:
<223> OTHER INFORMATION: synthetic peptide

<400> SEQUENCE: 457

Met Asn Lys Val Met Ala Arg Phe Val Arg Gly Asp Ala Trp Pro Ala
1               5                   10                  15

Glu Ile Asp Ser
            20

<210> SEQ ID NO 458
<211> LENGTH: 20
<212> TYPE: PRT
<213> ORGANISM: Artificial Sequence
<220> FEATURE:
<223> OTHER INFORMATION: synthetic peptide

<400> SEQUENCE: 458

Phe Val Arg Gly Asp Ala Trp Pro Ala Glu Ile Asp Ser Leu Trp Glu
1               5                   10                  15

Ile Ser Lys Gln
            20

<210> SEQ ID NO 459
<211> LENGTH: 20
<212> TYPE: PRT
<213> ORGANISM: Artificial Sequence
<220> FEATURE:
<223> OTHER INFORMATION: synthetic peptide

<400> SEQUENCE: 459

Gly Pro Lys Gly Asn Val Gly Pro Gln Gly Glu Pro Gly Ser Pro Gly
1               5                   10                  15

Gln Gln Gly Asn
            20

<210> SEQ ID NO 460
<211> LENGTH: 20
<212> TYPE: PRT
<213> ORGANISM: Artificial Sequence
<220> FEATURE:
<223> OTHER INFORMATION: synthetic peptide
```

```
<400> SEQUENCE: 460

Pro Gln Gly Glu Pro Gly Ser Pro Gly Gln Gln Gly Asn Pro Gly Ala
1               5                   10                  15

Gln Gly Leu Pro
            20

<210> SEQ ID NO 461
<211> LENGTH: 20
<212> TYPE: PRT
<213> ORGANISM: Artificial Sequence
<220> FEATURE:
<223> OTHER INFORMATION: synthetic peptide

<400> SEQUENCE: 461

Ala Gln Gly Pro Pro Gly Pro Ala Gly Pro Ala Gly Glu Lys Gly Glu
1               5                   10                  15

Gln Gly Pro Ala
            20

<210> SEQ ID NO 462
<211> LENGTH: 20
<212> TYPE: PRT
<213> ORGANISM: Artificial Sequence
<220> FEATURE:
<223> OTHER INFORMATION: synthetic peptide

<400> SEQUENCE: 462

Ala Gly Pro Ala Gly Glu Lys Gly Glu Gln Gly Pro Ala Gly Ser Pro
1               5                   10                  15

Gly Phe Gln Gly
            20

<210> SEQ ID NO 463
<211> LENGTH: 20
<212> TYPE: PRT
<213> ORGANISM: Artificial Sequence
<220> FEATURE:
<223> OTHER INFORMATION: synthetic peptide

<400> SEQUENCE: 463

Ser Glu Thr Glu Cys Gly Gly Pro Asn Cys Arg Thr Asp Lys Gly Glu
1               5                   10                  15

Arg Lys Cys Gly
            20

<210> SEQ ID NO 464
<211> LENGTH: 20
<212> TYPE: PRT
<213> ORGANISM: Artificial Sequence
<220> FEATURE:
<223> OTHER INFORMATION: synthetic peptide

<400> SEQUENCE: 464

Pro Asn Cys Arg Thr Asp Lys Gly Glu Arg Lys Cys Gly Gly Pro Gly
1               5                   10                  15

Cys Gly Gly Leu
            20

<210> SEQ ID NO 465
<211> LENGTH: 20
<212> TYPE: PRT
<213> ORGANISM: Artificial Sequence
<220> FEATURE:
<223> OTHER INFORMATION: synthetic peptide
```

<400> SEQUENCE: 465

Pro Ser Thr Asp Lys Glu Lys Ser Trp Leu Tyr Thr Leu Asn Pro Ile
1               5                   10                  15

Leu Ile Thr Ile
            20

<210> SEQ ID NO 466
<211> LENGTH: 20
<212> TYPE: PRT
<213> ORGANISM: Artificial Sequence
<220> FEATURE:
<223> OTHER INFORMATION: synthetic peptide

<400> SEQUENCE: 466

Ser Trp Leu Tyr Thr Leu Asn Pro Ile Leu Ile Thr Ile Ile Ala Met
1               5                   10                  15

Ser Ser Leu Gly
            20

<210> SEQ ID NO 467
<211> LENGTH: 20
<212> TYPE: PRT
<213> ORGANISM: Artificial Sequence
<220> FEATURE:
<223> OTHER INFORMATION: synthetic peptide

<400> SEQUENCE: 467

Asp Leu Thr Gly Gln Lys Lys Gly Trp Lys Leu Arg Tyr Tyr Gly Asp
1               5                   10                  15

Pro Met Pro Cys
            20

<210> SEQ ID NO 468
<211> LENGTH: 20
<212> TYPE: PRT
<213> ORGANISM: Artificial Sequence
<220> FEATURE:
<223> OTHER INFORMATION: synthetic peptide

<400> SEQUENCE: 468

Gly Trp Lys Leu Arg Tyr Tyr Gly Asp Pro Met Pro Cys Pro Lys Glu
1               5                   10                  15

Asp Thr Pro Asn
            20

<210> SEQ ID NO 469
<211> LENGTH: 20
<212> TYPE: PRT
<213> ORGANISM: Artificial Sequence
<220> FEATURE:
<223> OTHER INFORMATION: synthetic peptide

<400> SEQUENCE: 469

Gln Thr Lys Pro Ser Ile Ser Gln Ile Ser Thr Thr Leu Ser Pro Thr
1               5                   10                  15

Thr Ser Thr Lys
            20

<210> SEQ ID NO 470
<211> LENGTH: 20
<212> TYPE: PRT
<213> ORGANISM: Artificial Sequence
<220> FEATURE:

<223> OTHER INFORMATION: synthetic peptide

<400> SEQUENCE: 470

Gln Ile Ser Thr Thr Leu Ser Pro Thr Thr Ser Thr Lys Lys Ser Gly
1               5                   10                  15

Gly Ala Ser Val
            20

<210> SEQ ID NO 471
<211> LENGTH: 20
<212> TYPE: PRT
<213> ORGANISM: Artificial Sequence
<220> FEATURE:
<223> OTHER INFORMATION: synthetic peptide

<400> SEQUENCE: 471

Gln Gly Asp Ala Phe His Gln Ser Asp Thr His Ile Phe Ser Ile Met
1               5                   10                  15

Gly Ala Ser Gly
            20

<210> SEQ ID NO 472
<211> LENGTH: 20
<212> TYPE: PRT
<213> ORGANISM: Artificial Sequence
<220> FEATURE:
<223> OTHER INFORMATION: synthetic peptide

<400> SEQUENCE: 472

Ser Asp Thr His Ile Phe Ser Ile Met Gly Ala Ser Gly Asp Leu Ala
1               5                   10                  15

Lys Lys Lys Ile
            20

<210> SEQ ID NO 473
<211> LENGTH: 20
<212> TYPE: PRT
<213> ORGANISM: Artificial Sequence
<220> FEATURE:
<223> OTHER INFORMATION: synthetic peptide

<400> SEQUENCE: 473

Leu Phe Ser Ser Gln Ala Ala Ala Ile Leu Ser Thr Leu Phe Ala Ala
1               5                   10                  15

Glu Val Ile Pro
            20

<210> SEQ ID NO 474
<211> LENGTH: 20
<212> TYPE: PRT
<213> ORGANISM: Artificial Sequence
<220> FEATURE:
<223> OTHER INFORMATION: synthetic peptide

<400> SEQUENCE: 474

Ala Ile Leu Ser Thr Leu Phe Ala Ala Glu Val Ile Pro Thr Thr Val
1               5                   10                  15

Arg Gly Arg Gly
            20

<210> SEQ ID NO 475
<211> LENGTH: 20
<212> TYPE: PRT
<213> ORGANISM: Artificial Sequence

```
<220> FEATURE:
<223> OTHER INFORMATION: synthetic peptide

<400> SEQUENCE: 475

Leu Pro Met Gly Ala Pro Val Pro Arg Pro Arg Gly Pro Leu Pro Pro
1               5                   10                  15

Pro Gly Asp Glu
            20

<210> SEQ ID NO 476
<211> LENGTH: 20
<212> TYPE: PRT
<213> ORGANISM: Artificial Sequence
<220> FEATURE:
<223> OTHER INFORMATION: synthetic peptide

<400> SEQUENCE: 476

Pro Arg Pro Arg Gly Pro Leu Pro Pro Pro Gly Asp Glu Asn Arg Glu
1               5                   10                  15

Met Asp Asp Pro
            20

<210> SEQ ID NO 477
<211> LENGTH: 20
<212> TYPE: PRT
<213> ORGANISM: Artificial Sequence
<220> FEATURE:
<223> OTHER INFORMATION: synthetic peptide

<400> SEQUENCE: 477

Lys Gly Asp Ile Gly Glu Lys Gly Asp Ser Gly Pro Ser Arg Ala Ala
1               5                   10                  15

Gly Pro Pro Gly
            20

<210> SEQ ID NO 478
<211> LENGTH: 20
<212> TYPE: PRT
<213> ORGANISM: Artificial Sequence
<220> FEATURE:
<223> OTHER INFORMATION: synthetic peptide

<400> SEQUENCE: 478

Gly Asp Ser Gly Pro Ser Arg Ala Ala Gly Pro Pro Gly Lys Lys Gly
1               5                   10                  15

Pro Pro Gly Glu
            20

<210> SEQ ID NO 479
<211> LENGTH: 20
<212> TYPE: PRT
<213> ORGANISM: Artificial Sequence
<220> FEATURE:
<223> OTHER INFORMATION: synthetic peptide

<400> SEQUENCE: 479

Ala Leu Ser Pro Leu Thr Pro Ala Arg Leu Leu Gly Pro Phe Leu Thr
1               5                   10                  15

Ser Thr Thr Pro
            20

<210> SEQ ID NO 480
<211> LENGTH: 20
<212> TYPE: PRT
```

-continued

```
<213> ORGANISM: Artificial Sequence
<220> FEATURE:
<223> OTHER INFORMATION: synthetic peptide

<400> SEQUENCE: 480

Ala Arg Leu Leu Gly Pro Phe Leu Thr Ser Thr Thr Pro Ala Ser Ser
1               5                   10                  15

Ser Ser Gly Ser
            20

<210> SEQ ID NO 481
<211> LENGTH: 20
<212> TYPE: PRT
<213> ORGANISM: Artificial Sequence
<220> FEATURE:
<223> OTHER INFORMATION: synthetic peptide

<400> SEQUENCE: 481

Asn His Ser Gly Ile Ser Val Asn Ile Gln Asp Leu Ala Ser Ser Cys
1               5                   10                  15

Ala Gly Phe Leu
            20

<210> SEQ ID NO 482
<211> LENGTH: 20
<212> TYPE: PRT
<213> ORGANISM: Artificial Sequence
<220> FEATURE:
<223> OTHER INFORMATION: synthetic peptide

<400> SEQUENCE: 482

Asn Ile Gln Asp Leu Ala Ser Ser Cys Ala Gly Phe Leu Phe Gly Val
1               5                   10                  15

Ala Asn Thr Ala
            20

<210> SEQ ID NO 483
<211> LENGTH: 20
<212> TYPE: PRT
<213> ORGANISM: Artificial Sequence
<220> FEATURE:
<223> OTHER INFORMATION: synthetic peptide

<400> SEQUENCE: 483

Gly Glu Pro Gly Thr Cys Lys Asp Arg Glu Ile Leu Arg Tyr Asp Pro
1               5                   10                  15

His Lys Leu Leu
            20

<210> SEQ ID NO 484
<211> LENGTH: 20
<212> TYPE: PRT
<213> ORGANISM: Artificial Sequence
<220> FEATURE:
<223> OTHER INFORMATION: synthetic peptide

<400> SEQUENCE: 484

Asp Arg Glu Ile Leu Arg Tyr Asp Pro His Lys Leu Leu Glu Gly Cys
1               5                   10                  15

Leu Val Gly Gly
            20

<210> SEQ ID NO 485
<211> LENGTH: 20
```

```
<212> TYPE: PRT
<213> ORGANISM: Artificial Sequence
<220> FEATURE:
<223> OTHER INFORMATION: synthetic peptide

<400> SEQUENCE: 485

Ile Lys Asn Leu Val Gly Ser Gly Ser Glu Ile Gln Phe Phe Ser Glu
1               5                   10                  15

Ala Gln Asp Asp
            20

<210> SEQ ID NO 486
<211> LENGTH: 20
<212> TYPE: PRT
<213> ORGANISM: Artificial Sequence
<220> FEATURE:
<223> OTHER INFORMATION: synthetic peptide

<400> SEQUENCE: 486

Gly Ser Glu Ile Gln Phe Phe Ser Glu Ala Gln Asp Asp Pro Gln Lys
1               5                   10                  15

Arg Lys Pro Asp
            20

<210> SEQ ID NO 487
<211> LENGTH: 20
<212> TYPE: PRT
<213> ORGANISM: Artificial Sequence
<220> FEATURE:
<223> OTHER INFORMATION: synthetic peptide

<400> SEQUENCE: 487

Ser Gly Gly Ala Leu Ser Pro Leu Arg Ala Ala Ser Asp Ser Leu Leu
1               5                   10                  15

Ser Ser Val Ser
            20

<210> SEQ ID NO 488
<211> LENGTH: 20
<212> TYPE: PRT
<213> ORGANISM: Artificial Sequence
<220> FEATURE:
<223> OTHER INFORMATION: synthetic peptide

<400> SEQUENCE: 488

Leu Arg Ala Ala Ser Asp Ser Leu Leu Ser Ser Val Ser Pro Ala Val
1               5                   10                  15

Ser Lys Ala Ser
            20

<210> SEQ ID NO 489
<211> LENGTH: 20
<212> TYPE: PRT
<213> ORGANISM: Artificial Sequence
<220> FEATURE:
<223> OTHER INFORMATION: synthetic peptide

<400> SEQUENCE: 489

Leu Glu Leu Asp Glu Gln Gln Lys Lys Arg Leu Glu Ala Tyr Leu Thr
1               5                   10                  15

Gln Lys Ala Lys
            20

<210> SEQ ID NO 490
```

```
<211> LENGTH: 20
<212> TYPE: PRT
<213> ORGANISM: Artificial Sequence
<220> FEATURE:
<223> OTHER INFORMATION: synthetic peptide

<400> SEQUENCE: 490

Lys Lys Arg Leu Glu Ala Tyr Leu Thr Gln Lys Ala Lys Val Gly Glu
1               5                   10                  15

Leu Lys Asp Asp
            20

<210> SEQ ID NO 491
<211> LENGTH: 20
<212> TYPE: PRT
<213> ORGANISM: Artificial Sequence
<220> FEATURE:
<223> OTHER INFORMATION: synthetic peptide

<400> SEQUENCE: 491

Pro Glu Tyr Val Ile Pro Val His Tyr Asp Leu Leu Ile Tyr Ala Asn
1               5                   10                  15

Leu Thr Thr Leu
            20

<210> SEQ ID NO 492
<211> LENGTH: 20
<212> TYPE: PRT
<213> ORGANISM: Artificial Sequence
<220> FEATURE:
<223> OTHER INFORMATION: synthetic peptide

<400> SEQUENCE: 492

His Tyr Asp Leu Leu Ile Tyr Ala Asn Leu Thr Thr Leu Thr Phe Trp
1               5                   10                  15

Gly Thr Thr Lys
            20

<210> SEQ ID NO 493
<211> LENGTH: 20
<212> TYPE: PRT
<213> ORGANISM: Artificial Sequence
<220> FEATURE:
<223> OTHER INFORMATION: synthetic peptide

<400> SEQUENCE: 493

Gly Ile Ala Ser Asp Ser Ser Ser Asp Ser Ser Ser Ser Phe Ser Ser
1               5                   10                  15

Ser Ser Ser Asp
            20

<210> SEQ ID NO 494
<211> LENGTH: 20
<212> TYPE: PRT
<213> ORGANISM: Artificial Sequence
<220> FEATURE:
<223> OTHER INFORMATION: synthetic peptide

<400> SEQUENCE: 494

Ser Asp Ser Ser Ser Ser Phe Ser Ser Ser Ser Asp Ser Asp Ser
1               5                   10                  15

Glu Cys Glu Ser
            20
```

```
<210> SEQ ID NO 495
<211> LENGTH: 20
<212> TYPE: PRT
<213> ORGANISM: Artificial Sequence
<220> FEATURE:
<223> OTHER INFORMATION: synthetic peptide

<400> SEQUENCE: 495

Pro Pro Gly His Leu Thr Ala Ala Leu Gly Asp Ile Met Arg His Tyr
1               5                   10                  15

Asp Glu Ser Met
            20

<210> SEQ ID NO 496
<211> LENGTH: 20
<212> TYPE: PRT
<213> ORGANISM: Artificial Sequence
<220> FEATURE:
<223> OTHER INFORMATION: synthetic peptide

<400> SEQUENCE: 496

Ala Leu Gly Asp Ile Met Arg His Tyr Asp Glu Ser Met Pro Asp Pro
1               5                   10                  15

Leu Pro Glu Phe
            20

<210> SEQ ID NO 497
<211> LENGTH: 20
<212> TYPE: PRT
<213> ORGANISM: Artificial Sequence
<220> FEATURE:
<223> OTHER INFORMATION: synthetic peptide

<400> SEQUENCE: 497

Met Pro Glu Cys Gln Cys Pro Pro His Met Thr Gly Pro Trp Cys Glu
1               5                   10                  15

Glu His Val Phe
            20

<210> SEQ ID NO 498
<211> LENGTH: 20
<212> TYPE: PRT
<213> ORGANISM: Artificial Sequence
<220> FEATURE:
<223> OTHER INFORMATION: synthetic peptide

<400> SEQUENCE: 498

Pro His Met Thr Gly Pro Trp Cys Glu Glu His Val Phe Ser Gln Gln
1               5                   10                  15

Gln Pro Gly His
            20

<210> SEQ ID NO 499
<211> LENGTH: 20
<212> TYPE: PRT
<213> ORGANISM: Artificial Sequence
<220> FEATURE:
<223> OTHER INFORMATION: synthetic peptide

<400> SEQUENCE: 499

Ser Asp Asp Ile Lys Glu Thr Gly Tyr Thr Tyr Ile Leu Leu Lys Asn
1               5                   10                  15

Val Leu Lys Lys
            20
```

```
<210> SEQ ID NO 500
<211> LENGTH: 20
<212> TYPE: PRT
<213> ORGANISM: Artificial Sequence
<220> FEATURE:
<223> OTHER INFORMATION: synthetic peptide

<400> SEQUENCE: 500

Gly Tyr Thr Tyr Ile Leu Leu Lys Asn Val Leu Lys Lys Phe Ile Cys
1               5                   10                  15

Ile Ser Asp Leu
            20

<210> SEQ ID NO 501
<211> LENGTH: 20
<212> TYPE: PRT
<213> ORGANISM: Artificial Sequence
<220> FEATURE:
<223> OTHER INFORMATION: synthetic peptide

<400> SEQUENCE: 501

Glu Pro Gly Pro Ala Thr Pro Asp Phe Tyr Ala Leu Val Val Gln Arg
1               5                   10                  15

Leu Glu Gln Leu
            20

<210> SEQ ID NO 502
<211> LENGTH: 20
<212> TYPE: PRT
<213> ORGANISM: Artificial Sequence
<220> FEATURE:
<223> OTHER INFORMATION: synthetic peptide

<400> SEQUENCE: 502

Asp Phe Tyr Ala Leu Val Val Gln Arg Leu Glu Gln Leu Val Gln Glu
1               5                   10                  15

Gln Leu Lys Ser
            20

<210> SEQ ID NO 503
<211> LENGTH: 20
<212> TYPE: PRT
<213> ORGANISM: Artificial Sequence
<220> FEATURE:
<223> OTHER INFORMATION: synthetic peptide

<400> SEQUENCE: 503

Arg Thr Gly Lys Ala Ala Gln Val Thr Ile Gln Ser Ser Glu Thr Phe
1               5                   10                  15

Ser Ser Lys Phe
            20

<210> SEQ ID NO 504
<211> LENGTH: 20
<212> TYPE: PRT
<213> ORGANISM: Artificial Sequence
<220> FEATURE:
<223> OTHER INFORMATION: synthetic peptide

<400> SEQUENCE: 504

Val Thr Ile Gln Ser Ser Glu Thr Phe Ser Ser Lys Phe Gln Val Asp
1               5                   10                  15

Asn Asn Asn Arg
            20
```

<210> SEQ ID NO 505
<211> LENGTH: 20
<212> TYPE: PRT
<213> ORGANISM: Artificial Sequence
<220> FEATURE:
<223> OTHER INFORMATION: synthetic peptide

<400> SEQUENCE: 505

Tyr Gly Ser Gln Thr Pro Leu His Asp Gly Ser Arg Thr Ser Ala Gln
1               5                   10                  15

Ser Gly Ala Trp
            20

<210> SEQ ID NO 506
<211> LENGTH: 20
<212> TYPE: PRT
<213> ORGANISM: Artificial Sequence
<220> FEATURE:
<223> OTHER INFORMATION: synthetic peptide

<400> SEQUENCE: 506

His Asp Gly Ser Arg Thr Ser Ala Gln Ser Gly Ala Trp Asp Pro Asn
1               5                   10                  15

Asn Pro Asn Thr
            20

<210> SEQ ID NO 507
<211> LENGTH: 20
<212> TYPE: PRT
<213> ORGANISM: Artificial Sequence
<220> FEATURE:
<223> OTHER INFORMATION: synthetic peptide

<400> SEQUENCE: 507

Lys Arg Thr Pro Ala Pro Glu Pro Glu Pro Cys Glu Ala Phe Glu Leu
1               5                   10                  15

Pro Ala Lys Arg
            20

<210> SEQ ID NO 508
<211> LENGTH: 20
<212> TYPE: PRT
<213> ORGANISM: Artificial Sequence
<220> FEATURE:
<223> OTHER INFORMATION: synthetic peptide

<400> SEQUENCE: 508

Pro Glu Pro Cys Glu Ala Phe Glu Leu Pro Ala Lys Arg Leu Arg Ser
1               5                   10                  15

Ser Glu Glu Pro
            20

<210> SEQ ID NO 509
<211> LENGTH: 20
<212> TYPE: PRT
<213> ORGANISM: Artificial Sequence
<220> FEATURE:
<223> OTHER INFORMATION: synthetic peptide

<400> SEQUENCE: 509

Val Lys Leu Thr Arg Gln Thr Met Ala Glu Val Phe Glu Met Glu Gln
1               5                   10                  15

Ser Ile Cys Ala

```
<210> SEQ ID NO 510
<211> LENGTH: 20
<212> TYPE: PRT
<213> ORGANISM: Artificial Sequence
<220> FEATURE:
<223> OTHER INFORMATION: synthetic peptide

<400> SEQUENCE: 510

Met Ala Glu Val Phe Glu Met Glu Gln Ser Ile Cys Ala Ala Glu Glu
1               5                   10                  15

Gln Pro Ala Glu
            20

<210> SEQ ID NO 511
<211> LENGTH: 20
<212> TYPE: PRT
<213> ORGANISM: Artificial Sequence
<220> FEATURE:
<223> OTHER INFORMATION: synthetic peptide

<400> SEQUENCE: 511

Arg Ser Thr Ile Ile Thr Leu Tyr Asn Gly Ala Phe Asp Phe Ser Ser
1               5                   10                  15

Ala Val Phe Leu
            20

<210> SEQ ID NO 512
<211> LENGTH: 20
<212> TYPE: PRT
<213> ORGANISM: Artificial Sequence
<220> FEATURE:
<223> OTHER INFORMATION: synthetic peptide

<400> SEQUENCE: 512

Tyr Asn Gly Ala Phe Asp Phe Ser Ser Ala Val Phe Leu Ile Ile Lys
1               5                   10                  15

Leu Leu Tyr Glu
            20

<210> SEQ ID NO 513
<211> LENGTH: 8
<212> TYPE: PRT
<213> ORGANISM: Artificial Sequence
<220> FEATURE:
<223> OTHER INFORMATION: ovalbumin epitope sequence

<400> SEQUENCE: 513

Ser Ile Ile Asn Phe Glu Lys Leu
1               5

<210> SEQ ID NO 514
<211> LENGTH: 12
<212> TYPE: PRT
<213> ORGANISM: Artificial Sequence
<220> FEATURE:
<223> OTHER INFORMATION: chicken ovalbumin and the LLO190 epitope

<400> SEQUENCE: 514

Asn Glu Lys Tyr Ala Gln Ala Tyr Pro Asn Val Ser
1               5                   10
```